United States Patent
Bhatia et al.

(10) Patent No.: US 7,528,134 B2
(45) Date of Patent: *May 5, 2009

(54) ACETAMIDES AND BENZAMIDES THAT ARE USEFUL IN TREATING SEXUAL DYSFUNCTION

(75) Inventors: Pramila A. Bhatia, Libertyville, IL (US); Jerome F. Daanen, Racine, WI (US); Ahmed A. Hakeem, Niles, IL (US); Teodozyj Kolasa, Lake Villa, IL (US); Mark A. Matulenko, Libertyville, IL (US); Kathleen H. Mortell, Chicago, IL (US); Meena V. Patel, Green Oaks, IL (US); Andrew O. Stewart, Libertyville, IL (US); Xueqing Wang, Evanston, IL (US); Zhiren Xia, Wadsworth, IL (US); Henry Q. Zhang, Grayslake, IL (US)

(73) Assignee: Abbott Laboratories Inc., Abbott Park, IL (US)

( * ) Notice: Subject to any disclaimer, the term of this patent is extended or adjusted under 35 U.S.C. 154(b) by 913 days.

This patent is subject to a terminal disclaimer.

(21) Appl. No.: 10/444,687

(22) Filed: May 23, 2003

(65) Prior Publication Data
US 2003/0229094 A1    Dec. 11, 2003

Related U.S. Application Data

(60) Provisional application No. 60/382,863, filed on May 23, 2002.

(51) Int. Cl.
*A61K 31/501* (2006.01)
*A61K 31/497* (2006.01)

(52) U.S. Cl. .............. 514/252.02; 514/252.14; 514/252.11; 514/253.1

(58) Field of Classification Search ............ 514/252.02, 514/252.03, 252.11, 252
See application file for complete search history.

(56) References Cited

U.S. PATENT DOCUMENTS

| 6,083,947 | A * | 7/2000 | Granger et al. ............... 514/249 |
| 6,960,589 | B2 * | 11/2005 | Cowart et al. ........... 514/252.14 |
| 7,022,728 | B2 * | 4/2006 | Cowart et al. ................ 514/395 |
| 2003/0229094 | A1 * | 12/2003 | Bhatia et al. ............ 514/252.02 |
| 2004/0073036 | A1 * | 4/2004 | Marzabadi et al. ........... 546/194 |

FOREIGN PATENT DOCUMENTS

| EP | 0512755 | 11/1992 |
| WO | WO 00/35892 | 6/2000 |

OTHER PUBLICATIONS

"IUPAC Commission on Nomenclature of Organic Chemistry, Rules for the Nomenclature of Organic Chemistry, Section E: Stereochemistry (Recommendations 1974)" IUPAC Pure and Applied Chemistry 45:13-30 (1976).

Abdel Rahman et al., "Synthesis and biological activities of some new 2-(N-heterocyclo carboxamidomehtyl thio) Naphth[1,2-d]oxazoles. Part VI," J. Indian Chem. Soc. 58:171-173 (1981).

Astles et al., "Acyl-CoA: cholesterol O-acyltransferase (ACAT) inhibitors. 2. 2-(1,3-dioxan-2-yl)-4,5-diphenyl-1-H-imidazoles as potent inhibitors of ACAT," J. Med. Chem. 39:1423 (1996).

Bendele et al., "Anti-inflammatory activity of pergolide, a dopamine receptor agonist," Journal of Pharmacology and Experimental Therapeutics (1991).

Bursavich et al., "From peptides to non-peptide peptidomimetics: design and synthesis of new peperidine inhibitors of aspartic peptidases," Org. Lett. 3(15):2317-2320 (2001).

Caroti et al., "Synthesis, Antilipidemic and platelet antiaggregatory activity of 2-aminobenzimidazole amide derivatives," Farmaco 44(3):227 (1989).

Carreno et al., "Enantioselective Diels—alder cycloadditions with (S,S)-2-(p-Tolylsulfinyl)-1,4-naphthoquinone: Efficient kinetic resolution of chiral racemic vinylcyclohexenes," J. Org. Chem. 63:8320-8330 (1998).

Chen et al., "Effects of dopamine, apomorphine, γ-hydroxybutyric acid, haloperidol and pimozide on reflex bradycardia in rats," Journal of Pharmacology and Experimental Therapeutics 214(2):427-432 (1980).

Coward et al., "Chimeric G proteins allow a high-throughput signaling assay of $G_i$—coupled receptors," Analytical Biochemistry 270:242-248 (1999).

Eastwood, "A versatile synthesis of 4-aryl tetrahydropyridines via palladium mediated Suzuki cross-coupling with cyclic vinyl boronates," Tetrahedron Letters 41:3705-3708 (2000).

Hahn et al., "Primate cardiovascular responses mediated by dopamine receptors: effects of N,N-di-n-propyldopamine and LY171555," Journal of Pharmacology and Experimental Therapeutics 229(1):132-138 (1983).

Hrib et al., "The dopamine $D_4$ receptor: a controversial therapeutic target," Drugs of the Future 25(6):587-611 (2000).

Lissoni et al., "Efficacy of bromocriptine in the treatment of metastatic breast cancer- and prostate cancer-related hyperprolactinemia," Neuroendocrinology Letters 21:405-408 (2000).

(Continued)

*Primary Examiner*—Shengjun Wang
*Assistant Examiner*—Timothy E Betton
(74) *Attorney, Agent, or Firm*—Andreas M. Danckers

(57) ABSTRACT

The present invention relates to the use of compounds of formula (I)

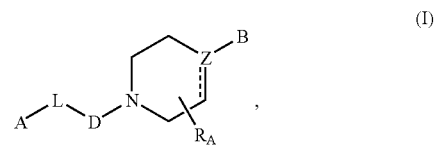

for the treatment of sexual dysfunction and to compositions containing compounds of formula (I) for the treatment of sexual dysfunction.

9 Claims, No Drawings

OTHER PUBLICATIONS

Melis et al., "Dopamine and sexual behavior," Neuroscience and Biobehavioral Reviews 19(1):19-38 (1995).

Missale et al., "Dopamine receptors: from structure to function," Physiol. Reviews 78(1):189-225 (1998).

Prescott et al., Methods in Cell Biology, Academic Press, New York, p. 33 et seq. (1976).

Saari et al., "Adrenoceptor and tetrabenazine antagonism activities of some pyridinyltetrahydropyridines," J. Med. Chem. 27:1182-1185 (1984).

* cited by examiner

ACETAMIDES AND BENZAMIDES THAT ARE USEFUL IN TREATING SEXUAL DYSFUNCTION

This application claims priority to U.S. Provisional Patent Application Ser. No. 60/382,863, filed May 23, 2002, which is hereby incorporated by reference.

TECHNICAL FIELD

The present invention relates to the use of acetamides and benzamides and compositions containing these compounds for the treatment of sexual dysfunction.

BACKGROUND OF THE INVENTION

Preclinical evidence indicates that dopamine (DA) plays a role in penile erection in mammals. Sexual stimulation can be initiated by sensory (erotic) information reaching the cerebral cortex in mammals. The cerebral cortex has extensive neuronal connections with limbic structures like the amygdala, as well as midbrain structures like the periaqueductal gray (PAG) and the hypothalamus. Two important nuclei in the hypothalamus are the medial preoptic area (MPOA) and the paraventricular nucleus (PVN). The MPOA and PVN nuclei play a critical role in sexual behavior as bilateral lesions of these areas completely eliminate male sexual behavior. The incerto-hypothalamic dopaminergic pathway that innervates the PVN and the MPOA nuclei has been associated with the pro-erectile effect of DA agents. Systemic administration of DA receptor agonists like apomorphine ((6aR) 5,6,6a,7-tetrahydro-6-methyl-4H-dibenzo[de,g]quinoline-10,11-diol), quinpirole and (−)3-(3-hydroxyphenyl)-N-propylpiperidine (3-PPP) facilitate penile erection in rats, an effect blocked by haloperidol, a central DA antagonist. As the erectogenic effect can not be blocked by domperidone, a peripheral DA antagonist, it is believed that the pro-erectile effect of DA agonists is centrally mediated.

Clinical data also indicates that DA systems in the CNS play a role on the regulation of male sexual behavior as indicated by the sexual stimulatory effect of L-dopa in Parkinson's patients and by the pro-erectile effect of apomorphine in humans.

DA receptors belong to a superfamily of protein receptors that signal across the cell membrane by coupling to intracellular GTP-binding proteins. Several G proteins have been identified (including Gs, Gq and Gi) that lead to specific intracellular events.

There are five known DA receptors which are classified into two groups, $D_1$-like and $D_2$-like. The $D_1$-like receptors include $D_1$ and $D_5$. The $D_2$-like receptors include $D_2$, $D_3$ and $D_4$. The $D_1$-like family receptor subtypes are $G_s$-coupled and can activate adenylate cyclase. The $D_2$-like family receptor subtypes are $G_i$-coupled and they increase intracellular calcium level and inhibit adenylate cyclase.

The $D_1$-like family members are $G_s$-coupled receptors that can activate adenylate cyclase. The $D_1$ receptor is the most abundant and widespread DA receptor in the CNS both by mRNA expression and by immunohistochemical studies. It is found in the striatum, nucleus accumbens and olfactory tubercle as well as the limbic system, hypothalamus and thalamus. The $D_1$ receptor expression has been reported in the heart and kidney, and despite that the function of these peripheral $D_1$ receptors remains to be clarified, its role on the control of hemodynamic variables has been confirmed. The $D_5$ receptor, while having a higher affinity for DA than the $D_1$ receptor, is sparsely distributed in the CNS with no evidence of expression outside the CNS.

The $D_2$-like family members are $G_i$ coupled receptors that inhibit adenylate cyclase and increase intracellular calcium levels. The $D_2$ receptor is the most abundant of the $D_2$-like receptors and is located in brain areas such as the striatum and substantia nigra, and in peripheral areas such as the heart, pituitary gland and kidney. The $D_3$ receptor is found abundantly in the islands of Calleja with distinct cluster populations in the ventral striatum/nucleus accumbens regions, olfactory tubercle, dendate gyrus and striatal cortex.

Expression of the $D_4$ receptor has been documented by in situ RNA hybridization and immunohistochemical studies. Recently, studies revealed that $D_4$ expression is highest in the entorhinal cortex, lateral septal nucleus, hippocampus and the medial preoptic area of the hypothalamus. Localization of $D_4$ is distinct from the distribution of $D_2$ in the brain, as $D_2$ receptors are most abundant in striatal areas. The expression of $D_4$ receptors in the MPOA of the hypothalamus is of importance to the facilitation of penile erection in view of the role of the hypothalamus as an area of integration between the cortex and the spinal pathways. The participation of $D_4$ receptors in other CNS regions, thalamic, subthalamic and spinal can not be excluded.

The present invention identifies a therapeutic use for acetamides and benzamides of formula (I) in the treatment of sexual dysfunction in mammals. More specifically, these compounds are useful in the treatment of sexual dysfunction including, but not limited to, male erectile dysfunction (MED).

SUMMARY OF THE INVENTION

The present invention relates to a method of treating sexual dysfunction in a mammal, in particular humans, comprising administering to the mammal a therapeutically effective amount of a compound of formula (I)

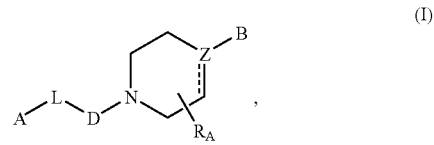

or a pharmaceutically acceptable salt, ester, amide, or prodrug thereof, wherein A is aryl, arylalkyl, cycloalkyl, cycloalkylalkyl, heterocycle, or heterocyclealkyl;

L is —N($R_7$)C(O)—, —C(O)N($R_7$)—, —N($R_7$)C(S)—, or —C(S)N($R_7$)— wherein the left end of said —N($R_7$)C(O)—, —C(O)N($R_7$)—, —N($R_7$)C(S)—, or —C(S)N($R_7$)— is attached to A and the right end is attached to D;

D is alkylene, fluoroalkylene, or hydroxyalkylene;

Z is N, C or $CR_B$;

$R_A$ is hydrogen or alkyl;

$R_B$ is hydrogen, alkyl, or halogen;

━ is a bond when Z is C and ━ is absent when Z is N or $CR_B$;

B is

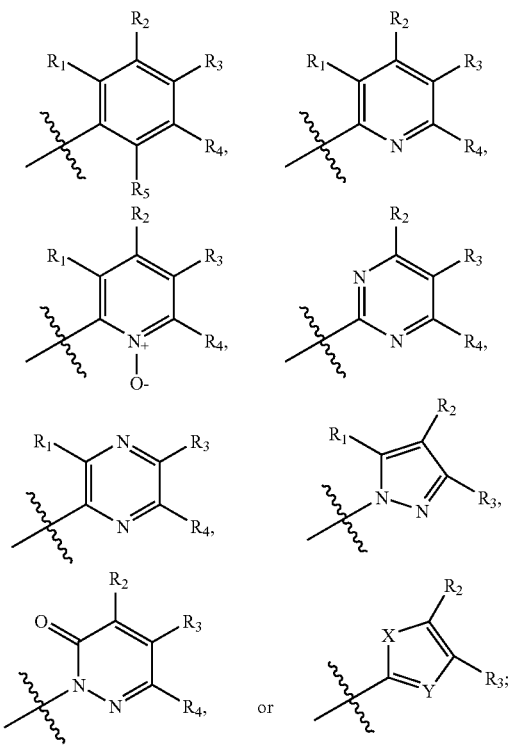

$R_1$, $R_2$, $R_3$, $R_4$ and $R_5$ are each independently hydrogen, alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, —$NZ_1Z_2$, ($NZ_3Z_4$) alkyl, ($NZ_3Z_4$)carbonyl, or ($NZ_3Z_4$)sulfonyl;

$Z_1$ and $Z_2$ are each independently hydrogen, alkyl, alkylcarbonyl, alkylsulfonyl, aryl, arylalkyl, arylalkylsulfonyl, arylsulfonyl, or formyl;

$Z_3$ and $Z_4$ are each independently hydrogen, alkyl, aryl, or arylalkyl;

X is N($R_6$), O or S;

Y is C($R_4$) or N;

$R_6$ is hydrogen or alkyl; and $R_7$ is hydrogen or alkyl.

DETAILED DESCRIPTION OF THE INVENTION

All patents, patent applications, and literature references cited in the specification are herein incorporated by reference in their entirety.

In its principle embodiment, the present invention relates to a method of treating sexual dysfunction in a mammal, in particular humans, comprising administering to the mammal a therapeutically effective amount of a compound of formula (I)

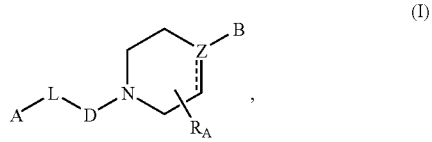
(I)

or a pharmaceutically acceptable salt, ester, amide, or prodrug thereof, wherein A is aryl, arylalkyl, cycloalkyl, cycloalkylalkyl, heterocycle, or heterocyclealkyl;

L is —N($R_7$)C(O)—, —C(O)N($R_7$)—, —N($R_7$)C(S)—, or —C(S)N($R_7$)— wherein the left end of said —N($R_7$)C(O)—, —C(O)N($R_7$)—, —N($R_7$)C(S)—, or —C(S)N($R_7$)— is attached to A and the right end is attached to D;

D is alkylene, fluoroalkylene, or hydroxyalkylene;

Z is N, C or C$R_B$;

$R_A$ is hydrogen or alkyl;

$R_B$ is hydrogen, alkyl, or halogen;

— is a bond when Z is C and — is absent when Z is N or C$R_B$;

B is

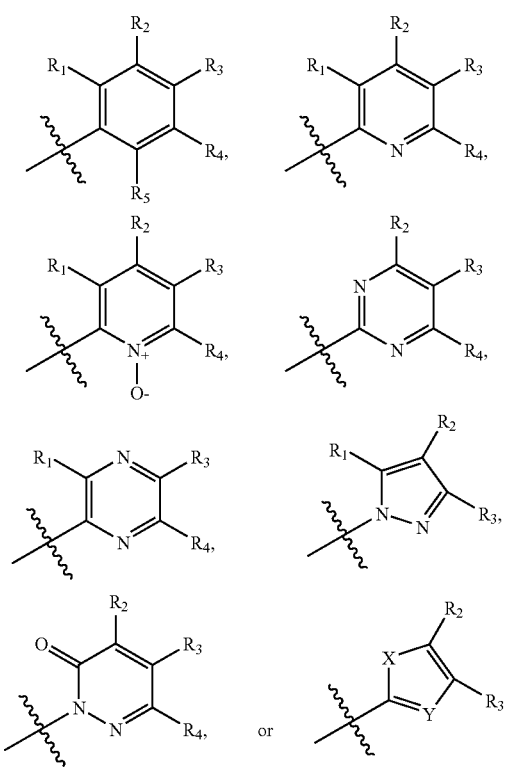

$R_1$, $R_2$, $R_3$, $R_4$ and $R_5$ are each independently hydrogen, alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, —$NZ_1Z_2$, ($NZ_3Z_4$) alkyl, ($NZ_3Z_4$)carbonyl, or ($NZ_3Z_4$)sulfonyl;

$Z_1$ and $Z_2$ are each independently hydrogen, alkyl, alkylcarbonyl, alkylsulfonyl, aryl, arylalkyl, arylalkylsulfonyl, arylsulfonyl, or formyl;

$Z_3$ and $Z_4$ are each independently hydrogen, alkyl, aryl, or arylalkyl;

X is N($R_6$), O or S;

Y is C($R_4$) or N;

$R_6$ is hydrogen or alkyl; and $R_7$ is hydrogen or alkyl.

In another embodiment, the present invention relates to a method of treating sexual dysfunction in a mammal compris ing administering to the mammal a therapeutically effective amount of a compound of formula (I) wherein A is aryl; B is

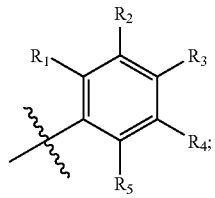

Z is N; — is absent; L is —N(R$_7$)C(O)—; and D, R$_1$, R$_2$, R$_3$, R$_4$, R$_5$, R$_7$, and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

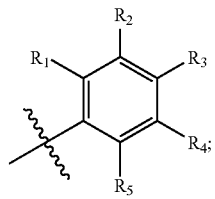

R$_1$ is hydrogen, alkoxy, alkyl, alkylthio, cyano, halogen, hydroxy, nitro, —NZ$_1$Z$_2$, or (NZ$_3$Z$_4$)alkyl; R$_2$ is hydrogen, alkoxy, cyano, halogen, or hydroxy; R$_3$ is hydrogen or hydroxy; R$_4$ and R$_5$ are hydrogen; Z is N; — is absent; D is —CH$_2$—; L is —N(R$_7$)C(O)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

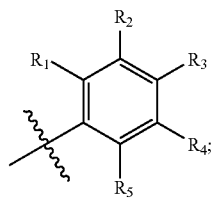

R$_1$ is hydrogen, alkoxy, alkyl, alkylthio, cyano, halogen, hydroxy, nitro, —NZ$_1$Z$_2$, or (NZ$_3$Z$_4$)alkyl; R$_2$ is hydrogen, alkoxy, cyano, halogen, or hydroxy; R$_3$ is hydrogen or hydroxy; R$_4$ and R$_5$ are hydrogen; Z is N; — is absent; D is —CH(CH$_3$)—; L is —N(R$_7$)C(O)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

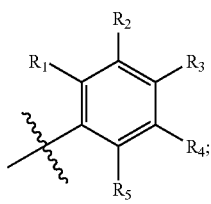

Z is N; — is absent; L is —N(R$_7$)C(O)—; and D, R$_1$, R$_2$, R$_3$, R$_4$, R$_5$, R$_7$, and R$_A$ are as defined in formula (I).

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

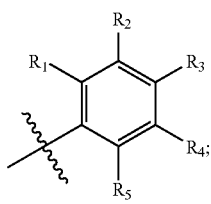

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH$_2$—; L is —N(R$_7$)C(O)—; and R$_7$ and R$_A$ are as defined on formula (I).

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, pyrazolyl, pyridinyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

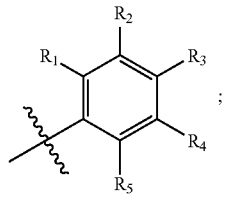

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is N; — is absent; D is —$CH_2$—; L is —$N(R_7)C(O)$—; and $R_7$ and $R_A$ are as defined on formula (I).

In another embodiment, the present invention relates to a method of treating sexual dysfunction in a mammal comprising administering to the mammal a therapeutically effective amount of a compound of formula (I) wherein A is aryl; B is

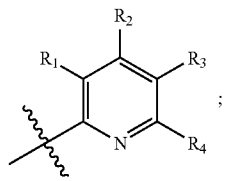

Z is N; — is absent; L is —$N(R_7)C(O)$—; and D, $R_1$, $R_2$, $R_3$, $R_4$, $R_7$, and $R_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

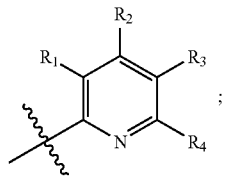

is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is N; — is absent; D is —$CH_2$—; L is —$N(R_7)C(O)$—; and $R_7$ and $R_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

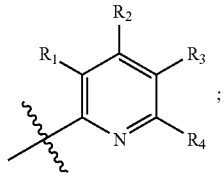

is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is N; — is absent; D is —$CH_2$—; L is —$N(R_7)C(S)$—; and $R_7$ and $R_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

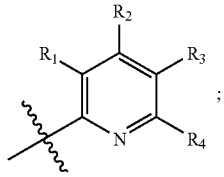

is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is N; — is absent; D is —$CH(CH_3)$—; L is —$N(R_7)C(O)$—; and $R_7$ and $R_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is tetrahydronaphthalenyl or 2,3-dihydro-1H-indenyl; B is

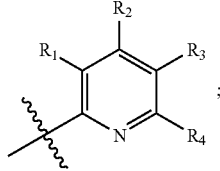

is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is N; — is absent; D is —$CH_2$—; L is —$N(R_7)C(O)$—; and $R_7$ and $R_A$ are as defined in formual (I).

In another embodiment, the present invention relates to a method of treating sexual dysfunction in a mammal comprising administering to the mammal a therapeutically effective amount of a compound of formula (I) wherein A is aryl wherein the aryl is tetrahydronaphthalenyl or 2,3-dihydro-1H-indenyl; B is

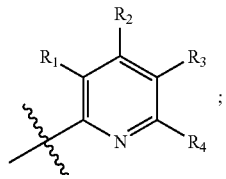

is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH(CH$_3$)—; L is —N(R$_7$)C(O)—; and R$_7$ and R$_A$ are as defined in formual (I).

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

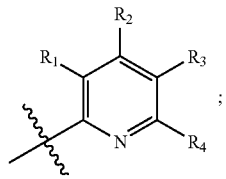

Z is N; — is absent; L is —N(R$_7$)C(O)—; and D, R$_1$, R$_2$, R$_3$, R$_4$, R$_5$, R$_7$, and R$_A$ are as defined in formula (I).

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

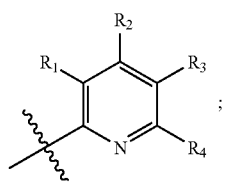

is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH$_2$—; L is —N(R$_7$)C(O)—; and R$_7$ and R$_A$ are as defined on formula (I).

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, pyrazolyl, pyridinyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

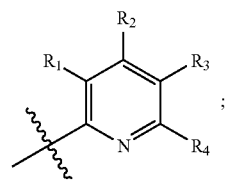

is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH$_2$—; L is —N(R$_7$)C(O)—; and R$_7$ and R$_A$ are as defined on formula (I).

In another embodiment, the present invention relates to a method of treating sexual dysfunction in a mammal comprising administering to the mammal a therapeutically effective amount of a compound of formula (I) wherein A is aryl; B is

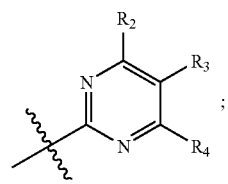

— is absent; L is —N(R$_7$)C(O)—; and D, R$_2$, R$_3$, R$_4$, R$_7$, and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

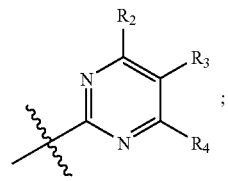

R$_2$, R$_3$, and R$_4$ are hydrogen; Z is N; — is absent; D is —CH$_2$—; L is —N(R$_7$)C(O)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

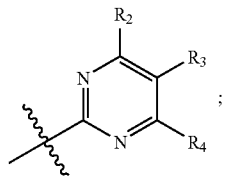

R$_2$, R$_3$, and R$_4$ are hydrogen; Z is N; — is absent; D is —CH(CH$_3$)—; L is —N(R$_7$)C(O)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl; B is

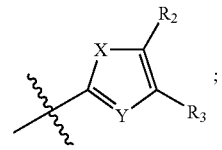

— is absent; L is —N(R$_7$)C(O)—; and D, X, Y, R$_2$, R$_3$, R$_7$, and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

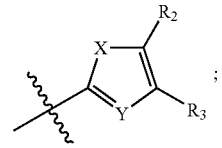

and R$_3$ are hydrogen; X is N(R$_6$), O, or S; Y is N; Z is N; — is absent; D is —CH$_2$—; L is —N(R$_7$)C(O)—; and R$_6$, R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

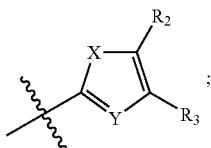

R$_2$ and R$_3$ are hydrogen; X is N(R$_6$), O, or S; Y is N; Z is N; — is absent; D is —CH(CH$_3$)—; L is —N(R$_7$)C(O)—; and R$_6$, R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is heterocycle; B is

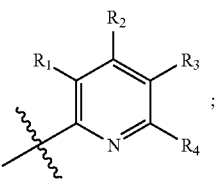

is N; — is absent; L is —N(R$_7$)C(O)—; and D, R$_1$, R$_2$, R$_3$, R$_4$, R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

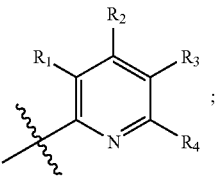

Z is N; — is absent; D is —CH$_2$—; L is —N(R$_7$)C(O)—; and R$_1$, R$_2$, R$_3$, R$_4$, R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

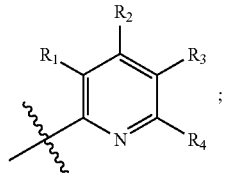

Z is N; — is absent; D is —CH(CH$_3$)—; L is —N(R$_7$)C(O)—; and R$_1$, R$_2$, R$_3$, R$_4$, R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, pyrazolyl, pyridinyl, or thienyl independently substituted with 0, 1, 2, or 3 substituents independently selected from alkoxy, alkoxycarbonyl, alkyl, cyano, halogen, haloalkoxy, haloalkyl, or nitro; B is

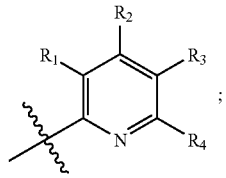

R$_1$ is the group consisting of hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH$_2$—; L is —N(R$_7$)C(O)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, pyrazolyl, pyridinyl, or thienyl independently substituted with 0, 1, 2, or 3 substituents independently selected from alkoxy, alkoxycarbonyl, alkyl, cyano, halogen, haloalkoxy, haloalkyl, or nitro; B is

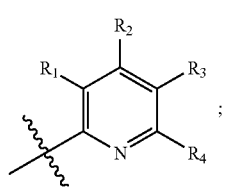

R$_1$ is the group consisting of hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH(CH$_3$)—; L is —N(R$_7$)C(O)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is cycloalkyl; B is

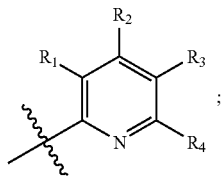

Z is N; — is absent; L is —N(R$_7$)C(O)—; and D, R$_1$, R$_2$, R$_3$, R$_4$, R$_7$, and R$_A$ are as defined in formula (I).

In another embodiment, the present invention relates to a method of treating sexual dysfunction in a mammal comprising administering to the mammal a therapeutically effective amount of a compound of formula (I) wherein A is cycloalkyl wherein the cycloalkyl is cyclohexyl or adamantyl; B is

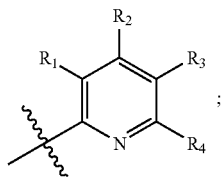

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH$_2$—; L is —N(R$_7$)C(O)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is cycloalkyl wherein the cycloalkyl is cyclohexyl or adamantyl; B is

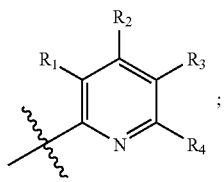

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH(CH$_3$)—; L is —N(R$_7$)C(O)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is arylalkyl; B is

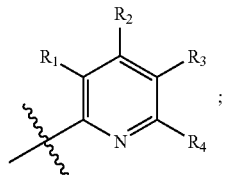

Z is N; — is absent; L is —N(R$_7$)C(O)—; and D, R$_1$, R$_2$, R$_3$, R$_4$, R$_7$, and R$_A$ are as defined in formula (I).

In another embodiment, the present invention relates to a method of treating sexual dysfunction in a mammal comprising administering to the mammal a therapeutically effective amount of a compound of formula (I) wherein A is arylalkyl wherein the aryl of arylalkyl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

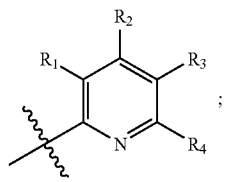

is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH$_2$—; L is —N(R$_7$)C(O)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is arylalkyl wherein the aryl of arylalkyl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

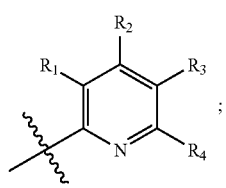

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH(CH$_3$)—; L is —N(R$_7$)C(O)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl; B is

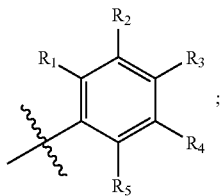

Z is CR$_B$; — is absent; L is —N(R$_7$)C(O)—; and D, R$_1$, R$_2$, R$_3$, R$_4$, R$_5$, R$_7$, R$_B$, and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, and —NZ$_1$Z$_2$; B is

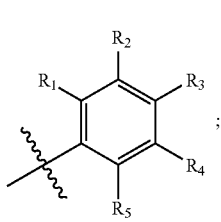

R$_1$ is hydrogen, alkoxy, alkyl, alkylthio, cyano, halogen, hydroxy, nitro, —NZ$_1$Z$_2$, or (NZ$_3$Z$_4$)alkyl; R$_2$ is hydrogen, alkoxy, cyano, halogen, or hydroxy; R$_3$ is hydrogen or hydroxy; R$_4$ and R$_5$ are hydrogen; Z is CR$_B$; — is absent; D is —CH$_2$—; L is —N(R$_7$)C(O)—; R$_B$ is hydrogen; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

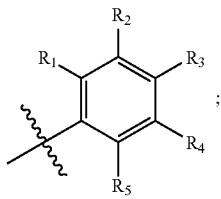

R$_1$ is hydrogen, alkoxy, alkyl, alkylthio, cyano, halogen, hydroxy, nitro, —NZ$_1$Z$_2$, or (NZ$_3$Z$_4$)alkyl; R$_2$ is hydrogen, alkoxy, cyano, halogen, or hydroxy; R$_3$ is hydrogen or hydroxy; R$_4$ and R$_5$ are hydrogen; Z is CR$_B$; — is absent; D is —CH$_2$—; L is —N(R$_7$)C(O)—; R$_B$ is halogen wherein a preferred halogen is —F; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

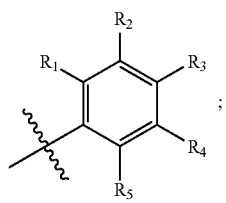

R$_1$ is hydrogen, alkoxy, alkyl, alkylthio, cyano, halogen, hydroxy, nitro, —NZ$_1$Z$_2$, or (NZ$_3$Z$_4$)alkyl; R$_2$ is hydrogen, alkoxy, cyano, halogen, or hydroxy; R$_3$ is hydrogen or hydroxy; R$_4$ and R$_5$ are hydrogen; Z is CR$_B$; — is absent; D is —CH(CH$_3$)—; L is —N(R$_7$)C(O)—; R$_B$ is hydrogen; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl; B is

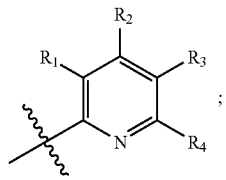

Z is CR$_B$; — is absent; L is —N(R$_7$)C(O)—; R$_B$ is hydrogen; and D, R$_1$, R$_2$, R$_3$, R$_4$, R$_7$, and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

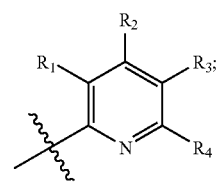

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is CR$_B$; — is absent; D is —CH$_2$—; L is —N(R$_7$)C(O)—; R$_B$ is hydrogen; and R$_7$ and R$_A$ are as defined on formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

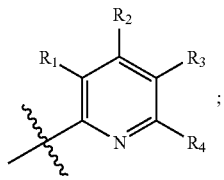

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is CR$_B$; — is absent; D is —CH$_2$—; L is —N(R$_7$)C(S)—; R$_B$ is hydrogen; and R$_7$ and R$_A$ are as defined on formula (I).

In another embodiment, the present invention relates to a method of treating sexual dysfunction in a mammal comprising administering to the mammal a therapeutically effective amount of a compound of formula (I) wherein A is aryl wherein the aryl is tetrahydronaphthalenyl or 2,3-dihydro-1H-indenyl; B is

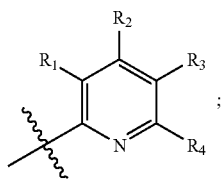

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is CR$_B$; — is absent; D is —CH$_2$—; L is —N(R$_7$)C(S)—; R$_B$ is hydrogen; and R$_7$ and R$_A$ are as defined on formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

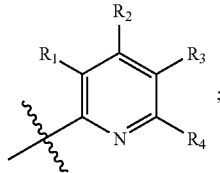

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is $CR_B$; — is absent; D is —CH(CH$_3$)—; L is —N(R$_7$)C(O)—; $R_B$ is hydrogen; and $R_7$, $R_B$, and $R_A$ are as defined on formula (I).

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

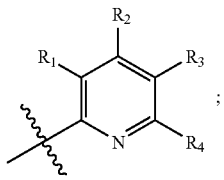

Z is $CR_B$; — is absent; L is —N(R$_7$)C(O)—; $R_B$ is hydrogen; and D, $R_1$, $R_2$, $R_3$, $R_4$, $R_7$, and $R_A$ are as defined in formula (I).

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

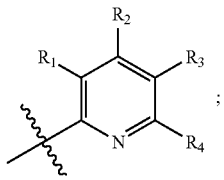

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is $CR_B$; — is absent; D is —CH$_2$—; L is —N(R$_7$)C(O)—; $R_B$ is hydrogen; and $R_7$ and $R_A$ are as defined on formula (I).

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, pyrazolyl, pyridinyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

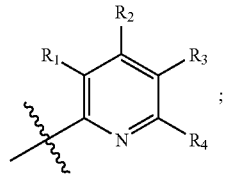

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is $CR_B$; — is absent; D is —CH$_2$—; L is —N(R$_7$)C(O)—; $R_B$ is hydrogen; and $R_7$ and $R_A$ are as defined on formula (I).

In another embodiment, the present invention relates to a method of treating sexual dysfunction in a mammal comprising administering to the mammal a therapeutically effective amount of a compound of formula (I) wherein A is aryl; B is

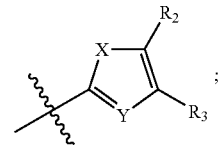

Z is $CR_B$; — is absent; L is —N(R$_7$)C(O)—; $R_B$ is hydrogen; and D, X, Y, $R_2$, $R_3$, $R_7$, and $R_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

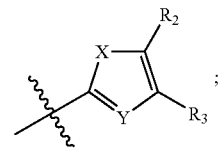

X is N(R$_6$), O, or S; Y is N; $R_2$ and $R_3$ are hydrogen; Z is $CR_B$; — is absent; D is —CH$_2$—; L is —N(R$_7$)C(O)—; $R_B$ is hydrogen; and $R_6$, $R_7$ and $R_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

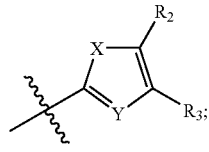

X is N(R$_6$), O, or S; Y is N; R$_2$ and R$_3$ are hydrogen; Z is CR$_B$; — is absent; D is —CH(CH$_3$)—; L is —N(R$_7$)C(O)—; R$_B$ is hydrogen; and R$_6$, R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl; B is

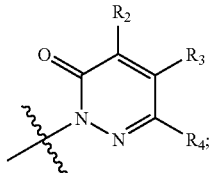

Z is CR$_B$; — is absent; L is —N(R$_7$)C(O)—; and D, R$_2$, R$_3$, R$_4$, R$_7$, R$_B$, and R$_A$.

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

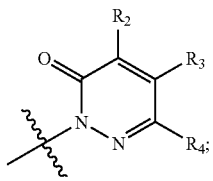

Z is CR$_B$; — is absent; D is —CH$_2$—; L is —N(R$_7$)C(O)—; R$_2$, R$_3$, and R$_4$ are hydrogen; R$_B$ is hydrogen; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

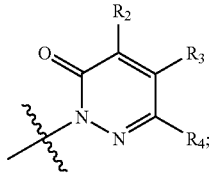

Z is CR$_B$; — is absent; D is —CH(CH$_3$)—; L is —N(R$_7$)C(O)—; R$_2$, R$_3$, and R$_4$ are hydrogen; R$_B$ is hydrogen; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl; B is

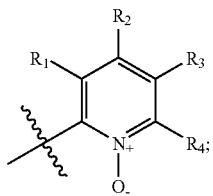

Z is CR$_B$; —is absent; L is —N(R$_7$)C(O)—; and D, R$_1$, R$_2$, R$_3$, R$_4$, R$_7$, R$_B$, and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

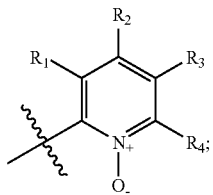

R$_1$, R$_2$, R$_3$, and R$_4$ are hydrogen; Z is CR$_B$; R$_B$ is hydrogen; — is absent; D is —CH$_2$—; L is —N(R$_7$)C(O)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

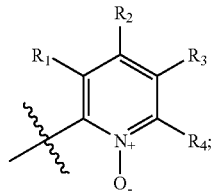

R$_1$, R$_2$, R$_3$, and R$_4$ are hydrogen; Z is CR$_B$; R$_B$ is hydrogen; — is absent; D is —CH$_2$—; L is —N(R$_7$)C(O)—; and R$_7$ and R$_A$ are hydrogen.

In another embodiment, the present invention relates to a method of treating sexual dysfunction in a mammal comprising administering to the mammal a therapeutically effective amount of a compound of formula (I) wherein A is aryl wherein the aryl is phenyl substituted with 1 alkyl substituent; B is

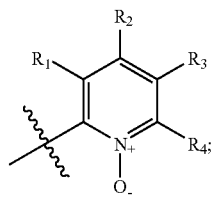

R$_1$, R$_2$, R$_3$, and R$_4$ are hydrogen; Z is CR$_B$; R$_B$ is hydrogen; — is absent; D is —CH$_2$—; L is —N(R$_7$)C(O)—; and R$_7$ and R$_A$ are hydrogen.

In another embodiment, the present invention relates to a method of treating sexual dysfunction in a mammal comprising administering to the mammal a therapeutically effective amount of a compound of formula (I) wherein A is aryl wherein the aryl is phenyl substituted with 1 alkyl substituent; B is

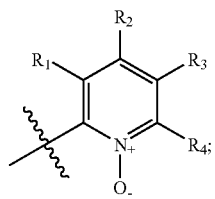

R$_1$, R$_2$, R$_3$, and R$_4$ are hydrogen; Z is CR$_B$; R$_B$ is hydrogen; — is absent; D is —CH$_2$—; L is —N(R$_7$)C(O)—; R$_7$ is alkyl wherein methyl is preferred; and R$_A$ is hydrogen.

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

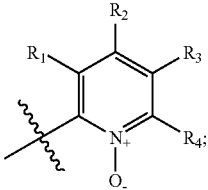

R$_1$, R$_2$, R$_3$, and R$_4$ are hydrogen; Z is CR$_B$; R$_B$ is hydrogen; — is absent; D is —CH(CH$_3$)—; L is —N(R$_7$)C(O)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is tetrahydronaphthalenyl or 2,3-dihydro-1H-indenyl; B is

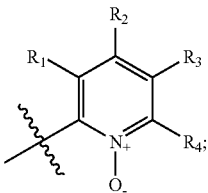

R$_1$, R$_2$, R$_3$, and R$_4$ are hydrogen; Z is CR$_B$; R$_B$ is hydrogen; — is absent; D is —CH$_2$—; L is —N(R$_7$)C(O)—; and R$_7$ and R$_A$ are hydrogen.

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

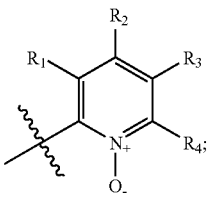

Z is CR$_B$; R$_B$ is hydrogen; — is absent; L is —N(R$_7$)C(O)—; and D, R$_1$, R$_2$, R$_3$, R$_4$, R$_7$, and R$_A$ are as defined in formula (I).

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

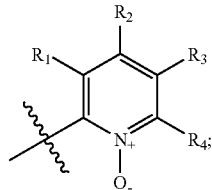

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is $CR_B$; $R_B$ is hydrogen; — is absent; D is —CH$_2$—; L is —N(R$_7$)C(O)—; and R$_7$ and R$_A$ are as defined on formula (I).

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, pyrazolyl, pyridinyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

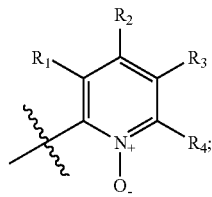

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is $CR_B$; $R_B$ is hydrogen; — is absent; D is —CH$_2$—; L is —N(R$_7$)C(O)—; and R$_7$ and R$_A$ are as defined on formula (I).

In another embodiment, the present invention relates to a method of treating sexual dysfunction in a mammal comprising administering to the mammal a therapeutically effective amount of a compound of formula (I) wherein A is cycloalkyl; B is

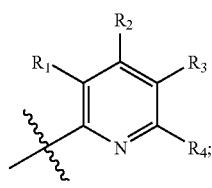

Z is $CR_B$; — is absent; L is —N(R$_7$)C(O)—; and D, R$_1$, R$_2$, R$_3$, R$_4$, R$_7$, R$_B$, and R$_A$ are as defined in formula (I).

In another embodiment, the present invention relates to a method of treating sexual dysfunction in a mammal comprising administering to the mammal a therapeutically effective amount of a compound of formula (I) wherein A is cycloalkyl wherein the cycloalkyl is cyclohexyl or adamantyl; B is

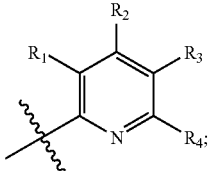

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is $CR_B$; $R_B$ is hydrogen; — is absent; D is —CH$_2$—; L is —N(R$_7$)C(O)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is cycloalkyl wherein the cycloalkyl is cyclohexyl or adamantyl; B is

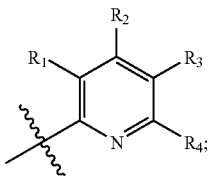

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is $CR_B$; $R_B$ is hydrogen; — is absent; D is —CH(CH$_3$)—; L is —N(R$_7$)C(O)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl; B is

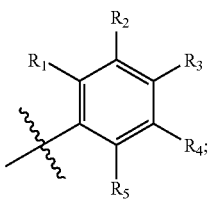

Z is C; — is a bond; L is —N(R$_7$)C(O)—; and D, R$_1$, R$_2$, R$_3$, R$_4$, R$_5$, R$_7$, and R$_A$ are as defined on formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

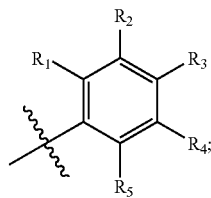

R$_1$ is hydrogen, alkoxy, alkyl, alkylthio, cyano, halogen, hydroxy, nitro, —NZ$_1$Z$_2$, or (NZ$_3$Z$_4$)alkyl; R$_2$ is hydrogen, alkoxy, cyano, halogen, or hydroxy; R$_3$ is hydrogen or hydroxy; R$_4$ and R$_5$ are hydrogen; Z is C; — is a bond; D is —CH$_2$—; L is —N(R$_7$)C(O)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

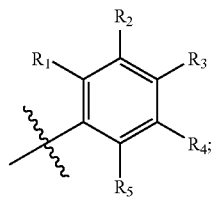

R$_1$ is hydrogen, alkoxy, alkyl, alkylthio, cyano, halogen, hydroxy, nitro, —NZ$_1$Z$_2$, or (NZ$_3$Z$_4$)alkyl; R$_2$ is hydrogen, alkoxy, cyano, halogen, or hydroxy; R$_3$ is hydrogen or hydroxy; R$_4$ and R$_5$ are hydrogen; Z is C; — is a bond; D is —CH(CH$_3$)—; L is —N(R$_7$)C(O)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl; B is

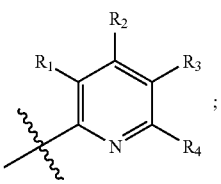

Z is C; — is a bond; L is —N(R$_7$)C(O)—; and D, R$_1$, R$_2$, R$_3$, R$_4$, R$_7$, and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

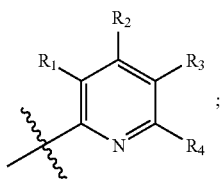

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is C; — is a bond; D is —CH$_2$—; L is —N(R$_7$)C(O)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

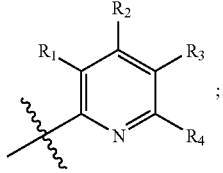

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is C; — is a bond; D is —CH(CH$_3$)—; L is —N(R$_7$)C(O)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

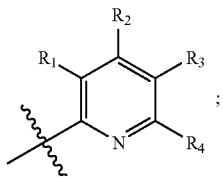

Z is C; — is a bond; L is —N(R$_7$)C(O)—; and D, R$_1$, R$_2$, R$_3$, R$_4$, R$_7$, and R$_A$ are as defined in formula (I).

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

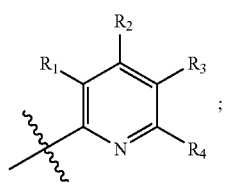

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is C; — is a bond; D is —CH$_2$—; L is —N(R$_7$)C(O)—; and R$_7$ and R$_A$ are as defined on formula (I).

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, pyrazolyl, pyridinyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

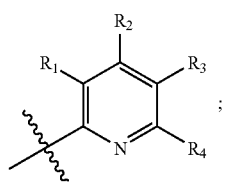

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is C; — is a bond; D is —CH$_2$—; L is —N(R$_7$)C(O)—; and R$_7$ and R$_A$ are as defined on formula (I).

In another embodiment, the present invention relates to a method of treating sexual dysfunction in a mammal comprising administering to the mammal a therapeutically effective amount of a compound of formula (I) wherein A is aryl; B is

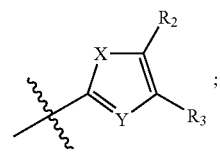

Z is C; — is a bond; L is —N(R$_7$)C(O)—; and D, X, Y, R$_2$, R$_3$, R$_7$, and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

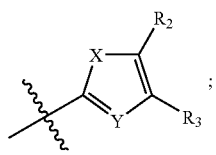

X is N(R$_6$), O, or S; Y is C(R$_4$); R$_2$ and R$_3$ are hydrogen; R$_4$ is hydrogen, alkyl, or cyano; Z is C; — is a bond; D is —CH$_2$—; L is —N(R$_7$)C(O)—; and R$_6$, R$_7$, and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

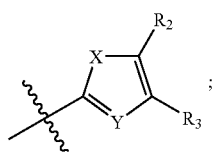

X is N(R$_6$), O, or S; Y is C(R$_4$); R$_2$ and R$_3$ are hydrogen; R$_4$ is hydrogen, alkyl, or cyano; Z is C; — is a bond; D is —CH(CH$_3$)—; L is —N(R$_7$)C(O)—; and R$_6$, R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is cycloalkyl; B is

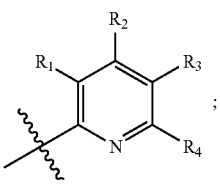

Z is C; — is a bond; L is —N(R$_7$)C(O)—; and D, R$_1$, R$_2$, R$_3$, R$_4$, R$_7$, and R$_A$ are as defined in formula (I).

In another embodiment, the present invention relates to a method of treating sexual dysfunction in a mammal comprising administering to the mammal a therapeutically effective amount of a compound of formula (I) wherein A is cycloalkyl wherein the cycloalkyl is cyclohexyl or adamantyl; B is

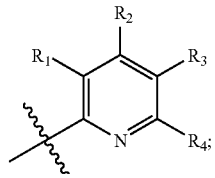

$R_1$ is hydrogen, alkyl, cyano, haloalkyl, halogen, nitro, (NZ$_3$Z$_4$)alkyl, or (NZ$_3$Z$_4$)carbonyl; $R_2$ and $R_4$ are hydrogen; $R_3$ is hydrogen or hydroxy; Z is C; — is a bond; D is —CH$_2$—; L is —N(R$_7$)C(O)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is cycloalkyl wherein the cycloalkyl is cyclohexyl or adamantyl; B is

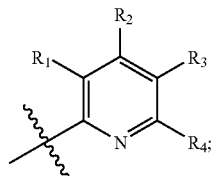

$R_1$ is hydrogen, alkyl, cyano, haloalkyl, halogen, nitro, (NZ$_3$Z$_4$)alkyl, or (NZ$_3$Z$_4$)carbonyl; $R_2$ and $R_4$ are hydrogen; $R_3$ is hydrogen or hydroxy; Z is C; — is a bond; D is —CH(CH$_3$)—; L is —N(R$_7$)C(O)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl; B is

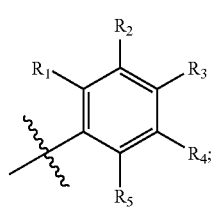

Z is N; — is absent; L is —C(O)N(R$_7$)—; and D, $R_1$, $R_2$, $R_3$, $R_4$, $R_5$, $R_7$, and $R_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

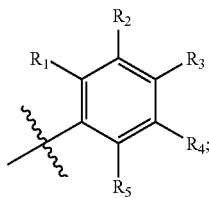

$R_1$ is hydrogen, alkoxy, alkyl, alkylthio, cyano, halogen, hydroxy, nitro, —NZ$_1$Z$_2$, or (NZ$_3$Z$_4$)alkyl; $R_2$ is hydrogen, alkoxy, cyano, halogen, or hydroxy; $R_3$ is hydrogen or hydroxy; $R_4$ and $R_5$ are hydrogen; Z is N; — is absent; D is —CH$_2$—; L is —C(O)N(R$_7$)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

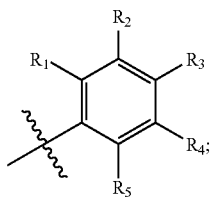

$R_1$ is hydrogen, alkoxy, alkyl, alkylthio, cyano, halogen, hydroxy, nitro, —NZ$_1$Z$_2$, or (NZ$_3$Z$_4$)alkyl; $R_2$ is hydrogen, alkoxy, cyano, halogen, or hydroxy; $R_3$ is hydrogen or hydroxy; $R_4$ and $R_5$ are hydrogen; Z is N; — is absent; D is —CH(CH$_3$)—; L is —C(O)N(R$_7$)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl; B is

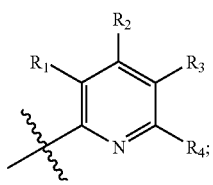

Z is N; — is absent; L is —C(O)N(R$_7$)—; and D, $R_1$, $R_2$, $R_3$, $R_4$, $R_7$, and $R_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

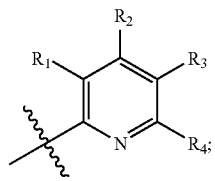

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH$_2$—; L is —C(O)N(R$_7$)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

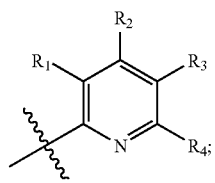

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH(CH$_3$)—; L is —C(O)N(R$_7$)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

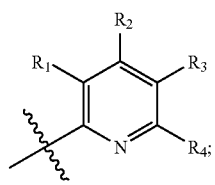

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH$_2$CH$_2$—; L is —C(O)N(R$_7$)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl; B is

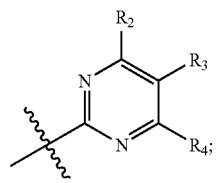

Z is N; — is absent; L is —C(O)N(R$_7$)—; and D, R$_2$, R$_3$, R$_4$, R$_7$, and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

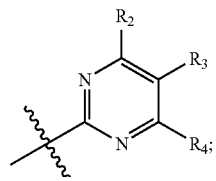

R$_2$, R$_3$, and R$_4$ are hydrogen; Z is N; — is absent; D is —CH$_2$—; L is —C(O)N(R$_7$)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

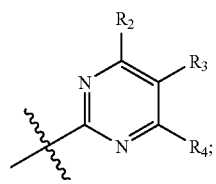

R$_2$, R$_3$, and R$_4$ are hydrogen; Z is N; — is absent; D is —CH(CH$_3$)—; L is —C(O)N(R$_7$)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is cycloalkyl; B is

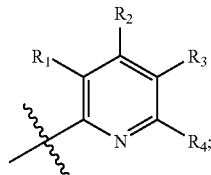

Z is N; — is absent; L is —C(O)N(R$_7$)—; and D, R$_1$, R$_2$, R$_3$, R$_4$, R$_7$, and R$_A$ are as defined in formula (I).

In another embodiment, the present invention relates to a method of treating sexual dysfunction in a mammal comprising administering to the mammal a therapeutically effective amount of a compound of formula (I) wherein A is cycloalkyl wherein the cycloalkyl is cyclohexyl or adamantyl; B is

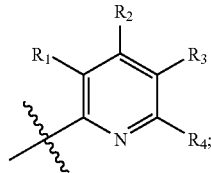

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH$_2$—; L is —C(O)N(R$_7$)—; and R$_7$ and R$_A$ are as defined as in formula (I).

In another embodiment, the present invention relates to a method of treating sexual dysfunction in a mammal comprising administering to the mammal a therapeutically effective amount of a compound of formula (I) wherein A is cycloalkyl wherein the cycloalkyl is cyclohexyl or adamantyl; B is

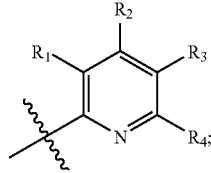

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH(CH$_3$)—; L is —C(O)N(R$_7$)—; and R$_7$ and R$_A$ are defined as in formula (I).

In another embodiment, the present invention relates to a method of treating sexual dysfunction in a mammal comprising administering to the mammal a therapeutically effective amount of a compound of formula (I) wherein A is aryl; B is

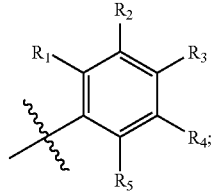

Z is CR$_B$; R$_B$ is hydrogen; — is absent; L is —C(O)N(R$_7$)—; and D, R$_1$, R$_2$, R$_3$, R$_4$, R$_5$, R$_7$, and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

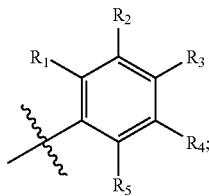

R$_1$ is hydrogen, alkoxy, alkyl, alkylthio, cyano, halogen, hydroxy, nitro, —NZ$_1$Z$_2$, or (NZ$_3$Z$_4$)alkyl; R$_2$ is hydrogen, alkoxy, cyano, halogen, or hydroxy; R$_3$ is hydrogen or hydroxy; R$_4$ and R$_5$ are hydrogen; Z is CR$_B$; R$_B$ is hydrogen; — is absent; D is —CH$_2$—; L is —C(O)N(R$_7$)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

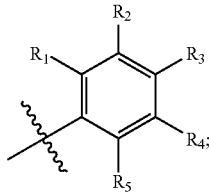

R$_1$ is hydrogen, alkoxy, alkyl, alkylthio, cyano, halogen, hydroxy, nitro, —NZ$_1$Z$_2$, or (NZ$_3$Z$_4$)alkyl; R$_2$ is hydrogen, alkoxy, cyano, halogen, or hydroxy; R$_3$ is hydrogen or hydroxy; R$_4$ and R$_5$ are hydrogen; Z is CR$_B$; R$_B$ is hydrogen; — is absent; D is —CH(CH$_3$)—; L is —C(O)N(R$_7$)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl; B is

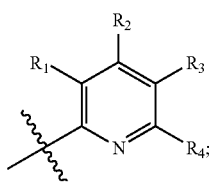

Z is CR$_B$; R$_B$ is hydrogen; — is absent; L is —C(O)N(R$_7$)—; and D, R$_1$, R$_2$, R$_3$, R$_4$, R$_7$, and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

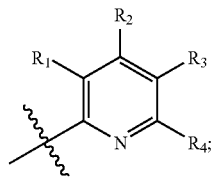

$R_1$ is hydrogen, alkyl, cyano, haloalkyl, halogen, nitro, ($NZ_3Z_4$)alkyl, or ($NZ_3Z_4$)carbonyl; $R_2$ and $R_4$ are hydrogen; $R_3$ is hydrogen or hydroxy; Z is $CR_B$; $R_B$ is hydrogen; — is absent; D is —$CH_2$—; L is —C(O)N($R_7$)—; and $R_7$ and $R_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

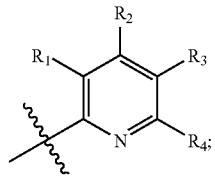

$R_1$ is hydrogen, alkyl, cyano, haloalkyl, halogen, nitro, ($NZ_3Z_4$)alkyl, or ($NZ_3Z_4$)carbonyl; $R_2$ and $R_4$ are hydrogen; $R_3$ is hydrogen or hydroxy; Z is $CR_B$; $R_B$ is hydrogen; — is absent; D is —CH($CH_3$)—; L is —C(O)N($R_7$)—; and $R_7$ and $R_A$ are as defined in formula (I).

In another embodiment, the present invention relates to a method of treating sexual dysfunction in a mammal comprising administering to the mammal a therapeutically effective amount of a compound of formula (I) wherein A is aryl; B is

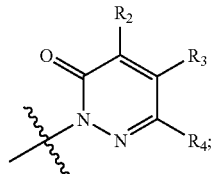

Z is $CR_B$; $R_B$ is hydrogen; — is absent; L is —C(O)N($R_7$)—; and D, $R_2$, $R_3$, $R_4$, $R_7$, and $R_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

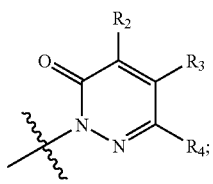

$R_2$, $R_3$, and $R_4$ are hydrogen; Z is $CR_B$; $R_B$ is hydrogen; — is absent; D is —$CH_2$—; L is —C(O)N($R_7$)—; and $R_7$ and $R_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

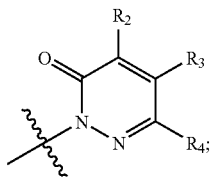

$R_2$, $R_3$, and $R_4$ are hydrogen; Z is $CR_B$; $R_B$ is hydrogen; — is absent; D is —CH($CH_3$)—; L is —C(O)N($R_7$)—; and $R_7$ and $R_A$ are as defined in formula (I).

In another embodiment, the present invention relates to a method of treating sexual dysfunction in a mammal comprising administering to the mammal a therapeutically effective amount of a compound of formula (I) wherein A is aryl; B is

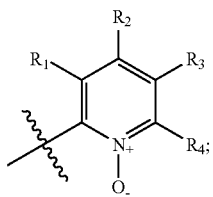

Z is $CR_B$; $R_B$ is hydrogen; — is absent; L is —C(O)N($R_7$)—; and D, $R_1$, $R_2$, $R_3$, $R_4$, $R_7$, and $R_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

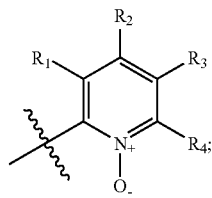

R$_1$, R$_2$, R$_3$, and R$_4$ are hydrogen; Z is CR$_B$; R$_B$ is hydrogen; — is absent; D is —CH$_2$—; L is —C(O)N(R$_7$)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

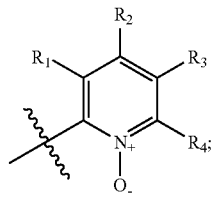

R$_1$, R$_2$, R$_3$, and R$_4$ are hydrogen; Z is CR$_B$; R$_B$ is hydrogen; — is absent; D is —CH$_2$—; L is —C(O)N(R$_7$)—; and R$_7$ and R$_A$ are hydrogen.

In another embodiment, the present invention relates to a method of treating sexual dysfunction in a mammal comprising administering to the mammal a therapeutically effective amount of a compound of formula (I) wherein A is aryl wherein the aryl is phenyl substituted with 1 alkyl substituent; B is

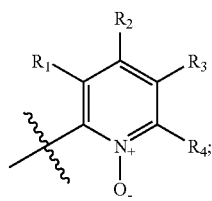

R$_1$, R$_2$, R$_3$, and R$_4$ are hydrogen; Z is CR$_B$; R$_B$ is hydrogen; — is absent; D is —CH$_2$—; L is —C(O)N(R$_7$)—; and R$_7$ and R$_A$ are hydrogen.

In another embodiment, the present invention relates to a method of treating sexual dysfunction in a mammal comprising administering to the mammal a therapeutically effective amount of a compound of formula (I) wherein A is aryl wherein the aryl is phenyl substituted with 1 alkyl substituent wherein a preferred alkyl substituent is methyl; B is

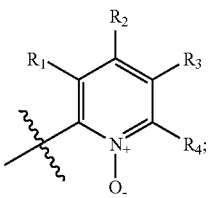

R$_1$, R$_2$, R$_3$, and R$_4$ are hydrogen; Z is CR$_B$; R$_B$ is hydrogen; — is absent; D is —CH$_2$—; L is —C(O)N(R$_7$)—; and R$_7$ and R$_A$ are hydrogen.

In another embodiment, the present invention relates to a method of treating sexual dysfunction in a mammal comprising administering to the mammal a therapeutically effective amount of a compound of formula (I) wherein A is aryl wherein the aryl is phenyl substituted with 1 alkyl substituent wherein a preferred alkyl substituent is methyl; B is

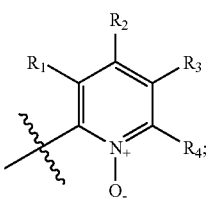

R$_1$, R$_2$, R$_3$, and R$_4$ are hydrogen; Z is CR$_B$; R$_B$ is hydrogen; — is absent; D is —CH$_2$—; L is —C(S)N(R$_7$)—; and R$_7$ and R$_A$ are hydrogen.

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

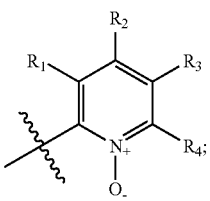

R$_1$, R$_2$, R$_3$, and R$_4$ are hydrogen; Z is CR$_B$; R$_B$ is hydrogen; — is absent; D is —CH(CH$_3$)—; L is —C(O)N(R$_7$)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 1 alkyl substituent wherein a preferred alkyl substituent is methyl; B is

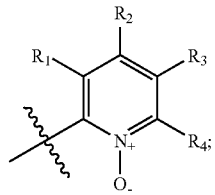

$R_1$, $R_2$, $R_3$, and $R_4$ are hydrogen; Z is $CR_B$; $R_B$ is hydrogen; — is absent; D is —CH(CH$_3$)—; L is —C(O)N(R$_7$)—; and $R_7$ and $R_A$ are hydrogen.

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

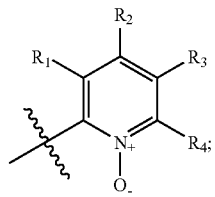

Z is $CR_B$; $R_B$ is hydrogen; — is absent; L is —C(O)N(R$_7$)—; and D, $R_1$, $R_2$, $R_3$, $R_4$, $R_7$, and $R_A$ are as defined in formula (I).

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

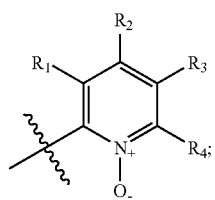

$R_1$ is hydrogen, alkyl, cyano, haloalkyl, halogen, nitro, (NZ$_3$Z$_4$)alkyl, or (NZ$_3$Z$_4$)carbonyl; $R_2$ and $R_4$ are hydrogen; $R_3$ is hydrogen or hydroxy; Z is $CR_B$; $R_B$ is hydrogen; — is absent; D is —CH$_2$—; L is —C(O)N(R$_7$)—; and $R_7$ and $R_A$ are as defined on formula (I).

In another embodiment, the present invention relates to a method of treating sexual dysfunction in a mammal comprising administering to the mammal a therapeutically effective amount of a compound of formula (I) wherein A is heterocycle wherein the heterocycle is benzimidazolyl, benzothiazolyl, pyrazolyl, pyridinyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

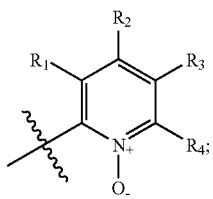

$R_1$ is hydrogen, alkyl, cyano, haloalkyl, halogen, nitro, (NZ$_3$Z$_4$)alkyl, or (NZ$_3$Z$_4$)carbonyl; $R_2$ and $R_4$ are hydrogen; $R_3$ is hydrogen or hydroxy; Z is $CR_B$; $R_B$ is hydrogen; — is absent; D is —CH$_2$—; L is —C(O)N(R$_7$)—; and $R_7$ and $R_A$ are as defined on formula (I).

In another embodiment, the present invention relates to a method of treating sexual dysfunction in a mammal comprising administering to the mammal a therapeutically effective amount of a compound of formula (I) wherein A is cycloalkyl; B is

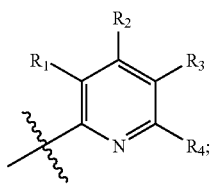

Z is $CR_B$; $R_B$ is hydrogen; — is absent; L is —C(O)N(R$_7$)—; and D, $R_1$, $R_2$, $R_3$, $R_4$, $R_7$, and $R_A$ are as defined in formula (I).

In another embodiment, the present invention relates to a method of treating sexual dysfunction in a mammal comprising administering to the mammal a therapeutically effective amount of a compound of formula (I) wherein A is cycloalkyl wherein the cycloalkyl is cyclohexyl or adamantyl; B is

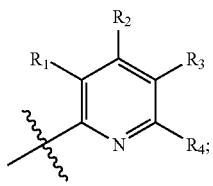

$R_1$ is hydrogen, alkyl, cyano, haloalkyl, halogen, nitro, (NZ$_3$Z$_4$)alkyl, or (NZ$_3$Z$_4$)carbonyl; $R_2$ and $R_4$ are hydrogen; $R_3$ is hydrogen or hydroxy; Z is $CR_B$; $R_B$ is hydrogen; — is absent; D is —CH$_2$—; L is —C(O)N(R$_7$)—; and $R_7$ and $R_A$ are as defined in formula (I).

In another embodiment, the present invention relates to a method of treating sexual dysfunction in a mammal comprising administering to the mammal a therapeutically effective amount of a compound of formula (I) wherein A is cycloalkyl wherein the cycloalkyl is cyclohexyl or adamantyl; B is

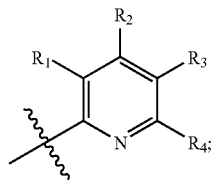

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is $CR_B$; $R_B$ is hydrogen; — is absent; D is —CH(CH$_3$)—; L is —C(O)N(R$_7$)—; and $R_7$ and $R_A$ are as defined in formula (I).

In another embodiment, the present invention relates to a method of treating sexual dysfunction in a mammal comprising administering to the mammal a therapeutically effective amount of a compound of formula (I) wherein A is aryl; B is

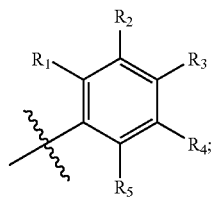

Z is C; — is a bond; L is —C(O)N(R$_7$)—; and D, $R_1$, $R_2$, $R_3$, $R_4$, $R_5$, $R_7$, and $R_A$ are as defined in formula (1).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

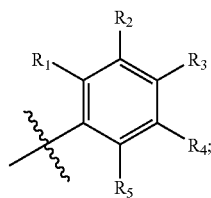

$R_1$ is hydrogen, alkoxy, alkyl, alkylthio, cyano, halogen, hydroxy, nitro, —NZ$_1$Z$_2$, or $(NZ_3Z_4)$alkyl; $R_2$ is hydrogen, alkoxy, cyano, halogen, or hydroxy; $R_3$ is hydrogen or hydroxy; $R_4$ and $R_5$ are hydrogen; Z is C; — is a bond; D is —CH$_2$—; L is —C(O)N(R$_7$)—; and $R_7$ and $R_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

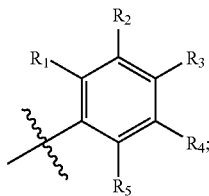

$R_1$ is hydrogen, alkoxy, alkyl, alkylthio, cyano, halogen, hydroxy, nitro, —NZ$_1$Z$_2$, or $(NZ_3Z_4)$alkyl; $R_2$ is hydrogen, alkoxy, cyano, halogen, or hydroxy; $R_3$ is hydrogen or hydroxy; $R_4$ and $R_5$ are hydrogen; Z is C; — is a bond; D is CH(CH$_3$)—; L is —C(O)N(R$_7$)—; and $R_7$ and $R_A$ are as defined in formula (I).

In another embodiment, the present invention relates to a method of treating sexual dysfunction in a mammal comprising administering to the mammal a therapeutically effective amount of a compound of formula (I) wherein A is aryl; B is

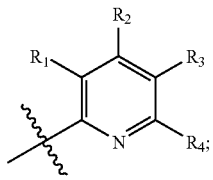

Z is C; — is a bond; L is —C(O)N(R$_7$)—; and D, $R_1$, $R_2$, $R_3$, $R_4$, $R_7$, and $R_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

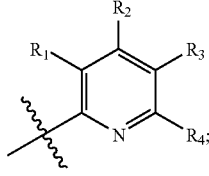

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is C; — is a bond; D is —CH$_2$—; L is —C(O)N(R$_7$)—; and $R_7$ and $R_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

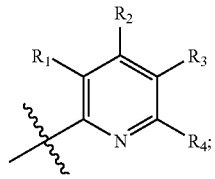

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is C; — is a bond; D is —CH(CH$_3$)—; L is —C(O)N(R$_7$)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is naphthyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

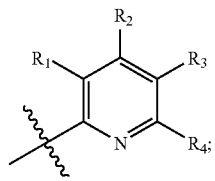

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is C; — is a bond; D is —CH$_2$—; L is —C(O)N(R$_7$)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is naphthyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

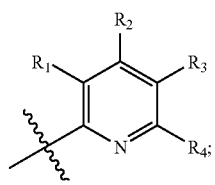

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is C; — is a bond; D is —CH(CH$_3$)—; L is —C(O)N(R$_7$)—; and R$_7$ and R$_A$ are as defined in formula (I).

In another embodiment, the present invention relates to a method of treating sexual dysfunction in a mammal comprising administering to the mammal a therapeutically effective amount of a compound of formula (I) wherein A is aryl; B is

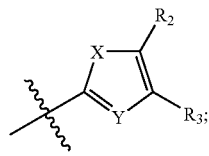

is C; — is a bond; L is —C(O)N(R$_7$)—; and D, X, Y, R$_2$, R$_3$, R$_7$, and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

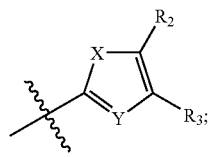

R$_2$ and R$_3$ are hydrogen; X is N(R$_6$), O, or S; Y is N; Z is C; — is a bond; D is —CH$_2$—; L is —C(O)N(R$_7$)—; and R$_6$, R$_7$, and R$_A$ are as defined in formula (I).

In another embodiment, the present invention relates to a method of treating sexual dysfunction in a mammal comprising administering to the mammal a therapeutically effective amount of a compound of formula (I) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

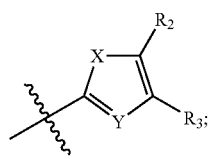

R$_2$ and R$_3$ are hydrogen; X is N(R$_6$), O, or S; Y is N; Z is C; — is a bond; D is —CH(CH$_3$)—; L is —C(O)N(R$_7$)—; and R$_6$, R$_7$, and R$_A$ are as defined in formula (I).

In another embodiment, the present invention relates to a method of treating sexual dysfunction in a mammal comprising administering to the mammal a therapeutically effective amount of a compound of formula (I) wherein A is cycloalkyl; B is

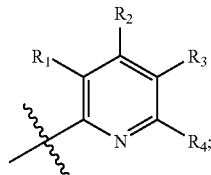

Z is C; — is a bond; L is —C(O)N(R₇)—; and D, R₁, R₂, R₃, R₄, R₇, and R_A are as defined in formula (I).

In another embodiment, the present invention relates to a method of treating sexual dysfunction in a mammal comprising administering to the mammal a therapeutically effective amount of a compound of formula (I) wherein A is cycloalkyl wherein the cycloalkyl is cyclohexyl or adamantyl; B is

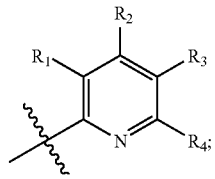

R₁ is hydrogen, alkyl, cyano, haloalkyl, halogen, nitro, (NZ₃Z₄)alkyl, or (NZ₃Z₄)carbonyl; R₂ and R₄ are hydrogen; R₃ is hydrogen or hydroxy; Z is C; — is a bond; D is —CH₂—; L is —C(O)N(R₇)—; and R₇ and R_A are as defined in formula (I).

In another embodiment, the present invention relates to a method of treating sexual dysfunction in a mammal comprising administering to the mammal a therapeutically effective amount of a compound of formula (I) wherein A is cycloalkyl wherein the cycloalkyl is cyclohexyl or adamantyl; B is

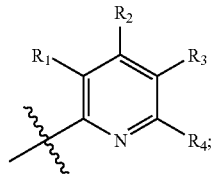

R₁ is hydrogen, alkyl, cyano, haloalkyl, halogen, nitro, (NZ₃Z₄)alkyl, or (NZ₃Z₄)carbonyl; R₂ and R₄ are hydrogen; R₃ is hydrogen or hydroxy; Z is C; — is a bond; D is —CH(CH₃)—; L is —C(O)N(R₇)—; and R₇ and R_A are as defined in formula (I).

In another embodiment, the present invention relates to compounds of formula (II)

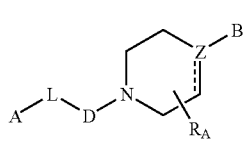

(II)

or a pharmaceutically acceptable salt, ester, amide, or prodrug thereof, wherein A is aryl, arylalkyl, cycloalkyl, cycloalkylalkyl, heterocycle, or heterocyclealkyl;

L is —N(R₇)C(O)—, —C(O)N(R₇)—, —N(R₇)C(S)—, or —C(S)N(R₇)— wherein the left end of the —N(R₇)C(O)—, —C(O)N(R₇)—, —N(R₇)C(S)—, or —C(S)N(R₇)— is attached to A and the right end is attached to D;

D is alkylene, fluoroalkylene, or hydroxyalkylene;

Z is N, C or CR_B;

R_A is hydrogen or alkyl;

R_B is hydrogen, alkyl, or halogen;

— is a bond when Z is C and — is absent when Z is N or CR_B;

B is

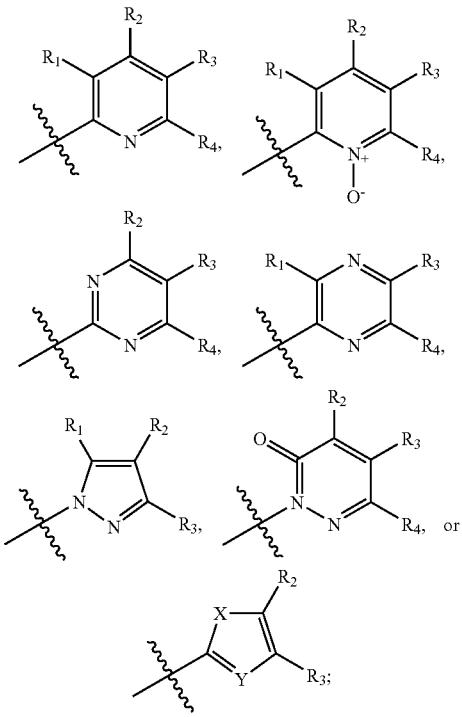

R₁, R₂, R₃, R₄ and R₅ are each independently hydrogen, alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, —NZ₁Z₂, (NZ₃Z₄)alkyl, (NZ₃Z₄)carbonyl, or (NZ₃Z₄)sulfonyl;

Z₁ and Z₂ are each independently hydrogen, alkyl, alkylcarbonyl, alkylsulfonyl, aryl, arylalkyl, arylalkylsulfonyl, arylsulfonyl, or formyl;

Z₃ and Z₄ are each independently hydrogen, alkyl, aryl, or arylalkyl;

X is N(R₆), O or S;

Y is C(R₄) or N;

R₆ is hydrogen or alkyl; and

R₇ is hydrogen or alkyl.

In another embodiment of the present invention, compounds of formula (II) are disclosed wherein A is aryl; B is

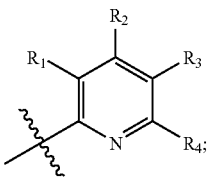

Z is N; — is absent; L is —N(R$_7$)C(O)—; and D, R$_1$, R$_2$, R$_3$, R$_4$, R$_7$, and R$_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

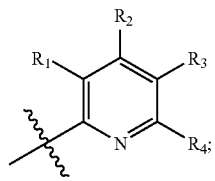

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH$_2$—; L is —N(R$_7$)C(O)—; and R$_7$ and R$_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

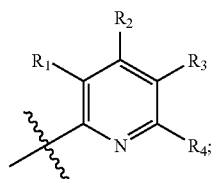

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; R$_3$ is hydrogen or hydroxy; Z is N; — is absent; D is —CH(CH$_3$)—; L is —N(R$_7$)C(O)—; and R$_7$ and R$_A$ are as defined in formula (II).

In another embodiment of the present invention, compounds of formula (II) are disclosed wherein A is aryl wherein the aryl is tetrahydronaphthalenyl or 2,3-dihydro-1H-indenyl; B is

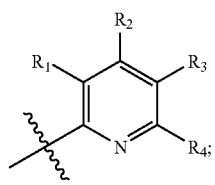

R$_1$ is selected from hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH$_2$—; L is —N(R$_7$)C(O)—; and R$_7$ and R$_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

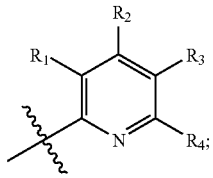

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH$_2$—; L is —N(R$_7$)C(S)—; and R$_7$ and R$_A$ are as defined in formula (II).

In another embodiment of the present invention, compounds of formula (II) are disclosed wherein A is aryl wherein the aryl is tetrahydronaphthalenyl or 2,3-dihydro-1H-indenyl; B is

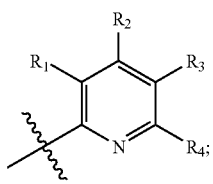

R$_1$ is selected from hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH(CH$_3$)—; L is —N(R$_7$)C(O)—; and R$_7$ and R$_A$ are as defined in formula (II).

In another embodiment of the present invention, compounds of formula (II) are disclosed wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

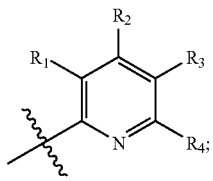

Z is N; — is absent; L is —N(R$_7$)C(O)—; and D, R$_1$, R$_2$, R$_3$, R$_4$, R$_7$, and R$_A$ are as defined in formula (II).

In another embodiment of the present invention, compounds of formula (II) are disclosed wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

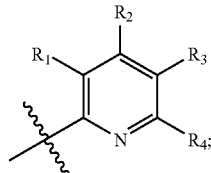

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is N; — is absent; D is —$CH_2$—; L is —$N(R_7)C(O)$—; and $R_7$ and $R_A$ are as defined on formula (II).

In another embodiment of the present invention, compounds of formula (II) are disclosed wherein A is heterocycle wherein the heterocycle is benzimidazolyl, benzothiazolyl, pyrazolyl, pyridinyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

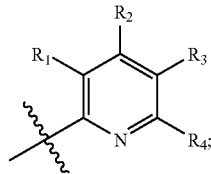

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is N; — is absent; D is —$CH_2$—; L is —$N(R_7)C(O)$—; and $R_7$ and $R_A$ are as defined on formula (II).

In another embodiment of the present invention, compounds of formula (II) are disclosed wherein A is aryl; B is

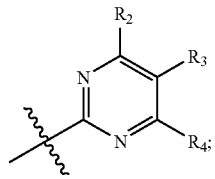

is N; — is absent; L is —$N(R_7)C(O)$—; and D, $R_2$, $R_3$, $R_4$, $R_7$, and $R_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

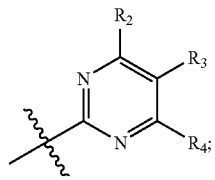

$R_2$, $R_3$, and $R_4$ are hydrogen; Z is N; — is absent; D is —$CH_2$—; L is —$N(R_7)C(O)$—; $R_7$ and $R_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

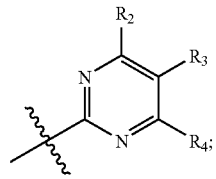

$R_2$, $R_3$, and $R_4$ are hydrogen; Z is N; — is absent; D is —$CH(CH_3)$—; L is —$N(R_7)C(O)$—; $R_7$ and $R_A$ are as defined in formula (II).

In another embodiment of the present invention, compounds of formula (II) are disclosed wherein A is aryl; B is

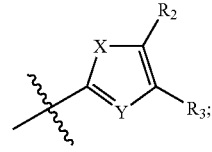

Z is N; — is absent; L is —$N(R_7)C(O)$—; and D, X, Y, $R_2$, $R_3$, $R_7$, and $R_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

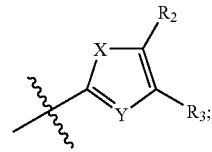

$R_2$ and $R_3$ are hydrogen; X is $N(R_6)$, O, or S; Y is N; Z is N; — is absent; D is —$CH_2$—; L is —$N(R_7)C(O)$—; and $R_6$, $R_7$, and $R_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

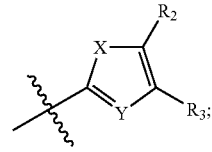

$R_2$ and $R_3$ are hydrogen; X is $N(R_6)$, O, or S; Y is N; Z is N; — is absent; D is —$CH(CH_3)$—; L is —$N(R_7)C(O)$—; and $R_6$, $R_7$, and $R_A$ are as defined in formula (II).

In another embodiment of the present invention, compounds of formula (II) are disclosed wherein A is cycloalkyl; B is

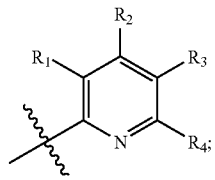

Z is N; — is absent; L is —N(R$_7$)C(O)—; and D, R$_1$, R$_2$, R$_3$, R$_4$, R$_7$, and R$_A$ are as defined in formula (II).

In another embodiment of the present invention, compounds of formula (II) are disclosed wherein A is cycloalkyl wherein the cycloalkyl is cyclohexyl or adamantyl; B is

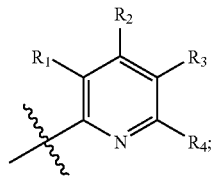

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH$_2$—; L is —N(R$_7$)C(O)—; and R$_7$ and R$_A$ are as defined in formula (II).

In another embodiment of the present invention, compounds of formula (II) are disclosed wherein A is cycloalkyl wherein the cycloalkyl is cyclohexyl or adamantyl; B is

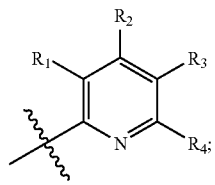

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH(CH$_3$)—; L is —N(R$_7$)C(O)—; and R$_7$ and R$_A$ are as defined in formula (II).

In another embodiment of the present invention, compounds of formula (II) are disclosed wherein A is arylalkyl; B is

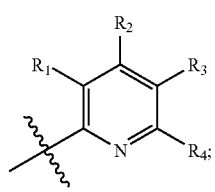

Z is N; — is absent; L is —N(R$_7$)C(O)—; and D, R$_1$, R$_2$, R$_3$, R$_4$, R$_7$, and R$_A$ are as defined in formula (II).

In another embodiment of the present invention, compounds of formula (II) are disclosed wherein A is arylalkyl wherein the aryl of arylalkyl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

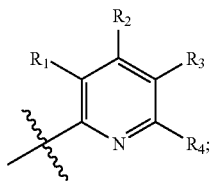

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH$_2$—; L is —N(R$_7$)C(O)—; and R$_7$ and R$_A$ are as defined in formula (II).

In another embodiment of the present invention, compounds of formula (II) are disclosed wherein A is arylalkyl wherein the aryl of arylalkyl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

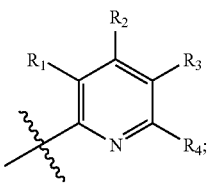

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH(CH$_3$)—; L is —N(R$_7$)C(O)—; and R$_7$ and R$_A$ are as defined in formula (II).

In another embodiment of the present invention, compounds of formula (II) are disclosed wherein A is aryl; B is

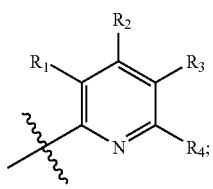

Z is CR$_B$; — is absent; L is —N(R$_7$)C(O)—; and D, R$_1$, R$_2$, R$_3$, R$_4$, R$_7$, R$_B$, and R$_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

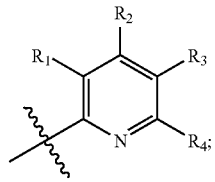

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is CR$_B$; R$_B$ is hydrogen; — is absent; D is —CH$_2$—; L is —N(R$_7$)C(O)—; and R$_7$ and R$_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

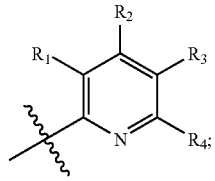

R$_1$ is hydrogen, alkyl, cyano, haloalkyl, halogen, nitro, (NZ$_3$Z$_4$)alkyl, or (NZ$_3$Z$_4$)carbonyl, or (NZ$_3$Z$_4$)carbonyl; R$_2$ and R$_4$ are hydrogen; R$_3$ is hydrogen or hydroxy; Z is CR$_B$; R$_B$ is hydrogen; — is absent; D is —CH$_2$—; L is —N(R$_7$)C(S)—; and R$_7$ and R$_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

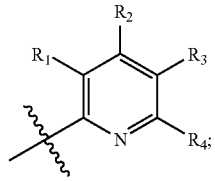

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is CR$_B$; R$_B$ is hydrogen; — is absent; D is —CH(CH$_3$)—; L is —N(R$_7$)C(O)—; and R$_7$ and R$_A$ are as defined in formula (II).

In another embodiment of the present invention, compounds of formula (II) are disclosed wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

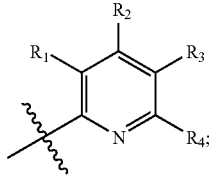

Z is CR$_B$; — is absent; L is —N(R$_7$)C(O)—; R$_B$ is hydrogen; and D, R$_1$, R$_2$, R$_3$, R$_4$, R$_7$, and R$_A$ are as defined in formula (II).

In another embodiment of the present invention, compounds of formula (II) are disclosed wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

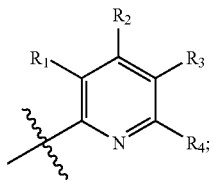

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is CR$_B$; — is absent; D is —CH$_2$—; L is —N(R$_7$)C(O)—; R$_B$ is hydrogen; and R$_7$ and R$_A$ are as defined on formula (II).

In another embodiment of the present invention, compounds of formula (II) are disclosed wherein A is heterocycle wherein the heterocycle is benzimidazolyl, benzothiazolyl, pyrazolyl, pyridinyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is CR$_B$; — is absent; D is —CH$_2$—; L is —N(R$_7$)C(O)—; R$_B$ is hydrogen; and R$_7$ and R$_A$ are as defined on formula (II).

In another embodiment of the present invention, compounds of formula (II) are disclosed wherein A is aryl; B is

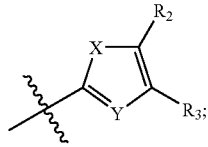

Z is $CR_B$; — is absent; L is —N($R_7$)C(O)—; and D, X, Y, $R_2$, $R_3$, $R_7$, $R_B$, and $R_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

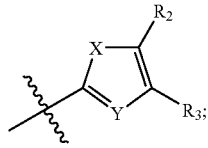

X is N($R_6$), O, or S; Y is N; $R_2$ and $R_3$ are hydrogen; Z is $CR_B$; $R_B$ is hydrogen; — is absent; D is —$CH_2$—; L is —N($R_7$)C(O)—; and $R_6$, $R_7$, and $R_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

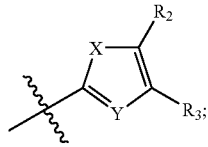

X is N($R_6$), O, or S; Y is N; $R_2$ and $R_3$ are hydrogen; Z is $CR_B$; $R_B$ is hydrogen; — is absent; D is —CH($CH_3$)—; L is —N($R_7$)C(O)—; and $R_6$, $R_7$ and $R_A$ are as defined in formula (II)

In another embodiment of the present invention, compounds of formula (II) are disclosed wherein A is aryl; B is

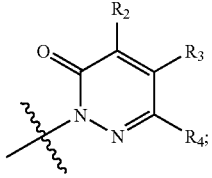

Z is $CR_B$; — is absent; L is —N($R_7$)C(O)—; and D, $R_2$, $R_3$, $R_4$, $R_7$, $R_B$, and $R_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

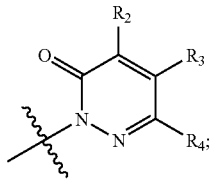

Z is $CR_B$; $R_B$ is hydrogen; — is absent; D is —$CH_2$—; L is —N($R_7$)C(O)—; $R_2$, $R_3$, and $R_4$ are hydrogen; and $R_7$ and $R_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

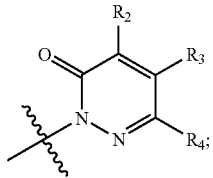

Z is $CR_B$; $R_B$ is hydrogen; — is absent; D is —CH($CH_3$)—; L is —N($R_7$)C(O)—; $R_2$, $R_3$, and $R_4$ are hydrogen; and $R_7$ and $R_A$ are as defined in formula (II).

In another embodiment of the present invention, compounds of formula (II) are disclosed wherein A is aryl; B is

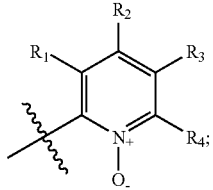

Z is $CR_B$; — is absent; L is —N($R_7$)C(O)—; and D, $R_1$, $R_2$, $R_3$, $R_4$, $R_7$, $R_B$, and $R_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

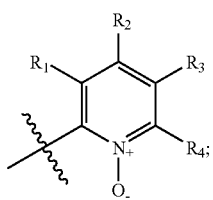

$R_1$, $R_2$, $R_3$, and $R_4$ are hydrogen; Z is $CR_B$; $R_B$ is hydrogen; — is absent; D is —$CH_2$—; L is —N($R_7$)C(O)—; and $R_7$ and $R_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

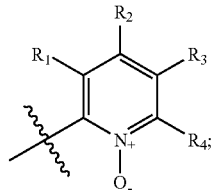

R$_1$, R$_2$, R$_3$, and R$_4$ are hydrogen; Z is CR$_B$; R$_B$ is hydrogen; — is absent; D is —CH$_2$—; L is —N(R$_7$)C(O)—; and R$_7$ and R$_A$ are hydrogen.

In another embodiment of the present invention, compounds of formula (II) are disclosed wherein A is aryl wherein the aryl is phenyl substituted with 1 alkyl substituent; B is

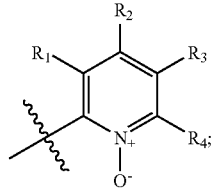

R$_1$, R$_2$, R$_3$, and R$_4$ are hydrogen; Z is CR$_B$; R$_B$ is hydrogen; — is absent; D is —CH$_2$—; L is —N(R$_7$)C(O)—; and R$_7$ and R$_A$ are hydrogen.

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

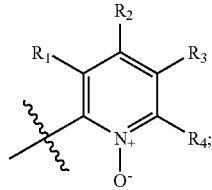

R$_1$, R$_2$, R$_3$, and R$_4$ are hydrogen; Z is CR$_B$; R$_B$ is hydrogen; — is absent; D is —CH(CH$_3$)—; L is —N(R$_7$)C(O)—; and R$_7$ and R$_A$ are as defined in formula (II).

In another embodiment of the present invention, compounds of formula (II) are disclosed wherein A is aryl wherein the aryl is tetrahydronaphthalenyl or 2,3-dihydro-1H-indenyl; B is

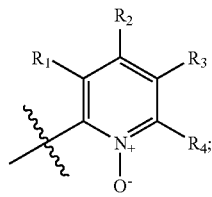

R$_1$, R$_2$, R$_3$, and R$_4$ are hydrogen; Z is CR$_B$; R$_B$ is hydrogen; — is absent; D is —CH$_2$—; L is —N(R$_7$)C(O)—; and R$_7$ and R$_A$ are hydrogen.

In another embodiment of the present invention, compounds of formula (II) are disclosed wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

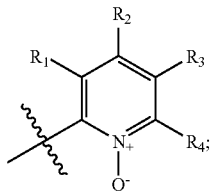

Z is CR$_B$; R$_B$ is hydrogen; — is absent; L is —N(R$_7$)C(O)—; and D, R$_1$, R$_2$, R$_3$, R$_4$, R$_7$, and R$_A$ are as defined in formula (II).

In another embodiment of the present invention, compounds of formula (II) are disclosed wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

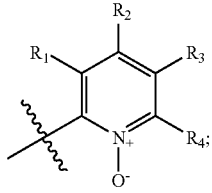

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is CR$_B$; R$_B$ is hydrogen; — is absent; D is —CH$_2$—; L is —N(R$_7$)C(O)—; and R$_7$ and R$_A$ are as defined on formula (II).

In another embodiment of the present invention, compounds of formula (II) are disclosed wherein A is heterocycle wherein the heterocycle is benzimidazolyl, benzothiazolyl, pyrazolyl, pyridinyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

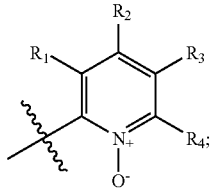

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen;

$R_3$ is hydrogen or hydroxy; Z is $CR_B$; $R_B$ is hydrogen; — is absent; D is —$CH_2$—; L is —$N(R_7)C(O)$—; and $R_7$ and $R_A$ are as defined on formula (II).

In another embodiment of the present invention, compounds of formula (II) are disclosed wherein A is cycloalkyl; B is

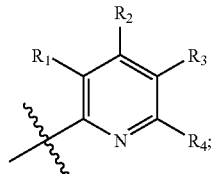

Z is $CR_B$; — is absent; L is —$N(R_7)C(O)$—; and D, $R_1$, $R_2$, $R_3$, $R_4$, $R_7$, $R_B$, and $R_A$ are as defined in formula (II).

In another embodiment of the present invention, compounds of formula (II) are disclosed wherein A is cycloalkyl wherein the cycloalkyl is cyclohexyl or adamantyl; B is

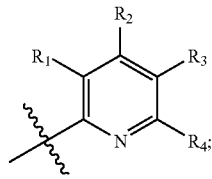

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is $CR_B$; $R_B$ is hydrogen; — is absent; D is —$CH_2$—; L is —$N(R_7)C(O)$—; and $R_7$ and $R_A$ are as defined in formula (II).

In another embodiment of the present invention, compounds of formula (II) are disclosed wherein A is cycloalkyl wherein the cycloalkyl is cyclohexyl or adamantyl; B is

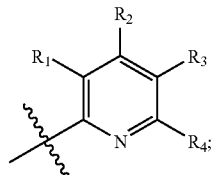

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is $CR_B$; $R_B$ is hydrogen; — is absent; D is —$CH(CH_3)$—; L is —$N(R_7)C(O)$—; and $R_7$ and $R_A$ are as defined in formula (II).

In another embodiment of the present invention, compounds of formula (II) are disclosed wherein A is aryl; B is

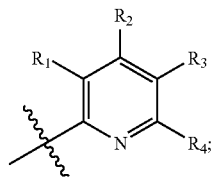

Z is C; — is a bond; L is —$N(R_7)C(O)$—; and D, $R_1$, $R_2$, $R_3$, $R_4$, $R_7$, and $R_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

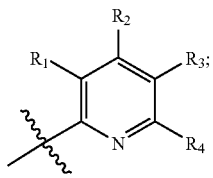

$R_1$ is hydrogen, alkyl, cyano, halolkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is C; — is a bond; D is —$CH_2$—; L is —$N(R_7)C(O)$—; and $R_7$ and $R_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

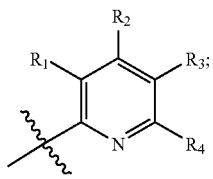

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is C; — is a bond; D is —CH$(CH_3)$—; L is —$N(R_7)C(O)$—; and $R_7$ and $R_A$ are as defined in formula (II).

In another embodiment of the present invention, compounds of formula (II) are disclosed wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

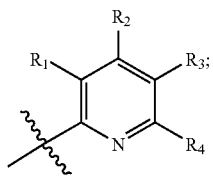

C; — is a bond; L is —$N(R_7)C(O)$—; $R_B$ is hydrogen; and D, $R_1$, $R_2$, $R_3$, $R_4$, $R_7$, and $R_A$ are as defined in formula (II).

In another embodiment of the present invention, compounds of formula (II) are disclosed wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

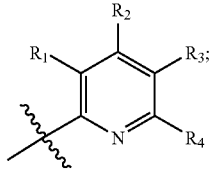

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is C; — is a bond; D is —CH$_2$—; L is —N(R$_7$)C(O)—; R$_B$ is hydrogen; and R$_7$ and R$_A$ are as defined on formula (II).

In another embodiment of the present invention, compounds of formula (II) are disclosed wherein A is heterocycle wherein the heterocycle is benzimidazolyl, benzothiazolyl, pyrazolyl, pyridinyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

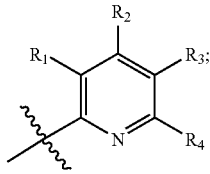

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is C; — is a bond; D is —CH$_2$—; L is —N(R$_7$)C(O)—; R$_B$ is hydrogen; and R$_7$ and R$_A$ are as defined on formula (II).

In another embodiment of the present invention, compounds of formula (II) are disclosed wherein A is aryl; B is

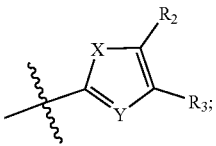

Z is C; — is a bond; L is —N(R$_7$)C(O)—; and D, X, Y, $R_2$, $R_3$, $R_7$, and $R_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

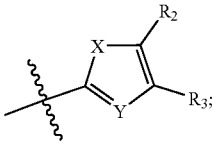

X is N(R$_6$), O, or S; Y is C(R$_4$); R$_2$ and R$_3$ are hydrogen; R$_4$ is hydrogen, alkyl, or cyano; Z is C; — is a bond; D is —CH$_2$—; L is —N(R$_7$)C(O)—; and R$_6$, R$_7$, and R$_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

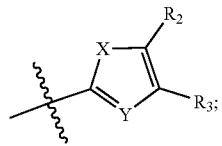

X is N(R$_6$), O, or S; Y is C(R$_4$); R$_2$ and R$_3$ are hydrogen; R$_4$ is hydrogen, alkyl, or cyano; Z is C; — is a bond; D is —CH (CH$_3$)—; L is —N(R$_7$)C(O)—; and R$_6$, R$_7$, and R$_A$ are as defined in formula (II).

In another embodiment of the present invention, compounds of formula (II) are disclosed wherein A is cycloalkyl; B is

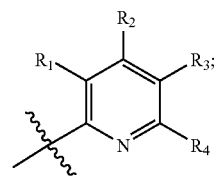

Z is C; — is a bond; L is —N(R$_7$)C(O)—; and D, $R_1$, $R_2$, $R_3$, $R_4$, $R_7$, and $R_A$ are as defined in formula (II).

In another embodiment of the present invention, compounds of formula (II) are disclosed wherein A is cycloalkyl wherein the cycloalkyl is cyclohexyl or adamantyl; B is

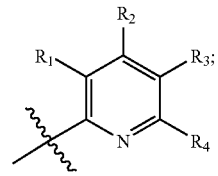

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is C; — is a bond; D is —CH$_2$—; L is —N(R$_7$)C(O)—; and R$_7$ and R$_A$ are as defined in formula (II).

In another embodiment of the present invention, compounds of formula (II) are disclosed wherein A is cycloalkyl wherein the cycloalkyl is cyclohexyl or adamantyl; B is

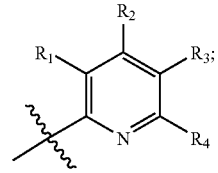

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is C; — is a bond; D is —CH($CH_3$)—; L is —N($R_7$)C(O)—; and $R_7$ and $R_A$ are as defined in formula (II).

In another embodiment of the present invention, compounds of formula (II) are disclosed wherein A is aryl; B is

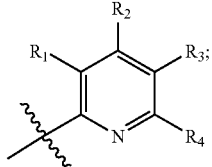

Z is N; — is absent; L is —C(O)N($R_7$)—; and D, $R_1$, $R_2$, $R_3$, $R_4$, $R_7$, and $R_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

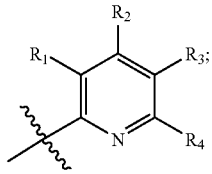

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is N; — is absent; D is —$CH_2$—; L is —C(O)N($R_7$)—; and $R_7$ and $R_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

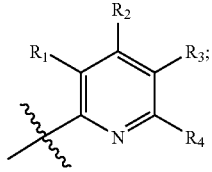

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is N; — is absent; D is —CH($CH_3$)—; L is —C(O)N($R_7$)—; and $R_7$ and $R_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

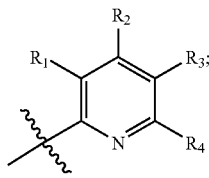

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is N; — is absent; D is —$CH_2CH_2$—; L is —C(O)N($R_7$)—; and $R_7$ and $R_A$ are as defined in formula (II).

In another embodiment of the present invention, compounds of formula (II) are disclosed wherein A is aryl; B is

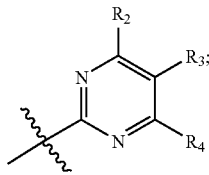

Z is N; — is absent; L is —C(O)N($R_7$)—; and D, $R_2$, $R_3$, $R_4$, $R_7$, and $R_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

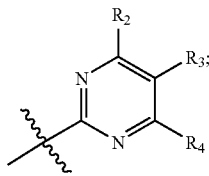

$R_2$, $R_3$, and $R_4$ are hydrogen; Z is N; — is absent; D is —$CH_2$—; L is —C(O)N($R_7$)—; and $R_7$ and $R_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

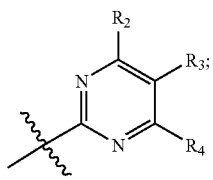

$R_2$, $R_3$, and $R_4$ are hydrogen; Z is N; — is absent; D is —CH($CH_3$)—; L is —C(O)N($R_7$)—; and $R_7$ and $R_A$ are as defined in formula (II).

In another embodiment of the present invention, compounds of formula (II) are disclosed wherein A is cycloalkyl; B is

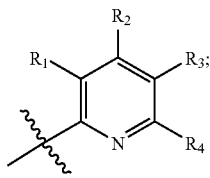

Z is N; — is absent; L is —C(O)N(R$_7$)—; and D, R$_1$, R$_2$, R$_3$, R$_4$, R$_7$, and R$_A$ are as defined in formula (II).

In another embodiment of the present invention, compounds of formula (II) are disclosed wherein A is cycloalkyl wherein the cycloalkyl is cyclohexyl or adamantyl; B is

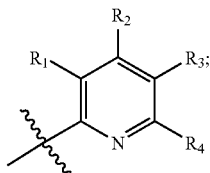

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH$_2$—; L is —C(O)N(R$_7$)—; and R$_7$ and R$_A$ are as defined in formula (II).

In another embodiment of the present invention, compounds of formula (II) are disclosed wherein A is cycloalkyl wherein the cycloalkyl is cyclohexyl or adamantyl; B is

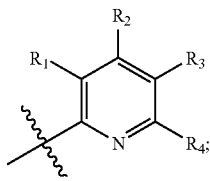

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is N; — is absent; D is —CH(CH$_3$)—; L is —C(O)N(R$_7$)—; and R$_7$ and R$_A$ are as defined in formula (II).

In another embodiment of the present invention, compounds of formula (II) are disclosed wherein A is aryl; B is

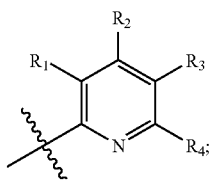

Z is CR$_B$; — is absent; L is —C(O)N(R$_7$)—; and D, R$_1$, R$_2$, R$_3$, R$_4$, R$_7$, R$_B$, and R$_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

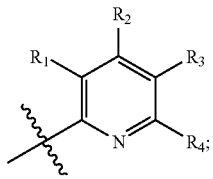

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is CR$_B$; R$_B$ is hydrogen; — is absent; D is —CH$_2$—; L is —C(O)N(R$_7$)—; and R$_7$ and R$_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

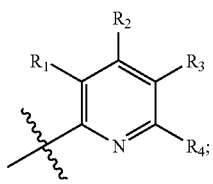

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is CR$_B$; R$_B$ is hydrogen; — is absent; D is —CH(CH$_3$)—; L is —C(O)N(R$_7$)—; and R$_7$ and R$_A$ are as defined in formula (II).

In another embodiment of the present invention, compounds of formula (II) are disclosed wherein A is aryl; B is

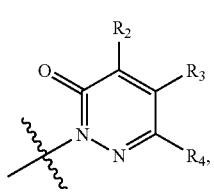

Z is CR$_B$; — is absent; L is —C(O)N(R$_7$)—; and D, R$_2$, R$_3$, R$_4$, R$_7$, R$_B$, and R$_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycar bonyl, alkyl alkythio, benzyl, cyano, halogen, haloalkoxy, haloalkyl, methylenedioxy, nitro, phenyl, or —NZ$_1$Z$_2$; B is

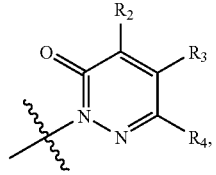

R$_2$, R$_3$, and R$_4$ are hydrogen; Z is CR$_B$; R$_B$ is hydrogen; — is absent; D is —CH$_2$—; L is —C(O)N(R$_7$)—; and R$_7$ and R$_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

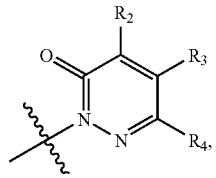

R$_2$, R$_3$, and R$_4$ are hydrogen; Z is CR$_B$; R$_B$ is hydrogen; — is absent; D is —CH(CH$_3$)—; L is —C(O)N(R$_7$)—; and R$_7$ and R$_A$ are as defined in formula (II).

In another embodiment of the present invention, compounds of formula (II) are disclosed wherein A is aryl; B is

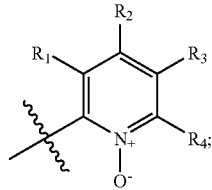

Z is CR$_B$; — is absent; L is —C(O)N(R$_7$)—; and D, R$_1$, R$_2$, R$_3$, R$_4$, R$_7$, R$_B$, and R$_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

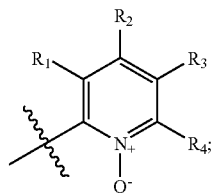

R$_1$, R$_2$, R$_3$, and R$_4$ are hydrogen; Z is CR$_B$; R$_B$ is hydrogen; — is absent; D is —CH$_2$—; L is —C(O)N(R$_7$)—; and R$_7$ and R$_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

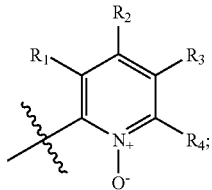

R$_1$, R$_2$, R$_3$, and R$_4$ are hydrogen; Z is CR$_B$; R$_B$ is hydrogen; — is absent; D is —CH$_2$—; L is —C(O)N(R$_7$)—; and R$_7$ and R$_A$ are hydrogen.

In another embodiment of the present invention, compounds of formula (II) are disclosed wherein A is aryl wherein the aryl is phenyl substituted with 1 alkyl substituent; B is

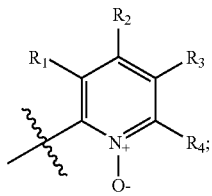

R$_1$, R$_2$, R$_3$, and R$_4$ are hydrogen; Z is CR$_B$; R$_B$ is hydrogen; — is absent; D is —CH$_2$—; L is —C(O)N(R$_7$)—; and R$_7$ and R$_A$ are hydrogen.

In another embodiment of the present invention, compounds of formula (II) are disclosed wherein A is aryl wherein the aryl is phenyl substituted with 1 alkyl substituent wherein a preferred alkyl substituent is methyl; B is

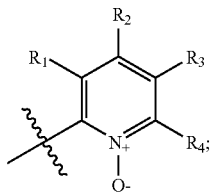

R$_1$, R$_2$, R$_3$, and R$_4$ are hydrogen; Z is CR$_B$; R$_B$ is hydrogen; — is absent; D is —CH$_2$—; L is —C(O)N(R$_7$)—; and R$_7$ and R$_A$ are hydrogen.

In another embodiment of the present invention, compounds of formula (II) are disclosed wherein A is aryl wherein the aryl is phenyl substituted with 1 alkyl substituent wherein a preferred alkyl substituent is methyl; B is

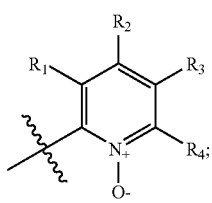

R$_1$, R$_2$, R$_3$, and R$_4$ are hydrogen; Z is CR$_B$; R$_B$ is hydrogen; — is absent; D is —CH$_2$—; L is —C(S)N(R$_7$)—; and R$_7$ and R$_A$ are hydrogen.

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

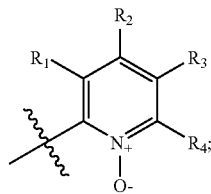

$R_1$, $R_2$, $R_3$, and $R_4$ are hydrogen; Z is $CR_B$; $R_B$ is hydrogen; — is absent; D is —CH($CH_3$)—; L is —C(O)N($R_7$)—; and $R_7$ and $R_A$ are as defined in formula (II).

In another embodiment of the present invention, compounds of formula (II) are disclosed wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

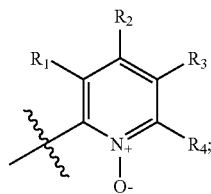

Z is $CR_B$; $R_B$ is hydrogen; — is absent; L is —C(O)N($R_7$)—; and D, $R_1$, $R_2$, $R_3$, $R_4$, $R_7$, and $R_A$ are as defined in formula (II).

In another embodiment of the present invention, compounds of formula (II) are disclosed wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

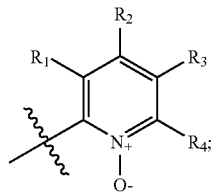

$R_1$ is hydrogen, alkyl, cyano, haloalkyl, halogen, nitro, ($NZ_3Z_4$)alkyl, or ($NZ_3Z_4$)carbonyl; $R_2$ and $R_4$ are hydrogen; $R_3$ is hydrogen or hydroxy; Z is $CR_B$; $R_B$ is hydrogen; — is absent; D is —$CH_2$—; L is —C(O)N($R_7$)—; and $R_7$ and $R_A$ are as defined on formula (II).

In another embodiment of the present invention, compounds of formula (II) are disclosed wherein A is heterocycle wherein the heterocycle is benzimidazolyl, benzothiazolyl, pyrazolyl, pyridinyl, or thienyl wherein the heterocycle is independently substituted with 0, 1, 2, or 3 substituents independently selected from alkoxy, alkoxycarbonyl, alkyl, cyano, halogen, haloalkoxy, haloalkyl, or nitro; B is

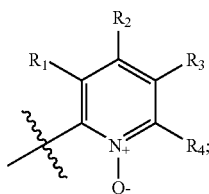

$R_1$ is hydrogen, alkyl, cyano, haloalkyl, halogen, nitro, ($NZ_3Z_4$)alkyl, or ($NZ_3Z_4$)carbonyl; $R_2$ and $R_4$ are hydrogen; $R_3$ is hydrogen or hydroxy; Z is $CR_B$; $R_B$ is hydrogen; — is absent; D is —$CH_2$—; L is —C(O)N($R_7$)—; and $R_7$ and $R_A$ are as defined on formula (II).

In another embodiment of the present invention, compounds of formula (II) are disclosed wherein A is cycloalkyl; B is

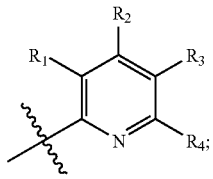

Z is $CR_B$; — is absent; L is —C(O)N($R_7$)—; and D, $R_1$, $R_2$, $R_3$, $R_4$, $R_7$, $R_B$, and $R_A$ are as defined in formula (II).

In another embodiment of the present invention, compounds of formula (II) are disclosed wherein A is cycloalkyl wherein the cycloalkyl is cyclohexyl or adamantyl; B is

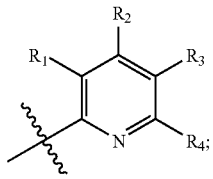

$R_1$ is hydrogen, alkyl, cyano, haloalkyl, halogen, nitro, ($NZ_3Z_4$)alkyl, or ($NZ_3Z_4$)carbonyl; $R_2$ and $R_4$ are hydrogen; $R_3$ is hydrogen or hydroxy; Z is $CR_B$; $R_B$ is hydrogen; — is absent; D is —$CH_2$—; L is —C(O)N($R_7$)—; and $R_7$ and $R_A$ are as defined in formula (II).

In another embodiment of the present invention, compounds of formula (II) are disclosed wherein A is cycloalkyl wherein the cycloalkyl is cyclohexyl or adamantyl; B is

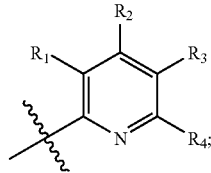

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is $CR_B$; $R_B$ is hydrogen; — is absent; D is —CH(CH$_3$)—; L is —C(O)N(R$_7$)—; and $R_7$ and $R_A$ are as defined in formula (II).

In another embodiment of the present invention, compounds of formula (II) are disclosed wherein A is aryl; B is

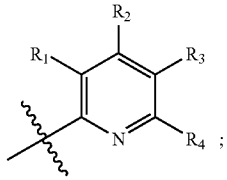

Z is C; — is a bond; L is —C(O)N(R$_7$)—; and D, $R_1$, $R_2$, $R_3$, $R_4$, $R_7$, and $R_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

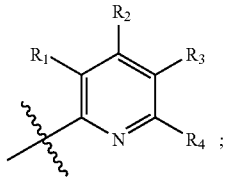

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is C; — is a bond; D is —CH$_2$—; L is —C(O)N(R$_7$)—; and $R_7$ and $R_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

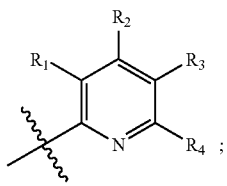

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is C; — is a bond; D is —CH(CH$_3$)—; L is —C(O)N(R$_7$)—; and $R_7$ and $R_A$ are as defined in formula (II).

In another embodiment of the present invention, compounds of formula (II) are disclosed wherein A is aryl wherein the aryl is naphthyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

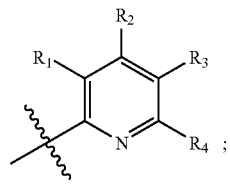

$R_1$ is hydrogen, alkyl, cyano, halogen, nitro, $(NZ_3Z_4)$alkyl, or $(NZ_3Z_4)$carbonyl; $R_2$, $R_3$, and $R_4$ are hydrogen; Z is C; — is a bond; D is —CH$_2$—; L is —C(O)N(R$_7$)—; and $R_7$ and $R_A$ are as defined in formula (II).

In another embodiment of the present invention, compounds of formula (II) are disclosed wherein A is aryl wherein the aryl is naphthyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

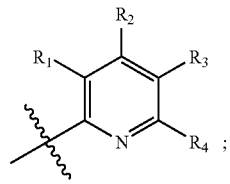

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; Z is C; — is a bond; D is —CH(CH$_3$)—; L is —C(O)N(R$_7$)—; and $R_7$ and $R_A$ are as defined in formula (II).

In another embodiment of the present invention, compounds of formula (II) are disclosed wherein A is aryl; B is

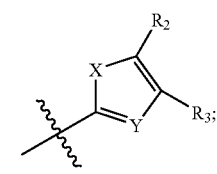

Z is C; — is a bond; L is —C(O)N(R$_7$)—; and D, X, Y, $R_2$, $R_3$, $R_7$ and $R_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycar bonyl, alkyl, alkythio, benzyl, cyano, halogen, haloalkoxy, haloalkyl, methylenedioxy, nitro, phenyl, or —NZ$_1$Z$_2$; B is

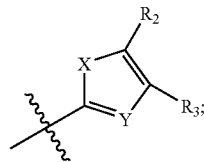

R$_2$ and R$_3$ are hydrogen; X is N(R$_6$), O, or S; Y is N; Z is C; — is a bond; D is —CH$_2$—; L is —C(O)N(R$_7$)—; and R$_6$, R$_7$, and R$_A$ are as defined in formula (II).

In another embodiment of the present invention, compounds of formula (II) are disclosed wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

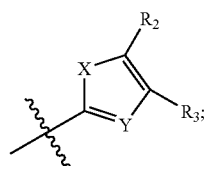

R$_2$ and R$_3$ are hydrogen; X is N(R$_6$), O, or S; Y is N; Z is C; — is a bond; D is —CH(CH$_3$)—; L is —C(O)N(R$_7$)—; and R$_6$, R$_7$, and R$_A$ are as defined in formula (II).

In another embodiment of the present invention, compounds of formula (II) are disclosed wherein A is cycloalkyl; B is

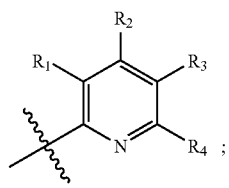

Z is C; — is a bond; L is —C(O)N(R$_7$)—; and D, R$_1$, R$_2$, R$_3$, R$_4$, R$_7$, and R$_A$ are as defined in formula (II).

In another embodiment of the present invention, compounds of formula (II) are disclosed wherein A is cycloalkyl wherein the cycloalkyl is cyclohexyl or adamantyl; B is

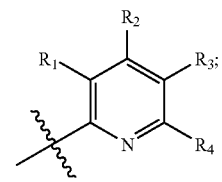

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is C; — is a bond; D is —CH$_2$—; L is —C(O)N(R$_7$)—; and R$_7$ and R$_A$ are as defined in formula (II).

In another embodiment of the present invention, compounds of formula (II) are disclosed wherein A is cycloalkyl wherein the cycloalkyl is cyclohexyl or adamantyl; B is

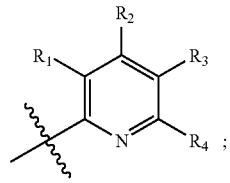

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; Z is C; — is a bond; D is —CH(CH$_3$)—; L is —C(O)N(R$_7$)—; and R$_7$ and R$_A$ are as defined in formula (II).

In another embodiment, the present invention relates to method of treating sexual dysfunction in a mammal comprising administering to the mammal a therapeutically effective amount of a compound of formula (I) or a pharmaceutically acceptable salt, ester, amide, or prodrug thereof in combination with a pharmaceutically acceptable carrier.

In another embodiment, the present invention relates to method of treating sexual dysfunction in a mammal comprising administering to the mammal a therapeutically effective amount of 2-(1-{[(3-methylbenzoyl)amino]methyl}-4-piperidinyl)pyridinium N-oxide or a pharmaceutically acceptable salt, ester, amide, or prodrug thereof in combination with a pharmaceutically acceptable carrier.

In another embodiment, the present invention relates to method of treating sexual dysfunction in a mammal comprising administering to the mammal a therapeutically effective amount of a compound of formula (I) or a pharmaceutically acceptable salt, ester, amide, or prodrug thereof in combination with a phosphodiesterase 5 inhibitor.

In another embodiment, the present invention relates to method of treating sexual dysfunction in a mammal comprising administering to the mammal a therapeutically effective amount of 2-(1-{[(3-methylbenzoyl)amino]methyl}-4-piperidinyl)pyridinium N-oxide or a pharmaceutically acceptable salt, ester, amide, or prodrug thereof in combination with a phosphodiesterase 5 inhibitor.

In another embodiment, the present invention relates to method of treating sexual dysfunction in a mammal comprising administering to the mammal a therapeutically effective amount of a compound of formula (I) or a pharmaceutically acceptable salt, ester, amide, or prodrug thereof in combination with an adrenergic receptor antagonist.

In another embodiment, the present invention relates to method of treating sexual dysfunction in a mammal comprising administering to the mammal a therapeutically effective amount of 2-(1-{[(3-methylbenzoyl)amino]methyl}-4-piperidinyl)pyridinium N-oxide or a pharmaceutically acceptable salt, ester, amide, or prodrug thereof in combination with an adrenergic receptor antagonist.

In another embodiment, the present invention relates to method of treating sexual dysfunction in a mammal comprising administering to the mammal a therapeutically effective amount of a compound of formula (I) or a pharmaceutically acceptable salt, ester, amide, or prodrug thereof in combination with a dopamine agonist.

In another embodiment, the present invention relates to method of treating sexual dysfunction in a mammal comprising administering to the mammal a therapeutically effective amount of 2-(1-{[(3-methylbenzoyl)amino]methyl}-4-piperidinyl)pyridinium N-oxide or a pharmaceutically acceptable salt, ester, amide, or prodrug thereof in combination with a dopamine agonist.

In another embodiment, the present invention relates to method of treating male erectile dysfunction in a male human comprising administering to the male human in need of such treatment a therapeutically effective amount of a compound of formula (I) or a pharmaceutically acceptable salt, ester, amide, or prodrug thereof in combination with a pharmaceutically acceptable carrier.

In another embodiment, the present invention relates to method of treating male erectile dysfunction in a male human comprising administering to the male human in need of such treatment a therapeutically effective amount of 2-(1-{[(3-methylbenzoyl)amino]methyl}-4-piperidinyl)pyridinium N-oxide or a pharmaceutically acceptable salt, ester, amide, or prodrug thereof in combination with a pharmaceutically acceptable carrier.

In another embodiment, the present invention relates to method of treating male erectile dysfunction in a mammal comprising administering to the mammal a therapeutically effective amount of a compound of formula (I) or a pharmaceutically acceptable salt, ester, amide, or prodrug thereof in combination with a phosphodiesterase 5 inhibitor.

In another embodiment, the present invention relates to method of treating male erectile dysfunction in a mammal comprising administering to the mammal a therapeutically effective amount of 2-(1-{[(3-methylbenzoyl)amino]methyl}-4-piperidinyl)pyridinium N-oxide or a pharmaceutically acceptable salt, ester, amide, or prodrug thereof in combination with a phosphodiesterase 5 inhibitor.

In another embodiment, the present invention relates to method of treating male erectile dysfunction in a mammal comprising administering to the mammal a therapeutically effective amount of a compound of formula (I) or a pharmaceutically acceptable salt, ester, amide, or prodrug thereof in combination with an adrenergic receptor antagonist.

In another embodiment, the present invention relates to method of treating male erectile dysfunction in a mammal comprising administering to the mammal a therapeutically effective amount of 2-(1-{[(3-methylbenzoyl)amino]methyl}-4-piperidinyl)pyridinium N-oxide or a pharmaceutically acceptable salt, ester, amide, or prodrug thereof in combination with an adrenergic receptor antagonist.

In another embodiment, the present invention relates to method of treating male erectile dysfunction in a mammal comprising administering to the mammal a therapeutically effective amount of a compound of formula (I) or a pharmaceutically acceptable salt, ester, amide, or prodrug thereof in combination with a dopamine agonist.

In another embodiment, the present invention relates to method of treating male erectile dysfunction in a mammal comprising administering to the mammal a therapeutically effective amount of 2-(1-{[(3-methylbenzoyl)amino]methyl}-4-piperidinyl)pyridinium N-oxide or a pharmaceutically acceptable salt, ester, amide, or prodrug thereof in combination with a dopamine agonist.

In another embodiment, the present invention relates to method of treating female sexual dysfunction in a mammal comprising administering to the mammal in need of such treatment a therapeutically effective amount of a compound of formula (I) or a pharmaceutically acceptable salt, ester, amide, or prodrug thereof in combination with a pharmaceutically acceptable carrier.

In another embodiment, the present invention relates to method of treating female sexual dysfunction in a mammal comprising administering to the mammal in need of such treatment a therapeutically effective amount of 2-(1-{[(3-methylbenzoyl)amino]methyl}-4-piperidinyl)pyridinium N-oxide or a pharmaceutically acceptable salt, ester, amide, or prodrug thereof in combination with a pharmaceutically acceptable carrier.

In another embodiment, the present invention relates to method of treating female sexual dysfunction in a mammal comprising administering to the mammal a therapeutically effective amount of a compound of formula (I) or a pharmaceutically acceptable salt, ester, amide, or prodrug thereof in combination with a phosphodiesterase 5 inhibitor.

In another embodiment, the present invention relates to method of treating female sexual dysfunction in a mammal comprising administering to the mammal a therapeutically effective amount of 2-(1-{[(3-methylbenzoyl)amino]methyl}-4-piperidinyl)pyridinium N-oxide or a pharmaceutically acceptable salt, ester, amide, or prodrug thereof in combination with a phosphodiesterase 5 inhibitor.

In another embodiment, the present invention relates to method of treating female sexual dysfunction in a mammal comprising administering to the mammal a therapeutically effective amount of a compound of formula (I) or a pharmaceutically acceptable salt, ester, amide, or prodrug thereof in combination with an adrenergic receptor antagonist.

In another embodiment, the present invention relates to method of treating female sexual dysfunction in a mammal comprising administering to the mammal a therapeutically effective amount of 2-(1-{[(3-methylbenzoyl)amino]methyl}-4-piperidinyl)pyridinium N-oxide or a pharmaceutically acceptable salt, ester, amide, or prodrug thereof in combination with an adrenergic receptor antagonist.

In another embodiment, the present invention relates to method of treating female sexual dysfunction in a mammal comprising administering to the mammal a therapeutically effective amount of a compound of formula (I) or a pharmaceutically acceptable salt, ester, amide, or prodrug thereof in combination with a dopamine agonist.

In another embodiment, the present invention relates to method of treating female sexual dysfunction in a mammal comprising administering to the mammal a therapeutically effective amount of 2-(1-{[(3-methylbenzoyl)amino]methyl}-4-piperidinyl)pyridinium N-oxide or a pharmaceutically acceptable salt, ester, amide, or prodrug thereof in combination with a dopamine agonist.

In another embodiment, the present invention relates to method of treating a disorder wherein the disorder is cardiovascular disorders, inflammatory disorders, attention deficit hyperactivity disorder, Alzheimer's disease, drug abuse, Parkinson's disease, schizophrenia, anxiety, mood disorders or depression in a mammal comprising administering to the mammal in need of such treatment a therapeutically effective amount of a compound of formula (I) or a pharmaceutically acceptable salt, ester, amide, or prodrug thereof.

In another embodiment, the present invention relates to method of treating a disorder wherein the disorder is cardiovascular disorders, inflammatory disorders, attention deficit hyperactivity disorder, Alzheimer's disease, drug abuse, Parkinson's disease, schizophrenia, anxiety, mood disorders or depression in a mammal comprising administering to the mammal in need of such treatment a therapeutically effective amount of 2-(1-{[(3-methylbenzoyl)amino]methyl}-4-piperidinyl)pyridinium N-oxide or a pharmaceutically acceptable salt, ester, amide, or prodrug thereof.

In another embodiment, the present invention relates to compounds of formula (III)

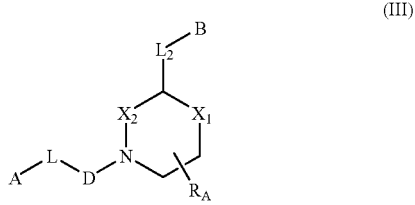

(III)

or a pharmaceutically acceptable salt, ester, amide, or prodrug thereof, wherein $X_1$ is a bond or $CR_BR_C$;
$X_2$ is a bond or $CR_DR_E$;
provided that when $X_1$ is a bond, then $X_2$ is $CR_DR_E$;
further provided that when $X_2$ is bond, then $X_1$ is $CR_BR_C$;
A is aryl, arylalkyl, cycloalkyl, or cycloalkylalkyl;
$L_1$ is —N($R_7$)C(O)—, —C(O)N($R_7$)—, —N($R_7$)C(S)—, or —C(S)N($R_7$)— wherein the left end of the —N($R_7$)C(O)—, —C(O)N($R_7$)—, —N($R_7$)C(S)—, and —C(S)N($R_7$)— is attached to A and the right end is attached to D;
$L_2$ is a bond or alkylene;
D is alkylene, fluoroalkylene, or hydroxyalkylene;
$R_4$, $R_B$, $R_C$, $R_D$, and $R_E$ are independently hydrogen or alkyl;
B is

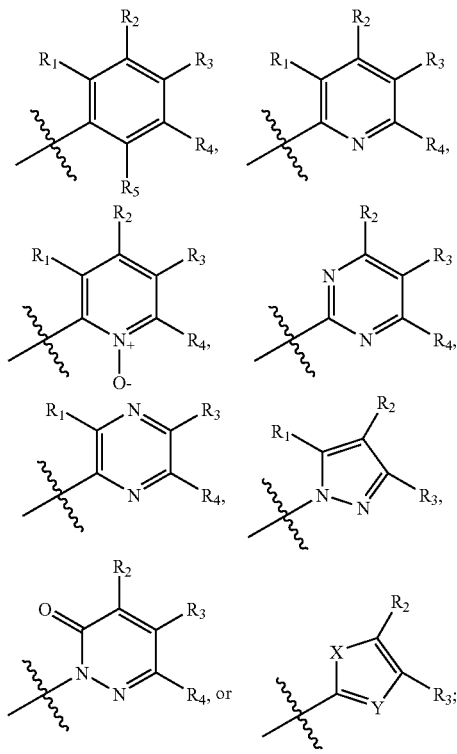

$R_1$, $R_2$, $R_3$, and $R_4$ are each independently hydrogen, alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, —$NZ_1Z_2$, ($NZ_3Z_4$)alkyl, ($NZ_3Z_4$)carbonyl, or ($NZ_3Z_4$)sulfonyl;

$Z_1$ and $Z_2$ are each independently hydrogen, alkyl, alkylcarbonyl, alkylsulfonyl, aryl, arylalkyl, arylalkylsulfonyl, arylsulfonyl, or formyl;

$Z_3$ and $Z_4$ are each independently hydrogen, alkyl, aryl, or arylalkyl;

X is $N(R_6)$, O, or S;
Y is $C(R_4)$ or N;
$R_6$ is hydrogen or alkyl; and
$R_7$ is hydrogen or alkyl.

In another embodiment, the present invention relates to compounds of formula (III) wherein A is aryl; B is

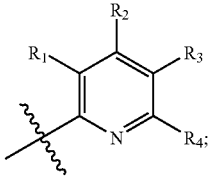

$X_1$ is $CR_BR_C$; $X_2$ is $CR_DR_E$; L is —N($R_7$)C(O)—; and $L_2$, D, $R_1$, $R_2$, $R_3$, $R_4$, $R_7$, $R_A$, $R_B$, $R_C$, $R_D$, and $R_E$ are as defined in formula (III).

In another embodiment, the present invention relates to compounds of formula (III) wherein A is aryl wherein the aryl is phenyl substituted with 0, 1, 2, 3, 4, or 5 substituents indpendently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

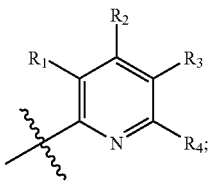

$R_1$ is hydrogen, alkyl, cyano, haloalkyl, halogen, nitro, ($NZ_3Z_4$)alkyl, or ($NZ_3Z_4$)carbonyl; $R_2$ and $R_4$ are hydrogen; $R_3$ is hydrogen or hydroxy; $X_1$ is $CR_BR_C$; $X_2$ is $CR_DR_E$; D is —$CH_2$—; $L_2$ is a bond; and L is —N($R_7$)C(O)—; and $R_A$, $R_B$, $R_C$, $R_D$, $R_E$, $R_1$, $R_2$, $R_3$, $R_4$, and $R_7$ are as defined in formula (III).

In another embodiment, the present invention relates to compounds of formula (III) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

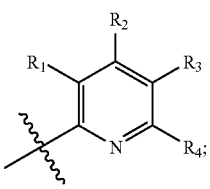

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; $X_1$ is $CR_BR_C$; $X_2$ is $R_DR_E$; D is —$CH_2$—; $L_2$ is a bond; and L is —$N(R_7)C(O)$—; and $R_A$, $R_B$, $R_C$, $R_E$, and $R_E$, and $R_7$ are hydrogen.

In another embodiment, the present invention relates to compounds of formula (III) wherein A is heterocycle; B is

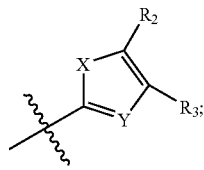

$X_1$ is $CR_BR_C$; $X_2$ is $CR_DR_E$; L is —$N(R_7)C(O)$—; and D, $L_2$, X, Y, $R_A$, $R_B$, $R_C$, $R_D$, $R_E$, $R_2$, $R_3$, and $R_7$ are as defined in formula (III).

In another embodiment, the present invention relates to compounds of formula (III) wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl, wherein the heterocycle is substituted with 0, 1, 2, or 3 substituents independently selected from alkoxy, alkoxycarbonyl, alkyl, cyano, halogen, haloalkoxy, haloalkyl, or nitro; B is

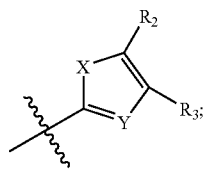

$R_2$ and $R_3$ are hydrogen; $X_1$ is $CR_BR_C$; $X_2$ is $CR_DR_E$; X is $N(R_6)$, O, or S; Y is N; D is —$CH_2$—; $L_2$ is a bond; L is —$N(R_7)C(O)$—; and $R_A$, $R_B$, $R_C$, $R_D$, $R_E$, $R_2$, $R_3$, and $R_7$ are hydrogen; and $R_6$ is hydrogen or alkyl wherein a preferred alkyl is methyl.

In another embodiment, the present invention relates to compounds of formula (III) wherein A is heterocycle wherein the heterocycle is benzimidazolyl substituted with 1 alkyl substitutuent wherein a preferred alkyl substituent is methyl; B is

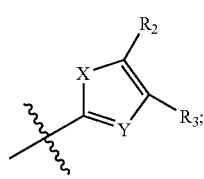

$R_2$ and $R_3$ are hydrogen; $X_1$ is $CR_BR_C$; $X_2$ is $CR_DR_E$; X is $N(R_6)$, O, or S; Y is N; D is —$CH_2$—; $L_2$ is a bond; L is —$N(R_7)C(O)$—; and $R_A$, $R_B$, $R_C$, $R_D$, $R_E$, $R_2$, $R_3$, and $R_7$ are hydrogen; and $R_6$ is hydrogen or alkyl wherein a preferred alkyl is methyl.

In another embodiment, the present invention relates to compounds of formula (III) wherein A is aryl; B is

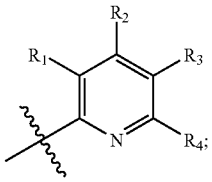

$X_1$ is a bond; $X_2$ is $CR_DR_E$; L is —$N(R_7)C(O)$—; and $L_2$, D, $R_1$, $R_2$, $R_3$, $R_4$, $R_7$, $R_A$, $R_B$, $R_C$, $R_D$, and $R_E$ are as defined in formula (III).

In another embodiment, the present invention relates to compounds of formula (III) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

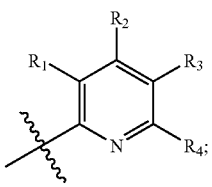

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; $X_1$ is a bond; $X_2$ is $CR_DR_E$; D is —$CH_2$—; $L_2$ is a bond; L is —$N(R_7)C(O)$—; and $R_7$, $R_A$, $R_D$, and $R_E$ are as defined in formula (III).

In another embodiment, the present invention relates to compounds of formula (III) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

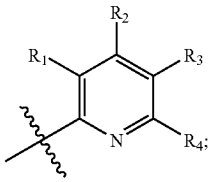

$R_1$ is hydrogen, alkyl, cyano, haloalkyl, halogen, nitro, $(NZ_3Z_4)$alkyl, or $(NZ_3Z_4)$carbonyl; $R_2$ and $R_4$ are hydrogen; $R_3$ is hydrogen or hydroxy; $X_1$ is a bond; $X_2$ is $CR_DR_E$; D is —$CH_2$—; $L_2$ is a bond; L is —$N(R_7)C(O)$—; and $R_7$, $R_A$, $R_D$, and $R_E$ are hydrogen.

In another embodiment, the present invention relates to compounds of formula (III) wherein A is heterocycle; B is

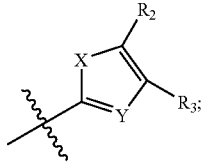

$X_1$ is a bond; $X_2$ is $CR_DR_E$; L is —N($R_7$)C(O)—; and D, $L_2$, X, Y, $R_A$, $R_D$, $R_E$, $R_2$, $R_3$, and $R_7$ are as defined in formula (III).

In another embodiment, the present invention relates to compounds of formula (III) wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl, wherein the heterocycle is substituted with 0, 1, 2, or 3 substituents independently selected from alkoxy, alkoxycarbonyl, alkyl, cyano, halogen, haloalkoxy, haloalkyl, or nitro; B is

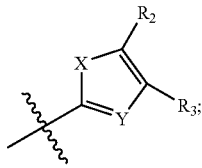

$R_2$ and $R_3$ are hydrogen; $X_1$ is a bond; $X_2$ is $CR_DR_E$; X is N($R_6$), O, or S; Y is N; D is —CH$_2$—; $L_2$ is a bond; L is —N($R_7$)C(O)—; and $R_6$, $R_A$, $R_D$, $R_E$, and $R_7$ are as defined in formula (III).

In another embodiment, the present invention relates to compounds of formula (III) wherein A is heterocycle wherein the heterocycle is benzimidazolyl substituted with 1 alkyl substitutuent wherein a preferred alkyl substituent is methyl; B is

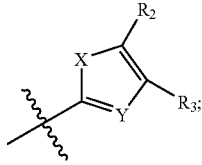

$R_2$ and $R_3$ are hydrogen; $X_1$ is a bond; $X_2$ is $CR_DR_E$; X is N($R_6$), O, or S; Y is N; D is —CH$_2$—; $L_2$ is a bond; L is —N($R_7$)C(O)—; and $R_A$, $R_D$, $R_E$, and $R_7$ are hydrogen; and $R_6$ is hydrogen or alkyl wherein a preferred alkyl is methyl.

In another embodiment, the present invention relates to compounds of formula (III) wherein A is aryl; B is

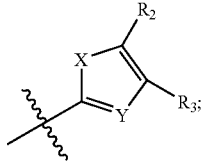

$X_1$ is a bond; $X_2$ is $CR_DR_E$; L is —N($R_7$)C(O)—; and D, $L_2$, X, Y, $R_A$, $R_D$, $R_E$, $R_2$, $R_3$, and $R_7$ are as defined in formula (III).

In another embodiment, the present invention relates to compounds of formula (III) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —N$Z_1Z_2$; B is

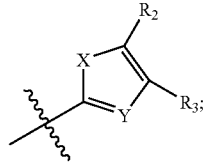

$R_2$ and $R_3$ are hydrogen; $X_1$ is a bond; $X_2$ is $CR_DR_E$; X is N($R_6$), O, or S; Y is C($R_4$); D is —CH$_2$—; $L_2$ is a bond; L is —N($R_7$)C(O)—; $R_4$ is hydrogen, alkyl, or cyano; and $R_6$, $R_A$, $R_D$, $R_E$, $R_4$, and $R_7$ are as defined in formula (III).

In another embodiment, the present invention relates to compounds of formula (III) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —N$Z_1Z_2$; B is

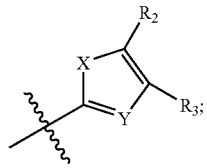

$R_2$ and $R_3$ are hydrogen; $X_1$ is a bond; $X_2$ is $CR_DR_E$; X is N($R_6$), O, or S; Y is C($R_4$); D is —CH$_2$—; $L_2$ is a bond; L is —N($R_7$)C(O)—; $R_4$ is hydrogen, alkyl, or cyano; $R_A$, $R_D$, $R_E$, $R_4$, and $R_7$ are hydrogen; and $R_6$ is hydrogen or alkyl wherein a preferred alkyl is methyl.

In another embodiment, the present invention relates to compounds of formula (III) wherein A is aryl; B is

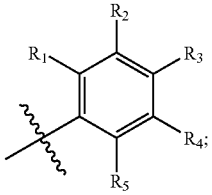

$X_1$ is $CR_BR_C$; $X_2$ is a bond; L is —N($R_7$)C(O)—; and $L_2$, D, $R_1$, $R_2$, $R_3$, $R_4$, $R_5$, $R_7$, $R_A$, $R_B$, and $R_C$ are as defined in formula (III).

In another embodiment, the present invention relates to compounds of formula (III) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —N$Z_1Z_2$; B is

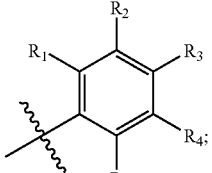

$R_1$, $R_2$, $R_3$, $R_4$, and $R_5$ are hydrogen; $X_1$ is $CR_BR_C$; $X_2$ is a bond; D is —CH$_2$—; $L_2$ is —CH$_2$—; L is —N($R_7$)C(O)—; and $R_B$, $R_C$, and $R_7$ are as defined in formula (III).

In another embodiment, the present invention relates to compounds of formula (III) wherein A is aryl wherein the aryl is phenyl substituted with 0, 1, 2, 3, 4, or 5 substituents independently selected from alkenyl, alkoxy, alkoxycarbonyl, alkyl, alkylthio, benzyl, cyano, halogen, haloalkoxy, haloalkyl, methylenedioxy, nitro, phenyl, or —NZ$_1$Z$_2$; B is

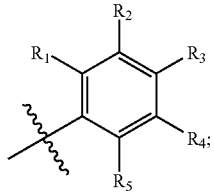

R$_1$, R$_2$, R$_3$, R$_4$, and R$_5$ are hydrogen; X$_1$ is CR$_B$R$_C$; X$_2$ is a bond; D is —CH$_2$—; L$_2$ is —CH$_2$—; L is —N(R$_7$)C(O)—; and R$_B$, R$_C$, and R$_7$ are hydrogen.

In another embodiment, the present invention relates to a method of treating sexual dysfunction in a mammal comprising administering to said mammal in need of such treatment a therapeutically effective amount of a compound of formula (IV)

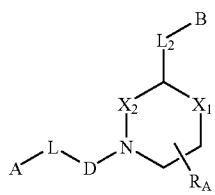

(IV)

or a pharmaceutically acceptable salt, ester, amide, or prodrug thereof, wherein X$_1$ is a bond or CR$_B$R$_C$;

X$_2$ is a bond or CR$_D$R$_E$;

provided that when X$_1$ is a bond, then X$_2$ is CR$_D$R$_E$;

further provided that when X$_2$ is bond, then X$_1$ is CR$_B$R$_C$;

A is aryl, arylalkyl, cycloalkyl, or cycloalkylalkyl;

L$_1$ is —N(R$_7$)C(O)—, —C(O)N(R$_7$)—, —N(R$_7$)C(S)—, or —C(S)N(R$_7$)— wherein the left end of the —N(R$_7$)C(O)—, —C(O)N(R$_7$)—, —N(R$_7$)C(S)—, and —C(S)N(R$_7$)— is attached to A and the right end is attached to D;

L$_2$ is a bond or alkylene;

D is alkylene, fluoroalkylene, or hydroxyalkylene;

R$_A$, R$_B$, R$_C$, R$_D$, and R$_E$ are independently hydrogen or alkyl;

B is

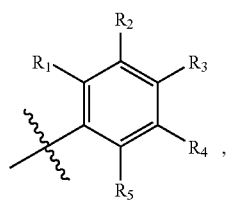 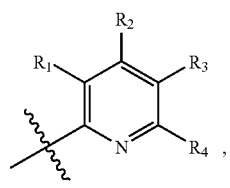

-continued

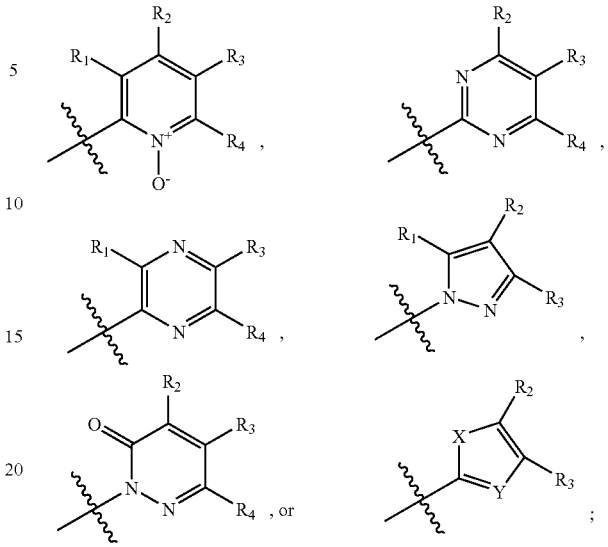

R$_1$, R$_2$, R$_3$, and R$_4$ are each independently hydrogen, alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, —NZ$_1$Z$_2$, (NZ$_3$Z$_4$) alkyl, (NZ$_3$Z$_4$)carbonyl, or (NZ$_3$Z$_4$)sulfonyl;

Z$_1$ and Z$_2$ are each independently hydrogen, alkyl, alkylcarbonyl, alkylsulfonyl, aryl, arylalkyl, arylalkylsulfonyl, arylsulfonyl, or formyl;

Z$_3$ and Z$_4$ are each independently hydrogen, alkyl, aryl, or arylalkyl;

X is N(R$_6$), O, or S;

Y is C(R$_4$) or N;

R$_6$ is hydrogen or alkyl; and

R$_7$ is hydrogen or alkyl.

In another embodiment, the present invention relates to a method of treating sexual dysfunction in a mammal comprising administering to the mammal a therapeutically effective amount of a compound of formula (IV) wherein A is aryl; B is

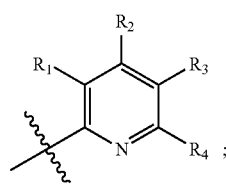

X$_1$ is CR$_B$R$_C$; X$_2$ is CR$_D$R$_E$; L is —N(R$_7$)C(O)—; and L$_2$, D, R$_1$, R$_2$, R$_3$, R$_4$, R$_7$, R$_A$, R$_B$, R$_C$, R$_D$, and R$_E$ are as defined in formula (IV).

In another embodiment, the present invention relates to a method of treating sexual dysfunction in a mammal comprising administering to the mammal a therapeutically effective amount of a compound of formula (IV) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

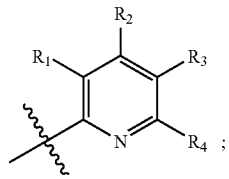

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; X1 is CR$_B$R$_C$; X$_2$ is CR$_D$R$_E$; D is —CH$_2$—; L$_2$ is a bond; L is —N(R$_7$)C(O)—; and R$_7$, R$_A$, R$_B$, R$_C$, R$_D$, and R$_E$ are as defined in formula (IV).

In another embodiment, the present invention relates to a method of treating sexual dysfunction in a mammal comprising administering to the mammal a therapeutically effective amount of a compound of formula (IV) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ$_1$Z$_2$; B is

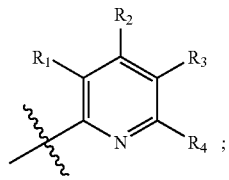

R$_1$ is hydrogen, alkyl, cyano, haloalkyl, halogen, nitro, (NZ$_3$Z$_4$)alkyl, or (NZ$_3$Z$_4$)carbonyl; R$_2$ and R$_4$ are hydrogen; R$_3$ is hydrogen or hydroxy; X1 is CR$_B$R$_C$; X$_2$ is CR$_D$R$_E$; D is —CH$_2$—; L$_2$ is a bond; L is —N(R$_7$)C(O)—; and R$_7$, R$_A$, R$_B$, R$_C$, R$_D$, and R$_E$ are hydrogen.

In another embodiment, the present invention relates to a method of treating sexual dysfunction in a mammal comprising administering to the mammal a therapeutically effective amount of a compound of formula (IV) wherein A is heterocycle; B is

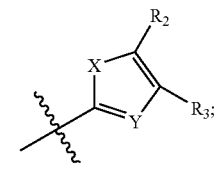

X$_1$ is CR$_B$R$_C$; X$_2$ is CR$_D$R$_E$; L is —N(R$_7$)C(O)—; and D, L$_2$, X, Y, R$_A$, R$_B$, R$_C$, R$_D$, R$_E$, R$_2$, R$_3$, and R$_7$ are as defined in formula (IV).

In another embodiment, the present invention relates to a method of treating sexual dysfunction in a mammal comprising administering to the mammal a therapeutically effective amount of a compound of formula (IV) wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl, wherein the heterocycle is substituted with 0, 1, 2, or 3 substituents independently selected from alkoxy, alkoxycarbonyl, alkyl, cyano, halogen, haloalkoxy, haloalkyl, or nitro; B is

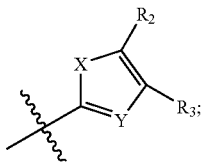

R$_2$ and R$_3$ are hydrogen; X$_1$ is CR$_B$R$_C$; X$_2$ is CR$_D$R$_E$; X is N(R$_6$), O, or S; Y is N; D is —CH$_2$—; L$_2$ is a bond; L is —N(R$_7$)C(O)—; and R$_6$, R$_A$, R$_B$, R$_C$, R$_D$, R$_E$, and R$_7$ are as defined in formula (IV).

In another embodiment, the present invention relates to a method of treating sexual dysfunction in a mammal comprising administering to the mammal a therapeutically effective amount of a compound of formula (IV) wherein A is heterocycle wherein the heterocycle is benzimidazolyl substituted with 1 alkyl substitutuent wherein a preferred alkyl substituent is methyl; B is

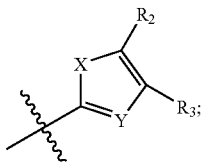

R$_2$ and R$_3$ are hydrogen; X$_1$ is CR$_B$R$_C$; X$_2$ is CR$_D$R$_E$; X is N(R$_6$), O, or S; Y is N; D is —CH$_2$—; L$_2$ is a bond; L is —N(R$_7$)C(O)—; and R$_A$, R$_B$, R$_C$, R$_D$, R$_E$, and R$_7$ are hydrogen; and R$_6$ is hydrogen or alkyl wherein a preferred alkyl is methyl.

In another embodiment, the present invention relates to a method of treating sexual dysfunction in a mammal comprising administering to the mammal a therapeutically effective amount of a compound of formula (IV) wherein A is aryl; B is

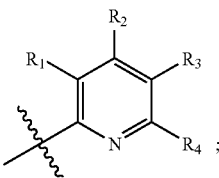

X$_1$ is a bond; X$_2$ is CR$_D$R$_E$; L is —N(R$_7$)C(O)—; and L$_2$, D, R$_1$, R$_2$, R$_3$, R$_4$, R$_7$, R$_A$, R$_D$, and R$_E$ are as defined in formula (IV).

In another embodiment, the present invention relates to a method of treating sexual dysfunction in a mammal comprising administering to the mammal a therapeutically effective amount of a compound of formula (IV) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ₁Z₂; B is

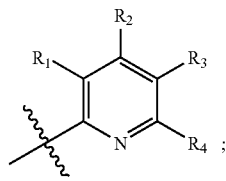

R¹ is hydrogen, alkyl, cyano, haloalkyl, halogen, nitro, (NZ₃Z₄)alkyl, or (NZ₃Z₄)carbonyl; R₂ and R₄ are hydrogen; R₃ is hydrogen or hydroxy; X₁ is a bond; X₂ is CR_DR_E; D is —CH₂—; L₂ is a bond; L is —N(R₇)C(O)—; and R₇, R₄, R_D, and R_E are as defined in formula (IV).

In another embodiment, the present invention relates to a method of treating sexual dysfunction in a mammal comprising administering to the mammal a therapeutically effective amount of a compound of formula (IV) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —NZ₁Z₂; B is

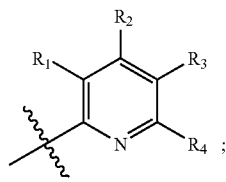

R₁ is hydrogen, alkyl, cyano, haloalkyl, halogen, nitro, (NZ₃Z₄)alkyl, or (NZ₃Z₄)carbonyl; R₂ and R₄ are hydrogen; R₃ is hydrogen or hydroxy; X₁ is a bond; X₂ is CR_DR_E; D is —CH₂—; L₂ is a bond; L is —N(R₇)C(O)—; and R₇, R₄, R_D, and R_E are hydrogen.

In another embodiment, the present invention relates to a method of treating sexual dysfunction in a mammal comprising administering to the mammal a therapeutically effective amount of a compound of formula (IV) wherein A is heterocycle; B is

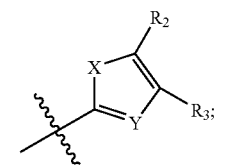

X₁ is a bond; X₂ is CR_DR_E; L is —N(R₇)C(O)—; and D, L₂, X, Y, R₄, R_D, R_E, R₂, R₃, and R₇ are as defined in formula (IV).

In another embodiment, the present invention relates to a method of treating sexual dysfunction in a mammal comprising administering to the mammal a therapeutically effective amount of a compound of formula (IV) wherein A is heterocycle wherein the heterocycle is benzimidazolyl, benzothiazolyl, furyl, imidazolyl, 1,3-oxazolyl, pyrazinyl, pyrazolyl, pyridazinyl, pyridinyl, pyrimidinyl, pyrrolyl, 1,3-thiazolyl, or thienyl, wherein the heterocycle is substituted with 0, 1, 2, or 3 substituents independently selected from alkoxy, alkoxycarbonyl, alkyl, cyano, halogen, haloalkoxy, haloalkyl, or nitro; B is

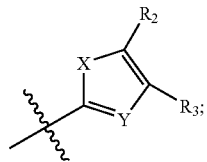

R₂ and R₃ are hydrogen; X₁ is a bond; X₂ is CR_DR_E; X is N(R₆), O, or S; Y is N; D is —CH₂—; L₂ is a bond; L is —N(R₇)C(O)—; and R₆, R₄, R_D, R_E, and R₇ are as defined in formula (IV).

In another embodiment, the present invention relates to a method of treating sexual dysfunction in a mammal comprising administering to the mammal a therapeutically effective amount of a compound of formula (IV) wherein A is heterocycle wherein the heterocycle is benzimidazolyl substituted with 1 alkyl substitutuent wherein a preferred alkyl substituent is methyl; B is

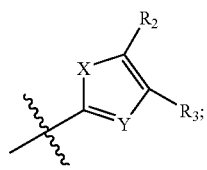

R₂ and R₃ are hydrogen; X₁ is a bond; X₂ is CR_DR_E; X is N(R₆), O, or S; Y is N; D is —CH₂—; L₂ is a bond; L is —N(R₇)C(O)—; R₄, R_D, R_E, and R₇ are hydrogen; and R₆ is hydrogen or alkyl wherein a preferred alkyl is methyl.

In another embodiment, the present invention relates to a method of treating sexual dysfunction in a mammal comprising administering to the mammal a therapeutically effective amount of a compound of formula (IV) wherein A is aryl; B is

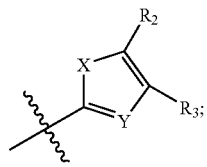

X₁ is a bond; X₂ is CR_DR_E; L is —N(R₇)C(O)—; and D, L₂, X, Y, R₄, R_D, R_E, R₂, R₃, and R₇ are as defined in formula (IV).

In another embodiment, the present invention relates to a method of treating sexual dysfunction in a mammal comprising administering to the mammal a therapeutically effective amount of a compound of formula (IV) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

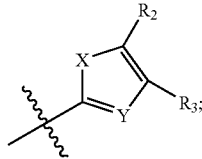

$R_2$ and $R_3$ are hydrogen; $X_1$ is a bond; $X_2$ is $CR_DR_E$; X is $N(R_6)$, O, or S; Y is $C(R_4)$; D is —$CH_2$—; $L_2$ is a bond; L is —$N(R_7)C(O)$—; $R_4$ is hydrogen, alkyl, or cyano; and $R_6$, $R_A$, $R_D$, $R_E$, and $R_7$ are as defined in formula (IV).

In another embodiment, the present invention relates to a method of treating sexual dysfunction in a mammal comprising administering to the mammal a therapeutically effective amount of a compound of formula (IV) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

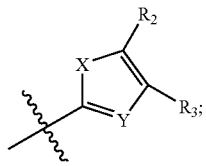

$R_2$ and $R_3$ are hydrogen; $X_1$ is a bond; $X_2$ is $CR_DR_E$; X is $N(R_6)$, O, or S; Y is $C(R_4)$; D is —$CH_2$—; $L_2$ is a bond; L is —$N(R_7)C(O)$—; $R_4$ is hydrogen, alkyl, or cyano; $R_A$, $R_D$, $R_E$, and $R_7$ are hydrogen; and $R_6$ is hydrogen or alkyl wherein a preferred alkyl is methyl.

In another embodiment, the present invention relates to a method of treating sexual dysfunction in a mammal comprising administering to the mammal a therapeutically effective amount of a compound of formula (IV) wherein A is aryl; B is

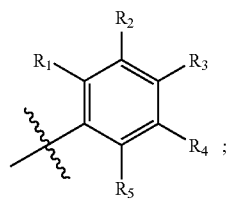

$X_1$ is $CR_BR_C$; $X_2$ is a bond; L is —$N(R_7)C(O)$—; and $L_2$, D, $R_1$, $R_2$, $R_3$, $R_4$, $R_5$, $R_7$, $R_A$, $R_B$, and $R_C$ are as defined in formula (IV).

In another embodiment, the present invention relates to a method of treating sexual dysfunction in a mammal comprising administering to the mammal a therapeutically effective amount of a compound of formula (IV) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

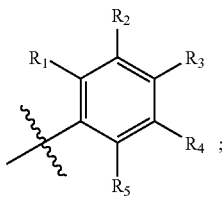

$R_1$, $R_2$, $R_3$, $R_4$, and $R_5$ are hydrogen; X1 is $CR_BR_C$; $X_2$ is a bond; D is —$CH_2$—; $L_2$ is —$CH_2$—; L is —$N(R_7)C(O)$—; and $R_B$, $R_C$, and $R_7$ are as defined in formula (IV).

In another embodiment, the present invention relates to a method of treating sexual dysfunction in a mammal comprising administering to the mammal a therapeutically effective amount of a compound of formula (IV) wherein A is aryl wherein the aryl is phenyl substituted with 0, 1, 2, 3, 4, or 5 substituents independently selected from alkenyl, alkoxy, alkoxycarbonyl, alkyl, alkythio, benzyl, cyano, halogen, haloalkoxy, haloalkyl, methylenedioxy, nitro, phenyl, or —$NZ_1Z_2$; B is

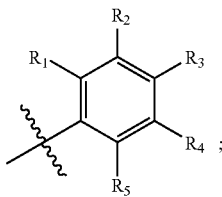

$R_1$, $R_2$, $R_3$, $R_4$, and $R_5$ are hydrogen; $X_1$ is $CR_BR_C$; $X_2$ is a bond; D is —$CH_2$—; $L_2$ is —$CH_2$—; L is —$N(R_7)C(O)$—; and $R_B$, $R_C$, and $R_7$ are hydrogen.

In another embodiment, the present invention relates to method of treating sexual dysfunction in a mammal comprising administering to the mammal a therapeutically effective amount of a compound of formula (IV) or a pharmaceutically acceptable salt, ester, amide, or prodrug thereof in combination with a pharmaceutically acceptable carrier.

In another embodiment, the present invention relates to method of treating sexual dysfunction in a mammal comprising administering to the mammal a therapeutically effective amount of a compound of formula (IV) or a pharmaceutically acceptable salt, ester, amide, or prodrug thereof in combination with a phosphodiesterase 5 inhibitor.

In another embodiment, the present invention relates to method of treating sexual dysfunction in a mammal comprising administering to the mammal a therapeutically effective amount of a compound of formula (IV) or a pharmaceutically acceptable salt, ester, amide, or prodrug thereof in combination with an adrenergic receptor antagonist.

In another embodiment, the present invention relates to method of treating sexual dysfunction in a mammal comprising administering to the mammal a therapeutically effective amount of a compound of formula (IV) or a pharmaceutically acceptable salt, ester, amide, or prodrug thereof in combination with a dopamine agonist.

In another embodiment, the present invention relates to method of treating male erectile dysfunction in a male human comprising administering to the male human in need of such treatment a therapeutically effective amount of a compound of formula (IV) or a pharmaceutically acceptable salt, ester, amide, or prodrug thereof in combination with a pharmaceutically acceptable carrier.

In another embodiment, the present invention relates to method of treating male erectile dysfunction in a mammal comprising administering to the mammal a therapeutically effective amount of a compound of formula (IV) or a pharmaceutically acceptable salt, ester, amide, or prodrug thereof in combination with a phosphodiesterase 5 inhibitor.

In another embodiment, the present invention relates to method of treating male erectile dysfunction in a mammal comprising administering to the mammal a therapeutically effective amount of a compound of formula (IV) or a pharmaceutically acceptable salt, ester, amide, or prodrug thereof in combination with an adrenergic receptor antagonist.

In another embodiment, the present invention relates to method of treating male erectile dysfunction in a mammal comprising administering to the mammal a therapeutically effective amount of a compound of formula (IV) or a pharmaceutically acceptable salt, ester, amide, or prodrug thereof in combination with a dopamine agonist.

In another embodiment, the present invention relates to method of treating female sexual dysfunction in a mammal comprising administering to the mammal in need of such treatment a therapeutically effective amount of a compound of formula (IV) or a pharmaceutically acceptable salt, ester, amide, or prodrug thereof in combination with a pharmaceutically acceptable carrier.

In another embodiment, the present invention relates to method of treating female sexual dysfunction in a mammal comprising administering to the mammal a therapeutically effective amount of a compound of formula (IV) or a pharmaceutically acceptable salt, ester, amide, or prodrug thereof in combination with a phosphodiesterase 5 inhibitor.

In another embodiment, the present invention relates to method of treating female sexual dysfunction in a mammal comprising administering to the mammal a therapeutically effective amount of a compound of formula (IV) or a pharmaceutically acceptable salt, ester, amide, or prodrug thereof in combination with an adrenergic receptor antagonist.

In another embodiment, the present invention relates to method of treating female sexual dysfunction in a mammal comprising administering to the mammal a therapeutically effective amount of a compound of formula (IV) or a pharmaceutically acceptable salt, ester, amide, or prodrug thereof in combination with a dopamine agonist.

In another embodiment, the present invention relates to method of treating a disorder wherein the disorder is cardiovascular disorders, inflammatory disorders, attention deficit hyperactivity disorder, Alzheimer's disease, drug abuse, Parkinson's disease, schizophrenia, anxiety, mood disorders or depression in a mammal comprising administering to the mammal in need of such treatment a therapeutically effective amount of a compound of formula (IV) or a pharmaceutically acceptable salt, ester, amide, or prodrug thereof.

Definitions of the Present Invention

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxysulfonyl" as used herein, means an alkoxy group, as defined herein, appended appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain hydrocarbon of from 1 to 10 carbon atoms. Examples are —$CH_2$—, —$CH_2CH_2$—, —$CH(CH_3)$—, —$CH(CH_2CH_3)$—, —$CH_2CH_2CH_2$—, and —$CH_2CH_2CH_2CH_2$—.

The term "alkylsulfinyl" as used herein, means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylsulfanyl, ethylsulfanyl, tert-butylsulfanyl, and hexylsulfanyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means a phenyl group, or a bicyclic fused ring system, or a tricyclic fused ring system wherein one or more of the fused rings is a phenyl group.

Bicyclic fused ring systems are exemplified by a phenyl group fused to another phenyl group or fused to a cycloalkyl group wherein the cycloalkyl group is selected from cyclopentane, cycloahexane, cycloheptane, or cyclooctane. Tricyclic fused ring systems are exemplified by a bicyclic fused ring system fused to a phenyl group. Representative examples of aryl include, but are not limited to, anthracenyl, azulenyl, fluorenyl, 5,6,7,8-tetrahydronaphthalenyl, 5,6,7,8-tetrahydro-1-naphthalenyl, 1,2,3,4-tetrahydro-1-naphthalenyl, (1S)-1,2,3,4-tetrahydro-1-naphthalenyl, (1R)-1,2,3,4-tetrahydro-1-naphthalenyl, indanyl, indenyl, 3-dihydro-1H-indenyl, 2,3-dihydro-1H-inden-5-yl, 1-naphthyl, 2-naphthyl, and phenyl.

The aryl groups of the present invention are substituted with 0, 1, 2, 3, 4, or 5 substituents independently selected from alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, methylenedioxy, nitro, $-NZ_1Z_2$, $(NZ_3Z_4)$carbonyl, and $(NZ_3Z_4)$sulfonyl. The aryl groups of this invention can be further substituted with an additional aryl or arylalkyl group, as defined herein, wherein the additional aryl group or the aryl portion of arylalkyl group are substituted with 0, 1, 2, 3, 4, or 5 substituents independently selected from alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, methylenedioxy, nitro, $-NZ_1Z_2$, $(NZ_3Z_4)$carbonyl, and $(NZ_3Z_4)$sulfonyl. Representative examples include, but are not limited to, 1,3-benzodioxol-5-yl, 3-benzylphenyl, 1,1'-biphenyl-3yl, 2-bromophenyl, 3-bromophenyl, 4-bromophenyl, 4-bromo-3-methylphenyl, 4-bromo-2-methylphenyl, 2-chlorophenyl, 3-chlorophenyl, 4-chlorophenyl, 3-chloro-4-fluorophenyl, 4-chloro-3-methoxyphenyl, 3-chloro-2-methylphenyl, 2-chloro-5-methylphenyl, 2-chloro-6-methylphenyl, 4-chloro-2,6-dimethylphenyl, 3-chloro-4-fluorophenyl, 5-chloro-2-methylphenyl, 4-chloro-3-methylphenyl, 3-chloro-4-methylphenyl, 2-chloro-5-trifluoromethylphenyl, 3-chloro-4-trifluoromethoxyphenyl, 2-cyanophenyl, 3-cyanophenyl, 4-cyanophenyl, 2,3-dibromo-5-methylphenyl, 2,3-dichlorophenyl, 3,4-dichlorophenyl, 3,5-dichlorophenyl, 2,6-dichloro-3-methylphenyl, 2,6-diethylphenyl, 3,4-difluorophenyl, 2,4-difluorophenyl, 3,5-difluorophenyl, 3,5-dimethoxyphenyl, 2,5-dimethoxyphenyl, 2,3-dimethylphenyl, 2,6-dimethylphenyl, 2,5-dimethylphenyl, 3,5-dimethylphenyl, 3,4-dimethylphenyl, 3-(dimethylamino)phenyl, 3-ethoxyphenyl, 4-(ethoxycarbonyl)phenyl, 3-ethylphenyl, 2-ethyl-6-methylphenyl, 2-fluorophenyl, 3-fluorophenyl, 4-fluorophenyl, 2-fluoro-5-methylphenyl, 4-fluoro-3-methylphenyl, 4-fluoro-2-methylphenyl, 4-fluoro-3-trifluoromethylphenyl, 3-fluoro-5-trifluoromethylphenyl, 2-fluoro-5-trifluoromethylphenyl, 2-fluoro-3-trifluoromethylphenyl, 4-iodo-3-methylphenyl, 3-isopropoxyphenyl, 3-isopropylphenyl, 2-isopropyl-6-methylphenyl, 2-methoxyphenyl, 3-methoxyphenyl, 4-methoxyphenyl, 2-methoxy-6-methylphenyl, 3-methoxy-2-methylphenyl, 3-methylphenyl, 2-methylphenyl, 4-methylphenyl, 5-methyl-2-nitrophenyl, 4-methyl-3-trifluoromethylphenyl, 3-methylthiophenyl, 2-nitrophenyl, 3-nitrophenyl, 4-nitrophenyl, 2,4,6-tribromo-3-methylphenyl, pentafluorophenyl, 3-(tert-butyl)phenyl, 2,4,6-trichlorophenyl, 2,4,6-trifluorophenyl, 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 3,4,5-trimethoxyphenyl, and 3-vinylphenyl.

The term "arylalkyl" as used herein, means an aryl group, as defined herein, appended to the parent molecular moiety through an alkyl group, as defined herein. Representative examples of arylalkyl include, but are not limited to, phenylmethyl, 2-phenylethyl, 3-phenylpropyl, and 3-(2-methylphenyl)propyl.

The term "arylsulfonyl" as used herein, means an aryl group, as defined herein, appended to the parent molecular moiety through a sulfonyl group, as defined herein. Representative examples of arylsulfonyl include, but are not limited to, phenylsulfonyl, 2-methylphenylsulfonyl, 2-nitrophenylsulfonyl, and 3-nitrophenylsulfonyl.

The term "arylalkylsulfonyl" as used herein, means an arylalkyl group, as defined herein, appended to the parent molecular moiety through a sulfonyl group, as defined herein. Representative examples of arylalkylsulfonyl include, but are not limited to, (phenylmethyl)sulfonyl, (2-phenylethyl)sulfonyl, and (3-phenylpropyl)sulfonyl.

The term "carbonyl" as used herein, means a $-C(O)-$ group.

The term "carboxy" as used herein, means a $-CO_2H$ group.

The term "cyano" as used herein, means a $-CN$ group.

The term "cycloalkyl" as used herein, means a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms ($-CH_2-$, $-CH_2CH_2-$, and $-CH_2CH_2CH_2-$). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic ring systems are exemplified by a bicyclic ring system in which two non-adjacent carbon atoms of the bicyclic ring are linked by a bond or an alkylene bridge of between one and three carbon atoms ($-CH_2-$, $-CH_2CH_2-$, and $-CH_2CH_2CH_2-$). Representative examples of tricyclic-ring systems include, but are not limited to, tricyclo[3.3.1.0$^{3,7}$]nonane and tricyclo[3.3.1.1$^{3,7}$]decane (adamantyl).

The cycloalkyl groups of the present invention are substituted with 0, 1, 2, 3, or 4 substituents independently selected from alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, $-NZ_1Z_2$, $(NZ_3Z_4)$carbonyl or $(NZ_3Z_4)$sulfonyl. Representative examples of cycloalkyl substituted with 0, 1, 2, 3, or 4 substituents include, but are not limited to, 2-methylcyclohexyl, 2-cyanocyclohexyl, and 2-methoxycyclohexyl.

The term "fluoroalkylene" as used herein, means at least one fluoride atom ($-F$) is appended to the parent molecular moiety through an alkylene group, as defined herein. Representative examples of fluoroalkylene are $-CH(F)-$, $-CH(F)CH_2-$, $-C(F)_2CH_2-$, $-CH(F)CH(F)-$, $-CH(CF_3)-$, $-CH(CH_2CF_3)-$, and $-CH_2CH_2CH_2CH(F)-$.

The term "formyl" as used herein, means a $-C(O)H$ group.

The term "halo" or "halogen" as used herein, refers to $-Cl$, $-Br$, $-I$ or $-F$.

The term "haloalkoxy" as used herein, means at least one halogen, as defined herein, appended to the parent molecular moiety through an alkoxy group, as defined herein. Representative examples of haloalkoxy include, but are not limited to, 2-fluoro-1-chloroethoxy, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocycle" or "heterocyclic" as used herein, means a monocyclic, bicyclic, or tricyclic ring system. Monocyclic ring systems are exemplified by any 3- or 4-membered ring containing a heteroatom independently selected from oxygen, nitrogen and sulfur; or a 5-, 6- or 7-membered ring containing one, two or three heteroatoms wherein the heteroatoms are independently selected from nitrogen, oxygen and sulfur. The 5-membered ring has from 0-2 double bonds and the 6- and 7-membered ring have from 0-3 double bonds. Representative examples of monocyclic ring systems include, but are not limited to, azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1, 1-dioxidothiomorpholinyl (thiomorpholine sulfone), thiopyranyl, triazinyl, triazolyl, and trithianyl. Bicyclic ring systems are exemplified by any of the above monocyclic ring systems fused to a phenyl group, a cyclohexyl group, a cyclopentyl group, or another monocyclic heterocycle. Representative examples of bicyclic ring systems include but are not limited to, for example, benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, naphthyridinyl, isobenzofuranyl, isobenzothienyl, isoindolyl, isoquinolinyl, phthalazinyl, pyranopyridinyl, quinolinyl, quinolizinyl, quinoxalinyl, quinazolinyl, tetrahydroisoquinolinyl, tetrahydroquinolinyl, and thiopyranopyridinyl. Tricyclic rings systems are exemplified by any of the above bicyclic ring systems fused to a phenyl group, a cyclohexyl group, a cyclopentyl group, or another monocyclic heterocycle. Representative examples of tricyclic ring systems include, but are not limited to, acridinyl, carbazolyl, carbolinyl, dibenzo[b,d]furanyl, dibenzo[b,d]thienyl, naphtho[2,3-b]furan, naphtho[2,3-b]thienyl, phenazinyl, phenothiazinyl, phenoxazinyl, thianthrenyl, thioxanthenyl and xanthenyl.

The heterocycles of this invention are substituted with 0, 1, 2,or 3 substituents independently selected from alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, —$NZ_1Z_2$, ($NZ_3Z_4$)carbonyl, and ($NZ_3Z_4$)sulfonyl. The heterocycle groups of this invention can be further substituted with an additional heterocycle group, as defined herein, wherein the additional heterocycle group is substituted with 0, 1, 2, or 3 substituents independently selected from alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, —$NZ_1Z_2$, ($NZ_3Z_4$)carbonyl, and ($NZ_3Z_4$)sulfonyl. Representative examples include, but are not limited to, 1,3-dimethyl-1H-pyrazol-5-yl, 5-fluoro-1,3-benzothiazol-2-yl, 1-methyl-1H-benzimidazol-2-yl, 6-chloropyridin-2-yl, and 4-pyridin-2-ylpiperazin-1-yl.

The term "heterocyclealkyl" as used herein, means a heterocycle, as defined herein, appended to the parent molecular moiety through an alkyl group, as defined herein. Representative examples of heterocyclealkyl include, but are not limited to, pyridin-3-ylmethyl, 2-pyrimidin-2-ylpropyl, and 4-pyridin-2-ylpiperazin-1-ylmethyl.

The term "heterocyclecarbonyl" as used herein, means a heterocycle, as defined herein, appended to the parent molecular moiety through a carbonyl group, as defined herein. Representative examples of heterocyclecarbonyl include, but are not limited to, pyridin-3-ylcarbonyl, quinolin-3-ylcarbonyl, and 4-pyridin-2-ylpiperazin-1-ylmethylcarbonyl.

The term "hydroxy" as used herein, means an —OH group.

The term "hydroxyalkyl" as used herein, means at least one hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl 2-ethyl-4-hydroxyheptyl and 2,4-dihydroxybutyl.

The term "hydroxyalkylene" as used herein, means at least one hydroxy group, as defined herein, is appended to the parent molecular moiety through an alkylene group, as defined herein. Representative examples of hydroxyalkylene are —$CH_2CH(OH)CH_2$—, —$CH(CH_2OH)$—, —$CH(CH_2CH_2OH)$—, and —$CH_2CH_2CH(OH)CH_2$—.

The term "mercapto" as used herein, means a —SH group.

The term "methylenedioxy" as used herein, means a —$OCH_2$— group wherein the oxygen atoms of the methylenedioxy are attached to the parent molecular moiety through two adjacent carbon atoms. A representative example includes, but is not limited to, 1,3-benzodioxol-5-yl.

The term "nitro" as used herein, means a —$NO_2$ group.

The term "nitrogen protecting group" as used herein, means those groups intended to protect an amino group against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl).

The term "—$NZ_1Z_2$" as used herein, means two groups, $Z_1$ and $Z_2$, which are appended to the parent molecular moiety through a nitrogen atom. $Z_1$ and $Z_2$ are each independently selected from hydrogen, alkyl, alkylcarbonyl, alkylsulfonyl, aryl, arylalkyl, arylalkylsulfonyl, arylsulfonyl, formyl, heterocycle, heterocyclealkyl, and heterocyclealkylcarbonyl. Representative examples of —$NZ_1Z_2$ include, but are not limited to, amino, methylamino, dimethylamino, acetylamino, (acetyl)(methyl)amino, and (methylsulfonyl)amino.

The term "—$NZ_3Z_4$" as used herein, means two groups, $Z_3$ and $Z_4$, which are appended to the parent molecular moiety through a nitrogen atom. $Z_3$ and $Z_4$ are each independently selected from hydrogen, alkyl, aryl, or arylalkyl. Representative examples of —$NZ_3Z_4$ include, but are not limited to, amino, methylamino, dimethylamino, ethylmethylamino, phenylamino, (phenylmethyl)amino, (2-phenylethyl)amino, (phenyl)(methyl)amino, and diethylamino.

The term "($NZ_3Z_4$)alkyl" as used herein, means a —$NZ_3Z_4$ group, as defined herein, appended to the parent molecular moiety through an alkyl group, as defined herein. Representative examples of (NZ$_3$Z$_4$)alkyl include, but are not limited to, aminomethyl, (dimethylamino)methyl, and (methylamino)methyl.

The term "(NZ$_3$Z$_4$)carbonyl" as used herein, means a —NZ$_3$Z$_4$ group, as defined herein, appended to the parent molecular moiety through a carbonyl group, as defined herein. Representative examples of (NZ$_3$Z$_4$)carbonyl include, but are not limited to, aminocarbonyl, (methylamino)carbonyl, (dimethylamino)carbonyl, (phenylmethylamino)carbonyl, ((phenyl)(methyl)amino)carbonyl, (phenylamino)carbonyl, (ethylmethylamino)carbonyl, and (diethylamino)carbonyl.

The term "(NZ$_3$Z$_4$)sulfonyl" as used herein, means a —NZ$_3$Z$_4$ group, as defined herein, appended to the parent molecular moiety through a sulfonyl group, as defined herein. Representative examples of (NZ$_3$Z$_4$)sulfonyl include, but are not limited to, aminosulfonyl, (methylamino)sulfonyl, (dimethylamino)sulfonyl, (phenylmethylamino)sulfonyl, ((phenylmethyl)(methyl)amino)sulfonyl, (phenylmethylamino) sulfonyl, (phenylamino)sulfonyl, and (ethylmethylamino) sulfonyl.

The term "sulfinyl" as used herein, means a —S(O)— group.

The term "sulfonyl" as used herein, means a —S(O)$_2$— group.

The term "sexual dysfunction" as used herein, means sexual dysfunction in mammals including human male and human female sexual dysfunction.

The term "male sexual dysfunction" as used herein includes, but is not limited to, male erectile dysfunction or premature ejacualtion.

The term "female sexual dysfunction" as used herein includes, but is not limited to, female anorgasmia, clitoral erectile insufficiency, vaginal engorgement, dyspareunia, or vaginismus.

Compounds of the present invention may exist as stereoisomers wherein, asymmetric or chiral centers are present. These stercoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The present invention contemplates various stereoisomers and mixtures thereof and are specifically included within the scope of this invention. Stercoisomers include enantiomers and diastereomers, and mixtures of enantiomers or diastereomers. In particular, the stereochemistry at the point of attachment of -L$_2$-B of compounds of formula (III) or formula (IV) wherein X$_1$ is a bond and X$_2$ is CR$_D$R$_E$ may independently be either (R) or (S). The stereochemistry at the point of attachment of -L$_2$-B of compounds of formula (III) or formula (IV) wherein X$_1$ is CR$_B$R$_C$ and X$_2$ is a bond may independently be either (R) or (S). The stereochemistry at the point of attachment of -L$_2$-B of compounds of formula (III) or formula (IV) wherein X$_1$ is CR$_B$R$_C$ and X$_2$ is CR$_D$R$_E$ may independently be either (R) or (S). Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) direct separation of the mixture of optical enantiomers on chiral chromatographic columns, or (3) formation of a diastereomeric salt followed by selective recrystallization of one of the diastereomeric salts.

Compounds of the present invention were named by ACD/ChemSketch version 5.0 (developed by Advanced Chemistry Development, Inc., Toronto, ON, Canada) or were given names which appeared to be consistent with ACD nomenclature.

Preferred compounds of the present invention include:

2-[4-(2-methoxyphenyl)-1-piperazinyl]-N-(3-methylphenyl)acetamide;

2-[4-(2-cyanophenyl)-1-piperazinyl]-N-(3-methylphenyl) acetamide;

N-(3-methylphenyl)-2-[4-(2-pyrimidinyl)-1-piperazinyl]acetamide;

N-(3-methylphenyl)-2-[4-(2-pyridinyl)-1-piperazinyl]acetamide;

2-[4-(3-cyano-2-pyridinyl)-1-piperazinyl]-N-(3-methylphenyl)acetamide;

N-(3-methylphenyl)-2-[4-(2-methylphenyl)-1-piperazinyl] acetamide;

N-(3-methylphenyl)-2-[4-(2-nitrophenyl)-1-piperazinyl]acetamide;

2-[4-(3-cyano-2-pyridinyl)-1-piperazinyl]-N-(3-nitrophenyl)acetamide;

2-[4-(3-cyano-2-pyridinyl)-1-piperazinyl]-N-[3-(trifluoromethyl)phenyl]acetamide;

N-(3-methylphenyl)-2-(4-phenyl-1-piperazinyl)acetamide;

N-(3-cyanophenyl)-2-[4-(3-cyano-2-pyridinyl)-1-piperazinyl]acetamide;

N-(4-bromo-3-methylphenyl)-2-[4-(2-cyanophenyl)-1-piperazinyl]acetamide;

2-[4-(2-cyanophenyl)-1-piperazinyl]-N-phenylacetamide;

2-[4-(3-cyano-2-pyridinyl)-1-piperazinyl]-N-phenylacetamide;

2-[4-(3-cyano-2-pyridinyl)-1-piperazinyl]-N-(4-fluorophenyl)acetamide;

2-[4-(3-cyano-2-pyridinyl)-1-piperazinyl]-N-(3,5-dimethylphenyl)acetamide;

2-[4-(3-cyano-2-pyridinyl)-1-piperazinyl]-N-(2,3-dimethylphenyl)acetamide;

2-[4-(3-cyano-2-pyridinyl)-1-piperazinyl]-N-(2-methylphenyl)acetamide;

2-[4-(3-cyano-2-pyridinyl)-1-piperazinyl]-N-(2,5-dimethylphenyl)acetamide;

N-(3-chlorophenyl)-2-[4-(3-cyano-2-pyridinyl)-1-piperazinyl]acetamide;

N-(3-chloro-4-fluorophenyl)-2-[4-(3-cyano-2-pyridinyl)-1-piperazinyl]acetamide;

2-[4-(3-cyano-2-pyridinyl)-1-piperazinyl]-N-(3,4,5-trimethoxyphenyl)acetamide;

2-[4-(3-cyano-2-pyridinyl)-1-piperazinyl]-N-[4-fluoro-3-(trifluoromethyl)phenyl]acetamide;

2-[4-(3-cyano-2-pyridinyl)-1-piperazinyl]-N-[3-fluoro-5-(trifluoromethyl)phenyl]acetamide;

2-[4-(3-cyano-2-pyridinyl)-1-piperazinyl]-N-[2-fluoro-5-(trifluoromethyl)phenyl]acetamide;

2-[4-(3-cyano-2-pyridinyl)-1-piperazinyl]-N-[2-fluoro-3-(trifluoromethyl)phenyl]acetamide;

2-[4-(3-cyano-2-pyridinyl)-1-piperazinyl]-N-(4-fluoro-3-methylphenyl)acetamide;

2-[4-(3-cyano-2-pyridinyl)-1-piperazinyl]-N-(2-fluorophenyl)acetamide;

2-[4-(3-cyano-2-pyridinyl)-1-piperazinyl]-N-(2-methoxyphenyl)acetamide;

2-[4-(3-cyano-2-pyridinyl)-1-piperazinyl]-N-(2-nitrophenyl)acetamide;

2-[4-(3-cyano-2-pyridinyl)-1-piperazinyl]-N-[2-(trifluoromethyl)phenyl]acetamide;
N-phenyl-2-[4-(2-pyridinyl)-1-piperazinyl]acetamide;
N-(3-methylphenyl)-2-[4-(1,3-thiazol-2-yl)-1-piperazinyl]acetamide;
2-[4-(3-cyano-2-pyridinyl)-1-piperazinyl]-N-(4-methylphenyl)acetamide;
2-[4-(2-methoxyphenyl)-1-piperidinyl]-N-(3-methylphenyl)acetamide;
2-[4-(2-fluorophenyl)-1-piperidinyl]-N-(3-methylphenyl)acetamide;
N-(3-methylphenyl)-2-[4-(2-methylphenyl)-1-piperidinyl]acetamide;
2-[4-(3-fluorophenyl)-1-piperidinyl]-N-(3-methylphenyl)acetamide;
N-(3-methylphenyl)-2-[4-(6-oxo-1 (6H)-pyridazinyl)-1-piperidinyl]acetamide;
N-(2,6-dimethylphenyl)-2-[4-(2-thienyl)-1-piperidinyl]acetamide;
N-(2,5-dimethylphenyl)-2-[4-(2-thienyl)-1-piperidinyl]acetamide;
N-(2-methylphenyl)-2-[4-(2-thienyl)-1-piperidinyl]acetamide;
N-(3-chloro-4-fluorophenyl)-2-[4-(2-thienyl)-1-piperidinyl]acetamide;
N-(4-bromophenyl)-2-[4-(2-pyridinyl)-1-piperidinyl]acetamide;
N-(2,6-dimethylphenyl)-2-[4-(2-pyridinyl)-1-piperidinyl]acetamide;
N-(2-nitrophenyl)-2-[4-(2-pyridinyl)-1-piperidinyl]acetamide;
N-(3-nitrophenyl)-2-[4-(2-pyridinyl)-1-piperidinyl]acetamide;
N-(2,4-difluorophenyl)-2-[4-(2-pyridinyl)-1-piperidinyl]acetamide;
N-(2,5-dimethylphenyl)-2-[4-(2-pyridinyl)-1-piperidinyl]acetamide;
N-(2-methylphenyl)-2-[4-(2-pyridinyl)-1-piperidinyl]acetamide;
N-(4-methylphenyl)-2-[4-(2-pyridinyl)-1-piperidinyl]acetamide;
2-[4-(2-pyridinyl)-1-piperidinyl]-N-[3-(trifluoromethyl)phenyl]acetamide;
ethyl 4-({[4-(2-pyridinyl)-1-piperidinyl]acetyl}amino)benzoate;
N-(3-chloro-4-methylphenyl)-2-[4-(2-pyridinyl)-1-piperidinyl]acetamide;
N-(2-cyanophenyl)-2-[4-(2-pyridinyl)-1-piperidinyl]acetamide;
N-(3-chlorophenyl)-2-[4-(2-pyridinyl)-1-piperidinyl]acetamide;
2-[4-(3-cyano-2-pyridinyl)-1-piperidinyl]-N-(3-methylphenyl)acetamide;
N-(3-methylphenyl)-2-(4-phenyl-3,6-dihydro-1 (2H)-pyridinyl)acetamide;
2-(3',6'-dihydro-2,4'-bipyridin-1'(2'H)-yl)-N-(3-methylphenyl)acetamide;
2-(3',6'-dihydro-2,4'-bipyridin-1'(2'H)-yl)-N-(2,6-dimethylphenyl)acetamide;
2-(3',6'-dihydro-2,4'-bipyridin-1'(2'H)-yl)-N-(2-nitrophenyl)acetamide;
2-(3',6'-dihydro-2,4'-bipyridin-1'(2'H)-yl)-N-(3-nitrophenyl)acetamide;
2-(3',6'-dihydro-2,4'-bipyridin-1'(2'H)-yl)-N-(4-fluorophenyl)acetamide;
N-(2,4-difluorophenyl)-2-(3',6'-dihydro-2,4'-bipyridin-1'(2'H)-yl)acetamide;
2-(3',6'-dihydro-2,4'-bipyridin-1'(2'H)-yl)-N-(2,5-dimethylphenyl)acetamide;
2-(3',6'-dihydro-2,4'-bipyridin-1'(2'H)-yl)-N-(2-methylphenyl)acetamide;
N-cyclohexyl-2-(3',6'-dihydro-2,4'-bipyridin-1'(2'H)-yl)acetamide;
2-(3',6'-dihydro-2,4'-bipyridin-1'(2'H)-yl)-N-(4-methylphenyl)acetamide;
2-(3',6'-dihydro-2,4'-bipyridin-1'(2'H)-yl)-N-[3-(trifluoromethyl)phenyl]acetamide;
ethyl 4-[(3',6'-dihydro-2,4'-bipyridin-1'(2'H)-ylacetyl)amino]benzoate;
N-[2-chloro-5-(trifluoromethyl)phenyl]-2-(3',6'-dihydro-2,4'-bipyridin-1'(2'H)-yl)acetamide;
N-(3-chloro-4-methylphenyl)-2-(3',6'-dihydro-2,4'-bipyridin-1'(2'H)-yl)acetamide;
N-(2-cyanophenyl)-2-(3',6'-dihydro-2,4'-bipyridin-1'(2'H)-yl)acetamide;
N-(3-chlorophenyl)-2-(3',6'-dihydro-2,4'-bipyridin-1'(2'H)-yl)acetamide;
N-(3-chloro-4-fluorophenyl)-2-(3',6'-dihydro-2,4'-bipyridin-1'(2'H)-yl)acetamide;
2-(3',6'-dihydro-2,4'-bipyridin-1'(2'H)-yl)-N-[4-(trifluoromethoxy)phenyl]acetamide;
2-(3',6'-dihydro-2,4'-bipyridin-1'(2'H)-yl)-N-[2-(trifluoromethyl)phenyl]acetamide;
N-(4-chlorophenyl)-2-(3',6'-dihydro-2,4'-bipyridin-1'(2'H)-yl)acetamide;
N-(2,3-dichlorophenyl)-2-(3',6'-dihydro-2,4'-bipyridin-1'(2'H)-yl)acetamide;
N-(3,5-dichlorophenyl)-2-(3',6'-dihydro-2,4'-bipyridin-1'(2'H)-yl)acetamide;
2-(3',6'-dihydro-2,4'-bipyridin-1'(2'H)-yl)-N-(4-fluoro-2-methylphenyl)acetamide;
N-(4-fluorophenyl)-2-[4-(2-pyridinyl)-1-piperidinyl]acetamide;
N-(3,5-dichlorophenyl)-2-[4-(2-pyridinyl)-1-piperidinyl]acetamide;
N-(2,3-dichlorophenyl)-2-[4-(2-pyridinyl)-1-piperidinyl]acetamide;
2-[4-(2-pyridinyl)-1-piperidinyl]-N-[2-(trifluoromethyl)phenyl]acetamide;
N-(3-chloro-4-fluorophenyl)-2-[4-(2-pyridinyl)-1-piperidinyl]acetamide;
2-[4-(2-pyridinyl)-1-piperidinyl]-N-[4-(trifluoromethoxy)phenyl]acetamide;
N-Cyclohexyl-2-(3',4',5',6'-tetrahydro-2'H-[2,4']bipyridinyl-1'-yl) acetamide;
N-{[4-(2-cyanophenyl)-1-piperazinyl]methyl}-3-methylbenzamide;
3-methyl-N-{[4-(2-pyrimidinyl)-1-piperazinyl]methyl}benzamide;
3-methyl-N-{[4-(2-pyridinyl)-1-piperazinyl]methyl}benzamide;
3-methyl-N-[(4-phenyl-1-piperazinyl)methyl]benzamide;
N-{[4-(2-methoxyphenyl)-1-piperazinyl]methyl}-3-methylbenzamide;
N-{[4-(2-cyanophenyl)-1-piperazinyl]methyl}-2-methylbenzamide;
N-{[4-(2-cyanophenyl)-1-piperazinyl]methyl}-4-methylbenzamide;
N-{[4-(3-cyano-2-pyridinyl)-1-piperazinyl]methyl}-3-methylbenzamide;
N-{[4-(3-cyanophenyl)-1-piperazinyl]methyl}-3-methylbenzamide;
N-{[4-(3-cyanophenyl)-1-piperazinyl]methyl}-2-methylbenzamide;

N-{[4-(3-cyano-2-pyridinyl)-1-piperazinyl]methyl}benzamide;
N-{[4-(3-cyano-2-pyridinyl)-1-piperazinyl]methyl}-4-methylbenzamide;
N-{[4-(3-cyano-2-pyridinyl)-1-piperazinyl]methyl}-2-methylbenzamide;
N-{[4-(2-pyridinyl)-1-piperazinyl]methyl}benzamide;
N-{[4-(2-chlorophenyl)-1-piperazinyl]methyl}benzamide;
3-chloro-N-{[4-(2-cyanophenyl)-1-piperazinyl]methyl}benzamide;
4-chloro-N-{[4-(2-methoxyphenyl)-1-piperazinyl]methyl}benzamide;
2-chloro-N-{[4-(3-cyano-2-pyridinyl)-1-piperazinyl]methyl}benzamide;
N-{[4-(3-cyano-2-pyridinyl)-1-piperazinyl]methyl}-2-(trifluoromethyl)benzamide;
N-{[4-(2-cyanophenyl)-1-piperazinyl]methyl}benzamide;
N-{[4-(2-methoxyphenyl)-1-piperidinyl]methyl}-3-methylbenzamide;
3-methyl-N-{[4-(2-pyridinyl)-1-piperidinyl]methyl}benzamide;
3-methyl-N-[(4-phenyl-3,6-dihydro-1(2H)-pyridinyl)methyl]benzamide;
N-(3',6'-dihydro-2,4'-bipyridin-1'(2'H)-ylmethyl)-3-methylbenzamide;
N-(3',6'-dihydro-2,4'-bipyridin-1'(2'H)-ylmethyl)-3-methoxybenzamide;
N-(3',6'-dihydro-2,4'-bipyridin-1'(2'H)-ylmethyl)-3-fluorobenzamide;
N-(3',6'-dihydro-2,4'-bipyridin-1'(2'H)-ylmethyl)-3,5-difluorobenzamide;
2-[4-(3-cyano-2-pyridinyl)-1-piperazinyl]-N-3-pyridinylacetamide;
2-(1-{2-[(3-methylphenyl)amino]-2-oxoethyl}piperidin-4-yl)pyridiniumn N-oxide;
N-(3-methylphenyl)-2-[4-(2-pyridinyl)-1-piperidinyl]acetamide;
N-2-adamantyl-2-[4-(3-cyano-2-pyridinyl)-1-piperazinyl]acetamide;
2-[4-(3-cyano-2-pyridinyl)-1-piperazinyl]-N-cyclohexylacetamide;
2-[4-(3-cyano-2-pyridinyl)-1-piperazinyl]-N-5,6,7,8-tetrahydro-1-naphthalenylacetamide;
2-(3',6'-dihydro-2,4'-bipyridin-1'(2'H)-yl)-N-(4-fluoro-2-methylphenyl)acetamide;
N-{[4-(2-pyridinyl)-1-piperidinyl]methyl}-3-(trifluoromethyl)benzamide;
3,5-dimethoxy-N-{[4-(2-pyridinyl)-1-piperidinyl]methyl}benzamide;
N-{[4-(2-pyridinyl)-1-piperidinyl]methyl}cyclohexanecarboxamide;
3,4-difluoro-N-{[4-(2-pyridinyl)-1-piperidinyl]methyl}benzamide;
3-chloro-N-{[4-(2-pyridinyl)-1-piperidinyl]methyl}benzamide;
2,3-dimethyl-N-{[4-(2-pyridinyl)-1-piperazinyl]methyl}benzamide;
N-(3',6'-dihydro-2,4'-bipyridin-1'(2'H)-ylmethyl)-3-(trifluoromethyl)benzamide;
3-chloro-N-(3',6'-dihydro-2,4'-bipyridin-1'(2'H)-ylmethyl)benzamide;
N-(3',6'-dihydro-2,4'-bipyridin-1'(2'H)-ylmethyl)cyclohexanecarboxamide;
N-(3',6'-dihydro-2,4'-bipyridin-1'(2'H)-ylmethyl)-3,4-difluorobenzamide;
N-(3',6'-dihydro-2,4'-bipyridin-1'(2'H)-ylmethyl)-3,5-dimethoxybenzamide;
N-(3-methylphenyl)-2-(4-phenyl-1-piperidinyl)acetamide;
2-(3',6'-dihydro-2,4'-bipyridin-1'(2'H)-yl)-N-(3-nitrophenyl)acetamide;
N-1-adamantyl-2-[4-(3-cyano-2-pyridinyl)-1-piperazinyl]acetamide;
3-methyl-N-{[2-methyl-4-(2-pyridinyl)-1-piperazinyl]methyl}benzamide;
N-(3-methylphenyl)-2-[2-methyl-4-(2-pyridinyl)-1-piperazinyl]acetamide;
3,5-dimethyl-N-{[4-(2-pyridinyl)-1-piperidinyl]methyl}benzamide;
N-(3',6'-dihydro-2,4'-bipyridin-1'(2'H)-ylmethyl)-3,5-dimethylbenzamide;
3-methyl-N-[(3-methyl-3',6'-dihydro-2,4'-bipyridin-1'(2'H)-yl)methyl]benzamide;
N-[(3-cyano-3',6'-dihydro-2,4'-bipyridin-1'(2'H)-yl)methyl]-3-methylbenzamide;
N-(2,6-dimethylphenyl)-2-(3-methyl-3',6'-dihydro-2,4'-bipyridin-1'(2'H)-yl)acetamide;
N-(4-fluorophenyl)-2-(3-methyl-3',6'-dihydro-2,4'-bipyridin-1'(2'H)-yl)acetamide;
N-(2,4-difluorophenyl)-2-(3-methyl-3',6'-dihydro-2,4'-bipyridin-1'(2'H)-yl)acetamide;
2-(3-methyl-3',6'-dihydro-2,4'-bipyridin-1'(2'H)-yl)-N-(2-methylphenyl)acetamide;
2-(3-methyl-3',6'-dihydro-2,4'-bipyridin-1'(2'H)-yl)-N-[3-(trifluoromethyl)phenyl]acetamide;
N-(3-chloro-4-fluorophenyl)-2-(3-methyl-3',6'-dihydro-2,4'-bipyridin-1'(2'H)-yl)acetamide;
2-(3-methyl-3',6'-dihydro-2,4'-bipyridin-1'(2'H)-yl)-N-[4-(trifluoromethoxy)phenyl]acetamide;
2-(3-methyl-3',6'-dihydro-2,4'-bipyridin-1'(2'H)-yl)-N-[2-(trifluoromethyl)phenyl]acetamide;
N-(2,3-dichlorophenyl)-2-(3-methyl-3',6'-dihydro-2,4'-bipyridin-1'(2'H)-yl)acetamide;
2-(3-methyl-3',6'-dihydro-2,4'-bipyridin-1'(2'H)-yl)-N-[4-(trifluoromethyl)phenyl]acetamide;
2-[4-(3-cyano-2-thienyl)-3,6-dihydro-1(2H)-pyridinyl]-N-(3-methylphenyl)acetamide;
2-(3-cyano-3',6'-dihydro-2,4'-bipyridin-1'(2'H)-yl)-N-(2,6-dimethylphenyl)acetamide;
2-(3-cyano-3',6'-dihydro-2,4'-bipyridin-1'(2'H)-yl)-N-(4-fluorophenyl)acetamide;
2-(3-cyano-3',6'-dihydro-2,4'-bipyridin-1'(2'H)-yl)-N-(2,4-difluorophenyl)acetamide;
2-(3-cyano-3',6'-dihydro-2,4'-bipyridin-1'(2'H)-yl)-N-(2-methylphenyl)acetamide;
2-(3-cyano-3',6'-dihydro-2,4'-bipyridin-1'(2'H)-yl)-N-[3-(trifluoromethyl)phenyl]acetamide;
2-(3-cyano-3',6'-dihydro-2,4'-bipyridin-1'(2'H)-yl)-N-[4-(trifluoromethoxy)phenyl]acetamide;
2-(3-cyano-3',6'-dihydro-2,4'-bipyridin-1'(2'H)-y)-N-[2-(trifluoromethyl)phenyl]acetamide;
2-(3-cyano-3',6'-dihydro-2,4'-bipyridin-1'(2'H)-yl)-N-(2,3-dichlorophenyl)acetamide;
3-methyl-N-{[4-(6-oxo-1(6H)-pyridazinyl)-1-piperidinyl]methyl}benzamide;
N-(3',6'-dihydro-2,4'-bipyridin-1'(2'H)-ylmethyl)-1-adamantanecarboxamide;
3-methyl-N-{[4-(1,3-thiazol-2-yl)-3,6-dihydro-1(2H)-pyridinyl]methyl}benzamide;
2-[4-(3-cyano-2-pyridinyl)-1-piperazinyl]-N-1,2,3,4-tetrahydro-1-naphthalenylacetamide;
2-[4-(3-cyano-2-pyridinyl)-1-piperazinyl]-N-[(1 S)-1,2,3,4-tetrahydro-1-naphthalenyl]acetamide;
2-[4-(3-cyano-2-pyridinyl)-1-piperazinyl]-N-[(1R)-1,2,3,4-tetrahydro-1-naphthalenyl]acetamide;

N-(2,6-diethylphenyl)-2-[4-(2-pyridinyl)-1-piperidinyl]acetamide;
2-[4-(2-pyridinyl)-1-piperidinyl]-N-(2,4,6-trifluorophenyl)acetamide;
N-(4-chloro-2,6-dimethylphenyl)-2-[4-(2-pyridinyl)-1-piperidinyl]acetamide;
2-[4-(2-pyridinyl)-1-piperidinyl]-N-(2,4,6-trichlorophenyl)acetamide;
N-(2,6-diethylphenyl)-2-(3',6'-dihydro-2,4'-bipyridin-1'(2'H)-yl)acetamide;
2-(3',6'-dihydro-2,4'-bipyridin-1'(2'H)-yl)-N-(2,4,6-trifluorophenyl)acetamide;
N-(4-chloro-2,6-dimethylphenyl)-2-(3',6'-dihydro-2,4'-bipyridin-1'(2'H)-yl)acetamide;
2-(3',6'-dihydro-2,4'-bipyridin-1'(2'H)-yl)-N-(2,4,6-trichlorophenyl)acetamide;
N-{[4-(2-pyridinyl)-1-piperazinyl]methyl}-3-(trifluoromethyl)benzamide;
3,5-dimethoxy-N-{[4-(2-pyridinyl)-1-piperazinyl]methyl}benzamide;
N-{[4-(2-pyridinyl)-1-piperazinyl]methyl}cyclohexanecarboxamide;
N-(2,6-dimethylphenyl)-2-[4-(2-pyridinyl)-1-piperazinyl]acetamide;
N-(4-fluorophenyl)-2-[4-(2-pyridinyl)-1-piperazinyl]acetamide;
N-(2,4-difluorophenyl)-2-[4-(2-pyridinyl)-1-piperazinyl]acetamide;
N-(2-methylphenyl)-2-[4-(2-pyridinyl)-1-piperazinyl]acetamide;
2-[4-(2-pyridinyl)-1-piperazinyl]-N-[3-(trifluoromethyl)phenyl]acetamide;
N-(3-chlorophenyl)-2-[4-(2-pyridinyl)-1-piperazinyl]acetamide;
N-benzyl-2-[4-(2-pyridinyl)-1-piperazinyl]acetamide;
2-[4-(2-pyridinyl)-1-piperazinyl]-N-[4-(trifluoromethoxy)phenyl]acetamide;
2-[4-(2-pyridinyl)-1-piperazinyl]-N-[2-(trifluoromethyl)phenyl]acetamide;
N-(4-chlorophenyl)-2-[4-(2-pyridinyl)-1-piperazinyl]acetamide;
N-(2,3-dichlorophenyl)-2-[4-(2-pyridinyl)-1-piperazinyl]acetamide;
N-(3,4-dichlorophenyl)-2-[4-(2-pyridinyl)-1-piperazinyl]acetamide;
2-[4-(2-pyridinyl)-1-piperazinyl]-N-[4-(trifluoromethyl)phenyl]acetamide;
3-chloro-N-{[4-(2-pyridinyl)-1-piperazinyl]methyl}benzamide;
4-fluoro-3-methyl-N-{[4-(2-pyridinyl)-1-piperazinyl]methyl}benzamide;
N-(3',6'-dihydro-2,4'-bipyridin-1'(2'H)-ylmethyl)-4-fluoro-3-methylbenzamide;
3-methyl-N-{[4-(1,3-oxazol-2-yl)-3',6'-dihydro-1(2H)-pyridinyl]methyl}benzamide;
2-methyl-N-[(3-methyl-3',6'-dihydro-2,4'-bipyridin-1'(2'H)-yl)methyl]benzamide;
2-[4-(3-cyano-2-pyridinyl)-1-piperidinyl]-N-(2,6-dimethylphenyl)acetamide;
N-(3-methylphenyl)-2-[4-(3-methyl-2-pyridinyl)-1-piperazinyl]acetamide;
2-[4-(3-cyano-2-pyridinyl)-1-piperazinyl]-N-[4-(trifluoromethyl)phenyl]acetamide;
N-(2-ethyl-6-methylphenyl)-2-[4-(2-pyridinyl)-1-piperidinyl]acetamide;
N-(2-isopropyl-6-methylphenyl)-2-[4-(2-pyridinyl)-1-piperidinyl]acetamide;
N-(2-chloro-6-methylphenyl)-2-[4-(2-pyridinyl)-1-piperidinyl]acetamide;
N-(2-methoxy-6-methylphenyl)-2-[4-(2-pyridinyl)-1-piperidinyl]acetamide;
2-(3',6'-dihydro-2,4'-bipyridin-1'(2'H)-yl)-N-(2-ethyl-6-methylphenyl)acetamide;
2-(3',6'-dihydro-2,4'-bipyridin-1'(2'H)-yl)-N-(2-isopropyl-6-methylphenyl)acetamide;
N-(2-chloro-6-methylphenyl)-2-(3',6'-dihydro-2,4'-bipyridin-1'(2'H)-yl)acetamide;
2-(3',6'-dihydro-2,4'-bipyridin-1'(2'H)-yl)-N-(2-methoxy-6-methylphenyl)acetamide;
3-chloro-N-[(3-methyl-3',6'-dihydro-2,4'-bipyridin-1'(2'H)-yl)methyl]benzamide;
3-fluoro-N-[(3-methyl-3',6'-dihydro-2,4'-bipyridin-1'(2'H)-yl)methyl]benzamide;
3-methyl-N-{[(2S)-2-methyl-4-(2-pyridinyl)-1-piperazinyl]methyl}benzamide;
N-(3-methylphenyl)-2-[(2S)-2-methyl-4-(2-pyridinyl)-1-piperazinyl]acetamide;
3-methyl-N-{[(2R)-2-methyl-4-(2-pyridinyl)-1-piperazinyl]methyl}benzamide;
N-(3-methylphenyl)-2-[(2R)-2-methyl-4-(2-pyridinyl)-1-piperazinyl]acetamide;
3-methoxy-N-[(3-methyl-3',6'-dihydro-2,4'-bipyridin-1'(2'H)-yl)methyl]benzamide;
4-fluoro-N-[(3-methyl-3',6'-dihydro-2,4'-bipyridin-1'(2'H)-yl)methyl]benzamide;
2-(3-chloro-3',6'-dihydro-2,4'-bipyridin-1'(2'H)-yl)-N-(2,6-dimethylphenyl)acetamide;
2-(3-chloro-3',6'-dihydro-2,4'-bipyridin-1'(2'H)-yl)-N-(2-methylphenyl)acetamide;
N-(3',6'-dihydro-2,4'-bipyridin-1'(2'H)-ylmethyl)-1-naphthamide;
N-{[4-(3-cyano-2-pyridinyl)-1-piperazinyl]methyl}-3-fluorobenzamide;
2-(1-{2-[(4-fluoro-2-methylphenyl)amino]-2-oxoethyl}-4-piperidinyl)pyridinium N-oxide;
2-(1-{2-[(4-fluoro-3-methylphenyl)amino]-2-oxoethyl}-4-piperidinyl)pyridinium N-oxide;
2-(1-{2-[(3-fluorophenyl)amino]-2-oxoethyl}-4-piperidinyl)pyridinium N-oxide;
2-(1-{2-[(2-fluoro-5-methylphenyl)amino]-2-oxoethyl}-4-piperidinyl)pyridinium N-oxide;
2-(1-{1-methyl-2-[(3-methylphenyl)amino]-2-oxoethyl}-4-piperidinyl)pyridinium N-oxide;
2-(1-{2-[(4-fluorophenyl)amino]-2-oxoethyl}-4-piperidinyl)pyridinium N-oxide; 2-(1-{2-[(2-fluorophenyl)amino]-2-oxoethyl}-4-piperidinyl)pyridinium N-oxide;
N-(3-methylphenyl)-2-{4-[3-(trifluoromethyl)-2-pyridinyl]-1-piperazinyl}acetamide;
N-(3-methylphenyl)-2-{4-[3-(trifluoromethyl)-2-pyridinyl]-1-piperazinyl}acetamide;
N-(3-methylphenyl)-2-[4-(1,3-thiazol-2-yl)-3,6-dihydropyridin-1(2H)-yl]acetamide;
N-(3-methylphenyl)-2-(4-thien-2-yl-3,6-dihydropyridin-1(2H)-yl)acetamide;
3-methyl-N-[(4-thien-2-yl-3,6-dihydropyridin-1(2H)-yl)methyl]benzamide;
2-(1-{2-[(3-chlorophenyl)amino]-2-oxoethyl}piperidin-4-yl)pyridinium N-oxide;
2-[4-(1-methyl-1H-imidazol-2-yl)-3,6-dihydropyridin-1(2H)-yl]-N-(3-methylphenyl)acetamide;
N-(3-methylphenyl)-2-[4-(3-nitropyridin-2-yl)piperazin-1-yl]acetamide;
2-[4-(3-chloropyridin-2-yl)piperazin-1-yl]-N-(3-methylphenyl)acetamide;

2-(1-{2-oxo-2-[(2,4,6-tribromo-3-methylphenyl)amino] ethyl}piperidin-4-yl)pyridinium N-oxide;
2-{4-[3-(aminomethyl)pyridin-2-yl]piperazin-1-yl}-N-(3-methylphenyl)acetamide;
2-[4-(2-isopropoxyphenyl)piperazin-1-yl]-N-(3-methylphenyl)acetamide;
2-(4-{2-[(3-methylphenyl)amino]-2-oxoethyl }piperazin-1-yl)nicotinamide;
N-(3-methylphenyl)-2-[(2S)-2-methyl-4-pyridin-2-ylpiperazin-1-yl]ethanethioamide;
2-(1-{[(4-bromo-3-methylbenzoyl)amino] methyl}piperidin-4-yl)pyridinium N-oxide;
2-[4-(3-cyanopyridin-2-yl)piperazin-1-yl]-N-[3-(methylthio)phenyl]acetamide;
N-(3-tert-butylphenyl)-2-[4-(3-cyanopyridin-2-yl)piperazin-1-yl]acetamide;
2-[4-(2-hydroxyphenyl)piperazin-1-yl]-N-(3-methylphenyl)acetamide;
2-[4-(3-hydroxyphenyl)piperazin-1-yl]-N-(3-methylphenyl)acetamide;
2-[4-(4-hydroxyphenyl)piperazin-1-yl]-N-(3-methylphenyl)acetamide;
2-[4-(2-ethoxyphenyl)piperazin-1-yl]-N-(3-methylphenyl)acetamide;
N-(3-methylphenyl)-2-{4-[2-(methylthio)phenyl]piperazin-1-yl}acetamide;
2-[4-(2-fluorophenyl)piperazin-1-yl]-N-(3-methylphenyl)acetamide;
2-[4-(3-cyanopyridin-2-yl)piperazin-1-yl]-N-(3-fluorophenyl)acetamide;
N-(3-bromophenyl)-2-[4-(3-cyanopyridin-2-yl)piperazin-1-yl]acetamide;
N-(3-methylphenyl)-2-(4-pyridin-2-ylpiperazin-1-yl) ethanethioamide;
2-[4-(2-aminophenyl)piperazin-1-yl]-N-(3-methylphenyl)acetamide;
N-(3-nitrophenyl)-2-(4-pyridin-2-ylpiperazin-1-yl)acetamide;
2-[4-(2-cyanophenyl)piperazin-1-yl]-N-(3-nitrophenyl)acetamide;
N-(3-cyanophenyl)-2-(4-pyridin-2-ylpiperazin-1-yl)acetamide;
N-(3-cyanophenyl)-2-[4-(2-cyanophenyl)piperazin-1-yl]acetamide;
2-[4-(3-cyanopyridin-2-yl)piperazin-1-yl]-N-(pentafluorophenyl)acetamide;
2-[4-(3-cyanopyridin-2-yl)piperazin-1-yl]-N-(1,3-dimethyl-1H-pyrazol-5-yl)acetamide;
N-(3-benzylphenyl)-2-[4-(3-cyanopyridin-2-yl)piperazin-1-yl]acetamide;
2-[4-(2-chlorophenyl)piperazin-1-yl]-N-(3-methylphenyl)acetamide;
2-[4-(3-cyanopyrazin-2-yl)piperazin-1-yl]-N-(3-methylphenyl)acetamide;
2-(4-pyridin-2-ylpiperazin-1-yl)-N-(2-{[(4-pyridin-2-ylpiperazin-1-yl)acetyl]amino}phenyl)acetamide;
N-(3-methylphenyl)-2-(4-pyridin-2-ylpiperidin-1-yl) ethanethioamide;
2-[4-(1-methyl-1H-imidazol-2-yl)piperidin-1-yl]-N-(3-methylphenyl)acetamide;
N-(3-methylphenyl)-2-[4-(1,3-thiazol-2-yl)piperidin-1-yl] acetamide;
N-(4-iodo-3-methylphenyl)-2-(4-pyridin-2-ylpiperidin-1-yl)acetamide;
2-(4-fluoro-4-phenylpiperidin-1-yl)-N-(3-methylphenyl)acetamide;
2-[4-(5-hydroxypyridin-2-yl)piperidin-1-yl]-N-(3-methylphenyl)acetamide;
N-(5-fluoro-1,3-benzothiazol-2-yl)-2-[4-(3-methoxyphenyl) piperazin-1-yl]acetamide;
2-[4-(2-methoxyphenyl)piperazin-1-yl]-N-(1-methyl-1H-benzimidazol-2-yl)acetamide;
N-(3-methylphenyl)-2-[4-(3-methylthien-2-yl)-3,6-dihydropyridin-1(2H)-yl]acetamide;
2-(1-{2-[(3,5-dichlorophenyl)amino]-2-oxoethyl}piperidin-4-yl)pyridinium N-oxide;
2-(1-{2-[(2,3-dichlorophenyl)amino]-2-oxoethyl }piperidin-4-yl)pyridinium N-oxide;
2-(1-{2-[(2-methoxy-6-methylphenyl)amino]-2-oxoethyl}piperidin-4-yl)pyridinium N-oxide;
2-{1-[2-(1,1'-biphenyl-3-ylamino)-2-oxoethyl]piperidin-4-yl}pyridinium N-oxide;
2-{2-[(3-ethylphenyl)amino]-2-oxoethyl}piperidin-4-yl)pyridinium N-oxide;
2-{1-[2-(2,3-dihydro-1H-inden-5-ylamino)-2-oxoethyl]piperidin-4-yl}pyridinium N-oxide;
2-{1-[2-oxo-2-(5,6,7,8-tetrahydronaphthalen-1-ylamino) ethyl]piperidin-4-yl}pyridinium N-oxide;
2-(1-{2-[(3-isopropoxyphenyl)amino]-2-oxoethyl}piperidin-4-yl)pyridinium N-oxide;
2-(1-{2-[(3,5-dimethylphenyl)amino]-2-oxoethyl}piperidin-4-yl)pyridinium N-oxide;
2-(1-{2-[(4-bromo-2-methylphenyl)amino]-2-oxoethyl}piperidin-4-yl)pyridinium N-oxide;
2-[1-(2-oxo-2-{[3-(trifluoromethoxy)phenyl]amino}ethyl) piperidin-4-yl]pyridinium N-oxide;
2-(1-{2-[(5-methyl-2-nitrophenyl)amino]-2-oxoethyl }piperidin-4-yl)pyridinium N-oxide;
2-(1-{2-[(2,6-dimethylphenyl)amino]-2-oxoethyl}piperidin-4-yl)pyridinium N-oxide;
2-(1-{2-[(2,6-dichloro-3-methylphenyl)amino]-2-oxoethyl}piperidin-4-yl)pyridinium N-oxide;
2-{1-[2-(1,3-benzodioxol-5-ylamino)-2-oxoethyl]piperidin-4-yl}pyridinium N-oxide;
2-[1-(2-{[3-(methylthio)phenyl]amino}-2-oxoethyl)piperidin-4-yl]pyridinium N-oxide;
2-(1-{2-[(5-chloro-2-methylphenyl)amino]-2-oxoethyl }piperidin-4-yl)pyridinium N-oxide;
2-(1-{2-[(2,5-dimethoxyphenyl)amino]-2-oxoethyl}piperidin-4-yl)pyridinium N-oxide;
2-(1-{2-[(3,5-dimethoxyphenyl)amino]-2-oxoethyl}piperidin-4-yl)pyridinium N-oxide;
2-[1-(2-{[3-(dimethylamino)phenyl]amino}-2-oxoethyl)piperidin-4-yl]pyridinium N-oxide;
2-(1-{2-[(3-isopropylphenyl)amino]-2-oxoethyl}piperidin-4-yl)pyridinium N-oxide;
2-(1-{2-[(3-chloro-2-methylphenyl)amino]-2-oxoethyl }piperidin-4-yl)pyridinium N-oxide;
3-methyl-N-[2-(4-pyridin-2-ylpiperazin-1-yl)ethyl]benzamide;
2-{[(2,3-dibromo-5-methylbenzoyl)amino] methyl}piperidin-4-yl)pyridinium N-oxide;
2-{1-[(benzoylamino)methyl]piperidin-4-yl}pyridinium N-oxide;
2-(1-{[(4-chloro-3-methylbenzoyl)amino]methyl}piperidin-4-yl)pyridinium N-oxide;
2-(1-{[(4-fluoro-3-methylbenzoyl)amino]methyl}piperidin-4-yl)pyridinium N-oxide;
2-[1-({[3-chloro-4-(trifluoromethoxy)benzoyl] amino}methyl)piperidin-4-yl]pyridinium N-oxide;
2-(1-{[(3-ethoxybenzoyl)amino]methyl}piperidin-4-yl)pyridinium N-oxide;

2-(1-{[(3,5-dichlorobenzoyl)amino]methyl}piperidin-4-yl) pyridinium N-oxide;
2-[1-({[4-methyl-3-(trifluoromethyl)benzoyl] amino}methyl)piperidin-4-yl]pyridinium N-oxide;
2-(1-{[(3,4-dimethylbenzoyl)amino]methyl}piperidin-4-yl) pyridinium N-oxide;
2-(1-{[(3-chloro-4-fluorobenzoyl)amino]methyl}piperidin-4-yl)pyridinium N-oxide;
2-(1-{[(pyridin-2-ylcarbonyl)amino]methyl }piperidin-4-yl) pyridinium N-oxide;
2-(1-{[(3,5-dimethylbenzoyl)amino]methyl}piperidin-4-yl) pyridinium N-oxide;
2-(1-{[(3-vinylbenzoyl)amino]methyl}piperidin-4-yl)pyridinium N-oxide;
2-(1-{[(4-bromo-3-methylbenzoyl)amino]methyl}-1,2,3,6-tetrahydropyridin-4-yl)pyridinium N-oxide;
2-{1-[(2-naphthoylamino)methyl]piperidin-4-yl}pyridinium N-oxide;
2-(1-{[(thien-2-ylcarbonyl)amino]methyl}piperidin-4-yl) pyridinium N-oxide;
2-[1-({[(6-chloropyridin-3-yl)carbonyl]amino }methyl)piperidin-4-yl]pyridinium N-oxide;
2-(1-{[(3-cyanobenzoyl)amino]methyl}piperidin-4-yl)pyridinium N-oxide;
2-(1-{[(2,3-dibromo-5-methylbenzoyl)amino]methyl}-1,2, 3,6-tetrahydropyridin-4-yl)pyridinium N-oxide;
12-(1-{[(4-bromobenzoyl)amino]methyl}piperidin-4-yl) pyridinium N-oxide;
2-(1-{[(3-chloro-4-methylbenzoyl)amino]methyl}piperidin-4-yl)pyridinium N-oxide;
2-(1-{[methyl(3-methylbenzoyl)amino]methyl}piperidin-4-yl)pyridinium N-oxide;
2-(1-{[(3-nitrobenzoyl)amino]methyl}piperidin-4-yl)pyridinium N-oxide;
2-(1-{[(2-chloro-5-methylbenzoyl)amino]methyl}piperidin-4-yl)pyridinium N-oxide;
2-(1-{[(3-methoxy-2-methylbenzoyl)amino] methyl}piperidin-4-yl)pyridinium N-oxide;
2-(1-{[(4-chloro-3-methoxybenzoyl)amino] methyl}piperidin-4-yl)pyridinium N-oxide;
N-(3-methylphenyl)-2-(3-pyridin-2-ylpiperidin-1-yl)acetamide;
N-(3-methylphenyl)-2-(3-pyridin-2-ylpyrrolidin-1-yl)acetamide;
N-(1-methyl-1H-benzimidazol-2-yl)-2-[3-(1,3-thiazol-2-yl) piperidin-1-yl]acetamide;
N-(1-methyl-1H-benzimidazol-2-yl)-2-[3-(1,3-thiazol-2-yl) pyrrolidin-1-yl]acetamide;
2-(2-benzylpyrrolidin-1-yl)-N-(3-fluorophenyl)acetamide; and
N-(4-fluorophenyl)-2-(3-thien-2-ylpyrrolidin-1-yl)acetamide; or pharmaceutically acceptable salts, esters, amides, or prodrugs thereof.

A most preferred compound of the present invention is 2-(1-{[(3-methylbenzoyl)amino]methyl}-4-piperidinyl)pyridinium N-oxide.

Abbreviations

Abbreviations which have been used in the descriptions of the Schemes and the Examples that follow are: Ac for acetyl; BINAP for 2,2'-bis(diphenylphosphino)-1,1'-binaphthyl; Boc for tert-butoxycarbonyl; nBuLi for n-butyllithium; dba for dibenzylideneacetone; DME for dimethoxyethane; DMF for N,N-dimethylformamide; DMSO for dimethylsulfoxide; EtOH for ethanol; HPLC for high pressure liquid chromatography; MeOH for methanol; TEA for triethylamine; TFA for trifluoroacetic acid; THF for tetrahydrofuran; THP for tetrahydropyran; TLC for thin layer chromatography.

Preparation of Compounds of the Present Invention

The compounds and processes of the present invention will be better understood in connection with the following synthetic Schemes and Examples which illustrate a means by which the compounds of the present invention can be prepared.

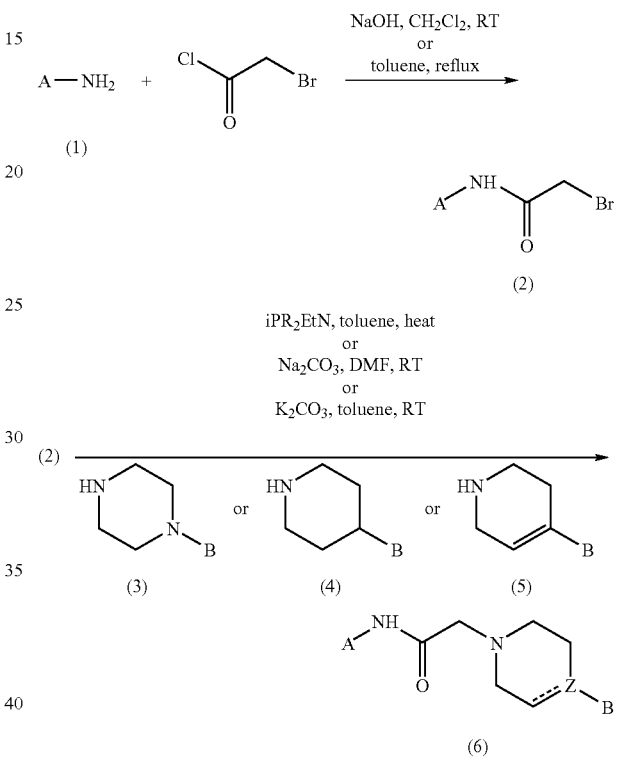

Compound of general formula (6), wherein A, Z, B, and — are as defined in formula (I), can be prepared as described in Scheme 1. Amines of general formula (1) can be treated with bromoacetyl chloride, sodium hydroxide in a solvent such as, but not limited to, toluene or methylene chloride to provide compounds of general formula (2). Compounds of general formula (2) can be treated with an amine of general formula (3) or (4) or (5) in the presence of a base such as, but not limited to, diisopropylethylamine, sodium carbonate, or potassium carbonate in a solvent such as, but not limited to, toluene or N,N-dimethylformamide to provide compounds of general formula (6).

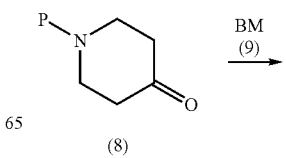

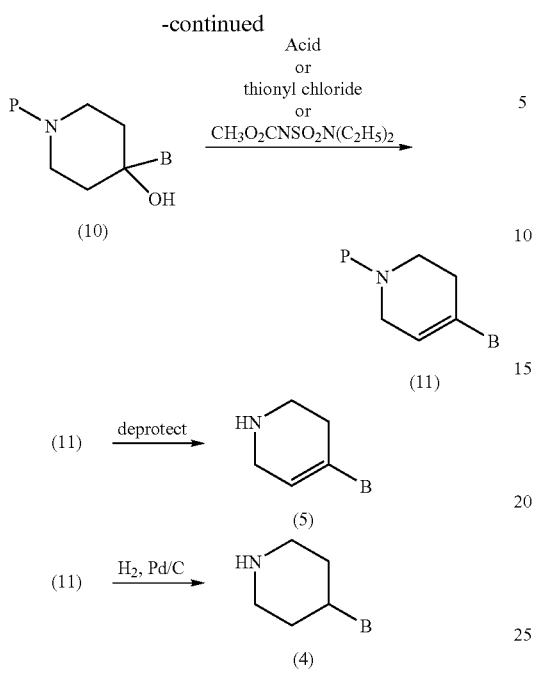

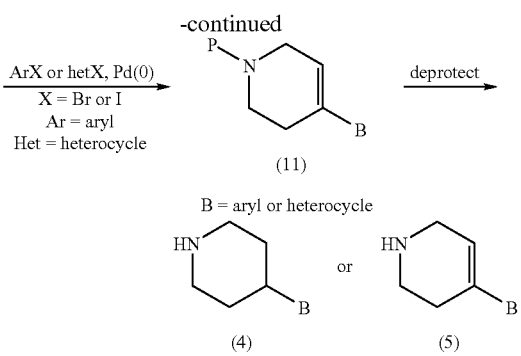

Compounds of general formula (4) and (5), wherein B is as defined in formula (I), can be prepared as described in Scheme 3. Piperidinones of general formula (8), purchased commercially or prepared using standard methods know to those of skill in the art wherein P is a nitrogen protecting group such as, but not limited to, $(CH_3)_3CO_2C-$ or $C_6H_5CH_2O_2C-$, can be treated with $Tf_2NPh$ to provide triflates of general formula (13). Triflates of general formula (13) can be treated with diborane pinacol ester to provide boranes of general formula (14). Boranes of general formula (14) can be treated with ArX or HetX in the presence of a Pd(0) catalyst to provide compounds of general formula (11). Compounds of general formula (11) can be deprotected using standard methods known to those of ordinary skill in the art to provide compounds of general formula (4) and (5).

Compounds of general formula (5) and (4), wherein B is as defined in formula (I) can be prepared as described in Scheme 2. Piperidinones of general formula (8), purchased commercially or prepared using standard methods know to those of skill in the art wherein P is a nitrogen protecting group such as, but not limited to, $(CH_3)_3CO_2C-$ or $C_6H_5CH_2O_2C-$, can be treated with compounds of general formula (9), wherein M is Li, MgBr, MgCl, Cu, or Zn to provide compounds of general formula (10). Compounds of general formula (10) can be treated with Burgess Reagent, thionyl chloride or an acid such as, but not limited to, sulfuric acid or trifluoracetic acid to provide dihyropyridines of general formula (11). Dihyropyridines of general formula (11) can be deprotected using standard methods known to those of ordinary skill in the art to provide compounds of general formula (4) and (5).

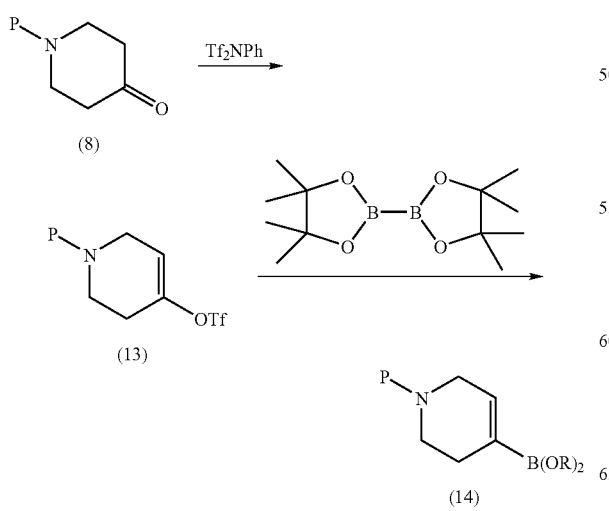

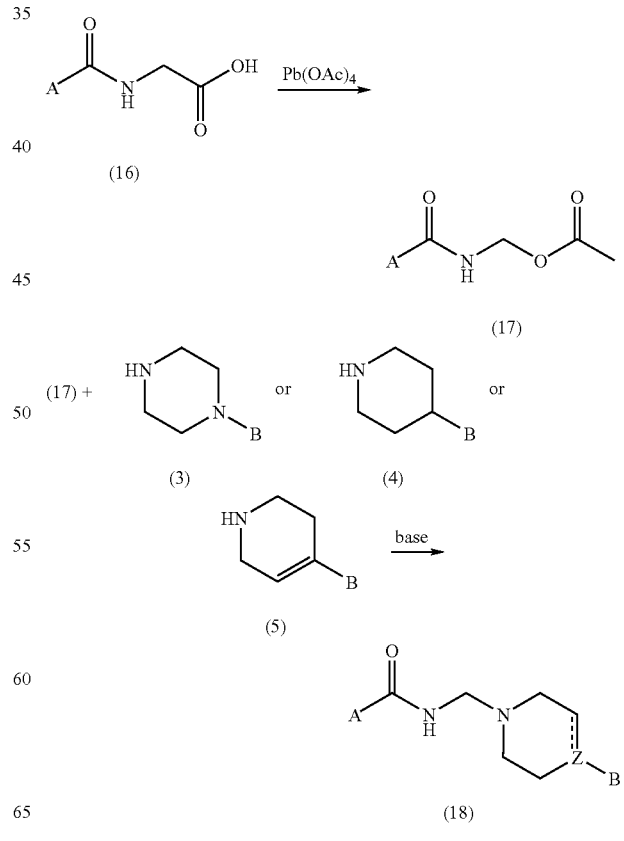

Compounds of general formula (18), wherein A, Z, B, and — are as defined in formula (I), can be prepared as described in Scheme 4. Acids of general formula (16), purchased commercially or prepared using standard methods known to those of ordinary skill in the art, can be treated with lead tetraacetate and copper(II) acetate in a solvent such as, but not limited to, toluene with heat to provide acetates of general formula (17). Acetates of general formula (17) can be treated with an amine of general formula (3) or (4) or (5) and a base such as, but not limited to, triethylamine in a solvent such as, but not limited to, acetonitrile to provide compounds of general formula (18).

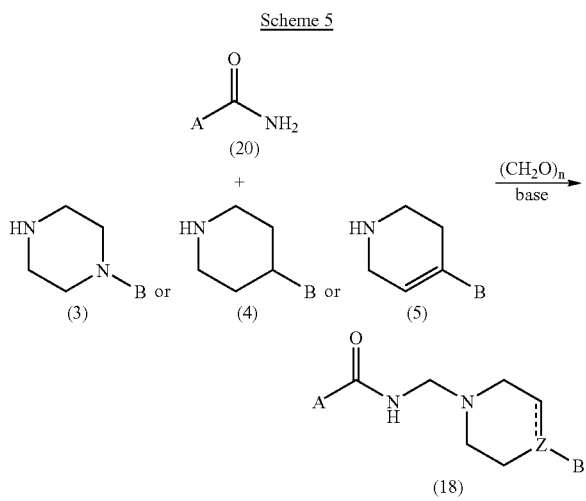

Scheme 5

Compounds of general formula (18), wherein A, Z, B, and — are as defined in formula (I), can be prepared as described in Scheme 5. Amides of general formula (20), purchased commercially or prepared using methods known to those of ordinary skill in the art, can be treated with paraformaldehyde and a base such as, but not limited to, potassium carbonate in a solvent such as, but not limited to, ethanol with heat to provide compounds of general formula (18).

The following Examples are intended as an illustration of and not a limitation upon the scope of the invention as defined in the appended claims.

EXAMPLE 1

2-[4-(2-methoxyphenyl)-1-piperazinyl]-N-(3-methylphenyl)acetamide

EXAMPLE 1A 2-bromo-N-(3-methylphenyl)acetamide

3-Methylaniline (Acros, 15.50 mL, 141.8 mmol) in 2N aqueous sodium hydroxide (200 mL) at room temperature was treated with bromoacetyl chloride (Sigma, 12.50 mL, 152.0 mmol) as a solution in dichloromethane (200 mL). After 30 minutes, the layers were separated and the aqueous phase extracted with additional portions of dichloromethane. The organic phases were combined, washed with an aqueous solution of 1N HCl, dried ($Na_2SO_4$), filtered, and the filtrate concentrated under reduced pressure to provide 16.69 g (52% yield) of the title compound as a white solid. $^1$H NMR (300 MHz, DMSO-$d_6$) δ2.28 (s, 3H), 4.01 (s, 2H), 6.91 (d, 1H, J=7.5 Hz), 7.20 (dd, 1H, J=7.5, 7.5 Hz), 7.36 (d, 1H, J=8.8 Hz), 7.42 (s, 1H), 10.28 (br s, 1H); MS (DCI/$NH_3$) m/e 228/230 (M+H)$^+$; 245/247 (M+$NH_4$)$^+$.

EXAMPLE 1B

2-[4-(2-methoxyphenyl)-1-piperazinyl]-N-(3-methylphenyl)acetamide 1-(2-methoxyphenyl)piperazine, (Aldrich, 1.50 g, 7.80 mmol) and N,N-diisopropylethylamine (2.0 mL) in toluene (30 mL) were treated with the product from Example 1A (1.12 g, 4.90 mmol) and heated at 60° C. for 18 hours. The mixture was allowed to cool to room temperature, transferred to a separatory funnel and washed with saturated aqueous sodium bicarbonate. The organic phase was dried ($Na_2SO_4$), filtered, and the filtrate concentrated under reduced pressure. The residue was purified by flash chromatography on silica gel (elution with 85% hexanes:ethyl acetate then 50% hexanes:ethyl acetate) to provide 1.39 g (83% yield) of the title compound as a yellow oil. $^1$H NMR (300 MHz, DMSO-$d_6$) δ 2.28 (s, 3H), 2.67 (m, 4H), 3.03 (m, 4H), 3.17 (s, 2H), 3.77 (s, 3H), 6.89 (m, 5H), 7.18 (dd, 1H, J=7.8, 7.8 Hz), 7.44 (m, 2H), 9.64 (br s, 1H); MS (DCI/$NH_3$) m/e 340 (M+H)$^+$.

HCl salt: white solid; mp 80° C. (dec); $^1$H NMR (300 MHz, DMSO-$d_6$) δ2.30 (s, 3H), 3.11 (br s, 2H), 3.46 (br s, 4H), 3.60 (br s, 2H), 3.80 (s, 3H), 4.25 (br s, 2H), 6.95 (m, 5H), 7.24 (dd, 1H, J=7.4, 7.4 Hz), 7.44 (m, 2H), 10.52 (br s, 0.5H), 10.82 (br s, 0.5H); Anal. calcd for $C_{20}H_{25}N_3O_2$.0.90 HCl: C, 64.53; H, 7.01; N, 11.29. Found: C, 64.38; H, 6.83; N, 11.17.

EXAMPLE 2

2-[4-(2-cyanophenyl)-1-piperazinyl]-N-(3-methylphenyl)acetamide

The procedure described in Example 1B was followed, substituting 1-(2-cyanophenyl)piperazine (Chess) for 1-(2-methoxyphenyl)piperazine, to provide the title compound (92% yield) as a colorless oil. $^1$H NMR (300 MHz, DMSO-$d_6$) δ 2.28 (s, 3H), 2.73 (m, 4H), 3.21 (s, 2H), 3.23 (m, 4H), 6.88 (br d, 1H, J=7.5 Hz), 7.10 (ddd, 1H, J=7.5, 7.5, 0.7 Hz), 7.19 (m, 2H), 7.44 (m, 2H), 7.61 (ddd, 1H, J=7.5, 7.5, 1.7 Hz), 7.70 (dd, 1H, J=7.8, 1.7 Hz), 9.68 (br s, 1H); MS (DCI/$NH_3$) m/e 335 (M+H)$^+$.

Maleate salt: white solid, mp 168-170° C.; $^1$H NMR (300 MHz, DMSO-$d_6$) δ 2.30 (s, 3H), 3.21 (br s, 4H), 3.37 (br s, 4 H), 3.82 (br s, 2H), 6.13 (s, 2H), 6.93 (br d, 1H, J=7.4 Hz), 7.18 (m, 3H), 7.42 (m, 2H), 7.64 (ddd, 1H, J=7.5, 7.5, 1.4 Hz), 7.74 (dd, 1H, J=7.8, 1.7 Hz), 10.15 (br s, 1H); Anal. calcd for $C_{20}H_{22}N_4$.1.0 $C_4H_4O_4$: C, 63.99; H, 5.82; N, 12.44. Found: C, 63.80; H, 5.80; N, 12.21.

EXAMPLE 3

N-(3-methylphenyl)-2-[4-(2-pyrimidinyl)-1-piperazinyl]acetamide

The procedure described in Example 1B was followed, substituting 1-(2-pyrimidinyl)piperazine (EMKA-Chemie) for 1-(2-methoxyphenyl)piperazine, to provide the title compound (70% yield) as a white solid. mp 113-116° C.; $^1$H NMR (300 MHz, DMSO-$d_6$) δ 2.28 (s, 3H), 2.57 (m, 4H), 3.17 (s, 2H), 3.80 (m, 4H), 6.62 (dd, 1H, J=4.8, 4.8 Hz), 6.88 (br d, 1H, J=7.4 Hz), 7.18 (dd, 1H, J=7.8, 7.8 Hz), 7.46 (m, 2H), 8.36 (d, 2H, J=4.7 Hz), 9.67 (br s, 1H); MS (DCI/$NH_3$) m/e 312 (M+H)$^+$; Anal. calcd for $C_{17}H_{21}N_5O$: C, 65.57; H, 6.80; N, 22.49. Found: C, 65.39; H, 6.77; N, 22.56.

EXAMPLE 4

N-(3-methylphenyl)-2-[4-(2-pyridinyl)-1-piperazinyl]acetamide

The procedure described in Example 1B was followed, substituting 1-(2-pyridinyl)piperazine (Aldrich) for 1-(2-methoxyphenyl)piperazine, to provide the title compound (65% yield) as a white solid. mp 126-127° C.; $^1$H NMR (300 MHz, DMSO-$d_6$) δ 2.27 (s, 3H), 2.60 (m, 4H), 3.17 (s, 2H), 3.55 (m, 4H), 6.63 (ddd, 1H, J=6.7, 4.7, 0.6 Hz), 6.82 (d, 1H, J=8.8 Hz), 6.88 (br d, 1H, J=7.8 Hz), 7.18 (dd, 1H, J=6.7, 4.7, 0.6 Hz), 7.46 (m, 2H), 7.52 (ddd, 1H, J=8.8, 7.1, 2.0 Hz), 8.11 (m, 1H), 9.67 (br s, 1H); MS (DCI/NH$_3$) m/e 311 (M+H)$^+$; Anal. calcd for $C_{18}H_{22}N_4O$: C, 69.65; H, 7.14; N, 18.05. Found: C, 69.72; H, 7.09; N, 18.22.

EXAMPLE 5

2-[4-(3-cyano-2-pyridinyl)-1-piperazinyl]-N-(3-methylphenyl)acetamide

The procedure described in Example 1B was followed, substituting 2-(1-piperazinyl)nicotinonitrile (Chess) for 1-(2-methoxyphenyl)piperazine, to provide the title compound (64% yield) as a white solid. mp 99-100° C.; $^1$H NMR (300 MHz, DMSO-$d_6$) δ 2.28 (s, 3H), 2.68 (m, 4H), 3.19 (s, 2H), 3.68 (m, 4H), 6.88 (br d, 1H, J=7.8 Hz), 6.93 (dd, 1H, J=7.8, 4.8 Hz), 7.18 (dd, 1H, J=7.5, 7.5 Hz), 7.44 (br d, 1H, J=8.2 Hz), 7.47 (br s, 1H), 8.07 (dd, 1H, J=7.8, 2.0 Hz), 8.42 (dd, 1H, J=5.1, 2.0 Hz), 9.68 (br s, 1H); MS (DCI/NH$_3$) m/e 336 (M+H)$^+$; Anal. calcd for $C_{19}H_{21}N_5O$: C, 68.04; H, 6.31; N, 20.88. Found: C, 68.19; H, 6.36; N, 21.15.

EXAMPLE 6

N-(3-methylphenyl)-2-[4-(2-methylphenyl)-1-piperazinyl]acetamide

The procedure described in Example 1B was followed, substituting 1-(2-methylphenyl)piperazine (EMKA Chemie) for 1-(2-methoxyphenyl)piperazine, to provide the title compound (75% yield) as a white solid. mp 104-106° C.; $^1$H NMR (300 MHz, DMSO-$d_6$) δ 2.24 (s, 3H), 2.28 (s, 3H), 2.69 (m, 4H), 2.91 (m, 4H), 3.19 (s, 2H), 6.88 (br d, 1H, J=7.4 Hz), 6.95 (dd, 1H, J=7.1, 7.1 Hz), 7.05 (m, 1H), 7.17 (m, 3H), 7.45 (m, 2H), 9.64 (br s, 1H); MS (DCI/NH$_3$) m/e 324 (M+H)$^+$; Anal. calcd for $C_{20}H_{25}N_3O$: C, 74.27; H, 7.79; N, 12.99. Found: C, 74.34; H, 7.85; N, 12.91.

EXAMPLE 7

N-(3-methylphenyl)-2-[4-(2-nitrophenyl)-1-piperazinyl]acetamide

The procedure described in Example 1B was followed, substituting 1-(2-nitrophenyl)piperazine (EMKA Chemie) for 1-(2-methoxyphenyl)piperazine, to provide the title compound (91% yield) as an orange oil. 1H NMR (300 MHz, DMSO-$d_6$) δ 2.28 (s, 3H), 2.66 (m, 4H), 3.07 (m, 4H), 3.18 (s, 2H), 6.88 (br d, 1H, J=7.8 Hz), 7.13 (ddd, 1H, J=8.5, 7.1, 1.0 Hz), 7.18 (dd, 1H, J=7.8, 7.8 Hz), 7.35 (dd, 1H, J=8.1, 1.0 Hz), 7.45 (m, 2H), 7.59 (ddd, 1H, J=8.1, 7.1, 1.3 Hz), 7.79 (dd, 1H, J=8.1, 1.7 Hz), 9.66 (br s, 1H); MS (DCI/NH$_3$) m/e 355 (M+H)$^+$.

maleate salt: yellow solid; mp 172-175° C.; Anal. calcd for $C_{19}H_{22}N_4O_3 \cdot 1.0\ C_4H_4O_4$: C, 58.72; H, 5.57; N, 11.91. Found: C, 58.38; H, 5.49; N, 11.64.

EXAMPLE 8

2-[4-(3-cyano-2-pyridinyl)-1-piperazinyl]-N-(3-nitrophenyl)acetamide 2-(1-Piperazinyl)-3-pyridinecarbonitrile (640 mg, 3.40 mmol) and N,N-diisopropylethylamine (1.0 mL) in toluene (15 mL) at room temperature were treated with N-chloroacetyl-3-nitroaniline (Lancaster, 610 mg, 2.84 mmol) and the reaction was heated at 90° C. for 18 hours. The mixture was allowed to cool to room temperature, transferred to a separatory funnel and washed with saturated aqueous sodium bicarbonate. The organic phase was dried ($Na_2SO_4$), filtered, and the filtrate concentrated under reduced pressure. The residue was purified by flash chromatography on silica gel (elution with 85% hexanes:ethyl acetate) to provide 256 mg (25% yield) of the title compound as a light tan solid. mp 143-145° C.; $^1$H NMR (300 MHz, DMSO-$d_6$) δ 2.69 (m, 4H), 3.27 (s, 2H), 3.70 (m, 4H), 6.93 (dd, 1H, J=7.4, 5.0 Hz), 7.61 (dd, 1H, J=8.1, 8.1 Hz), 7.93 (br d, 1H, J=8.2 Hz), 8.06 (dd, 2H, J=7.8, 7.8 Hz), 8.42 (m, 1H), 8.70 (br s, 1H), 10.28 (br s, 1H); MS (DCI/NH$_3$) m/e 367 (M+H)$^+$; Anal. calcd for $C_{18}H_{18}N_6O_3$: C, 59.01; H, 4.95; N, 22.94. Found: C, 59.31; H, 5.25; N, 22.66.

EXAMPLE 9

2-[4-(3-cyano-2-pyridinyl)-1-piperazinyl]-N-[3-(trifluoromethyl)phenyl]acetamide The procedure described in Example 8 was followed, substituting N-chloroacetyl-3-(trifluoromethyl)aniline for N-chloroacetyl-3-nitroaniline, to provide the title compound (84% yield) as a yellow oil. $^1$H NMR (300 MHz, DMSO-$d_6$) δ 2.69 (m, 4H), 3.25 (s, 2H), 3.69 (m, 4H), 6.93 (dd, 1H, J=7.8, 4.7 Hz), 7.41 (br d, 1H, J=7.8 Hz), 7.56 (dd, 1H, J=7.8, 7.8 Hz), 7.90 (br d, 1H, J=8.4 Hz), 8.07 (dd, 1H, J=7.8, 2.1 Hz), 8.15 (br s, 1H), 8.42 (dd, 1H, J=4.7, 1.7 Hz), 10.11 (br s, 1H); MS (DCI/NH$_3$) m/e 390 (M+H)$^+$.

maleate salt: tan solid; mp 157-158° C.; $^1$H NMR (300 MHz, DMSO-$d_6$) δ 3.07 (br s, 4H), 3.73 (br s, 2H), 3.79 (br s, 4H), 6.15 (s, 2H), 7.00 (dd, 1H, J=7.4, 4.7 Hz), 7.46 (br d, 1H, J=7.8 Hz), 7.59 (dd, 1H, J=7.8, 7.8 Hz), 7.85 (br d, 1H, J=8.2 Hz), 8.13 (m, 2H), 8.45 (dd, 1H, J=4.7, 2.0 Hz), 10.48 (br s, 1H); Anal. calcd for $C_{19}H_{18}F_3N_5O \cdot 1.0\ C_4H_4O_4$: C, 54.56; H, 4.39; N, 13.86. Found: C, 54.30; H, 4.42; N, 13.42.

EXAMPLE 10

N-(3-methylphenyl)-2-(4-phenyl-1-piperazinyl)acetamide

The procedure described in Example 1B was followed, substituting 1-phenylpiperazine (Aldrich) for 1-(2-methoxyphenyl)piperazine, to provide the title compound (86% yield) as a white solid. mp 120-121° C.; $^1$H NMR (300 MHz, DMSO-$d_6$) δ 2.27 (s, 3H), 2.66 (m, 4H), 3.17 (s, 2H), 3.20 (m, 4H), 6.77 (dd, 1H, J=7.1, 7.1 Hz), 6.88 (br d, 1H, J=7.5 Hz), 6.94 (d, 2H, J=7.8 Hz), 7.21 (m, 3H), 7.44 (m, 2H), 9.65 (br s, 1H); MS (DCI/NH$_3$) m/e 310 (M+H)$^+$; Anal. calcd for $C_{19}H_{23}N_3O$: C, 73.76; H, 7.49; N, 13.58. Found: C, 73.73; H, 7.50; N, 13.64.

EXAMPLE 11

N-(3-cyanophenyl)-2-[4-(3-cyano-2-pyridinyl)-1-piperazinyl]acetamide

The procedure described in Example 8 was followed, substituting N-chloroacetyl-3-cyanoaniline (Maybridge) for N-chloroacetyl-3-nitroaniline, to provide the title compound (60% yield) as a colorless oil. $^1$H NMR (300 MHz, DMSO-d$_6$) δ 2.68 (m, 4H), 3.25 (s, 2H), 3.69 (m, 4H), 6.92 (dd, 1H, J=7.5, 5.1 Hz), 7.52 (m, 2H), 7.94 (m, 1H), 8.07 (m, 1H), 8.15 (m, 1H), 8.41 (m, 1H), 10.10 (br s, 1H); MS (DCI/NH$_3$) m/e 347 (M+H)$^+$.

maleate salt: white solid; mp 166-167° C.; $^1$H NMR (300 MHz, DMSO-d$_6$) δ3.04 (br s, 4H), 3.69 (br s, 2H), 3.78 (br s, 4H), 6.16 (s, 2H), 6.99 (dd, 1H, J=7.5, 4.6 Hz), 7.58 (m, 2H), 7.89 (m, 1H), 8.12 (m, 2H), 8.45 (dd, 1H, J=4.7, 2.0 Hz), 10.46 (br s, 1H); Anal. calcd for C$_{19}$H$_{18}$N$_6$O.1.0 C$_4$H$_4$O$_4$: C, 59.73; H, 4.79; N, 18.17. Found: C, 59.73; H, 4.81; N, 18.45.

EXAMPLE 12

N-(4-bromo-3-methylphenyl)-2-[4-(2-cyanophenyl)-1-piperazinyl]acetamide

EXAMPLE 12A 2-bromo-N-(4-bromo-3-methylphenyl)acetamide

4-Bromo-3-methylaniline (10.08 g, 54.18 mmol) in 2N sodium hydroxide (200 mL) was treated with bromoacetyl chloride (5.00 mL, 60.8 mmol) as a solution in dichloromethane (200 mL) dropwise. After 15 minutes, the layers were separated. The organic phase was washed with 1N hydrochloric acid, dried (Na$_2$SO$_4$), filtered, and the filtrate concentrated under reduced pressure to provide 11.75 g (71%) of the title compound as a tan solid. $^1$H NMR (300 MHz, CDCl$_3$) δ 2.39 (s, 3H), 4.01 (s, 2H), 7.23 (m, 1H), 7.44 (d, 1H, J=2.4 Hz), 7.49 (d, 1H, J=8.8 Hz), 8.07 (br s, 1H); MS (DCI/NH$_3$) m/e 306 (M+H)$^+$.

EXAMPLE 12B

N-(4-bromo-3-methylphenyl)-2-[4-(2-cyanophenyl)-1-piperazinyl]acetamide

The product from Example 12A (3.51 g, 11.4 mmol) and N,N-diisopropylethylamine (2.50 mL) in toluene (50 mL) were treated with 1-(2-cyanophenyl)piperazine (Chess, 2.90 g, 15.5 mmol) and the reaction mixture was heated at 90° C. for 18 hours. The mixture was allowed to cool to room temperature and transferred to a separatory funnel with ethyl acetate and water. The organic phase was washed with saturated aqueous sodium bicarbonate, dried (Na$_2$SO$_4$), filtered, and the filtrate concentrated under reduced pressure. The residue was purified by flash chromatography on silica gel to provide 3.66 g (77%) of the title compound as a yellow solid. mp 143-145° C.; $^1$H NMR (300 MHz, DMSO-d$_6$) δ 2.32 (s, 3H), 2.72 (m, 4H), 3.22 (m, 6H), 7.10 (ddd, 1H, J=7.4, 7.4, 0.6 Hz), 7.19 (d, 1H, 8.1 Hz), 7.49 (m, 2H), 7.61 (m, 1H), 7.65 (d, 1H, J=2.1 Hz), 7.70 (dd, 1H, J=7.8, 1.7 Hz), 9.82 (br, s, 1H); MS (DCI/NH$_3$) m/e 413/415 (M+H)$^+$; Anal. calcd for C$_{20}$H$_{21}$BrN$_4$O: C, 58.12; H, 5.12; N, 13.56. Found: C, 58.13; H, 5.07; N, 13.54.

EXAMPLE 13

2-[4-(2-cyanophenyl)-1-piperazinyl]-N-phenylacetamide

The procedure described in Example 12B was followed, substituting 2-chloro-N-phenylacetamide (Maybridge) for the product from Example 12A, to provide the title compound (39% yield) as a yellow solid, mp 137-138° C.; $^1$H NMR (300 MHz, DMSO-d$_6$) δ 2.73 (m, 4H), 3.22 (m, 6H), 7.08 (m, 2H), 7.19 (d, 1H, J=8.5 Hz), 7.30 (m, 2H), 7.63 (m, 2H), 7.70 (dd, 1H, J=7.8, 1.7 Hz), 9.76 (br s, 1H); MS (DCI/NH$_3$) m/e 321 (M+H)$^+$; Anal. calcd for C$_{19}$H$_{20}$N$_4$O: C, 71.23; H, 6.29; N, 17.49. Found: C, 70.92; H, 6.34; N, 17.34.

EXAMPLE 14

2-[4-(3-cyano-2-pyridinyl)-1-piperazinyl]-N-phenylacetamide

The procedure described in Example 8 was followed, substituting 2-chloro-N-phenylacetamide (Maybridge) for N-chloroacetyl-3-nitroaniline to provide the title compound (52% yield) as a white solid. mp 110-112° C.; $^1$H NMR (300 MHz, DMSO-d$_6$) δ 2.68 (m, 4H), 3.21 (s, 2H), 3.68 (m, 4H), 6.93 (dd, 1H, J=7.8, 4.7 Hz), 7.06 (dd, 1H, J=7.8, 7.8 Hz), 7.31 (dd, 2H, J=7.8, 7.8 Hz), 7.64 (dd, 2H, J=8.8, 1.4 Hz), 8.07 (dd, 1H, J=7.8, 2.0 Hz), 8.42 (dd, 1H, J=4.8, 1.7 Hz), 9.76 (br s, 1H); MS (DCI/NH$_3$) m/e 322 (M+H)$^+$; Anal. calcd for C$_{18}$H$_{19}$N$_5$O: C, 67.27; H, 5.96; N, 21.79. Found: C, 67.21; H, 5.77; N, 21.59.

EXAMPLE 15

2-[4-(3-cyano-2-pyridinyl)-1-piperazinyl]-N-(4-fluorophenyl)acetamide

The procedure described in Example 8 was followed, substituting N-choroacetyl-4-fluoroaniline (Avocado) for N-chloroacetyl-3-nitroaniline, to provide the title compound (91% yield) as a white solid. mp 98-100° C.; $^1$H NMR (300 MHz, DMSO-d$_6$) δ 2.68 (m, 4H), 3.20 (s, 2H), 3.68 (m, 4H), 6.92 (dd, 1H, J=7.5, 4.8 Hz), 7.15 (m, 2H), 7.67 (m, 2H), 8.07 (dd, 1H, J=7.8, 2.0 Hz), 8.41 (dd, 1H, J=4.8, 1.7 Hz), 9.83 (br s, 1H); MS (DCI/NH$_3$) m/e 340 (M+H)$^+$; Anal. calcd for C$_{18}$H$_{18}$FN$_5$O: C, 63.71; H. 5.35; N, 20.64. Found: C, 63.57; H, 5.32; N, 20.79.

EXAMPLE 16

2-[4-(3-cyano-2-pyridinyl)-1-piperazinyl]-N-(3,5-dimethylphenyl)acetamide

EXAMPLE 16A 2-chloro-N-(3,5-dimethylphenyl)acetamide 3,5-Dimethylaniline (Acros, 10.50 mL, 84.05 mmol) in 2N sodium hydroxide (200 mL) was treated with chloroacetyl chloride (Acros, 10.00 mL, 125.7 mmol) as a solution in dichloromethane (200 mL) drop wise. After 18 hours, the layers were separated. The organic phase was washed with 1N hydrochloric acid, dried (Na$_2$SO$_4$), filtered, and the filtrate concentrated under reduced pressure to provide 15.64 g (94%) of the title compound as a white solid. $^1$H NMR (300 MHz, DMSO-d$_6$) δ 2.24 (s, 6H), 4.21 (s, 2H), 6.73 (s, 1H), 7.20 (s, 2H), 10.11 (br s, 1H); MS (DCI/NH$_3$) m/e 198 (M+H)$^+$.

EXAMPLE 16B

2-[4-(3-cyano-2-pyridinyl)-1-piperazinyl]-N-(3,5-dimethylphenyl)acetamide

The procedure described in Example 8 was followed, substituting the product from Example 16A for N-chloroacetyl- 3-nitroaniline to provide the title compound (63% yield) as a white solid. mp 139-140° C.; 1H NMR (300 MHz, DMSO-$d_6$) δ 2.23 (s, 6H), 2.70 (m, 4H), 3.18 (s, 2H), 3.68 (m, 4H), 6.70 (br s, 1H), 6.93 (dd, 1H, J=7.8, 4.7 Hz), 7.28 (br s, 2H), 8.07 (dd, 1H, J=7.8, 2.0 Hz), 8.42 (dd, 1H, J=4.7, 2.0 Hz), 9.60 (br s, 1H); MS (DCI/NH$_3$) m/e 350 (M+H)$^+$; Anal. calcd for $C_{20}H_{23}N_5O$: C, 68.74; H, 6.63; N, 20.04. Found: C, 68.56; H, 6.56; N, 20.05.

EXAMPLE 17

2-[4-(3-cyano-2-pyridinyl)-1-piperazinyl]-N-(2,3-dimethylphenyl)acetamide

EXAMPLE 17A 2-chloro-N-(2,3-dimethylphenyl)acetamide

The procedure described in Example 16A was followed, substituting 2,3-dimethylaniline for 3,5-dimethylaniline to provide the title compound (96% yield) as a white solid. $^1$H NMR (300 MHz, DMSO-$d_6$) δ 2.07 (s, 3H), 2.24 (s, 3H), 4.28 (s, 2H), 7.07 (m, 3H), 9.70 (br s, 1H); MS (DCI/NH$_3$) m/e 198 (M+H)$^+$.

EXAMPLE 17B

2-[4-(3-cyano-2-pyridinyl)-1-piperazinyl]-N-(2,3-dimethylphenyl)acetamide

The procedure described in Example 8 was followed, substituting the product from Example 17A for N-chloroacetyl-3-nitroaniline, to provide the title compound (32% yield as a white solid. mp 124-126° C.; $^1$H NMR (300 MHz, DMSO-$d_6$) δ 2.12 (s, 3H), 2.26 (s, 3H), 2.72 (m, 4H), 3.21 (s, 2H), 3.69 (m, 4H), 6.94 (dd, 1H, J=7.8, 4.8 Hz), 6.99 (br d, 1H, J=7.4 Hz), 7.07 (dd, 1H, J=7.4, 7.4 Hz), 7.45 (br d, 1H, J=7.8 Hz), 8.08 (dd, 1H, J=7.8, 2.0 Hz), 8.42 (dd, 1H, 4.8, 2.1 Hz), 9.42 (br s, 1H); MS (DCI/NH$_3$) m/e 350 (M+H)$^+$; Anal. calcd for $C_{20}H_{23}N_5O\cdot0.10\,H_2O$: C, 68.39; H, 6.66; N, 19.94. Found: C, 68.74; H, 6.58; N, 19.56.

EXAMPLE 18

2-[4-(3-cyano-2-pyridinyl)-1-piperazinyl]-N-(2-methylphenyl)acetamide

EXAMPLE 18A 2-chloro-N-(2-methylphenyl)acetamide

The procedure described in Example 16A was followed, substituting 2-methylaniline for 3,5-dimethylaniline to provide the title compound (90% yield) as a white solid. $^1$H NMR (300 MHz, DMSO-$d_6$) δ 2.20 (s, 3H), 4.30 (s, 2H), 7.16 (m, 3H), 7.38 (d, 1H, J=7.8 Hz), 9.63 (br s, 1H); MS (DCI/NH$_3$) m/e 184 (M+H)$^+$.

EXAMPLE 18B

2-[4-(3-cyano-2-pyridinyl)-1-piperazinyl]-N-(2-methylphenyl)acetamide

The procedure described in Example 8 was followed, substituting the product from Example 18A for N-chloroacetyl-3-nitroaniline, to provide the title compound (58% yield) as a light yellow solid. mp 123-125° C.; $^1$H NMR (300 MHz, DMSO-$d_6$) δ 2.25 (s, 3H), 2.73 (m, 4H), 3.22 (s, 2H), 3.69 (m, 4H), 6.94 (dd, 1H, J=7.8, 4.8 Hz), 7.06 (ddd, 1H, J=7.4, 7.4, 1.0 Hz), 7.17 (d, 1H, J=7.8 Hz), 7.21 (dd, 1H, 8.5, 8.5 Hz), 7.75 (d, 1H, J=7.8 Hz), 8.08 (dd, 1H, J=7.8, 1.7 Hz), 8.42 (dd, 1H, J=5.0, 1.7 Hz), 9.42 (br s, 1H); MS (DCI/NH$_3$) m/e 336 (M+H)$^+$; Anal. calcd for $C_{19}H_{21}N_5O\cdot0.20\,H_2O$: C, 67.32; H, 6.36; N, 20.66. Found: C, 67.29; H, 6.23; N, 20.66.

EXAMPLE 19

2-[4-(3-cyano-2-pyridinyl)-1-piperazinyl]-N-(2,5-dimethylphenyl)acetamide

EXAMPLE 19A 2-chloro-N-(2,5-dimethylphenyl) acetamide

The procedure described in Example 16A was followed, substituting 2,5-dimethylaniline for 3,5-dimethylaniline, to provide the title compound (89% yield) as a white solid. $^1$H NMR (300 MHz, DMSO-$d_6$) δ 2.14 (s, 3H), 2.24 (s, 3H), 4.28 (s, 2H), 6.93 (d, 1H, J=7.8 Hz), 7.10 (d, 1H, J=7.8 Hz), 7.20 (s, 1H), 9.57 (br s, 1H); MS (DCI/NH$_3$) m/e 198 (M+H)$^+$.

EXAMPLE 19B

2-[4-(3-cyano-2-pyridinyl)-1-piperazinyl]-N-(2,5-dimethylphenyl)acetamide

The procedure described in Example 8 was followed, substituting Example 19A for N-chloroacetyl-3-nitroaniline, to provide the title compound (34% yield) as a white solid. mp 106-108° C.; $^1$H NMR (300 MHz, DMSO-$d_6$) δ 2.19 (s, 3H), 2.26 (s, 3H), 2.72 (m, 4H), 3.20 (s, 2H), 3.69 (m, 4H), 6.87 (d, 1H, J=7.4 Hz), 6.94 (dd, 1H, J=7.5, 4.8 Hz), 7.10 (d, 1H, J=7.8 Hz), 7.59 (br s, 1H), 8.08 (dd, 1H, J=7.8, 2.0 Hz), 8.42 (dd, 1H, J=4.7, 2.0 Hz), 9.35 (br s, 1H); MS (DCI/NH$_3$) m/e 350 (M+H)$^+$; Anal. calcd for $C_{20}H_{23}N_5O\cdot0.20\,H_2O$: C, 68.04; H, 6.68; N, 19.84. Found: C, 67.89; H, 6.54; N, 19.88.

EXAMPLE 20

N-(3-chlorophenyl)-2-[4-(3-cyano-2-pyridinyl)-1-piperazinyl]acetamide

The procedure described in Example 8 was followed, substituting 3-chloro-N-(chloroacetyl)aniline (Maybridge) for N-chloroacetyl-3-nitroaniline to provide the title compound (79% yield) as a light tan solid. mp 108-109° C.; $^1$H NMR (300 MHz, DMSO-$d_6$) δ 2.68 (m, 4H), 3.23 (s, 2H), 3.69 (m, 4H), 6.93 (dd, 1H, J=7.8, 4.8 Hz), 7.12 (m, 1H), 7.34 (dd, 1H, J=8.1, 8.1 Hz), 7.57 (m, 1H), 7.86 (m, 1H), 8.07 (dd, 1H, J=7.8, 2.0 Hz), 8.42 (dd, 1H, J=4.7, 2.0 Hz), 9.96 (br s, 1H); MS (DCI/NH$_3$) m/e 356 (M+H)$^+$; Anal. calcd for $C_{18}H_{18}ClN_5O$: C, 60.76; H, 5.10; N, 19.68. Found: C, 60.71; H, 5.09; N, 19.58.

EXAMPLE 21

N-(3-chloro-4-fluorophenyl)-2-[4-(3-cyano-2-pyridinyl)-1-piperazinyl]acetamide

The procedure described in Example 8 was followed, substituting 3-chloro-N-(chloroacetyl)-4-fluoroaniline (Maybridge) for N-chloroacetyl-3-nitroaniline, to provide the title compound (39% yield) as a light tan solid. mp 137-140° C.; $^1$H NMR (300 MHz, DMSO-$d_6$) δ 2.67 (m, 4H), 3.22 (s, 2H), 3.69 (m, 4H), 6.93 (dd, 1H, J=7.5, 4.8 Hz), , 7.37 (dd, 1H, J=9.1, 9.1 Hz), 7.61 (ddd, 1H, J=9.2, 4.5, 2.8 Hz), 7.98 (dd, 1H, J=7.2, 2.8 Hz), 8.07 (dd, 1H, J=7.8, 2.0 Hz), 8.41 (dd, 1H, J=4.8, 1.7 Hz), 9.98 (br s, 1H); MS (DCI/NH$_3$) m/e 374 (M+H)$^+$; Anal. calcd for C$_{18}$H$_{17}$ClFN$_5$O: C, 57.84; H, 4.58; N, 18.73. Found: C, 57.98; H, 4.42; N, 18.65.

EXAMPLE 22

2-[4-(3-cyano-2-pyridinyl)-1-piperazinyl]-N-(3,4,5-trimethoxyphenyl)acetamide

EXAMPLE 22A 2-chloro-N-(3,4,5-trimethoxyphenyl)acetamide 3,4,5-Trimethoxyaniline (Aldrich, 4.06 g, 22.2 mmol) and chloroacetyl chloride (2.60 mL, 32.7 mmol) in toluene (50 mL) were heated at 100° C. for 24 hours. The mixture was allowed to cool to room temperature and the volatiles were removed under reduced pressure. The residue was taken up in toluene and concentrated (3×) to remove traces of starting acid chloride and placed under high vacuum to provide 5.26 g (91%) of the title compound as a light brown solid. $^1$H NMR (500 MHz, DMSO-d$_6$) δ 3.62 (s, 3H), 3.74 (s, 6H), 4.21 (s, 2H), 6.96 (s, 2H), 10.19 (br s, 1H); MS (DCI/NH$_3$) m/e 260 (M+H)$^+$.

EXAMPLE 22B

2-[4-(3-cyano-2-pyridinyl)-1-piperazinyl]-N-(3,4,5-trimethoxyphenyl)acetamide

The procedure described in Example 8 was followed, substituting Example 22A for N-chloroacetyl-3-nitroaniline, to provide the title compound (69%.yield) as a light tan solid. mp 123-124° C.; $^1$H NMR (300 MHz, DMSO-d$_6$) δ 2.68 (m, 4H), 3.19 (s, 2H), 3.61 (s, 3H), 3.69 (m, 4H), 3.74 (s, 6H), 6.93 (dd, 1H, J=7.8, 4.7 Hz), 7.07 (s, 2H), 8.07 (dd, 1H, J=7.4, 1.7 Hz), 8.42 (dd, 1H, J=4.8, 2.1 Hz), 9.67 (br s, 1H); MS (DCI/NH$_3$) m/e 412 (M+H)$^+$; Anal. calcd for C$_{21}$H$_{25}$N$_5$O: C, 61.30; H, 6.12; N, 17.02. Found: C, 61.27; H, 6.08; N, 16.95.

EXAMPLE 23

2-[4-(3-cyano-2-pyridinyl)-1-piperazinyl]-N-[4-fluoro-3-(trifluoromethyl)phenyl]acetamide

EXAMPLE 23A 2-chloro-N-(4-fluoro-3-trifluoromethylphenyl)acetamide

The procedure described in Example 16A was followed, substituting 4-fluoro-3-(trifluoromethyl)aniline (Acros) for 3,5-dimethylaniline, to provide the title compound (79% yield) as a white solid. $^1$H NMR (300 MHz, DMSO-d$_6$) δ 4.29 (s, 2H), 7.50 (dd, 1H, J=9.8, 9.8 Hz), 7.85 (m,1H), 8.08 (dd, 1H, J=6.5, 2.7 Hz), 10.64 (br s, 1H).

EXAMPLE 23B

2-[4-(3-cyano-2-pyridinyl)-1-piperazinyl]-N-[4-fluoro-3-(trifluoromethyl)phenyl]acetamide The procedure described in Example 8 was followed, substituting the product from Example 23A for N-chloroacetyl-3-nitroaniline, to provide the title compound (47% yield) as a white solid. mp 120-122° C.; $^1$H NMR (300 MHz, DMSO-d$_6$) δ 2.68 (m, 4H), 3.24 (s, 2H), 3.69 (m, 4H), 6.93 (dd, 1H, J=8.1, 5.1 Hz), 7.48 (dd, 1H, J=10.2, 10.2 Hz), 7.97 (m, 1H), 8.07 (dd, 1H, J=7.1, 2.0 Hz), 8.16 (dd, 1H, J=6.8, 2.7 Hz), 8.42 (dd, 1H, J=4.8, 2.0 Hz), 10.1 (br, s, 1H); MS (DCI/NH$_3$) m/e 408 (M+H)$^+$; Anal. calcd for C$_{19}$H$_{17}$F$_4$N$_5$O: C, 56.02; H, 4.21; N, 17.19. Found: C, 55.94; H, 4.14; N, 17.31.

EXAMPLE 24

2-[4-(3-cyano-2-pyridinyl)-1-piperazinyl]-N-[3-fluoro-5-(trifluoromethyl)phenyl]acetamide

EXAMPLE 24A 2-chloro-N-(3-fluoro-5-trifluoromethylphenyl)acetamide

The procedure described in Example 16A was followed, substituting 3-fluoro-5-(trifluoromethyl)aniline (Oakwood) for 3,5-dimethylaniline, to provide the title compound (79% yield) as a white solid. $^1$H NMR (300 MHz, CDCl$_3$) δ 4.22 (s, 2H), 7.14 (m, 1H), 7.49 (br s, 1H), 7.76 (ddd, 1H, J=10.1, 2.0, 2.0 Hz), 8.37 (br s, 1H).

EXAMPLE 24B

2-[4-(3-cyano-2-pyridinyl)-1-piperazinyl]-N-[3-fluoro-5-(trifluoromethyl)phenyl]acetamide The procedure described in Example 8 was followed, substituting the product from Example 24A for N-chloroacetyl-3-nitroaniline, to provide the title compound (41% yield) as a white solid. mp 108-110° C.; $^1$H NMR (300 MHz, DMSO-d$_6$) δ 2.68 (m, 4H), 3.26 (s, 2H), 3.70 (m, 4H), 6.93 (dd, 1H, J=7.8, 4.7 Hz), 7.36 (m, 1H), 7.93 (m, 2H), 8.08 (dd, 1H, 7.7, 2.0 Hz), 8.42 (dd, 1H, J=4.7, 2.0 Hz), 10.28 (br s, 1H); MS (DCI/NH$_3$) m/e 408 (M+H)$^+$; Anal. calcd for C$_{19}$H$_{17}$F$_4$N$_5$O: C, 56.02; H, 4.21; N, 17.19. Found: C, 56.17; H, 4.11; N, 17.43.

EXAMPLE 25

2-[4-(3-cyano-2-pyridinyl)-1-piperazinyl]-N-[2-fluoro-5-(trifluoromethyl)phenyl]acetamide

EXAMPLE 25A 2-chloro-N-(2-fluoro-5-(trifluoromethyl)phenyl)acetamide

The procedure described in Example 22A was followed, substituting 2-fluoro-5-(trifluoromethyl)aniline (Acros) for 3,4,5-trimethoxyaniline, to provide the title compound (66% yield) as a tan solid. $^1$H NMR (300 MHz, DMSO-d$_6$) δ 4.40 (s, 2H), 7.58 (m, 2H), 8.38 (dd, 1H, J=7.4, 2.0 Hz), 10.42 (br s, 1H).

EXAMPLE 25B

2-[4-(3-cyano-2-pyridinyl)-1-piperazinyl]-N-[2-fluoro-5-(trifluoromethyl)phenyl]acetamide The procedure described in Example 8 was followed, substituting the product from Example 25A for N-chloroacetyl-3-nitroaniline to provide the title compound (61% yield) as a white solid. mp 130-133° C.; $^1$H NMR (300 MHz, DMSO-d$_6$) δ 2.73 (m, 4H), 3.31 (s, 2H), 3.67 (m, 4H), 6.94 (dd, 1H, J=7.8, 5.1 Hz), 7.56 (m, 2H), 8.08 (dd, 1H, J=7.5, 2.1 Hz), 8.42 (m, 2H), 9.91 (br s, 1H); MS (DCI/NH$_3$) m/e 408 (M+H)$^+$; Anal. calcd for C$_{19}$H$_{17}$F$_4$N$_5$O: C, 56.02; H, 4.21; N, 17.19. Found: C, 55.88; H, 4.14; N, 17.15.

EXAMPLE 26

2-[4-(3-cyano-2-pyridinyl)-1-piperazinyl]-N-[2-fluoro-3-(trifluoromethyl)phenyl]acetamide

EXAMPLE 26A 2-chloro-N-(2-fluoro-3-trifluoromethylphenyl)acetamide

The procedure described in Example 22A was followed, substituting 2-fluoro-3-(trifluoromethyl)aniline (Acros) for 3,4,5-trimethoxyaniline, to provide the title compound (72% yield) as a white solid. $^1$H NMR (300 MHz, DMSO-d$_6$) δ 4.39 (m, 2H), 7.41 (dd, 1H, J=8.2, 8.2 Hz), 7.57 (dd, 1H, J=6.5 Hz), 8.18 (dd, 1H, J=7.1 Hz), 10.37 (br s, 1H).

EXAMPLE 26B

2-[4-(3-cyano-2-pyridinyl)-1-piperazinyl]-N-[2-fluoro-3-(trifluoromethyl)phenyl]acetamide The procedure described in Example 8 was followed, substituting the product from Example 26A for N-chloroacetyl-3-nitroaniline, to provide the title compound (66% yield) as a white solid. mp 118-121° C.; $^1$H NMR (300 MHz, DMSO-d$_6$) δ 2.72 (m, 4H), 3.30 (s, 2H), 3.68 (m, 4H), 6.94 (dd, 1H, J=7.5, 4.8 Hz), 7.40 (dd, 1H, J=8.1, 8.1 Hz), 7.54 (m, 1H), 8.08 (dd, 1H, J=7.8, 2.0 Hz), 8.23 (dd, 1H, J=8.5, 8.5 Hz), 8.42 (dd, 1H, J=5.1, 2.1 Hz), 9.90 (br s, 1H); MS (DCI/NH$_3$) m/e 408 (M+H)$^+$; Anal. calcd for C$_{19}$H$_{17}$F$_4$N$_5$O: C, 56.02; H, 4.21; N, 17.19. Found: C, 55.82; H, 4.20; N, 17.18.

EXAMPLE 27

2-[4-(3-cyano-2-pyridinyl)-1-piperazinyl]-N-(4-fluoro-3-methylphenyl)acetamide

EXAMPLE 27A 2-chloro-N-(4-fluoro-3-methylphenyl)acetamide

The procedure described in Example 16A was followed, substituting 4-fluoro-3-methylaniline (Lancaster) for 3,5-dimethylaniline, to provide the title compound (83% yield) as a white solid. $^1$H NMR (300 MHz, DMSO-d$_6$) δ 2.21 (d, 3H, J=2.1 Hz), 4.23 (s, 2H), 7.10 (dd, 1H, J=9.2, 9.2 Hz), 7.40 (m, 1H), 7.49 (dd, 1H, J=7.1, 2.4 Hz), 10.25 (br s, 1H); MS (DCI/NH$_3$) m/e 219 (M+NH$_4$)$^+$.

EXAMPLE 27B

2-[4-(3-cyano-2-pyridinyl)-1-piperazinyl]-N-(4-fluoro-3-methylphenyl)acetamide

The procedure described in Example 8 was followed, substituting the product from Example 27A for N-chloroacetyl-3-nitroaniline, to provide the title compound (67% yield) as a light tan solid. mp 111-113° C.; $^1$H NMR (300 MHz, DMSO-d$_6$) δ 2.21 (d, 3H, J=1.7 Hz), 2.67 (m, 4H), 3.19 (s, 2H), 3.68 (m, 4H), 6.93 (dd, 1H, J=7.6, 4.8 Hz), 7.07 (dd, 1H, J=9.2, 9.2 Hz), 7.49 (m, 1H), 7.55 (m, 1H), 8.07 (dd, 1H, J=7.5, 2.1 Hz), 8.41 (dd, 1H, J=4.7, 2.0 Hz), 9.74 (br s, 1H); MS (DCI/NH$_3$) m/e 354 (M+H)$^+$; Anal. calcd for C$_{19}$H$_{20}$FN$_5$O; C, 64.57; H, 5.70; N, 19.82. Found: C, 64.34; H, 5.73; N, 19.83.

EXAMPLE 28

2-[4-(3-cyano-2-pyridinyl)-1-piperazinyl]-N-(2-fluorophenyl)acetamide

EXAMPLE 28A 2-chloro-N-(2-fluorophenyl)acetamide

The procedure described in Example 22A was followed, substituting 2-fluoroaniline (Aldrich) for 3,4,5-trimethoxyaniline, to provide the title compound (88% yield) as a white solid. $^1$H NMR (300 MHz, DMSO-d$_6$) δ 4.35 (s, 2H), 7.23 (m, 3H), 7.87 (m, 1H), 10.17 (br s, 1H); MS (DCI/NH$_3$) m/e 188 (M+H)$^+$.

EXAMPLE 28B

2-[4-(3-cyano-2-pyridinyl)-1-piperazinyl]-N-(2-fluorophenyl)acetamide

The procedure described in Example 8 was followed, substituting the product from Example 28A for N-chloroacetyl-3-nitroaniline, to provide the title compound (42% yield) as a white solid. mp 78-79° C.; $^1$H NMR (300 MHz, DMSO-d$_6$) δ 2.71 (m, 4H), 3.27 (s, 2H), 3.67 (m, 4H), 6.94 (dd, 1H, J=7.8, 4.8 Hz), 7.18 (m, 2H), 7.26 (m, 1H), 7.98 (m, 1H), 8.08 (dd, 1H, J=7.8, 2.0 Hz), 8.42 (dd, 1H, J=5.1, 2.1 Hz), 9.65 (br s, 1H); MS (DCI/NH$_3$) m/e 340 (M+H)$^+$; Anal. calcd for C$_{18}$H$_{18}$FN$_5$O: C, 63.70; H, 5.35; N, 20.64. Found: C, 63.48; H, 5.32; N, 20.54.

EXAMPLE 29

2-[4-(3-cyano-2-pyridinyl)-1-piperazinyl]-N-(2-methoxyphenyl)acetamide

EXAMPLE 29A 2-chloro-N-(2-methoxyphenyl)acetamide

The procedure described in Example 22A was followed, substituting 2-methoxyaniline (Acros) for 3,4,5-trimethoxyaniline, to provide the title compound (83% yield) as a brown solid. $^1$H NMR (300 MHz, DMSO-d$_6$) δ 3.85 (s, 3H), 4.38 (s, 2H), 6.92 (m, 1H), 7.08 (m, 2H), 7.91 (d, 1H, J=7.8 Hz), 9.48 (br s, 1H); MS (DCI/NH$_3$) m/e 200 (M+H)$^+$.

EXAMPLE 29B

2-[4-(3-cyano-2-pyridinyl)-1-piperazinyl]-N-(2-methoxyphenyl)acetamide

The procedure described in Example 8 was followed, substituting the product from Example 29A for N-chloroacetyl-3-nitroaniline, to provide the title compound (34% yield) as a white solid. mp 174-175° C.; $^1$H NMR (300 MHz, DMSO-d$_6$) δ 2.71 (m, 4H), 3.22 (s, 2H), 3.70 (m, 4H), 3.88 (s, 3H), 6.96 (m, 2H), 7.07 (m, 2H), 8.10 (dd, 1H, J=7.8, 2.1 Hz), 8.21 (d, 1H, J=7.8 Hz), 8.44 (dd, 1H, 4.7, 1.7 Hz), 9.73 (br s, 1H); MS (DCI/NH$_3$) m/e 352 (M+H)$^+$;

Anal. calcd for $C_{19}H_{21}N_5O_2$: C, 64.94; H, 6.02; N, 19.93. Found: C, 64.70; H, 5.95; N, 19.71.

EXAMPLE 30

2-[4-(3-cyano-2-pyridinyl)-1-piperazinyl]-N-(2-nitrophenyl)acetamide

EXAMPLE 30A 2-chloro-N-(2-nitrophenyl)acetamide

The procedure described in Example 22A was followed, substituting 2-nitroaniline (Aldrich) for 3,4,5-trimethoxyaniline to provide the title compound (94% yield) as a yellow solid. $^1$H NMR (300 MHz, DMSO-d$_6$) δ 4.38 (s, 2H), 7.41 (ddd, 1H, J=8.1, 7.1, 1.7 Hz), 7.77 (m, 2H), 8.03 (dd, 1H, J=8.2, 1.4 Hz), 10.68 (br s, 1H); MS (DCI/NH$_3$) m/e 232 (M+NH$_4$)$^+$.

EXAMPLE 30B

2-[4-(3-cyano-2-pyridinyl)-1-piperazinyl]-N-(2-nitrophenyl)acetamide

The procedure described in Example 8 was followed, substituting the product from Example 30A for N-chloroacetyl-3-nitroaniline, to provide the title compound (39% yield) as a yellow solid. mp 134-136° C.; $^1$H NMR (300 MHz, DMSO-d$_6$) δ2.75 (m, 4H), 3.29 (s, 2H), 3.72 (m, 4H), 6.96 (dd, 1H, J=7.8, 4.8 Hz), 7.32 (ddd, 1H, J=8.5, 7.1, 1.4 Hz), 7.78(ddd, 1H, J=8.8, 7.4, 1.6 Hz), 8.10 (dd, 1H, J=7.8, 2.1 Hz), 8.20 (dd, 1H, J=8.2, 1.4 Hz), 8.44 (dd, 1H, J=5.1, 2.0 Hz), 8.61 (dd, 1H, J=8.5, 1.4 Hz), 11.55 (br s, 1H); MS (DCI/NH$_3$) m/e 367 (M+H)$^+$; Anal. calcd for $C_{18}H_{18}N_6O$: C, 59.01; H, 4.95; N, 22.94. Found: C, 58.87; H, 5.01; N, 23.08.

EXAMPLE 31

2-[4-(3-cyano-2-pyridinyl)-1-piperazinyl]-N-[2-(trifluoromethyl)phenyl]acetamide The procedure described in Example 8 was followed, substituting N-chloroacetyl-2-(trifluoromethyl)aniline (Apollo) for N-chloroacetyl-3-nitroaniline to provide the title compound (47% yield) as a colorless oil. $^1$H NMR (300 MHz, DMSO-d$_6$) δ 2.74 (m, 4H), 3.27 (s, 2H), 3.65 (m, 4H), 6.97 (dd, 1H, J=7.5, 4.8 Hz), 7.36 (dd, 1H, J=7.8, 7.8 Hz), 7.69 (d, 1H, J=7.5 Hz), 7.73 (dd, 1H, J=8.1, 8.1 Hz), 8.10 (dd, 1H, J=8.1, 2.0 Hz), 8.21 (d, 1H, J=8.5 Hz), 8.44 (dd, 1H, J=4.7, 2.3 Hz), 9.89 (br s, 1H); MS (DCI/NH$_3$) m/e 390 (M+H)$^+$. Maleate salt: white solid, mp 143-145° C.; Anal. calcd for $C_{19}H_{18}F_3N_5O \cdot 1.0\ C_4H_4O_4$: C, 54.65; H, 4.39; N, 13.86. Found: C, 54.61; H, 4.32; N, 13.83.

EXAMPLE 32

N-phenyl-2-[4-(2-pyridinyl)-1-piperazinyl]acetamide

N-Chloroacetylaniline (0.5 g, 2.95 mmol), 1-(2-pyridinyl) piperazine (0.72 g, 4.42 mmol), and N,N-diisopropylethylamine (1.03 mL, 5.9 mmol) were combined in toluene and heated at reflux overnight. The mixture was allowed to cool to room temperature, filtered, and the filtrate concentrated under reduced pressure. The residue was purified by flash column chromatography on silica gel (elution with 60% ethyl acetate: hexanes) to provide 400 mg (46% yield) of the title compound as a hygroscopic white solid. $^1$H NMR (300 MHz, CDCl$_3$) δ 2.60 (m, 4H), 3.18 (s, 2H), 3.55 (m, 4H), 6.65 (dd, 1H, J=12, 6 Hz), 6.85 (d, 1H, J=9 Hz), 7.05 (t, 1H, J=6 Hz), 7.3 (t, 2H, J=9 Hz), 7.51 (ddd, 1H, J=9, 7.5, 3 Hz) 7.68 (d, 2H, J=9 Hz) 8.1 (dd, 1H, J=6, 3 Hz) 9.75 (br s, 1H); MS (DCI/NH$_3$) m/e 297 (M+H)$^+$; Anal. calcd for $C_{17}H_{20}N_4O$: C, 68.89; H, 6.80; N, 18.90. Found: C, 68.97; H, 6.87; N, 19.01.

EXAMPLE 33

N-(3-methylphenyl)-2-[4-(1,3-thiazol-2-yl)-1-piperazinyl]acetamide

EXAMPLE 33A 2-chloro-N-(3-methylphenyl)acetamide

3-Methylaniline (1 g, 9.3 mmol) in 2N aqueous sodium hydroxide (30 mL) was treated with chloroacetyl chloride (0.82 mL, 10.27 mmol) dropwise at room temperature as a solution in dichloromethane. After 18 hours, the reaction mixture was quenched with water and the layers separated. The organic phase was washed with an aqueous solution of 1N HCl and dried over MgSO$_4$, filtered and the filtrate concentrated under reduced pressure to provide 1.3 g (76%) of the title compound as a white solid. $^1$H NMR (300 MHz, CDCl$_3$) δ 2.35 (s, 3H), 4.20 (s, 2H), 7.00 (s, 1H), 7.22 (m, 1H), 7.35-7.45 (m, 2H), 8.15 (br s, 1H); MS (DCI/NH$_3$) m/e 201 (M+NH$_4$)$^+$.

EXAMPLE 33B 1-(1,3-thiazol-2-yl)piperazine

The procedure described in J. Med. Chem 1996, 39(7), 1431 was followed to provide the title compound. A mixture of 2-bromothiazole (3 g, 18.3 mmol) and piperazine (3.15 g, 36.6 mmol) was refluxed in n-butanol for 18 hours. The reaction mixture was allowed to cool to room temperature and concentrated under reduced pressure. The residue was treated with an aqueous solution of 10% K$_2$CO$_3$ and extracted with ethyl acetate. The organic phase was dried over MgSO$_4$, filtered, and the filtrate concentrated under reduced pressure to provide 2.7 g (87%) of the title compound as brown oil used directly in the next step without further purification. $^1$H NMR (300 MHz, CDCl$_3$) δ 2.99 (m, 4H), 3.47 (m, 4H), 6.57 (d, 1H, J=4.5 Hz), 7.20 (d, 1H, J=4.5 Hz); MS (DCI/NH$_3$) m/e 170 (M+H)$^+$.

EXAMPLE 33C

N-(3-methylphenyl)-2-[4-(1,3-thiazol-2-yl)-1-piperazinyl]acetamide

The product from Example 33A (0.2 g, 1.18 mmol), the product from Example 33B (0.25 g, 1.48 mmol) and N,N-diisopropylethylamine (0.41 mL, 2.3 mmol) were combined in toluene (25 mL) and heated at reflux overnight. The reaction was allowed to cool to room temperature, filtered, and the filtrate was concentrated under reduced pressure. The residue was purified by column chromatography on silica gel (elution with 50% ethyl acetate:hexanes) to provide 0.08 g (22%) of the desired material as a white solid. mp 151-153° C.; $^1$H NMR (300 MHz, DMSO-d$_6$) δ 2.28 (s, 3H), 2.65 (m, 4H), 3.20 (s, 2H), 3.48 (m, 4H), 6.85 (m, 2H), 7.18 (m, 2H), 7.48 (m, 2H), 9.65 (s, 1H); MS (DCI/NH$_3$) m/e 317 (M+H)$^+$; Anal calcd for $C_{16}H_{20}N_4OS$: C, 60.73; H. 6.37; N, 17.71. Found: C, 60.66; H, 6.24; N, 17.35.

EXAMPLE 34

2-[4-(3-cyano-2-pyridinyl)-1-piperazinyl]-N-(4-methylphenyl)acetamide

EXAMPLE 34A 2-chloro-N-(4-methylphenyl)acetamide

The procedure described in Example 33A was followed, substituting 4-methylaniline for 3-methylaniline, to provide a white solid. $^1$H NMR (300 MHz, CDCl$_3$) δ 2.30 (s, 3H), 4.20 (s, 2H), 7.15 (d, 2H, J=9 Hz), 7.41 (m, 2H), 8.15 (br s, 1H); MS (DCI/NH$_3$) m/e 201 (M+NH$_4$)$^+$.

EXAMPLE 34B

2-[4-(3-cyano-2-pyridinyl)-1-piperazinyl]-N-(4-methylphenyl)acetamide

The product from Example 34A (0.4 g, 2.18 mmol), 1-(2-cyanopyridinyl)piperazine (0.62 g, 3.3 mmol) and N,N-diisopropylethylamine (0.76 mL, 4.36 mmol) in toluene (50 mL) were heated at reflux. After 18 hours, the reaction mixture was allowed to cool to room temperature, filtered, and the filtrate was concentrated under reduced pressure. The residue purified by column chromatography on silica gel (elution with 60% ethyl acetate:hexanes) to provide 0.51 g (70%) of the desired material as a yellow oil. $^1$H NMR (300 MHz, CDCl$_3$) δ 2.30 (s, 3H), 2.80 (m, 4H), 3.25 (s, 2H), 3.80 (m, 4H), 6.80 (dd, 1H, J=12, 6 Hz), 7.12 (d, 2H, J=9 Hz), 7.48 (d, 2H, J=9 Hz), 7.80 (dd, 1H, J=9, 3 Hz), 8.38 (dd, 1H, J=6, 3 Hz), 9.10 (br, s, 1H); MS (DCI/NH$_3$) m/e 336 (M+H)$^+$; maleate salt: obtained as an off-white powder; mp 156-158° C. ; Anal. calcd for C$_{23}$H$_{25}$N$_5$O$_5$.0.20 H$_2$O: C, 60.70; H, 5.63; N, 15.39. Found: C, 60.33; H, 5.55; N, 15.10.

EXAMPLE 35

2-[4-(2-methoxyphenyl)-1-piperidinyl]-N-(3-methylphenyl)acetamide 4-(2-Methoxyphenyl)piperidine (200 mg, 1 mmol), the product from Example 1A (228 mg, 1 mmol) and N,N-diisopropylethylamine (0.185 mL, 1.1 mmol) in toluene (8 mL) were stirred at 60° C. for 18 hours. The reaction mixture was poured into water (30 mL) and extracted with ethyl acetate (30 mL). The organic layer was washed with brine (2×30 mL), dried over MgSO$_4$, filtered and the filtrate concentrated under reduced pressure. The residue was purified by flash chromatography on silica gel (elution with dichloromethane:methanol, 9.5:0.5) to provide the title compound 177 mg (52.3%). $^1$H NMR (300 MHz, DMSO-d$_6$) δ 1.71 (m, 4H), 2.28 (m, 5H), 2.89 (m, 1H), 2.96 (m, 2H), 3.13 (s, 2H), 3.78 (s, 3H), 6.91 (m, 3H), 7.20 (m, 3H), 7.45 (m, 2H), 8.69 (s, 1H); MS (DCI/NH$_3$) m/e 339 (M+H)$^+$. Anal. calcd for C$_{21}$H$_{26}$N$_2$O$_2$: C, 74.52; H, 7.74; N, 8.28. Found: C, 74.23, H, 7.71, N, 8.26.

EXAMPLE 36

N-(3-methylphenyl)-2-[4-(2-pyridinyl)-1-piperidinyl]acetamide

EXAMPLE 36A benzyl 4-hydroxy-4-(2-pyridinyl)-1-piperidinecarboxylate

2-Bromopyridine (0.470 mL, 5 mmol) in THF (20 mL) was treated with n-BuLi 1.6M in hexanes (5.2 ml, 5.2 mmol) dropwise at −60° C. After stirring at -60° C. for 30 minutes, the reaction mixture and treated with benzyl 4-oxo-1-piperidinecarboxylate (1.14 g, 4.9 mmol) in THF (10 mL) slowly. After stirring an additional 15 minutes at −60° C., the reaction mixture was quenched with a saturated aqueous solution of NH$_4$Cl, allowed to warm to room temperature and was extracted into dichloromethane. The organics were combined, dried on MgSO$_4$, filtered, and the filtrate was concentrated under reduced pressure. The residue was purified by flash chromatography on silica gel (elution with hexanes:ethyl acetate, 1:1) to provide the title compound (400 mg, 27% yield). $^1$H NMR (300 MHz, DMSO-d$_6$) δ 1.54 (m, 2H), 2.05 (m, 2H), 3.25 (m, 2H), 3.95 (m, 2H), 5.11 (s, 2H), 5.35 (s, 1H), 7.25 (m, 1H), 7.35 (m, 5H), 7.68 (m, 1H), 7.79 (m, 1H), 8.5 (m, 1H); MS (DCI/NH$_3$) m/e 313 (M+H)$^+$.

EXAMPLE 36B benzyl 3',6'-dihydro-2,4'-bipyridine-1'(2'H)-carboxylate

The product from Example 36A (400 mg, 1.28 mmol) in thionyl chloride (6 mL) was refluxed for 3 hours, allowed to cool to room temperature, and concentrated under reduced pressure. The residue was treated with ice and 40% aqueous sodium hydroxide then extracted into dichloromethane, washed with brine, dried (Na$_2$SO$_4$), filtered, and the filtrate concentrated under reduced pressure to provide the title compound (332 mg).

EXAMPLE 36C 2-(4-piperidinyl)pyridine

The product from Example 36B was treated with 10% Pd/C (250 mg) at 60 psi and 50° C. for 40 hours to provide the title compound (150 mg, 88% yield). MS (DCI/NH$_3$) m/e 163 (M+H)$^+$.

EXAMPLE 36D

N-(3-methylphenyl)-2-[4-(2-pyridinyl)-1-piperidinyl]acetamide

The product from Example 36C (200 mg, 1 mmol), the product from Example 1A (228 mg, 1 mmol) and N,N-diisopropylethylamine (0.185 mL, 1.1 mmol) in toluene (8 mL) were stirred at 60° C. for 18 hours. The reaction mixture was poured into water (30 mL) and extracted with ethyl acetate (20 mL). The organic layer was washed with brine (2×30 mL), dried over MgSO$_4$, filtered, and the filtrate was concentrated under reduced pressure. The residue was purified by flash chromatography on silica gel (elution with ethyl acetate:ethanol, 9.2:0.8) to provide the title compound (169 mg, 55%). $^1$H NMR (300 MHz, DMSO-d$_6$) δ 1.83 (m, 4H), 2.24 (m, 5H), 2.64 (m, 1H), 2.98 (m, 2H), 3.12 (s, 2H), 6.88 (d, 1H, J=6 Hz), 7.20 (m, 2H), 7.30 (d, 1H, J=6 Hz), 7.45 (d, 2H, J=6 Hz), 7.71 (m, 1H), 8.51 (m, 1H), 9.59 (br s, 1H); MS (DCI/

NH$_3$) m/e 310 (M+H)$^+$. Anal. calcd for C$_{19}$H$_{23}$N$_3$O.0.15 H$_2$O: C, 73.12; H, 7.52; N, 13.46. Found: C, 72.72, H, 7.24, N, 13.28.

EXAMPLE 37

2-[4-(2-fluorophenyl)-1-piperidinyl]-N-(3-methylphenyl)acetamide

The procedure described in Example 35 was followed, substituting 4-(2-fluorophenyl)piperidine for 4-(2-methoxyphenyl)piperidine (89 mg, 80.9% yield), to provide the title compound (89 mg, 80.9% yield). $^1$H NMR (300 MHz, DMSO-d$_6$) δ 1.72 (m, 2H), 1.85 (m, 2H), 2.29 (m, 5H), 2.51 (m, 1H), 2.80 (m, 1H), 2.97 (m, 2H), 3.12 (s, 2H), 6.88 (d, 1H, J=6 Hz), 7.19 (m, 4H), 7.42 (m, 3H), 9.61 (br s, 1H); MS (DCI/NH$_3$) m/e 327 (M+H)$^+$.

Anal. calcd for C$_{20}$H$_{23}$FN$_2$O: C, 73.59; H, 7.10; N, 8.58. Found: C, 73.49, H, 6.97, N, 8.30.

EXAMPLE 38

N-(3-methylphenyl)-2-[4-(2-methylphenyl)-1-piperidinyl]acetamide

The procedure described in Example 35 was followed, substituting 4-(2-methylphenyl)piperidine for 4-(2-methoxyphenyl)piperidine, to provide the title compound (65 mg, 87.8% yield). $^1$H NMR (300 MHz, DMSO-d$_6$) δ 1.72 (m, 2H), 1.79 (m, 2H), 2.29 (m, 8H), 2.69 (m, 1H), 2.97 (m, 2H), 3.12 (s, 2H), 6.88 (d, 1H, J=6 Hz), 7.13 (m, 4H), 7.28 (d, 1H, J=6 Hz), 7.47 (m, 2H), 9.61 (br s, 1H); MS (DCI/NH$_3$) m/e 323 (M+H)$^+$. Anal. calcd for C$_{21}$H$_{26}$N$_2$O: C, 78.22; H, 8.13; N, 8.69. Found: C, 77.86, H, 8.12, N, 8.51.

EXAMPLE 39

2-[4-(3-fluorophenyl)-1-piperidinyl]-N-(3-methylphenyl)acetamide

The procedure described in Example 35 was followed, substituting 4-(3-fluorophenyl)piperidine for 4-(2-methoxyphenyl)piperidine to provide the title compound (68 mg, 61.8% yield). $^1$H NMR (300 MHz, DMSO-d$_6$) δ 1.75 (m, 4H), 2.29 (m, 5H), 2.55 (m, 1H), 2.96 (m, 2H), 3.12 (s, 2H), 6.88 (d, 1H, J=6 Hz), 7.01 (m, 1H), 7.14 (m, 3H), 7.35 (m, 1H), 7.45 (m, 2H), 9.61 (br s, 1H); MS (DCI/NH$_3$) m/e 327 (M+H)$^+$.

EXAMPLE 40

N-(3-methylphenyl)-2-[4-(6-oxo-1(6H)-pyridazinyl)-1-piperidinyl]acetamide

EXAMPLE 40A tert-butyl 4-(6-oxo-1(6H)-pyridazinyl)-1-piperidinecarboxylate tert-Butyl 4-bromo-1-piperidinecarboxylate (1.00 g, 3.78 mmol) in DMF (20 mL) was treated with K$_2$CO$_3$ (523 mg, 3.78 mmol) and 3(2H)-pyridazinone (340 mg, 3.78 mmol) and then heated at 45° C. for 60 hours. The reaction mixture was allowed to cool to room temperature, poured into water (80 mL) and extracted with ethyl acetate (80 mL). The organic layer was washed with brine (3×50 mL), dried over MgSO$_4$, filtered, and the filtrate concentrated under reduced pressure. The residue was purified by flash chromatography on silica gel (elution with hexanes:ethyl acetate, 3:1) to provide the title compound (180 mg, 17% yield). $^1$H NMR (300 MHz, DMSO-d$_6$) δ 1.41 (s, 9H), 1.66 (m, 4H), 2.91 (m, 2H), 4.05 (m, 2H), 4.96 (m, 1H), 6.93 (dd, 1H, J=1.5, 9.0 Hz), 7.39 (dd, 1H, J=3.0, 9.0 Hz), 7.95 (dd, 1H, J=3.0, 9.0 Hz); (MS (DCI/NH$_3$) m/e 280 (M+H)$^+$.

EXAMPLE 40B 2-(4-piperidinyl)-3 (2H)-pyridazinone

The product from Example 40A (180 mg, 0.6 mmol) in dichloromethane (5 mL) was cooled to 0° C. and treated with trifluoroacetic acid (TFA) (0.46 mL, 6 mmol). After stirring at 0° C. for 3 hours, the reaction mixture was allowed to warm to room temperature and stirred an additional 3 hours. The reaction mixture was concentrated under reduced pressure and the residue was azeotroped with toluene (2×30 mL) to provide the title compound as the TFA salt (180 mg). $^1$H NMR (300 MHz, DMSO-d$_6$) δ 2.05 (m, 4H), 3.14 (m, 2H), 3.4 (m, 2H), 5.08 (m, 1H), 6.97 (dd, 1H, J=1.5, 9.0 Hz), 7.43 (dd, 1H, J=3.0, 9.0 Hz), 8.0 (dd, 1H, J=3.0, 9.0 Hz), 8.36 (br s, 1H), 8.70 (br s, 1H); (MS (DCI/NH$_3$) m/e 180 (M+H)$^+$.

EXAMPLE 40C

N-(3-methylphenyl)-2-[4-(6-oxo-1(6H)-pyridazinyl)-1-piperidinyl]acetamide

The product from Example 40B, as the TFA salt, (80 mg, 0.27 mmol), the product from Example 1A (0.062 g, 0.27 mmol), and K$_2$CO$_3$ (0.113 g, 0.81 mmol) were combined in toluene (8 mL) and stirred at room temperature for 18 hours. The reaction mixture was poured into water (30 mL) and extracted with ethyl acetate (20 mL). The organic layer was washed with brine (2×30 mL), dried over MgSO$_4$, filtered, and the filtrate concentrated under reduced pressure. The residue was purified by flash chromatography using ethyl acetate:ethanol, 9.7:0.3 to provide the title compound (89 mg, (100% yield). $^1$H NMR (300 MHz, DMSO-d$_6$) δ 1.74 (m, 2H), 2.01 (m, 2H), 2.29 (s, 3H), 2.35 (m, 2H), 3.0 (m, 2H), 3.15 (s, 2H), 4.78 (m, 1H), 6.88 (d, 1H, J=7.5 Hz), 6.93 (dd, 1H, J=1.5, 9.0 Hz), 7.19 (t, 1H J=7.5 Hz), 7.38 (dd, 1H, J=3.0, 9.0 Hz), 7.43 (d, 2H, J=7.5 Hz), 7.98 (dd, 1H, J=3.0, 9.0 Hz), 9.31 (br s, 1H); MS (DCI/NH$_3$) m/e 327 (M+H)$^+$.

EXAMPLE 41

N-(2,6-dimethylphenyl)-2-[4-(2-thienyl)-1-piperidinyl]acetamide 4-(2-Thienyl)piperidine hydrochloride (22 mg, 0.11 mmol), 2-chloro-N-(2,6-dimethylphenyl)acetamide (24 mg, 0.12 mmol), and sodium carbonate (50 mg) in N,N-dimethylformamide:water (2:1, 2 mL) was shaken at ambient temperature for 18 hours. The resulting mixture was concentrated under reduced pressure. The residue was purified by preparative HPLC to provide the title compound as a trifluoroacetic acid salt (30 mg, 62% yield). $^1$H NMR (300 MHz, DMSO-d$_6$) δ 2.00 (m, 2H), 2.19 (s, 6H), 2.20 (m, 2H), 3.15-3.30 (m, 3H), 3.60 (m, 2H), 4.22 (s, 2H), 6.97 (m, 1H), 7.00 (m, 1H), 7.16 (m, 3H), 7.40 (d, 1H, J=3 Hz), 9.85 (br s, 1H), 9.95 (s, 1H); MS (ESI APCI+) m/e 329 (M+H)$^+$.

EXAMPLE 42

N-(2,5-dimethylphenyl)-2-[4-(2-thienyl)-1-piperidinyl]acetamide

The procedure described in Example 41 was followed, substituting 2-chloro-N-(2,5-dimethylphenyl)acetamide for 2-chloro-N-(2,6-dimethylphenyl)acetamide, to provide the title compound (35 mg, 72% yield). $^1$H NMR (300 MHz, DMSO-$d_6$) δ 2.00 (m, 2H), 2.19 (s, 3H), 2.20 (m, 2H), 2.25 (s, 3H), 3.18-3.30 (m, 3H), 3.60 (m, 2H), 4.20 (s, 2H), 6.97 (m, 1H), 7.00 (m, 2H), 7.18 (d, 1H, J=6 Hz), 7.22 (s, 1H), 7.40 (d, 1H, J=3 Hz), 9.80 (br s, 1H), 9.90 (s, 1H); MS (ESI APCI+) m/e 329 (M+H)$^+$.

EXAMPLE 43

N-(2-methylphenyl)-2-[4-(2-thienyl)-1-piperidinyl]acetamide

The procedure described in Example 41 was followed, substituting 2-chloro-N-(2-methylphenyl)acetamide for 2-chloro-N-(2,6-dimethylphenyl)acetamide, to provide the title compound (30 mg, 64% yield). $^1$H NMR (300 MHz, DMSO-$d_6$) δ 2.00 (m, 2H), 2.20 (m, 2H), 2.22 (s, 3H), 3.18-3.30 (m, 3H), 3.60 (m, 2H), 4.20 (s, 2H), 6.97 (m, 1H), 7.00 (m, 1H), 7.18 (m, 1H), 7.22 (m, 1H), 7.28 (m, 1H), 7.40 (m, 2H), 9.82 (br s, 1H), 10.00 (s, 1H); MS (ESI APCI+) m/e 315 (M+H)$^+$.

EXAMPLE 44

N-(3-chloro-4-fluorophenyl)-2-[4-(2-thienyl)-1-piperidinyl]acetamide

The procedure described in Example 41 was followed, substituting 2-chloro-N-(3-chloro-4-fluorophenyl)acetamide for 2-chloro-N-(2,6-dimethylphenyl) acetamide, to provide the title compound (29 mg, 57% yield). 1H NMR (300 MHz, DMSO-$d_6$) δ 2.00 (m, 2H), 2.20 (m, 2H), 3.18-3.30 (m, 3H), 3.60 (m, 2H), 4.20 (s, 2H), 6.97 (m, 1H), 7.00 (m, 1H), 7.42 (m, 3H), 7.95 (d, 1H, J=3 Hz), 9.90 (br s, 1H), 10.75 (br s, 1H); MS (ESI APCI+) m/e 353 (M+H)$^+$.

EXAMPLE 45

N-(4-bromophenyl)-2-[4-(2-pyridinyl)-1-piperidinyl]acetamide

The product from Example 36C (hydrochloride, 20 mg, 0.10 mmol), N-(4-bromophenyl)-2-chloroacetamide (27 mg, 0.11 mmol), and sodium carbonate (50 mg) in DMF:water (2:1, 2 mL) was shaken at ambient temperature for 18 hours. The resulting mixture was decanted and concentrated under reduced pressure. The residue was purified by preparative HPLC to provide the title compound as a trifluoroacetic acid salt (34 mg, 70.9% yield). $^1$H NMR (500 MHz, DMSO-$d_6$) δ 2.10 (m, 4H), 3.02 (m, 1H), 3.26 (m, 2H), 3.62 (m, 2H), 4.21 (s, 2H), 7.28 (m, 2H), 7.56 (m, 4H), 7.82 (t, 1H, J=6 Hz), 8.26 (d, 1H, J=6 Hz), 9.90 (br s, 1H), 10.20 (br s, 1H); MS (ESI APCI+) m/e 373 (M–H)$^+$.

EXAMPLE 46

N-(2,6-dimethylphenyl)-2-[4-(2-pyridinyl)-1-piperidinyl]acetamide

The procedure described in Example 45 was followed, substituting 2-chloro-N-(2,6-dimethylphenyl)acetamide for N-(4-bromophenyl)-2-chloroacetamide, to provide the title compound (31 mg, 70.3% yield). $^1$H NMR (500 MHz, DMSO-$d_6$) δ 2.10 (m, 4H), 2.18 (s, 6H), 3.02 (m, 1H), 3.31 (m, 2H), 3.62 (m, 2H), 4.25 (s, 2H), 7.12 (m, 3H), 7.32 (t, 1H, J=4 Hz), 7.28 (d, 1H, J=6 Hz), 7.82 (t, 1H, J=6 Hz), 8.66 (d, 1H, J=4 Hz), 9.90 (br s, 1H), 9.98 (s, 1H); MS (ESI APCI+) m/e 324 (M+H)$^+$.

EXAMPLE 47

N-(2-nitrophenyl)-2-[4-(2-pyridinyl)-1-piperidinyl]acetamide

The procedure described in Example 45 was followed, substituting 2-chloro-N-(2-nitrophenyl)acetamide for N-(4-bromophenyl)-2-chloroacetamide, to provide the title compound (43 mg, 90% yield). $^1$H NMR (500 MHz, DMSO-$d_6$) δ 2.10 (m, 4H), 3.02 (m, 1H), 3.31 (m, 2H), 3.62 (m, 2H), 4.25 (s, 2H), 7.22 (m, 2H), 7.45 (t, 1H, J=4 Hz), 7.65 (m, 1H), 7.80 (m, 2H), 8.01 (d, 1H, J=6 Hz), 8.58 (d, 1H, J=4 Hz), 10.00 (br s, 1H), 11.02 (s, 1H); MS (ESI APCI+) m/e 341 (M+H)$^+$.

EXAMPLE 48

N-(3-nitrophenyl)-2-[4-(2-pyridinyl)-1-piperidinyl]acetamide

The procedure described in Example 45 was followed, substituting 2-chloro-N-(3-nitrophenyl)acetamide for N-(4-bromophenyl)-2-chloroacetamide, to provide the title compound (25 mg, 55% yield). $^1$H NMR (500 MHz, DMSO-$d_6$) δ 2.10 (m, 4H), 3.02 (m, 1H), 3.31 (m, 2H), 3.62 (m, 2H), 4.25 (s, 2H), 7.38 (m, 2H), 7.70 (t, 1H, J=6 Hz), 7.82 (t, 1H, J=4 Hz), 7.92 (d, 1H, J=6 Hz), 9.02 (d, 1H, J=4 Hz), 8.58 (d, 1H, J=4 Hz), 8.65 (s, 1H), 10.00 (br s, 1H), 11.12 (s, 1H); MS (ESI APCI+) m/e 341 (M+H)$^+$.

EXAMPLE 49

N-(2,4-difluorophenyl)-2-[4-(2-pyridinyl)-1-piperidinyl]acetamide

The procedure described in Example 45 was followed, substituting 2-chloro-N-(2,4-difluorophenyl)acetamide for N-(4-bromophenyl)-2-chloroacetamide, to provide the title compound (26 mg, 59% yield). $^1$H NMR (500 MHz, DMSO-$d_6$) δ 2.08 (m, 4H), 3.02 (m, 1H), 3.31 (m, 2H), 3.62 (m, 2H), 4.20 (s, 2H), 7.15 (m, 1H), 7.28 (m, 3H), 7.82 (m, 2H), 8.58 (d, 1H, J=4 Hz), 9.92 (br s, 1H), 10.52 (s, 1H); MS (ESI APCI+) m/e 332 (M+H)$^+$.

EXAMPLE 50

N-(2,5-dimethylphenyl)-2-[4-(2-pyridinyl)-1-piperidinyl]acetamide

The procedure described in Example 45 was followed, substituting 2-chloro-N-(2,5-dimethylphenyl)acetamide for N-(4-bromophenyl)-2-chloroacetamide, to provide the title compound (12.2 mg, 28% yield). $^1$H NMR (500 MHz, DMSO-$d_6$) δ 2.10 (m, 4H), 2.18 (s, 3H), 2.28 (s, 3H), 3.05 (m, 1H), 3.31 (m, 2H), 3.65 (m, 2H), 4.25 (s, 2H), 6.98 (d, 1H, J=6 Hz), 7.15 (d, 1H, J=6 Hz), 7.22 (s, 1H), 7.38 (m, 2H), 7.82 (t, 1H, J=4 Hz), 8.58 (d, 1H, J=4 Hz), 9.90 (br s, 1H), 9.98 (s, 1H); MS (ESI APCI+) m/e 324 (M+H)$^+$.

EXAMPLE 51

N-(2-methylphenyl)-2-[4-(2-pyridinyl)-1-piperidinyl]acetamide

The procedure described in Example 45 was followed, substituting 2-chloro-N-(2-methylphenyl)acetamide for N-(4-bromophenyl)-2-chloroacetamide, to provide the title compound (16 mg, 37% yield). $^1$HNMR (500 MHz, DMSO-d$_6$) δ 2.10 (m, 4H), 2.12 (s, 3H), 3.05 (m, 1H), 3.28 (m, 2H), 3.65 (m, 2H), 4.22 (s, 2H), 7.10 (m, 3H), 7.85 (t, 1H, J=4 Hz), 8.58 (d, 1H, J=4 Hz), 9.90 (br s, 1H), 9.98 (s, 1H); MS (ESI APCI +) m/e 310 (M+H)$^+$.

EXAMPLE 52

N-(4-methylphenyl)-2-[4-(2-pyridinyl)-1-piperidinyl]acetamide

The procedure described in Example 45 was followed, substituting 2-chloro-N-(4-methylphenyl) acetamide for N-(4-bromophenyl)-2-chloroacetamide, to provide the title compound (29 mg, 68% yield). $^1$H NMR (500 MHz, DMSO-d$_6$) δ 2.10 (m, 4H), 2.32 (s, 3H), 3.05 (m, 1H), 3.28 (m, 2H), 3.65 (m, 2H), 4.22 (s, 2H), 7.18 (d, 2H, J=6 Hz), 7.38 (t, 1H, J=4 Hz), 7.42 (d, 1H, J=4 Hz), 7.50 (d, 2H, J=6 Hz), 7.85 (t, 1H, J=4 Hz), 8.58 (d, 1H, J=4 Hz), 9.90 (br s, 1H), 10.55 (s, 1H); MS (ESI APCI+) m/e 310 (M+H)$^+$.

EXAMPLE 53

2-[4-(2-pyridinyl)-1-piperidinyl]-N-[3-(trifluoromethyl)phenyl]acetamide

The procedure described in Example 45 was followed, substituting 2-chloro-N-(3-trifluromethylphenyl)acetamide for N-(4-bromophenyl)-2-chloroacetamide, to provide the title compound (34 mg, 71% yield). $^1$H NMR (500 MHz, DMSO-d$_6$) δ 2.05 (m, 4H), 2.95 (m, 1H), 3.28 (m, 2H), 3.65 (m, 2H), 4.12 (s, 2H), 7.22 (t, 1H, J=4 Hz), 7.35 (d, 1H, J=4 Hz), 7.42 (d, 1H, J=4 Hz), 7.60 (t, 1H, J=4 Hz), 7.75 (t, 1H, J=4 Hz), 7.85 (d, 1H, J=4 Hz), 8.12 (s, 1H), 8.52 (d, 1H, J=4 Hz), 9.95 (br s, 1H), 10.75 (br s, 1H); MS (ESI APCI+) m/e 364 (M+H)$^+$.

EXAMPLE 54 ethyl 4-({[4-(2-pyridinyl)-1-piperidinyl]acetyl}amino)benzoate

The procedure described in Example 45 was followed, substituting ethyl 4-[(chloroacetyl)amino]benzoate for N-(4-bromophenyl)-2-chloroacetamide, to provide the title compound (30 mg, 62% yield). $^1$H NMR (500 MHz, DMSO-d$_6$) δ 1.28 (t, 3H, J=4 Hz), 1.98 (m, 6H), 2.41 (m, 2H), 2.72 (m, 1H), 3.01 (m, 2H), 3.20 (s, 2H), 4.28 (dd, 2H, J=4, 4 Hz), 7.22 (t, 1H, J=3 Hz), 7.30 (d, 1H, J=4 Hz), 7.78 (m, 3H), 7.95 (d, 2H, J=3 Hz), 8.55 (s, 1H), 9.90 (br s, 1H), 10.55 (br s, 1H); MS (ESI APCI+) m/e 368 (M+H)$^+$.

EXAMPLE 55

N-(3-chloro-4-methylphenyl)-2-[4-(2-pyridinyl)-1-piperidinyl]acetamide

The procedure described in Example 45 was followed, substituting 2-chloro-N-(3-chloro-4-methylphenyl)acetamide for N-(4-bromophenyl)-2-chloroacetamide, to provide the title compound (33 mg, 72% yield). $^1$H NMR (500 MHz, DMSO-d$_6$) δ 2.02 (m, 5H), 2.28 (s, 3H), 2.91 (m, 1H), 3.28 (m, 3H), 4.02 (s, 2H), 7.22 (t, 1H, J=4 Hz), 7.35 (d, 1H, J=4 Hz), 7.45 (d, 1H, J=4 Hz), 7.75 (t, 2H, J=4 Hz), 7.80 (s, 1H), 8.52 (d, 1H, J=4 Hz), 9.95 (br s, 1H), 10.75 (br s, 1H); MS (ESI APCI+) m/e 344 (M+H)$^+$.

EXAMPLE 56

N-(2-cyanophenyl)-2-[4-(2-pyridinyl)-1-piperidinyl]acetamide

The procedure described in Example 45 was followed, substituting 2-chloro-N-(2-cyanophenyl)acetamide for N-(4-bromophenyl)-2-chloroacetamide, to provide the title compound (27 mg, 63% yield). $^1$H NMR (500 MHz, DMSO-d$_6$) δ 2.02 (m, 4H), 2.91 (m, 1H), 3.28 (m, 2H), 3.65 (m, 2H), 4.22 (s, 2H), 7.22-7.45 (m, 3H), 7.75-7.85 (m, 4H), 8.52 (m, 1H), 9.95 (br s, 1H), 10.85 (br s, 1H); MS (ESI APCI+) m/e 321 (M+H)$^+$.

EXAMPLE 57

N-(3-chlorophenyl)-2-[4-(2-pyridinyl)-1-piperidinyl]acetamide

The procedure described in Example 45 was followed, substituting 2-chloro-N-(3-chlorophenyl)acetamide for N-(4-bromophenyl)-2-chloroacetamide, to provide the title compound (16 mg, 36% yield). $^1$H NMR (500 MHz, DMSO-d$_6$) δ 2.05 (m, 4H), 2.98 (m, 3H), 3.65 (m, 2H), 4.02 (s, 2H), 7.22 (t, 1H, J=4 Hz), 7.35 (d, 1H, J=4 Hz), 7.42 (d, 1H, J=4 Hz), 7.60 (t, 1H, J=4 Hz), 7.75 (t, 1H, J=4 Hz), 7.85 (d, 1H, J=4 Hz), 8.12 (s, 1H), 8.52 (d, 1H, J=4 Hz), 9.95 (br s, 1H), 10.75 (br s, 1H); MS (ESI APCI+) m/e 330 (M+H)$^+$.

EXAMPLE 58

2-[4-(3-cyano-2-pyridinyl)-1-piperidinyl]-N-(3-methylphenyl)acetamide

EXAMPLE 58A benzyl 4-{[(trifluoromethyl)sulfonyl]oxy}-3,6-dihydro-1(2H)-pyridinecarboxylate The title compound was prepared according to the procedure described in J. Org. Chem. 1998, 63, 8320. Benzyl 4-oxo-1-piperidinecarboxylate (0.5 g, 2.1 mmol) and N-phenytrifluoromethanesulfonimide (1.15 g, 3.2 mmol) in tetrahydrofuran (10 mL) at −78° C. was treated with lithium hexamethyldisilazide (2.14 mL, 2.1 mmol). After 4 hours at −78° C., the mixture was quenched with water and extracted with a large excess of diethyl ether (3×). The ethereal layers were combined, dried over sodium sulfate, filtered, and the filtrate concentrated under reduced pressure. The residue was chromatographed on flash silica gel (20% ethyl acetate:hexanes) to provide the title compound (0.471 g, 60% yield). $^1$H NMR (300 MHz, CDCl$_3$) δ 2.47 (m, 2H), 3.72 (m, 2H), 4.13 (m, 2H), 5.16 (s, 2H), 5.78 (br m, 1H), 7.36 (m, 5H); MS (ESI) m/e 366 (M+H)$^+$.

EXAMPLE 58B benzyl 4-(4,4,5,5-tetramethyl-1,3,2-dioxaborolan-2-yl)-3,6-dihydro-1(2H)-pyridinecarboxylate The title compound was prepared according to the procedure described in Tetrahedron Lett. 2000, 41 3705. Bis(pinacolato)diborane (338 mg, 1.33 mmol), potassium acetate (356 mg, 3.63 mmol), [1,1'-bis(diphenylphosphino)ferrocene]dichloropalladium(II) (PdCl$_2$dppf; 30 mg, 0.04 mmol), and 1,1'-bis(diphenylphosphino)ferrocene (20 mg, 0.04 mmol) were combined and treated with the product from Example 58A (440 mg, 1.21 mmol) in degassed 1,4-dioxane (7 mL). The reaction mixture was heated at 80° C. for 16 hours, allowed to cool to 23° C., diluted with water, and extracted with dichloromethane (3×). The dichloromethane extracts were combined, dried over sodium sulfate, filtered, and the filtrate concentrated under reduced pressure. The residue was chromatographed on flash silica gel (20% ethyl acetate:hexanes) to provide the title compound (323 mg, 78% yield). $^1$H NMR (300 MHz, CDCl$_3$) δ 1.25 (s, 12H), 2.24 (m, 2H), 3.52 (dd, 2H, J=5.7, 5.7 Hz), 4.03 (dd, 2H, J=6 Hz), 5.14 (s, 2H), 6.46 (br m, 1H), 7.32 (m, 5H); MS (ESI) m/e 344 (M+H)$^+$.

EXAMPLE 58C benzyl 3-cyano-3',6'-dihydro-2,4'-bipyridine-1'(2'H)-carboxylate4,4,5,5-tetramethyl-1,3,2-dioxaborolan-2-ol complex The product from Example 58B (200 mg, 0.58 mmol), potassium carbonate (241 mg, 1.75 mmol), PdCl$_2$dppf (29 mg, 0.035 mmol), and 2-chloro-3-cyanopyridine (85 mg, 0.61 mmol) were combined in degassed N,N-dimethylformamide (4 mL). The reaction mixture was heated at 80° C. for 16 hours, allowed to cool to 23° C., diluted with water, dichloromethane, and the layers separated. The aqueous phase was extracted with dichloromethane (2×). All the dichloromethane phases were combined, dried over sodium sulfate, filtered, and the filtrate concentrated under reduced pressure. The residue was chromatographed on flash silica gel (50% ethyl acetate:hexanes) to provide the title compound sufficiently pure to carry on in further reactions (323 mg, 78% yield). $^1$H NMR (300 MHz, CDCl$_3$) δ 1.13 (s, 12H), 2.74 (br s, 2H), 3.75 (dd, 2H, J=6 Hz), 4.26 (m, 2H), 5.19 (s, 2H), 6.57 (br m, 1H), 7.32 (m, 6H), 7.98 (dd, 1H, J=1.8, 7.8 Hz), 8.76 (dd, 1H, J=1.8, 4.5 Hz); MS (ESI) m/e 320 (M+H)$^+$.

EXAMPLE 58D 2-(4-piperidinyl)nicotinonitrile

A steady stream of H$_2$ was bubbled through a stirred solution of the product from Example 58C (70 mg, 0.15 mmol), Pd/C (5 mg), and ethanol (2 mL) at 23° C. for 24 hours. The H$_2$ bubbling was stopped and N$_2$ was bubbled through for a few minutes. The reaction mixture was passed through Celite and the filtrate concentrated under reduced pressure to provide the title compound sufficiently pure to carry into further reactions (30 mg). MS (ESI) m/e 188 (M+H)$^+$.

EXAMPLE 58E

2-[4-(3-cyano-2-pyridinyl)-1-piperidinyl]-N-(3-methylphenyl)acetamide

The product from Example 58D, the product from Example 1A (37 mg, 0.16 mmol), N,N-diisopropylethylamine (31 mg, 0.24 mmol), and toluene (3 mL) were combined and heated at 60° C. After 16 hours, the mixture was allowed to cool to 23° C. and concentrated under reduced pressure. The residue was purified by thin layer chromatography (7% ethyl acetate:hexanes) to provide the title compound (9 mg, 17% yield). $^1$H NMR (400 MHz, DMSO-d$_6$) δ 1.79 (br d, 2H, J=12 Hz), 2.02 (m, 2H), 2.27 (s, 3H), 2.32 (m, 2H), 3.04 (m, 3H), 3.16 (s, 2H), 6.88 (bd, 1H, J=8 Hz), 7.18 (dd, 1H, J=7.2, 7.2 Hz), 7.45 (m, 3H), 8.26 (dd, 1H, J=1, 2 Hz), 8.82 (dd, 1H, J=1, 4.4 Hz), 9.58 (s, 1H); MS (APCI/ESI) m/e 335 (M+H)$^+$.

EXAMPLE 59

N-(3-methylphenyl)-2-(4-phenyl-3,6-dihydro-1(2H)-pyridinyl)acetamide

The procedure described in Example 35 was followed, substituting 4-phenyl-1,2,3,6-tetrahydropyridine hydrochloride for 4-(2-methoxyphenyl)piperidine, to provide the title compound (180 mg, 39% yield). $^1$H NMR (300 MHz, DMSO-d$_6$) δ 2.27 (s, 3H), 2.55 (m, 2H), 2.78 (t, 2H, J=6 Hz), 3.26 (m, 4H), 6.18 (m, 1H), 6.88 (m, 1H). 7.17 (t, 1H, J=7.5 Hz), 7.25 (m, 1H), 7.35 (m, 2H), 7.45 (m, 4H), 9.64 (s, 1H); MS (DCI/NH$_3$) m/e 307 (M+H)$^+$. Anal. calcd for C$_{20}$H$_{22}$N$_2$O.0.10 H$_2$O: C, 77.94; H, 7.26; N, 9.09. Found: C, 77.72, H, 7.28, N, 9.03.

EXAMPLE 60

2-(3',6'-dihydro-2,4'-bipyridin-1'(2'H)-yl)-N-(3-methylphenyl)acetamide

The procedure described in Example 35 was followed, substituting 1',2',3',6'-tetrahydro-2,4'-bipyridine hydrochloride (Saari, W. S.; et al. J. Med. Chem. 1984, 27, 1182) for 4-(2-methoxyphenyl)piperidine, to provide the title compound (210 mg, 53.8% yield). $^1$H NMR (300 MHz, DMSO-d$_6$) δ 2.27 (s, 3H), 2.65 (m, 2H), 2.78 (t, 2H, J=6 Hz), 3.25 (s, 2H), 3.30 (m, 2H), 6.71 (m, 1H), 6.88 (m, 1H). 7.18 (t, 1H, J=7.5 Hz), 7.23 (m, 1H), 7.45 (m, 2H), 7.55 (d, 1H, J=9 Hz), 7.75 (m, 1H), 8.53 (m, 1H), 9.64 (br s, 1H); MS (DCI/NH$_3$) m/w 308 (M+H)$^+$. Anal. calcd for C$_{19}$H$_{21}$N$_3$O.0.30 H$_2$O: C, 72.96; H, 6.96; N, 13.43. Found: 72.73, H, 6.57, N, 13.47.

EXAMPLE 61

2-(3',6'-dihydro-2,4'-bipyridin-1'(2'H)-yl)-N-(2,6-dimethylphenyl)acetamide

1',2',3',6'-Tetrahydro-2,4'-bipyridine hydrochloride (22 mg, 0.11 mmol), 2-chloro-N-(2,6-dimethylphenyl)acetamide (24 mg, 0.12 mmol), and sodium carbonate (50 mg) in DMF: water (2:1, 2 mL) were combined and shaken at ambient temperature for 18 hours. The mixture was concentrated under reduced pressure. The residue was purified by preparative HPLC to provide the title compound as a trifluoroacetic acid salt (43 mg, 90% yield). $^1$H NMR (300 MHz, DMSO-d$_6$) δ 2.20 (s, 6H), 2.96 (br s, 2H), 3.43-3.63 (m, 2H), 4.03-4.20 (m, 2H), 4.39 (s, 2H), 6.72 (br s, 1H), 7.12 (m, 3H), 7.38 (m, 1H), 7.62 (d, 1H, J=6 Hz), 7.82 (m, 1H), 8.59 (m, 1H), 10.00 (m, 1H), 10.40 (br s, 1H); MS (ESI APCI+) m/e 322 (M+H)$^+$.

EXAMPLE 62

2-(3',6'-dihydro-2,4'-bipyridin-1'(2'H)-yl)-N-(2-nitrophenyl)acetamide

The procedure described in Example 61 was followed, substituting 2-chloro-N-(2-nitrophenyl)acetamide for 2-chloro-N-(2,6-dimethylphenyl)acetamide, to provide the title compound (27 mg, 54% yield). $^1$H NMR (300 MHz, DMSO-d$_6$) δ 2.93 (br s, 2H), 3.40-3.70 (m, 2H), 4.00-4.20 (m, 2H), 4.38 (s, 2H), 6.75 (br s, 1H), 7.38 (m, 1H), 7.48 (t, 1H, J=6 Hz), 7.62 (m, 2H), 7.80 (t, 1H, J=6 Hz), 7.88 (t, 1H, J=6 Hz), 8.03 (m, 1H), 8.60 (br s, 1H), 10.44 (br s, 1H), 10.98 (br s, 1H); MS (ESI APCI+) m/e 339 (M+H)$^+$.

EXAMPLE 63

2-(3',6'-dihydro-2,4'-bipyridin-1'(2'H)-yl)-N-(3-nitrophenyl)acetamide

The procedure described in Example 61 was followed, substituting 2-chloro-N-(3-nitrophenyl)acetamide for 2-chloro-N-(2,6-dimethylphenyl)acetamide, to provide the title compound (48 mg, 97% yield). $^1$H NMR (300 MHz, DMSO-$d_6$) δ 2.96 (br s, 2H), 3.45-3.75 (m, 2H), 4.05-4.20 (m, 2H), 4.38 (s, 2H), 6.75 (br s, 1H), 7.38 (m, 1H), 7.66 (m, 2H), 7.89 (m, 2H), 8.00 (d, 1H, J=6 Hz), 8.60 (m, 1H), 8.63 (br s, 1H), 10.45 (br s, 1H), 11.08 (br s, 1H); MS (ESI APCI+) m/e 339 (M+H)$^+$.

EXAMPLE 64

2-(3',6'-dihydro-2,4'-bipyridin-1'(2'H)-yl)-N-(4-fluorophenyl)acetamide

The procedure described in Example 61 was followed, substituting 2-chloro-N-(4-fluorophenyl)acetamide for 2-chloro-N-(2,6-dimethylphenyl)acetamide, to provide the title compound (40 mg, 86% yield). $^1$H NMR (300 MHz, DMSO-$d_6$) δ 2.96 (br s, 2H), 3.45-3.75 (m, 2H), 4.00-4.20 (m, 2H), 4.35 (s, 2H), 6.72 (br s, 1H), 7.22 (t, 2H, J=7 Hz), 7.38 (m, 1H), 7.63 (m, 3H), 7.82 (m, 1H), 8.60 (m, 1H), 10.38 (br s, 1H), 10.62 (br s, 1H); MS (ESI APCI+) m/e 312 (M+H)$^+$.

EXAMPLE 65

N-(2,4-difluorophenyl)-2-(3',6'-dihydro-2,4'-bipyridin-1'(2'H)-yl)acetamide

The procedure described in Example 61 was followed, substituting 2-chloro-N-(2,4-difluorophenyl)acetamide for 2-chloro-N-(2,6-dimethylphenyl)acetamide, to provide the title compound (45 mg, 92% yield). $^1$H NMR (300 MHz, DMSO-$d_6$) δ 2.95 (br s, 2H), 3.45-3.70 (m, 2H), 4.00-4.20 (m, 2H), 4.35 (s, 2H), 6.74 (br s, 1H), 7.18 (t, 1H, J=7 Hz), 7.36 (m, 2H), 7.63 (m, 1H), 7.85 (m, 2H), 8.60 (m, 1H), 10.40 (br s, 1H), 10.45 (br s, 1H); MS (ESI APCI+) m/e 330 (M+H)$^+$.

EXAMPLE 66

2-(3',6'-dihydro-2,4'-bipyridin-1'(2'H)-yl)-N-(2,5-dimethylphenyl)acetamide

The procedure described in Example 61 was followed, substituting 2-chloro-N-(2,5-dimethylphenyl)acetamide for 2-chloro-N-(2,6-dimethylphenyl)acetamide, to provide the title compound (28 mg, 59% yield). $^1$H NMR (300 MHz, DMSO-$d_6$) δ 2.20 (s, 3H), 2.25 (s, 3H), 2.95 (br s, 2H), 3.45-3.70 (m, 2H), 4.00-4.20 (m, 2H), 4.35 (s, 2H), 6.74 (br s, 1H), 7.00 (d, 1H, J=7 Hz), 7.18 (d, 1H, J=7 Hz), 7.22 (s, 1H), 7.38 (m, 1H), 7.63 (d, 1H, J=7 Hz), 7.82 (m, 1H), 8.60 (m, 1H), 9.92 (br s, 1H), 10.35 (br s, 1H); MS (ESI APCI+) m/e 322 (M+H)$^+$.

EXAMPLE 67

2-(3',6'-dihydro-2,4'-bipyridin-1'(2'H)-yl)-N-(2-methylphenyl)acetamide

The procedure described in Example 61 was followed, substituting 2-chloro-N-(2-methylphenyl)acetamide for 2-chloro-N-(2,6-dimethylphenyl)acetamide, to provide the title compound (30 mg, 65% yield). $^1$H NMR (300 MHz, DMSO-$d_6$) δ 2.25 (s, 3H), 2.95 (br s, 2H), 3.45-3.70 (m, 2H), 4.00-4.20 (m, 2H), 4.35 (s, 2H), 6.75 (br s, 1H), 7.18 (m, 1H), 7.22 (m, 1H), 7.28 (m, 1H), 7.38 (m, 1H), 7.43 (d, 1H, J=7 Hz), 7.63 (d, 1H, J=7 Hz), 7.82 (m, 1H), 8.60 (m, 1H), 9.96 (br s, 1H), 10.35 (br s, 1H); MS (ESI APCI+) m/e 308 (M+H)$^+$.

EXAMPLE 68

N-cyclohexyl-2-(3',6'-dihydro-2,4'-bipyridin-1'(2'H)-yl)acetamide

The procedure described in Example 61 was followed, substituting 2-chloro-N-cyclohexylacetamide for 2-chloro-N-(2,6-dimethylphenyl)acetamide, to provide the title compound (20 mg, 44% yield). $^1$H NMR (300 MHz, DMSO-$d_6$) δ 1.10-1.35 (m, 5H), 1.60-1.80 (m, 5H), 2.95 (br s, 2H), 3.45-3.70 (m, 3H), 4.00-4.20 (m, 2H), 4.35 (s, 2H), 6.68 (br s, 1H), 7.38 (m, 1H), 7.63 (d, 1H, J=7 Hz), 7.82 (m, 1H), 8.42 (d, 1H, J=7 Hz), 8.60 (m, 1H), 10.25 (br s, 1H); MS (ESI APCI+) m/e 300 (M+H)$^+$.

EXAMPLE 70

2-(3',6'-dihydro-2,4'-bipyridin-1'(2'H)-yl)-N-(4-methylphenyl)acetamide

The procedure described in Example 61 was followed, substituting 2-chloro-N-(4-methylphenyl)acetamide for 2-chloro-N-(2,6-dimethylphenyl)acetamide, to provide the title compound (26 mg, 56% yield). $^1$H NMR (300 MHz, DMSO-$d_6$) δ 2.24 (s, 3H), 2.95 (br s, 2H), 3.45-3.70 (m, 2H), 4.00-4.20 (m, 2H), 4.35 (s, 2H), 6.74 (br s, 1H), 7.19 (d, 2H, J=7 Hz), 7.38 (m, 1H), 7.49 (d, 2H, J=7 Hz), 7.63 (d, 1H, J=7 Hz), 7.82 (m, 1H), 8.60 (m, 1H), 10.35 (br s, 1H), 10.45 (br s, 1H); MS (ESI APCI+) m/e 308 (M+H)$^+$.

EXAMPLE 71

2-(3',6'-dihydro-2,4'-bipyridin-1'(2'H)-yl)-N-[3-(trifluoromethyl)phenyl]acetamide The procedure described in Example 61 was followed, substituting 2-chloro-N-[3-(trifluoromethyl)phenyl]acetamide for 2-chloro-N-(2,6-dimethylphenyl) acetamide, to provide the title compound (47 mg, 90% yield). $^1$H NMR (300 MHz, DMSO-$d_6$) δ 2.95 (br s, 2H), 3.45-3.70 (m, 2H), 4.00-4.20 (m, 2H), 4.35 (s, 2H), 6.74 (br s, 1H), 7.38 (m, 1H), 7.49 (d, 1H, J=6 Hz), 7.63 (m, 2H), 7.79 (d, 1H, J=6 Hz), 7.82 (m, 1H), 8.08 (s, 1H), 8.60 (m, 1H), 10.45 (br s, 1H), 10.98 (br s, 1H); MS (ESI APCI+) m/e 362 (M+H)$^+$.

EXAMPLE 72 ethyl 4-[(3',6'-dihydro-2,4'-bipyridin-1'(2'H)-ylacetyl)amino]benzoate

The procedure described in Example 61 was followed, substituting ethyl 4-[(chloroacetyl)amino]benzoate for 2-chloro-N-(2,6-dimethylphenyl)acetamide, to provide the title compound (51 mg, 97% yield). $^1$H NMR (300 MHz, DMSO-$d_6$) δ 1.35 (t, 3H, J=7 Hz), 2.95 (br s, 2H), 3.45-3.70 (m, 2H), 4.00-4.20 (m, 2H), 4.22 (q, 2H, J=7 Hz), 4.36 (s, 2H), 6.74 (br s, 1H), 7.38 (m, 1H), 7.62 (d, 1H, J=6 Hz), 7.74 (d, 2H, J=8 Hz), 7.82 (m, 1H), 7.98 (d, 2H, J=8 Hz), 8.60 (m, 1H), 10.40 (br s, 1H), 10.92 (br s, 1H); MS (ESI APCI+) m/e 366 (M+H)$^+$.

EXAMPLE 73

N-[2-chloro-5-(trifluoromethyl)phenyl]-2-(3',6'-dihydro-2,4'-bipyridin-1'(2'H)-yl)acetamide The procedure described in Example 61 was followed, substituting 2-chloro-N-[2-chloro-5-(trifluoromethyl)phenyl]acetamide for 2-chloro-N-(2,6-dimethylphenyl)acetamide, to provide the title compound (18 mg, 32% yield). $^1$H NMR (300 MHz, DMSO-$d_6$) δ 2.95 (br s, 2H), 3.45-3.70 (m, 2H), 4.00-4.20 (m, 2H), 4.35 (s, 2H), 6.73 (br s, 1H), 7.38 (m, 1H), 7.63 (m, 2H), 7.82 (m, 2H), 8.22 (s, 1H), 8.60 (m, 1H), 10.40 (br s, 1H), 10.50 (br s, 1H); MS (ESI APCI+) m/e 396 (M+H)$^+$.

EXAMPLE 74

N-(3-chloro-4-methylphenyl)-2-(3',6'-dihydro-2,4'-bipyridin-1'(2'H)-yl)acetamide The procedure described in Example 61 was followed, substituting 2-chloro-N-(3-chloro-4-methylphenyl)acetamide for 2-chloro-N-(2,6-dimethylphenyl)acetamide, to provide the title compound (44 mg, 88% yield). $^1$H NMR (300 MHz, DMSO-$d_6$) δ 2.28 (s, 3H), 2.95 (br s, 2H), 3.45-3.75 (m, 2H), 4.00-4.20 (m, 2H), 4.30 (s, 2H), 6.73 (br s, 1H), 7.38 (m, 3H), 7.63 (d, 1H, J=6 Hz), 7.80 (s, 1H), 7.83 (m, 1H), 8.60 (m, 1H), 10.38 (br s, 1H), 10.63 (br s, 1H); MS (ESI APCI+) m/e 342 (M+H)$^+$.

EXAMPLE 75

N-(2-cyanophenyl)-2-(3',6'-dihydro-2,4'-bipyridin-1'(2'H)-yl)acetamide

The procedure described in Example 61 was followed, substituting 2-chloro-N-(2-cyanophenyl)acetamide for 2-chloro-N-(2,6-dimethylphenyl)acetamide, to provide the title compound (46 mg, 97% yield). $^1$H NMR (300 MHz, DMSO-$d_6$) δ 2.95 (br s, 2H), 3.45-3.75 (m, 2H), 4.00-4.20 (m, 2H), 4.40 (s, 2H), 6.75 (br s, 1H), 7.38 (m, 1H), 7.42 (t, 1H, J=6 Hz), 7.63 (m, 2H), 7.78 (m, 1H), 7.83 (m, 1H), 7.88 (m, 1H), 8.60 (m, 1H), 10.42 (br s, 1H), 10.93 (br s, 1H); MS (ESI APCI+) m/e 319 (M+H)$^+$.

EXAMPLE 76

N-(3-chlorophenyl)-2-(3',6'-dihydro-2,4'-bipyridin-1'(2'H)-yl)acetamide

The procedure described in Example 61 was followed, substituting 2-chloro-N-(3-chlorophenyl)acetamide for 2-chloro-N-(2,6-dimethylphenyl)acetamide, to provide the title compound (42 mg, 86% yield). $^1$H NMR (300 MHz, DMSO-$d_6$) δ 2.95 (br s, 2H), 3.45-3.75 (m, 2H), 4.00-4.20 (m, 2H), 4.34 (s, 2H), 6.75 (br s, 1H), 7.20 (d, 1H, J=6 Hz), 7.38 (m, 1H), 7.42 (m, 2H), 7.63 (d, 1H, J=6 Hz), 7.80 (s, 1H), 7.83 (m, 1H), 8.60 (m, 1H), 10.40 (br s, 1H), 10.80 (br s, 1H); MS (ESI APCI+) m/e 328 (M+H)$^+$.

EXAMPLE 77

N-(3-chloro-4-fluorophenyl)-2-(3',6'-dihydro-2,4'-bipyridin-1'(2'H)-yl)acetamide The procedure described in Example 61 was followed, substituting 2-chloro-N-(3-chloro-4-fluorophenyl)acetamide for 2-chloro-N-(2,6-dimethylphenyl)acetamide, to provide the title compound (43 mg, 85% yield). $^1$H NMR (300 MHz, DMSO-$d_6$) δ 2.95 (br s, 2H), 3.45-3.75 (m, 2H), 4.00-4.20 (m, 2H), 4.38 (s, 2H), 6.73 (br s, 1H), 7.38 (m, 2H), 7.63 (d, 1H, J=6 Hz), 7.83 (m, 1H), 7.92 (d, 1H, J=5Hz), 8.60 (m, 1H), 10.38 (br s, 1H), 10.83 (br s, 1H); MS (ESI APCI+) m/e 346 (M+H)$^+$.

EXAMPLE 78

2-(3',6'-dihydro-2,4'-bipyridin-1'(2'H)-yl)-N-[4-(trifluoromethoxy)phenyl]acetamide The procedure described in Example 61 was followed, substituting 2-chloro-N-[4-(trifluoromethoxy)phenyl]acetamide for 2-chloro-N-(2,6-dimethylphenyl) acetamide, to provide the title compound (44 mg, 81% yield). $^1$H NMR (300 MHz, DMSO-$d_6$) δ 2.95 (br s, 2H), 3.45-3.75 (m, 2H), 4.00-4.20 (m, 2H), 4.35 (s, 2H), 6.73 (br s, 1H), 7.38 (m, 1H), 7.41 (d, 2H, J=7 Hz), 7.63 (d, 1H, J=6 Hz), 7.73 (d, 2H, J=7 Hz), 7.84 (m, 1H), 8.60 (m, 1H), 10.40 (br s, 1H), 10.80 (br s, 1H); MS (ESI APCI+) m/e 378 (M+H)$^+$.

EXAMPLE 79

2-(3',6'-dihydro-2,4'-bipyridin-1'(2'H)-yl)-N-[2-(trifluoromethyl)phenyl]acetamide The procedure described in Example 61 was followed, substituting 2-chloro-N-[2-(trifluoromethyl)phenyl]acetamide 2-chloro-N-(2,6-dimethylphenyl)acetamide, to provide the title compound (41 mg, 78% yield). $^1$H NMR (300 MHz, DMSO-$d_6$) δ 2.95 (br s, 2H), 3.45-3.75 (m, 2H), 4.00-4.20 (m, 2H), 4.35 (s, 2H), 6.73 (br s, 1H), 7.38 (m, 1H), 7.50-7.70 (m, 3H), 7.80-7.90 (m, 3H), 8.60 (m, 1H), 10.40 (s, 1H), 10.43 (br s, 1H); MS (ESI APCI+) m/e 362 (M+H)$^+$.

EXAMPLE 80

N-(4-chlorophenyl)-2-(3',6'-dihydro-2,4'-bipyridin-1'(2'H)-yl)acetamide

The procedure described in Example 61 was followed, substituting 2-chloro-N-(4-chlorophenyl)acetamide for 2-chloro-N-(2,6-dimethylphenyl)acetamide, to provide the title compound (39 mg, 80% yield). $^1$H NMR (300 MHz, DMSO-$d_6$) δ 2.95 (br s, 2H), 3.45-3.75 (m, 2H), 4.00-4.20 (m, 2H), 4.30 (s, 2H), 6.73 (br s, 1H), 7.38 (m, 1H), 7.44 (d, 2H), J=7 Hz), 7.63 (m, 3H), 7.83 (m, 1H), 8.60 (m, 1H), 10.40 (br s, 1H), 10.63 (s, 1H); MS (ESI APCI+) m/e 328 (M+H)$^+$.

EXAMPLE 81

N-(2,3-dichlorophenyl)-2-(3',6'-dihydro-2,4'-bipyridin-1'(2'H)-yl)acetamide

The procedure described in Example 61 was followed, substituting 2-chloro-N-(2,3-dichlorophenyl)acetamide for 2-chloro-N-(2,6-dimethylphenyl)acetamide, to provide the title compound (37 mg, 70% yield). $^1$H NMR (300 MHz, DMSO-$d_6$) δ 2.95 (br s, 2H), 3.45-3.75 (m, 2H), 4.00-4.20 (m, 2H), 4.40 (s, 2H), 6.73 (br s, 1H), 7.38 (m, 1H), 7.42 (t, 1H, J=7 Hz), 7.58 (d, 1H, J=7 Hz), 7.64 (d, 1H, J=7 Hz), 7.72 (d, 1H, J=7 Hz), 7.83 (m, 1H), 8.60 (m, 1H), 10.40 (s, 1H), 10.43 (br s, 1H); MS (ESI APCI+) m/e 363 (M+H)+.

EXAMPLE 82

N-(3,5-dichlorophenyl)-2-(3',6'-dihydro-2,4'-bipyridin-1'(2'H)-yl)acetamide

The procedure described in Example 61 was followed, substituting 2-chloro-N-(3,5-dichlorophenyl)acetamide for 2-chloro-N-(2,6-dimethylphenyl)acetamide, to provide the title compound (31 mg, 59% yield). $^1$H NMR (300 MHz, DMSO-$d_6$) δ 2.95 (br s, 2H), 3.45-3.75 (m, 2H), 4.00-4.20 (m, 2H), 4.34 (s, 2H), 6.73 (br s, 1H), 7.38 (m, 1H), 7.40 (s, 1H), 7.63 (m, 3H), 7.83 (m, 1H), 8.60 (m, 1H), 10.40 (br s, 1H), 10.90 (s, 1H); MS (ESI APCI+) m/e (M+H)+.

EXAMPLE 83

2-(3',6'-dihydro-2,4'-bipyridin-1'(2'H)-yl)-N-(4-fluoro-2-methylphenyl)acetamide The procedure described in Example 61 was followed, substituting 2-chloro-N-(4-fluoro-2-methylphenyl)acetamide for 2-chloro-N-(2,6-dimethylphenyl)acetamide, to provide the title compound (34 mg, 70% yield). $^1$H NMR (300 MHz, DMSO-$d_6$) δ 2.20 (s, 3H), 2.96 (br s, 2H), 3.43-3.63 (m, 2H), 4.03-4.20 (m, 2H), 4.39 (s, 2H), 6.72 (br s, 1(br s, 1H), 7.10 (m, 2H), 7.38 (m, 1H), 7.43 (m, 1H), 7.64 (d, 1H, J=7 Hz), 7.84 (m, 1H), 8.60 (m, 1H), 10.00 (m, 1H), 10.40 (br s, 1H); MS (ESI APCI+) m/e 326 (M+H)+.

EXAMPLE 84

N-(4-fluorophenyl)-2-[4-(2-pyridinyl)-1-piperidinyl] acetamide

The procedure described in Example 45 was followed, substituting 2-chloro-N-(4-fluorophenyl)acetamide for N-(4-bromophenyl)-2-chloroacetamide, to provide the title compound (57.5 mg, 59% yield). $^1$H NMR (500 MHz, DMSO-$d_6$) δ 2.15 (m, 4H), 3.01 (m, 1H), 3.26 (m, 2H), 3.65 (m, 2H), 4.18 (s, 2H), 7.22 (m, 2H), 7.35 (m, 2H), 7.58 (m, 2H), 7.82 (m, 1H), 8.60 (m, 1H), 9.95 (br s, 1H), 10.65 (br s, 1H); MS (ESI APCI+) m/e 314 (M+H)+.

EXAMPLE 85

N-(3,5-dichlorophenyl)-2-[4-(2-pyridinyl)-1-piperidinyl]acetamide

The procedure described in Example 45 was followed, substituting 2-chloro-N-(4-fluorophenyl)acetamide for N-(4-bromophenyl)-2-chloroacetamide, to provide the title compound (18.5 mg, 39% yield). $^1$H NMR (500 MHz, DMSO-$d_6$) δ 1.85 (m, 2H), 1.95 (m, 2H), 2.25 (m, 2H), 2.68 (m, 1H), 2.95 (m, 2H), 3.20 (s, 2H), 7.20 (m, 1H), 7.30 (m, 2H), 7.75 (m, 2H), 7.82 (s, 2H), 8.52 (s, 1H), 10.05 (br s, 1H); MS (ESI APCI+) m/e 365 (M+H)+.

EXAMPLE 86

N-(2,3-dichlorophenyl)-2-[4-(2-pyridinyl)-1-piperidinyl]acetamide

The procedure described in Example 45 was followed, substituting 2-chloro-N-(2,3-dichlorophenyl)acetamide for N-(4-bromophenyl)-2-chloroacetamide, to provide the title compound (18 mg, 38% yield). $^1$H NMR (500 MHz, DMSO-$d_6$) δ 1.90 (m, 4H), 2.42 (m, 2H), 2.75 (m, 1H), 3.05 (m, 2H), 3.28 (s, 2H), 7.22 (t, 11H, J=3 Hz), 7.30 (d, 1H, J=3 Hz), 7.42 (m, 3H), 7.75 (t, 1H, J=3 Hz), 8.25 (s, 1H), 8.50 (s, 1H), 10.18 (br s, 1H), MS (ESI APCI+) m/e 365 (M+H)+.

EXAMPLE 87

2-[4-(2-pyridinyl)-1-piperidinyl]-N-[2-(trifluoromethyl)phenyl]acetamide

The procedure described in Example 45 was followed, substituting 2-chloro-N-[2-(trifluoromethyl)phenyl]acetamide for N-(4-bromophenyl)-2-chloroacetamide, to provide the title compound (22 mg, 46% yield). $^1$H NMR (500 MHz, DMSO-$d_6$) δ 1.85 (m, 4H), 2.41 (m, 2H), 2.72 (m, 1H), 3.01 (m, 2H), 3.20 (s, 2H), 7.22 (t, 1H, J=3 Hz), 7.30 (d, 1H, J=3 Hz), 7.38 (m, 1H), 7.72 (m, 4H), 8.25 (br s, 1H), 8.50 (s, 1H), 9.98 (br s, 1H); MS (ESI APCI+) m/e 364 (M+H)+.

EXAMPLE 88

N-(3-chloro-4-fluorophenyl)-2-[4-(2-pyridinyl)-1-piperidinyl]acetamide

The procedure described in Example 45 was followed, substituting 2-chloro-N-(3-chloro-4-fluorophenyl)acetamide for N-(4-bromophenyl)-2-chloroacetamide, to provide the title compound (19 mg, 43% yield). $^1$H NMR (500 MHz, DMSO-$d_6$) δ 1.95 (m, 4H), 2.41 (m, 2H), 2.72 (m, 1H), 3.01 (m, 2H), 3.20 (s, 2H), 7.25 (t, 1H, J=3 Hz), 7.30 (d, 1H, J=3 Hz), 7.40 (t, 1H, J=3 Hz), 7.55 (s, 1H), 7.75 (t, 1H, J=3 Hz), 7.95 (t, 1H, J=3 Hz), 8.45 (s, 1H), 9.90 (br s, 1H), 10.35 (br s, 1H); MS (ESI APCI+) m/e 348 (M+H)+.

EXAMPLE 89

2-[4-(2-pyridinyl)-1-piperidinyl]-N-[4-(trifluoromethoxy)phenyl]acetamide

The procedure described in Example 45 was followed, substituting 2-chloro-N-[4-(trifluoromethoxy)phenyl]acetamide for N-(4-bromophenyl)-2-chloroacetamide, to provide the title compound (21 mg, 43% yield). $^1$H NMR (500 MHz, DMSO-$d_6$) δ 1.91 (m, 4H), 2.41 (m, 2H), 2.65 (m, 1H), 3.05 (m, 2H), 3.20 (s, 2H), 7.12 (m, 1H), 7.25 (m, 3H), 7.85 (m, 4H), 8.50 (s, 1H), 9.90 (br s, 1H); MS (ESI APCI+) m/e 380 (M+H)+.

EXAMPLE 90

N-Cyclohexyl-2-(3',4',5',6'-tetrahydro-2'H-[2,4']bipyridinyl-1'-yl) acetamide The procedure described in Example 45 was followed, substituting 2-chloro-N-cyclohexylacetamide for N-(4-bromophenyl)-2-chloroacetamide, to provide the title compound (49 mg, 53% yield). $^1$H NMR (500 MHz, DMSO-$d_6$) δ 1.10-1.35 (m, 6H), 1.55 (m, 1H), 1.70 (m, 2H), 1.79 (m, 2H), 2.08 (m, 4H), 2.98 (m, 1H), 3.18 (m, 2H), 3.68 (m, 2H), 3.88 (s, 2H), 7.38 (m, 2H), 7.82 (t, 1H, J=4 Hz), 8.45 (d, 1H, J=4 Hz), 8.58 (d, 1H, J=3 Hz), 9.70 (br s, 1H); MS (ESI APCI+) m/e 302 (M+H)+.

EXAMPLE 91

N-{[4-(2-cyanophenyl)-1-piperazinyl]methyl}-3-methylbenzamide

EXAMPLE 91A

[(3-methylbenzoyl)amino]methyl acetate

N-(3-Methylbenzoyl)glycine (10 g, 51.7 mmol), lead tetraacetate (25.25 g, 56.94 mmol), and copper (II) acetate monohydrate (0.94 g, 5.17 mmol) were combined in toluene and heated at reflux overnight. The reaction mixture was to cool to room temperature, filtered through Celite and the fitlrate concentrated under reduced pressure. The residue was purified by flash column chromatography on silica gel (elution with 25% ethyl acetate/hexanes) to provide the title compound (7.95 g, 74% yield). $^1$H NMR (300 MHz, CDCl$_3$) δ 2.10 (s, 3H), 2.40 (s, 3H), 5.45 (d, 2H, J=9 Hz), 7.35 (m, 2H), 7.55 (m, 1H), 7.62 (s, 1H); MS (DCI/NH$_3$) m/e 208 (M+H)$^+$.

EXAMPLE 91B

N-[4-(2-Cyanophenyl)piperazin-1-ylmethyl]-3-methyl benzamide

The product from Example 91A (4.00 g, 19.2 mmol), 1-(2-cyanophenyl)piperazine (3.6 g, 19.2 mmol), and triethylamine (5.3 ml, 38.4 mmol) were combined in acetonitrile (100 mL) and stirred overnight room temperature. The reaction mixture was concentrated under reduced pressure and the residue was purified by flash column chromatography on silica gel (elution with ethyl acetate) to provide the title compound as a colorless oil (2.85 g, 44% yield). $^1$H NMR (300 MHz, CDCl$_3$) δ 2.40 (s, 3H), 2.90 (m, 4H), 3.25 (m, 4H), 4.45 (d, 2H, J=6 Hz), 6.66 (br s, 1H), 7.0 (m, 2H), 7.35 (m, 2H), 7.48 (m, 1H), 7.55 (m, 2H), 7.58 (s, 1H); MS (DCI/NH$_3$) m/e 335 (M+H)$^+$. maleate salt: mp 131-133° C.; Anal. calcd for C$_{24}$H$_{26}$N$_4$O$_5$.0.30 H$_2$O: C, 63.23; H, 5.88; N, 12.29. Found: C, 63.04; H, 5.74; N, 12.05.

EXAMPLE 92

3-methyl-N-{[4-(2-pyrimidinyl)-1-piperazinyl]methyl}benzamide

The procedure described in Example 91B was followed, substituting 1-(2-pyrimidinyl)piperazine for 1-(2-cyanophenyl)piperazine, to provide the title compound as a colorless oil. $^1$H NMR (300 MHz, CDCl$_3$) δ 2.40 (s, 3H), 2.75 (m, 4H), 3.88 (m, 4H), 4.44 (d, 2H, J=6 Hz), 6.50 (t, 1H, J=4.5 Hz), 6.7 (br s, 1H), 7.32 (d, 2H, J=6 Hz), 7.55 (m, 1H), 7.65 (s, 1H), 8.30 (d, 2H, J=6 Hz); MS (DCI/NH$_3$) m/e 312 (M+H)$^+$.

maleate salt: Obtained as white powder (0.31 g); mp 163-165° C.; Anal. calcd for C$_{21}$H$_{25}$N$_5$O$_5$: C, 59.01; H, 5.90; N, 16.38. Found: C, 59.05; H, 5.93; N, 16.31.

EXAMPLE 93

3-methyl-N-{[4-(2-pyridinyl)-1-piperazinyl]methyl}benzamide

The procedure described in Example 91B was followed, substituting 1-(2-pyridinyl)piperazine for 1-(2-cyanophenyl)piperazine, to provide the title compound as an off-white residue. $^1$H NMR (300 MHz, CDCl$_3$) δ 2.40 (s, 3H), 2.75 (m, 4H), 3.60 (m, 4H), 4.40 (d, 2H, J=6 Hz), 6.58 (br s, 1H), 6.65 (m, 2H), 7.32 (d, 2H, J=6 Hz), 7.40-7.55 (m, 2H), 7.55 (s, 1H), 8.2 (m, 1H); MS (DCI/NH$_3$) m/e 311 (M+H)$^+$; maleate salt: Off-white solid; mp 141-143° C.; Anal. calcd for C$_{22}$H$_{26}$N$_4$O$_5$: C, 61.96; H, 6.15; N, 13.14. Found: C, 61.78; H, 6.08; N, 13.09.

EXAMPLE 94

3-methyl-N-[(4-phenyl-1-piperazinyl)methyl]benzamide

The procedure described in Example 91B was followed, substituting 1-phenylpiperazine for 1-(2-cyanophenyl)piperazine, to provide the title compound as a colorless oil. $^1$H NMR (300 MHz, CDCl$_3$) δ 2.40 (s, 3H), 2.82 (m, 4H), 3.21 (m, 4H), 4.44 (d, 2H, J=6 Hz), 6.60 (br s, 1H), 6.82-6.95 (m, 3H), 7.20 (m, 2H), 7.35 (d, 2H, J=6 Hz), 7.58 (m, 1H) 7.63 (s, 1H); MS (DCI/NH$_3$) m/e 310 (M+H)$^+$; maleate salt: Obtained as off-white powder; mp 145-147° C.; Anal. calcd for C$_{23}$H$_{27}$N$_3$O$_5$: C, 64.93; H, 6.40; N, 9.88. Found: C, 64.83; H, 6.38; N, 9.89.

EXAMPLE 95

N-{[4-(2-methoxyphenyl)-1-piperazinyl]methyl}-3-methylbenzamide

EXAMPLE 95A

[(3-chlorobenzoyl)amino]methyl acetate

The procedure described in Example 91A was followed, substituting N-(3-chlorobenzoyl)glycine for N-(3-methylbenzoyl)glycine, to provide the title compound.

EXAMPLE 95B

N-{[4-(2-methoxyphenyl)-1-piperazinyl]methyl}-3-methylbenzamide

The procedure described in Example 91 B was followed, substituting the product from Example 95A for the product from Example 91A and substituting 1-(2-methoxyphenyl)piperazine for 1-(2-cyanophenyl)piperazine, to provide the title compound (1.95 g). $^1$H NMR (300 MHz, CDCl$_3$) δ 2.90 (m, 4H), 3.15 (m, 4H), 3.85 (s, 3H), 4.45 (d, 2H, J=6 Hz), 6.55 (br s, 1H), 6.84 (d, 1H, J=7.5 Hz), 6.9-7.15 (m, 3H,), 7.40 (t, 1H, J=7.5 Hz), 7.5 (m, 1H), 7.68 (m, 1H) 7.8 (t, 1H, J=3 Hz); MS (DCI/NH$_3$) m/e 360 (M+H)$^+$; maleate salt: brown powder; mp 139-142° C.; Anal. calcd for C$_{23}$H$_{26}$ClN$_3$O$_6$: C, 57.61; H, 5.55; 8.76. Found: C, 57.26; H, 5.65; N, 8.69.

EXAMPLE 96

N-{[4-(2-cyanophenyl)-1-piperazinyl]methyl}-2-methylbenzamide

EXAMPLE 96A

[(2-methylbenzoyl)amino]methyl acetate

The procedure described in Example 91A was followed, substituting N-(2-methylbenzoyl)glycine for N-(3-methylbenzoyl)glycine, to provide the title compound.

EXAMPLE 96B

N-{[4-(2-cyanophenyl)-1-piperazinyl]methyl}-2-methylbenzamide

The procedure described in Example 91B was followed, substituting the product from Example 96A for the product from Example 91A to provide the title compound as an off-white powder. $^1$H NMR (300 MHz, CDCl$_3$) δ 2.50 (s, 3H), 2.90 (t, 4H, J=6 Hz), 3.25 (t, 4H, J=6 Hz), 4.45 (d, 2H, J=6

Hz), 6.18 (br s, 1H), 7.0 (m, 2H), 7.20-7.60 (m, 6H), MS (DCI/NH$_3$) m/e 335 (M+H)$^+$; maleate salt: Yellow powder; mp 62-64° C.; Anal. calcd for C$_{24}$H$_{26}$N$_4$O$_5$.0.20 H$_2$O: C, 63.48; H, 5.86; N, 12.34. Found: C, 63.19; H, 5.77; N, 11.97.

405145 EXAMPLE 97

N-{[4-(2-cyanophenyl)-1-piperazinyl]methyl}-4-methylbenzamide

EXAMPLE 97A

[(4-methylbenzoyl)amino]methyl acetate

The procedure described in Example 91 A was followed, substituting N-(4-methylbenzoyl)glycine for N-(3-methylbenzoyl)glycine, to provide the title compound.

EXAMPLE 97B

N-{[4-(2-cyanophenyl)-1-piperazinyl]methyl}-4-methylbenzamide

The procedure described in Example 91B was followed, substituting the product from Example 97A for the product from Example 91A to provide the title compound as a colorless oil. $^1$H NMR (300 MHz, CDCl$_3$) δ 2.45 (s, 3H), 2.9 (t, 4H, J=6 Hz), 3.25 (t, 4H, J=6 Hz), 4.45 (d, 2H, J=6 Hz), 6.60 (br s, 1H), 7.0 (m, 2H), 7.25 (m, 2H), 7.45-7.60 (m, 2H), 7.7 (d, 2H, J=9 Hz); MS (DCI/NH$_3$) m/e 335 (M+H)$^+$; maleate salt: Brown powder; Anal. calcd for C$_{24}$H$_{26}$N$_4$O$_5$: C, 63.99; H, 5.82; N, 12.44. Found: C, 63.71; H, 5.78; N, 12.18.

EXAMPLE 98

N-{[4-(3-cyano-2-pyridinyl)-1-piperazinyl]methyl}-3-methylbenzamide

The procedure described in Example 91B was followed, substituting 1-(2-cyanopyridinyl)piperazine for 1-(2-cyanophenyl)piperazine to provide the title compound as a brown oil. $^1$H NMR (300 MHz, CHCl$_3$) δ 2.40 (s, 3H), 2.80 (t, 4H, J=6 Hz), 3.75 (t, 4H, J=6 Hz), 4.40 (d, 2H, J=6 Hz), 6.55 (br s, 1H), 6.75 (dd, 1H, J=12, 6 Hz), 7.32 (d, 2 H, J=6 Hz), 7.52-7.65 (m, 2H), 7.75 (dd, 1H, J=7.5, 3 Hz), 8.33 (dd, 1H, J=6, 3 Hz); MS (DCI/NH$_3$) m/e 336 (M+H)$^+$; maleate salt: Pale yellow powder; mp 128-130° C.; Anal. calcd for C$_{23}$H$_{25}$N$_5$O$_5$:C, 61.19; H, 5.58; N, 15.51. Found: C, 61.46; H, 5.57; N, 15.57.

EXAMPLE 99

N-{[4-(3-cyanophenyl)-1-piperazinyl]methyl}-3-methylbenzamide

The procedure described in Example 91B was followed, substituting 1-(3-cyanophenyl)piperazine for 1-(2-cyanophenyl)piperazine to provide the title compound as a glassy solid. $^1$H NMR (300 MHz, CDCl$_3$) δ 2.40 (s, 3H), 2.80 (t, 4H, J=6 Hz), 3.25 (t, 4H, J=6 Hz), 4.40 (d, 2H, J=6 Hz), 6.50 (br s, 1H), 7.1 (m, 3H), 7.35 (m, 3H), 7.55-7.70 (m, 2H); MS (DCI/NH$_3$) m/e 335 (M+H)$^+$; maleate salt: Off-white powder. mp 59-61° C.; Anal. calcd for C$_{24}$H$_{26}$N$_4$O$_5$: C, 63.99; H, 5.82; N, 12.44. Found: C, 63.76; H, 5.75; N, 12.17.

EXAMPLE 100

N-{[4-(3-cyanophenyl)-1-piperazinyl]methyl}-2-methylbenzamide

The procedure described in Example 91B was followed, substituting the product from Example 96A for the product from Example 91A and substituting 1-(3-cyanophenyl)piperazine for 1-(2-cyanophenyl)piperazine to provide the title compound. $^1$H NMR (300 MHz, CDCl$_3$) δ 2.48 (s, 3H), 2.85 (t, 4H, J=6 Hz), 3.25 (t, 4H, J=6 Hz), 4.4 (d, 2H, J=6 Hz), 6.18 (br s, 1H), 7.10 (m, 3H), 7.22 (m, 2H), 7.30-7.45 (m, 3H); MS (DCI/NH$_3$) m/e 335 (M+H)$^+$; maleate salt: Off-white powder; mp 156-159° C.; Anal. calcd for C$_{24}$H$_{26}$N$_4$O$_5$: C, 63.99; H, 5.82; N, 12.44. Found: C, 63.79; H, 5.67; N, 12.29.

EXAMPLE 101

N-{[4-(3-cyano-2-pyridinyl)-1-piperazinyl]methyl}benzamide

EXAMPLE 101A (benzoylamino)methyl acetate

The procedure described in Example 91A was followed, substituting N-(benzoyl)glycine for N-(3-methylbenzoyl)glycine, to provide the title compound.

EXAMPLE 101B

N-{[4-(3-cyano-2-pyridinyl)-1-piperazinyl]methyl}benzamide

The procedure described in Example 91B was followed, substituting the product from Example 101A for the product from Example 91A and substituting 1-(2-cyanopyridinyl)piperazine for 1-(2-cyanophenyl)piperazine to provide the title compound as a colorless oil. $^1$H NMR (300 MHz, CDCl$_3$) δ 2.80 (t, 4H, J=6 Hz), 3.75 (t, 4H, J=6 Hz), 4.40 (d, 2H, J=6 Hz), 6.55 (br s, 1H), 6.75 (dd, 1H, J=12, 6Hz), 7.40-7.60 (m, 3H), 7.72-7.85 (m, 3H), 8.35 (dd, 1H, 6, 3Hz); MS (DCI/NH$_3$) m/e 322 (M+H)$^+$.

maleate salt: White solid; mp 133-136° C.; Anal. calcd for C$_{22}$H$_{23}$N$_5$O$_5$: C, 60.40; H, 5.30; N, 16.01. Found: C, 60.97; H, 5.26; N, 16.31.

EXAMPLE 102

N-{[4-(3-cyano-2-pyridinyl)-1-piperazinyl]methyl}-4-methylbenzamide

The procedure described in Example 91B was followed, substituting the product from Example 97A for the product from Example 91A and substituting 1-(2-cyanopyridinyl) piperazine for 1-(2-cyanophenyl)piperazine to provide the title compound as a white solid. $^1$H NMR (300 MHz, CDCl$_3$) δ 2.40 (s, 3H), 2.85 (m, 4H,), 3.75 (m, 4H), 4.43 (m, 2H), 6.75 (m, 1H), 7.22 (m, 2H), 7.70 (d, 2H, J=9 Hz), 7.78 (dd, 1H, J=9, 3 Hz), 8.323 (dd, 1H, J=6, 3 Hz); MS (DCI/NH$_3$) m/e 336 (M+H)$^+$; maleate salt: White solid; mp 134-136° C.;

Anal. calcd for C$_{23}$H$_{25}$N$_5$O$_5$: C, 61.19; H, 5.58; N, 15.51. Found: C, 60.91; H, 5.60; N,

EXAMPLE 103

N-{[4-(3-cyano-2-pyridinyl)-1-piperazinyl]methyl}-2-methylbenzamide

The procedure described in Example 91B was followed, substituting the product from Example 96A for the product from Example 91A and substituting 1-(2-cyanopyridinyl)piperazine for 1-(2-cyanophenyl)piperazine to provide the title compound as a glassy solid. $^1$H NMR (300 MHz, CDCl$_3$) δ 2.48 (s, 3H), 2.8 (t, 4H, J=6 Hz), 3.75 (t, 4H, J=6 Hz), 4.4 (d, 2H, J=6 Hz), 6.14 (br s, 1H), 6.75 (dd, 1H, J=12, 6 Hz), 7.18-7.41 (m, 4H), 7.78 (dd, 1H, J=9, 3 Hz), 8.35 (dd, 1H, 6, 3 Hz); MS (DCI/NH$_3$) m/e 336 (M+H)$^+$; maleate salt: Off-white powder; mp 124-127° C.; Anal. calcd for C$_{23}$H$_{25}$N$_5$O$_5$: C, 61.19; H, 5.58; 15.51. Found: C, 61.43; H, 5.39; N, 15.81.

EXAMPLE 104

N-{[4-(2-pyridinyl)-1-piperazinyl]methyl}benzamide

The procedure described in Example 91B was followed, substituting the product from Example 101A for the product from Example 91A and substituting 1-(2-pyridinyl)piperazine for 1-(2-cyanophenyl)piperazine to provide the title compound as a white sticky residue. $^1$H NMR (300 MHz, CDCl$_3$) δ 2.75 (t, 4H, J=6 Hz), 3.55 (t, 4H, J=6 Hz), 4.4 (d, 2H, J=6 Hz), 6.50 (br s, 1H), 6.65 (m, 2H), 7.40-7.55 (m, 4H), 7.75 (m, 2H), 8.20 (m, 1H); MS (DCI/NH$_3$) m/e 297 (M+H)$^+$; maleate salt: White solid; mp 125-127° C.; Anal. calcd for C$_{21}$H$_{24}$N$_4$O$_5$; C, 61.15; H, 5.87; N, 13.58. Found: C, 60.86; H, 5.89; N, 13.52.

EXAMPLE 105

N-{[4-(2-chlorophenyl)-1-piperazinyl]methyl}benzamide

The procedure described in Example 91B was followed, substituting the product from Example 101A for the product from Example 91A and substituting 1-(2-chlororphenyl)piperazine for 1-(2-cyanophenyl)piperazine to provide the title compound as a colorless oil. $^1$H NMR (300 MHz, CDCl$_3$) δ 2.86 (m, 4H), 3.1 (m, 4H), 4.45 (d, 2H, J=6 Hz), 6.70 (br s, 1H), 7.1 (m, 3H), 7.00 (m, 2H), 7.25 (m, 2H), 7.4-7.26 (m, 2H); MS (DCI/NH$_3$) m/e 330 (M+H)$^+$; maleate salt: Tan solid; mp 145-147° C.; Anal. calcd for C$_{22}$H$_{24}$ClN$_3$O$_5$; C, 59.26; H, 5.43; N, 9.42. Found: C, 58.98; H, 5.34; N, 9.15.

EXAMPLE 106

3-chloro-N-{[4-(2-cyanophenyl)-1-piperazinyl]methyl}benzamide

The procedure described in Example 91B was followed, substituting the product from Example 95A for the product from Example 91A, to provide the title compound as a colorless oil. $^1$H NMR (300 MHz, CDCl$_3$) δ 2.92 (m, 4H), 3.25 (m, 4H), 4.45 (d, 2H, J=6 Hz), 6.75 (br s, 1H), 7.00 (t, 2H, J=6 Hz), 7.35-7.70 (m, 5H), 7.82 (m, 1H); MS (DCI/NH$_3$) m/e 355 (M+H)$^+$; maleate salt: White solid; mp 143-146° C.; Anal. calcd for C$_{23}$H$_{23}$ClN$_4$O$_5$: C, 58.66; H, 4.92; N, 11.90. Found: C, 58.30; H, 5.01; N, 11.67.

EXAMPLE 107

4-chloro-N-{[4-(2-methoxyphenyl)-1-piperazinyl]methyl}benzamide

EXAMPLE 107A

[(4-chlorobenzoyl)amino]methyl acetate

The procedure described in Example 91A was followed, substituting N-(4-chlorobenzoyl)glycine for N-(3-methylbenzoyl)glycine, to provide the title compound.

EXAMPLE 107B 4-chloro-N-{[4-(2-methoxyphenyl)-1-piperazinyl]methyl}benzamide The procedure described in Example 91B was followed, substituting the product from Example 107A for the product from Example 91A and substituting 1-(2-methoxyphenyl)piperazine for 1-(2-cyanophenyl)piperazine to provide the title compound as a colorless oil. $^1$H NMR (300 MHz, CDCl$_3$) δ 2.92 (m, 4H), 3.15 (m, 4H), 3.85 (s, 3H), 4.45 (d, 2H, J=6 Hz), 6.7 (br s, 1H), 6.82-7.05 (m, 4H), 7.44 (m, 2H), 7.75 (m, 2H); MS (DCI/NH$_3$) m/e 360 (M+H)$^+$; maleate salt: White solid; mp 145-147° C.; Anal. calcd for C$_{23}$H$_{26}$ClN$_3$O$_6$: C, 58.04; H, 5.51; N, 8.83. Found: C, 58.24; H, 5.18; N, 8.83.

EXAMPLE 108

2-chloro-N-{[4-(3-cyano-2-pyridinyl)-1-piperazinyl]methyl}benzamide

EXAMPLE 108A

[(2-chlorobenzoyl)amino]methyl acetate

The procedure described in Example 91A was followed, substituting N-(2-chlorobenzoyl)glycine for N-(3-methylbenzoyl)glycine, to provide the title compound.

EXAMPLE 108B 2-chloro-N-{[4-(3-cyano-2-pyridinyl)-1-piperazinyl]methyl}benzamide The procedure described in Example 91B was followed, substituting the product from Example 108A for the product from Example 91A and substituting 1-(2-cyanopyridinyl)piperazine for 1-(2-cyanophenyl)piperazine to provide the title compound as a yellow oil. $^1$H NMR (300 MHz, CDCl$_3$) δ 2.75 (t, 4H, J=6 Hz), 3.55 (t, 4H, J=6 Hz), 4.4 (d, 2H, J=6 Hz), 6.50 (br s, 1H), 6.65 (m, 2H), 7.40-7.55 (m, 4H), 7.75 (m, 2 H), 8.20 (m, 1H); MS (DCI/NH$_3$) m/e 356 (M+H)$^+$; maleate salt: White solid; mp 137-139° C.; Anal. calcd for C$_{22}$H$_{22}$ClN$_5$O$_5$: C, 55.99; H, 4.70; N, 14.84. Found: C, 55.76; H, 4.74; N, 14.60.

EXAMPLE 109

N-{[4-(3-cyano-2-pyridinyl)-1-piperazinyl]methyl}-2-(trifluoromethyl)benzamide

EXAMPLE 109A

{[2-(trifluoromethyl)benzoyl]amino}methyl acetate

The procedure described in Example 91A was followed, substituting N-[2-(trifluoromethyl)benzoyl]glycine for N-(3-methylbenzoyl)glycine, to provide the title compound.

EXAMPLE 109B

N-{[4-(3-cyano-2-pyridinyl)-1-piperazinyl]methyl}-2-(trifluoromethyl)benzamide The procedure described in Example 91B was followed, substituting the product from Example 109A for the product from Example 91A and substituting 1-(2-cyanopyridinyl)piperazine for 1-(2-cyanophenyl)piperazine to provide the title compound as a colorless oil. $^1$H NMR (300 MHz, CDCl$_3$) δ 2.90 (m, 4H), 3.80 (m, 4H), 4.45 (d, 2H, J=6 Hz), 6.80 (dd, 1H, J=12, 6 Hz), 7.55-7.80 (m, 5H), 8.35 (dd, 1H, J=6, 3 Hz), 11.00 (br s, 1H); MS (DCI/NH$_3$) m/e 390 (M+H)$^+$. maleate salt: Hygroscopic white solid.

EXAMPLE 110

N-{[4-(2-cyanophenyl)-1-piperazinyl]methyl}benzamide

The procedure described in Example 91B was followed, substituting the product from Example 101A for the product from Example 91A, to provide the title compound as a yellow oil. $^1$H NMR (300 MHz, DMSO-d$_6$) δ 2.71 (m, 4H), 3.15 (m, 4H), 4.22 (d, 2H, J=6.1 Hz), 7.08 (dd, 1H, J=7.8, 7.8 Hz), 7.15 (d, 1H, J=8.5 Hz), 7.55 (m, 4H), 7.68 (dd, 1H, J=7.4, 1.3 Hz), 7.90 (m, 2H), 8.95 (t, 1H, J=6.1 Hz); MS (DCI/NH$_3$) m/e 321 (M+H)$^+$; maleate salt: Tan solid, mp 148-150° C.; Anal. calcd for C$_{19}$H$_{20}$N$_4$O.1.0 C$_4$H$_4$O$_4$: C, 63.29 12.84. Found: C, 63.03; H, 5.47; N, 12.79.

EXAMPLE 111

N-{[4-(2-methoxyphenyl)-1-piperidinyl]methyl}-3-methylbenzamide 4-(2-Methoxyphenyl)piperidine (286 mg, 1.5 mmol), the product from Example 91A (310 mg, 1 mmol), and triethylamine (0.42 mL, 3 mmol) were combined in acetonitrile (8 mL) and stirred at room temperature for 18 hours. The reaction mixture was concentrated under reduced pressure and the residue was purified by flash chromatography on silica gel (elution with dichloromethane:methanol 9.5:0.5) to provide the title compound (285 mg, 56.2% yield). $^1$H NMR (300 MHz, DMSO-d$_6$) δ 1.65 (m, 4H), 2.31 (m, 2H), 2.37 (s, 3H), 2.79 (m, 1H), 2.93 (m, 2H), 3.75 (s, 3H), 4.15 (d, 2H, J=6 Hz), 6.90 (m, 2H), 7.15 (m, 2H), 7.36 (m, 2H), 7.68 (m, 2H), 8.69 (t, 1H, J=6 Hz); MS (DCI/NH$_3$) m/e 339 (M+H)$^+$; Anal. calcd for C$_{21}$H$_{26}$N$_2$O$_2$.0.15 H$_2$O: C, 73.94; H, 7.77; N, 8.21. Found: C, 73.56, H, 7.72, N, 8.15.

EXAMPLE 112

3-methyl-N-{[4-(2-pyridinyl)-1-piperidinyl]methyl}benzamide

The procedure described in Example 111 was followed, substituting the product from Example 36C for 4-(2-methoxyphenyl)piperidine, to provide the title compound (480 mg, 64% yield). $^1$H NMR (300 MHz, DMSO-d$_6$) δ 1.75 (m, 4H), 2.31 (m, 2H), 2.36 (s, 3H), 2.59 (m, 1H), 2.95 (m, 2H), 4.17 (d, 2H, J=6 Hz), 7.18 (m, 1H), 7.25 (d, 1H, J=6 Hz), 7.35 (m, 2H), 7.69 (m, 3H), 8.48 (m, 1H), 8.71 (m, 1H); MS (DCI/NH$_3$) m/e 310 (M+H)$^+$. Anal. calcd for C$_{19}$H$_{23}$N$_3$O.0.25 H$_2$O: C, 72.70; H, 7.50; N, 13.39. Found: C, 72.60, H, 7.50, N, 13.21.

EXAMPLE 113

3-methyl-N-[(4-phenyl-3,6-dihydro-1(2H)-pyridinyl)methyl]benzamide

The procedure described in Example 111 was followed, substituting 4-phenyl-1,2,3,6-tetrahydropyridine for 4-(2-methoxyphenyl)piperidine, to provide the title compound (196 mg, 64% yield). $^1$H NMR (300 MHz, DMSO-d$_6$) δ 2.35 (s, 3H), 2.76 (t, 2H, J=6 Hz), 3.24 (d, 2H), 4.25 (d, 4H, J=9 Hz), 6.16 (m, 1H), 7.22 (t, 1H, J =6 Hz), 7.32 (m, 4H), 7.40 (m, 2H), 7.66 (m, 2H), 8.75 (t, 1H, J=6 Hz); MS (DCI/NH$_3$) m/e 307 (M+H)$^+$. Anal. calcd for C$_{20}$H$_{22}$N$_2$O.0.10 H$_2$O: C, 77.94; H, 7.26; N, 9.09. Found: C, 77.64, H, 7.34, N, 8.86.

EXAMPLE 114

N-(3',6'-dihydro-2,4'-bipyridin-1'(2'H)-ylmethyl)-3-methylbenzamide

The procedure described in Example 111 was followed, substituting 1',2',3',6'-tetrahydro-2,4'-bipyridine hydrochloride for 4-(2-methoxyphenyl)piperidine, to provide the title compound (310 mg, 81.5% yield). $^1$H NMR (300 MHz, DMSO-d$_6$) δ 2.35 (s, 3H), 2.58 (m, 2H), 2.76 (t, 2H, J=6 Hz), 3.29 (m, 2H), 4.27 (d, 2H, J=6 Hz), 6.70 (m, 1H), 7.22 (m, 1H), 7.35 (d, 2H, J=6 Hz), 7.51 (d, 1H, J=9 Hz), 7.70 (m, 3H), 8.51 (m, 1H), 8.76 (m, 1H); MS (DCI/NH$_3$) m/e 308 (M+H)$^+$.

EXAMPLE 115

N-(3',6'-dihydro-2,4'-bipyridin-1'(2'H)-ylmethyl)-3-methoxybenzamide

3-Methoxybenzamide (1.13 g, 7.5 mmol), K$_2$CO$_3$ (345 mg, 2.5 mmol), paraformaldehyde (0.5 g, 16 mmol), and 1',2',3',6'-tetrahydro-2,4'-bipyridine hydrochloride (393 mg, 2 mmol) were combined in ethanol (25 ml) and refluxed for 18 hours. The reaction mixture was allowed to cool to room temperature and concentrated under reduced pressure. The residue was partitioned between ethyl acetate (80 mL) and water (80 mL). The organic layer was washed with brine (2×50 mL), dried over MgSO$_4$, filtered, and the filtrate concentrated under reduced pressure. The residue was purified by flash chromatography on silica gel (elution with ethyl acetate:ethanol, 9.0:1.0) to provide the title compound (180 mg, 49% yield). $^1$H NMR (300 MHz, DMSO-d$_6$) δ 2.58 (m, 2H), 2.76 (t, 2H, J=6 Hz), 3.29 (m, 2H), 3.80 (s, 3H), 4.27 (d, 2H, J=6 Hz), 6.70 (m, 1H), 7.09 (m, 1H), 7.22 (m, 1H), 7.42 (m, 4H), 7.72 (m, 1H), 8.51 (m, 1H), 8.83 (t, 1H, J=6 Hz); MS (DCI/NH$_3$) m/e 324 (M+H)$^+$.

Anal. calcd for C$_{19}$H$_{21}$N$_3$O$_2$.0.60 H$_2$O: C, 68,28; H, 6.70; N, 12.57. Found: C, 68.19, H, 6.84, N, 11.77.

EXAMPLE 116

N-(3',6'-dihydro-2,4'-bipyridin-1'(2'H)-ylmethyl)-3-fluorobenzamide

The procedure described in Example 115 was followed, substituting 3-fluorobenzamide for 3-methoxybenzamide, to provide the title compound (260 mg, 42.6% yield). $^1$H NMR (300 MHz, DMSO-d$_6$) δ 2.58 (m, 2H), 2.76 (t, 2H, J=6 Hz), 3.29 (m, 2H), 4.27 (d, J=6 Hz), 6.70 (m, 1H), 7.21 (m, 1H), 7.39 (m, 1H), 7.51 (m, 2H), 7.72 (m, 3H), 8.51 (m, 1H), 8.93 (t, 1H, J=6 Hz); MS (DCI/NH$_3$) m/e 312 (M+H)$^+$.

EXAMPLE 117

N-(3',6'-dihydro-2,4'-bipyridin-1'(2'H)-ylmethyl)-3, 5-difluorobenzamide

The procedure described in Example 115 was followed, substituting 3,5-difluorobenzamide for 3-methoxybenzamide, to provide the title compound (140 mg, 21% yield). $^1$H NMR (300 MHz, DMSO-d$_6$) δ 2.58 (m, 2H), 2.76 (t, 2H, J=6 Hz), 3.29 (m, 2H), 4.27 (d, 2H, J=6 Hz), 6.70 (m, 1H), 7.21 (m, 1H), 7.51 (m, 2H), 7.60 (m, 2H), 7.75 (m, 1H), 8.51 (m, 1H), 9.01 (t, 1H, J=6 Hz); MS (DCI/NH$_3$) m/e 330 (M+H)$^+$. Anal. calcd for C$_{18}$H$_{17}$N$_3$OF$_2$.0.70 H$_2$O: C, 63.22; H, 5.42; N, 12.29. Found: C, 62.76, H, 5.02, N, 12.09.

EXAMPLE 118

2-[4-(3-cyano-2-pyridinyl)-1-piperazinyl]-N-3-pyridinylacetamide

The procedure described in Example 8 was followed, substituting 2-chloro-N-3-pyridinylacetamide (Abdel Rahman, A. E.; et al. J. Ind. Chem. Soc. 1981, 58, 171-173) for N-chloroacetyl-3-nitroaniline, to provide the title compound in 13% yield. The free base was treated with maleic acid to provide the maleate salt as a yellow solid. $^1$H NMR (300 MHz, MeOH-d$_4$) δ 8.43 (dd, 1 H, J=4.7, 1.7 Hz), 8.33 (br d, 1 H, J=4.1 Hz), 8.17 (ddd, 1 H, J=8.85, 2.4, 1.4 Hz), 8.00 (dd, 1 H, J=7.8, 2.0 Hz), 7.47 (dd, 1 H, J=8.5, 5.1 Hz), 7.00 (dd, 1 H, J=7.8, 5.1 Hz), 6.27 (s, 2 H), 3.88 (m, 6 H), 3.28 (m, 4 H); MS (DCI/NH$_3$) m/e 323 (M+H)$^+$; Anal. calcd for C$_{17}$H$_{18}$N$_6$O.1.2 C$_4$H$_4$O$_4$.0.40 H$_2$O: C, 55.85; H, 5.07; N, 17.92; Found: C, 55.66; H, 5.14; N, 17.91.

EXAMPLE 119

2-(1-{2-[(3-methylphenyl)amino]-2-oxoethyl}piperidin-4-yl)pyridiniumn N-oxide

EXAMPLE 119A

2-piperidin-4-ylpyridinium N-oxide hydrochloride

2-[1-(tert-butoxycarbonyl)piperidin-4-yl]pyridinium N-oxide (1.24 g, 4.15 mmol) in dichloromethane (30 mL) was cooled to 0° C. and treated with m-chloroperbenzoic acid 77% (1.4 g, 8.3 mmol). After stirring at 0° C. for 30 minutes, the mixture was allowed to warm to room temperature and stir an additional for 2 hrs. The mixture was diluted with methylene chloride (50 mL), washed with saturated NaHCO$_3$, brine, dried over MgSO$_4$, filtered, and the filtrate concentrated under reduced pressure to provide white solid. The white solid was dissolved in ethyl acetate (50 mL) and cooled to −78° C. HCl gas was bubbled through the reaction mixture for 15 minutes and the mixture was allowed to warm to room temperature. The mixture was filtered and the filter cake washed with ethyl acetate and then dried under high vaccum to provide the title compound (0.85 g, 96% yield). $^1$H NMR (300 MHz, DMSO-d$_6$) δ 1.82 (m, 2H), 2.10 (m, 2H), 3.06 (m, 2H), 3.36 (m, 2H), 3.58 (m, 1H), 7.45 (m, 3H), 8.39 (d, J=9Hz, 1H), 9.04 (bs, 1H); MS (DCI/NH$_3$) m/z 179 (M+H)$^+$.

EXAMPLE 119B

2-(1-{2-[(3-methylphenyl)amino]-2-oxoethyl}piperidin-4-yl)pyridiniumn N-oxide The procedure described in Example 36D was followed, substituting the product from Example 119A for the product from Example 36C, to provide the title compound (159 mg, 48.8% yield). $^1$H NMR (300 MHz, DMSO-d$_6$) δ 1.89 (m, 2H), 1.91(m, 2H), 2.30 (m, 5H), 2.99 (m, 2H), 3.14 (s, 2H), 3.25 (m, 1H), 6.88 (d, J=7.5Hz, 1H), 7.19 (t, J=7.5 Hz, 1H), 7.31 (m, 2H), 7.45 (m, 2H), 8.24 (m, 1H), 9.6 (bs, 1H); MS (DCI-NH$_3$) m/z 310 (M+H)$^+$. The free base (156.7 mg) in ethanol (20 mL) was treated with maleic acid (55.93 mg) and the solution was stirred for 10 minutes, concentrated under reduced pressure to provide the maleate salt as an off white solid (212.6 mg). $^1$H NMR (300 MHz, DMSO-d$_6$) δ 1.91 (m, 2H), 2.15 (m, 2H), 2.29 (s, 3H), 3.30 (m, 4H), 3.50 (m, 2H), 4.02 (m, 1H), 6.04 (s, 2H), 6.95 (d, J=7.5 Hz, 1H), 7.23 (t, J=7.5 Hz, 1H), 7.39 (m, 5H), 8.29 (m, 1H), 10.36 (bs, 1H); MS (DCI-NH$_3$) m/z 310 (M+H)$^+$; Analysis calculated for 0.25 H$_2$O.C$_{23}$H$_{27}$N$_3$O$_6$: C, 61.94; H, 6.22; N, 9.42; Found: C, 61.56, H, 6.21, N, 8.99.

EXAMPLE 121

N-2-adamantyl-2-[4-(3-cyano-2-pyridinyl)-1-piperazinyl]acetamide

EXAMPLE 121A

N-2-adamantyl-2-bromoacetamide

The procedure described in Example 1A was followed, substituting 2-adamantaneamine hydrochloride for 3-methylaniline to provide the title compound (68% yield) as a white solid. $^1$H NMR (300 MHz, DMSO-d$_6$) δ 1.51 (d, 2H, J=12.9 Hz), 1.78 (m, 10H), 1.95 (d, 2H, J=12.5 Hz), 3.82 (br d, 1H, J=7.5 Hz), 3.92 (s, 2H), 8.11 (br d, 1H, J=7.1 Hz); MS (DCI/NH$_3$) m/e 272 (M+H)$^+$; 290 (M+NH$_4$)$^+$.

EXAMPLE 121B

N-2-adamantyl-2-[4-(3-cyano-2-pyridinyl)-1-piperazinyl]acetamide 1-(2-cyanopyridyl)piperazine (680 mg, 3.61 mmol) and N,N-diisopropylamine (2 mL) in toluene (30 mL) were treated with the product from Example 121A (800 mg, 2.94 mmol) and heated to 60° C. for 18 hours. The mixture was allowed to cool to room temperature, transferred to a separatory funnel and washed with saturated aqueous sodium bicarbonate. The organic phase was dried (sodium sulfate), filtered, and the filtrate concentrated under reduced pressure. The residue was purified by flash column chromatography on silica gel (elution with 20% ethyl acetate:hexanes) to provide 917 mg (82% yield) of the title compound as a white solid. $^1$H NMR (300 MHz, DMSO-d$_6$) δ 1.57 (d, 2H, J=12.5 Hz), 1.79 (m, 12H), 2.63 (m, 4H), 3.04 (s, 2H), 3.62 (m, 4H), 3.88 (br d, 1H, J=7.8 Hz), 6.94 (dd, 1H, J=7.5, 4.7 Hz), 7.69 (br d, 1H, J=7.8 Hz), 8.08 (dd, 1H, J=7.8, 2.0 Hz), 8.41 (dd, 1H, J=4.8, 1.7 Hz); MS (DCI/NH$_3$) m/e 380 (M+H)$^+$; Anal. calcd for C$_{22}$H$_{29}$N$_5$O: C, 69.63; H, 7.70; N, 18.45. Found: C, 69.45; H, 7.90; N, 18.07.

EXAMPLE 122

2-[4-(3-cyano-2-pyridinyl)-1-piperazinyl]-N-cyclohexylacetamide

EXAMPLE 122A

2-bromo-N-cyclohexylacetamide

To a solution of bromoacetyl chloride (5.50 mL, 66.9 mmol) in tetrahydrofuran (120 mL) at 0° C. was added a mixture of 4-dimethylaminepyridine (2.80 g, 22.9 mmol) and cyclohexylamine (5.00 mL, 43.7 mmol) in tetrahydrofuran (60 mL). The mixture was warmed to room temperature and stirred an additional 18 hours. The reaction was quenched with water and extracted with dichloromethane. The organic phase was dried (sodium sulfate), filtered, and the filtrate concentrated under reduced pressure. The residue was purified by flash column chromatography on silica gel (elution with 10% ethyl acetate:hexanes) to provide of the title compound (25% yield) as a white solid. $^1$H NMR (300 MHz, DMSO-$d_6$) δ 1.18 (m, 5H), 1.64 (m, 5H), 3.52 (m, 1H), 3.99 (s, 2H), 8.04 (br d, 1H, J=7.1 Hz); MS (DCI/NH$_3$) m/e 237/239 (M+NH$_4$)$^+$.

EXAMPLE 122B

2-[4-(3-cyano-2-pyridinyl)-1-piperazinyl]-N-cyclohexylacetamide

The procedure described in Example 121B was followed, substituting the product from Example 122A for the product from Example 121A to provide the title compound (46% yield) as a white solid. $^1$H NMR (300 MHz, DMSO-$d_6$) δ 1.22 (m, 3H), 1.38 (m, 2H), 1.67 (m, 3H), 1.89 (m, 2H), 2.68 (m, 4H), 3.05 (s, 2H), 3.75 (m, 4H), 3.83 (m, 1H), 6.79 (dd, 1H, J=7.5, 4.8 Hz), 7.02 (br s, 1H), 7.78 (dd, 1H, J=7.6, 1.9 Hz), 8.35 (dd, 1H, J=4.8, 2.0 Hz); MS (DCI/NH$_3$) m/e 328 (M+H)$^+$; Anal. calcd for $C_{18}H_{25}N_5O$: C, 66.03; H, 7.70; N, 21.39. Found: C, 65.88; H, 7.70; N, 21.28.

EXAMPLE 123

2-[4-(3-cyano-2-pyridinyl)-1-piperazinyl]-N-5,6,7,8-tetrahydro-1-naphthalenylacetamide

EXAMPLE 123A 2-bromo-N-5,6,7,8-tetrahydro-1-naphthalenylacetamide

The procedure described in Example 1A was followed, substituting 5,6,7,8-tetrahydro-1-naphthylamine for 3-methylaniline to provide the title compound (14% yield) as a white solid. $^1$H NMR (300 MHz, DMSO-$d_6$) δ 1.70 (m, 4H), 2.58 (m, 2H), 2.73 (m, 2H), 4.07 (s, 2H), 6.93 (d, 1H, J=7.5 Hz), 7.07 (dd, 1H, J=7.8, 7.8 Hz), 7.17 (d, 1H, J=6.8 Hz), 9.55 (br s, 1H); MS (DCI/NH$_3$) m/e 268/270 (M+H)$^+$; 285/287 (M+NH$_4$)$^+$.

EXAMPLE 123B

2-[4-(3-cyano-2-pyridinyl)-1-piperazinyl]-N-5,6,7,8-tetrahydro-1-naphthalenylacetamide The procedure described in Example 121B was followed, substituting the product from Example 123A for the product from Example 121A to provide the title compound (75% yield) as a white solid. $^1$H NMR (300 MHz, DMSO-$d_6$) δ 1.74 (m, 4H), 2.62 (m, 2H), 2.72 (m, 6H), 3.20 (s, 2H), 3.69 (m, 4H), 6.88 (d, 1H, J=7.5 Hz), 6.94 (dd, 1H, J=7.8, 4.7 Hz), 7.07 (dd, 1H, J=7.8 Hz), 7.59 (d, 1H, J=7.8 Hz), 8.08 (dd, 1H, J=7.5, 1.7 Hz), 8.42 (dd, 1H, J=4.8, 1.7 Hz), 9.33 (br s, 1H); MS (DCI/NH$_3$) m/e 376 (M+H)$^+$; Anal. calcd for $C_{22}H_{25}N_5O \cdot 0.3 H_2O$: C, 69.38; H, 6.77; N, 18.39. Found: C, 69.40; H, 6.63; N, 18.13.

EXAMPLE 124

2-(3',6'-dihydro-2,4'-bipyridin-1'(2'H)-yl)-N-(4-fluoro-2-methylphenyl)acetamide

EXAMPLE 124A 2-chloro-N-(4-fluoro-2-methylphenyl)acetamide

The procedure described in Example 22A was followed, substituting 4-fluoro-2-methylphenylamine for 3,4,5-trimethoxyaniline to provide the title compound (51 % yield) as a white solid. $^1$H NMR (300 MHz, DMSO-$d_6$) δ 2.19 (s, 3H), 4.29 (s, 2H), 7.01 (ddd, 1H, J=8.5, 8.5, 3.1 Hz), 7.10 (dd, 1H, J=9.8, 3.1 Hz), 7.35 (dd, 1H, J=8.8, 5.8 Hz), 9.67 (br s, 1H); MS (DCI/NH$_3$) m/e 202 (M+H)$^+$; 219 (M+NH$_4$)$^+$.

EXAMPLE 124B 2-(3',6'-dihydro-2,4'-bipyridin-1'(2'H)-yl)-N-(4-fluoro-2-methylphenyl)acetamide A mixture of 1',2',3',6'-tetrahydro-[2,4']bipyridinyl hydrochloride (30 mg, 0.15 mmol, Saari, W. S.; et al. J. Med. Chem. 1984, 27, 1182), the product from Example 124A (40 mg, 0.20 mmol) and sodium carbonate (70 mg) in N,N-dimethylformamide/water (2:1, 2 mL) was shaken at room temperature for 18 hours. The resulting mixture was concentrated under reduced pressure. The residue was purified by preparative HPLC to provide 46 mg (70%) of the desired product as a trifluoroacetic acid salt. $^1$H NMR (300 MHz, DMSO-$d_6$) δ 2.20 (s, 3H), 2.96 (br s, 2H), 3.43-3.63 (m, 2H), 4.03-4.20 (m, 2H), 4.39 (s, 2H), 6.72 (br s, 1H), 7.10 (m, 2H), 7.38 (m, 1H), 7.43 (m, 1H), 7.64 (d, J=7 Hz, 1H), 7.84 (m, 1H), 8.60 (m, 1H), 10.00 (m, 1H), 10.40 (br s, 1H); MS (ESI/APCI+) m/e 326 (M+H)$^+$.

EXAMPLE 125

N-{[4-(2-pyridinyl)-1-piperidinyl]methyl}-3-(trifluoromethyl)benzamide

A mixture of product from Example 36C (20 mg, 0.10 mmol), paraformaldehyde (30 mg, 1 mmol), 3-trifluoromethylbenzamide (95 mg, 0.5 mmol, Lancaster), and 42 mg of potassium carbonate (0.3 mmol) in 2.5 mL absolute ethyl alcohol was heated to reflux under nitrogen overnight. The mixture was cooled to room temperature, filtered, and the solvent was removed. The residue was purified by flash column chromatography on silica gel (10% methanol:ethyl acetate) to give 11.2 mg (34%) pure compound. $^1$H NMR (500 MHz, DMSO-$d_6$) δ 1.72 (m, 2H), 1.82 (m, 2H), 2.34 (m, 2H), 2.60 (m, 1H), 2.96 (m, 2H), 4.20 (d, J=6.2 Hz, 2H), 7.18 (ddd, J=7.5, 4.8, 1.1 Hz, 1H), 7.25 (m, 1H), 7.69 (td, J=7.6, 1.9 Hz, 1H), 7.74 (t, J=7.8 Hz, 1H), 7.92 (d, J=7.8 Hz, 1H), 8.20 (d, J=7.8 Hz, 1H), 8.24 (s, 1H), 8.47 (ddd, J=5.0, 1.9, 0.9 Hz, 1H), 9.02 (t, J=6.1 Hz, 1H); MS (ESI/APCI−) m/e 362 (M−H)$^+$.

EXAMPLE 126

3,5-dimethoxy-N-{[4-(2-pyridinyl)-1-piperidinyl]methyl}benzamide

A mixture of product from Example 36C (20 mg, 0.10 mmol), paraformaldehyde (30 mg, 1 mmol), 3,5-dimethoxybenzamide (91 mg, 0.5 mmol, Aldrich), and 42 mg of potassium carbonate (0.3 mmol) in 2.5 mL absolute ethyl alcohol was heated to reflux under nitrogen overnight. The mixture was cooled to room temperature, filtered, and the solvent was removed. The residue was purified by flash column chromatography on silica gel (10% methanol:ethyl acetate) to give 11.8 mg (34%) pure compound. $^1$H NMR (500 MHz, DMSO-$d_6$) δ 1.73 (m, 2H), 1.82 (m, 2H), 2.36 (m, 2H), 2.61 (m, 1H), 2.96 (m, 2H), 3.79 (s, 6H), 4.18 (d, J=6.0 Hz, 2H), 6.65 (s, 1H), 7.05 (s, 2H), 7.18 (t, J=5 Hz, 1H), 7.25 (d, J=7 Hz, 1H), 7.69 (t, J=7 Hz, 1H), 8.47 (d, J=4 Hz, 1H), 8.75 (t, J=6 Hz, 1H); MS (ESI/APCI−) m/e 354 (M−H)$^+$.

EXAMPLE 127

N-{[4-(2-pyridinyl)-1-piperidinyl]methyl}cyclohexanecarboxamide

A mixture of product from Example 36C (20 mg, 0.10 mmol), paraformaldehyde (30 mg, 1 mmol), cyclohexanecarboxylic acid amide (63 mg, 0.5 mmol, Aldrich), and 42 mg of potassium carbonate (0.3 mmol) in 2.5 mL absolute ethyl alcohol was heated to reflux under nitrogen overnight. The mixture was cooled to room temperature, filtered, and the solvent was removed. The residue was purified by flash column chromatography on silica gel (10% methanol:ethyl acetate) to give 16 mg (56%) pure compound. $^1$H NMR (500 MHz, DMSO-$d_6$) δ 1.38 (m, 2H), 1.19 (m, 4H), 1.73 (m, 2H), 1.68 (m, 4H), 1.80 (m, 2H), 2.18 (m, 3H), 2.58 (m, 1H), 2.92 (m, 2H), 3.92 (d, J=5 Hz, 2H), 7.18 (t, J=5 Hz, 1H), 7.26 (d, J=7 Hz, 1H), 7.69 (t, J=7 Hz, 1H), 7.95 (t, J=5 Hz, 1H), 8.55 (d, J=4 Hz, 1H); MS (ESI/APCI+) m/e 302 (M+H)$^+$.

EXAMPLE 128

3,4-difluoro-N-{[4-(2-pyridinyl)-1-piperidinyl]methyl}benzamide

A mixture of product from Example 36C (20 mg, 0.10 mmol), paraformaldehyde (30 mg, 1 mmol), 3,4-difluorobenzamide (79 mg, 0.5 mmol, Lancaster), and 42 mg of potassium carbonate (0.3 mmol) in 2.5 mL absolute ethyl alcohol was heated to reflux under nitrogen overnight. The mixture was cooled to room temperature, filtered, and the solvent was removed. The residue was purified by flash column chromatography on silica gel (10% methanol:ethyl acetate) to give 16 mg (56%) pure compound. $^1$H NMR (500 MHz, DMSO-$d_6$) δ 1.73 (m, 2H), 1.82 (m, 2H), 2.33 (m, 2H), 2.60 (m, 1H), 2.95 (m, 2H), 4.18 (d, J=5 Hz, 2H), 7.18 (t, J=5 Hz, 1H), 7.25 (d, J=7 Hz, 1H), 7.58 (t, J=7 Hz, 1H), 7.70 (t, J=7 Hz, 1H), 7.80 (m, 1H), 7.95 (t, J=7 Hz, 1H), 8.45 (d, J=4 Hz, 1H), 8.95 (t, J=5 Hz, 1H), (ESI/APCI−) m/e 330 (M−H)$^+$.

EXAMPLE 129

3-chloro-N-{[4-(2-pyridinyl)-1-piperidinyl]methyl}benzamide

A mixture of product from Example 36C (20 mg, 0.10 mmol), paraformaldehyde (30 mg, 1 mmol), 3-chlorobenzamide (165 mg, 0.5 mmol, Lancaster), and 42 mg of potassium carbonate (0.3 mmol) in 2.5 mL absolute ethyl alcohol was heated to reflux under nitrogen overnight. The mixture was cooled to room temperature, filtered, and the solvent was removed. The residue was purified by flash column chromatography on silica gel (10% methanol:ethyl acetate) to give 11 mg (36%) pure compound. $^1$H NMR (500 MHz, DMSO-$d_6$) δ 1.73 (m, 2H), 1.82 (m, 2H), 2.33 (m, 2H), 2.60 (m, 1H), 2.95 (m, 2H), 4.18 (d, J=5 Hz, 2H), 7.18 (t, J=6 Hz, 1H), 7.25 (d, J=7 Hz, 1H), 7.56 (t, J=7 Hz, 1H), 7.62 (d, J=6 Hz, 1H), 7.72 (t, J=7 Hz, 1H), 7.85 (d, J=6 Hz, 1H), 7.95 (s, 1H), 8.48 (d, J=6 Hz, 1H), 8.95 (t, J=5 Hz, 1H); MS (ESI/APCI−) m/e 328 (M−H)$^+$.

EXAMPLE 130

2,3-dimethyl-N-{[4-(2-pyridinyl)-1-piperazinyl]methyl}benzamide

A mixture of 1-pyridin-2-ylpiperazine (16 mg, 0.1 mmol, Aldrich), paraformaldehyde (30 mg, 1 mmol), 2,3-dimethylbenzamide (75 mg, 0.5 mmol, Lancaster), and 42 mg of potassium carbonate (0.3 mmol) in 2 mL absolute ethyl alcohol was heated to reflux under nitrogen overnight. The mixture was cooled to room temperature, filtered, and the solvent was removed. The residue was purified by flash column chromatography on silica gel (10% methanol:ethyl acetate) to give 29 mg (88%) pure compound. $^1$H NMR (500 MHz, DMSO-$d_6$) δ 2.20 (s, 3H), 2.24 (s, 3H), 2.61 (t, J=4 Hz, 4H), 3.48 (t, J=4 Hz, 4H), 4.15 (d, J=5 Hz, 1H), 6.62 (t, J=5 Hz, 1H), 6.81 (d, J=6 Hz, 1H), 7.03 (m, 2H), 7.21 (t, J=5 Hz, 1H), 7.51 (t, J=6 Hz, 1H), 8.12 (d, J=5 Hz, 1H), 8.52 (t, J=5 Hz, 1H); MS (ESI/APCI−) m/e 323 (M−H)$^+$.

EXAMPLE 131

N-(3',6'-dihydro-2,4'-bipyridin-1'(2'H)-ylmethyl)-3-(trifluoromethyl)benzamide A mixture of 1',2',3',6'-tetrahydro-[2,4']bipyridinyl hydrochloride (20 mg, 0.10 mmol, Saari, W. S.; et al. J. Med. Chem. 1984, 27, 1182), paraformaldehyde (30 mg, 1 mmol), 3-trifluoromethylbenzamide (95 mg, 0.5 mmol), and 42 mg of potassium carbonate (0.3 mmol) in 2.5 mL absolute ethyl alcohol was heated to reflux under nitrogen overnight. The mixture was cooled to room temperature, filtered, and the solvent was removed. The residue was purified by flash column chromatography on silica gel (10% methanol:ethyl acetate) to give 15 mg (41%) pure compound. $^1$H NMR (500 MHz, DMSO-$d_6$) δ 2.58 (m, 2H), 2.80 (t, J=4 Hz, 2H), 3.28 (m, 2H), 4.32 (d, J=5 Hz, 2H), 6.71 (m, 1H), 7.22 (m, 1H), 7.52 (d, J=6 Hz, 1H), 7.72 (m, 2H), 7.95 (d, J=6 Hz, 1H), 8.22 (m, 2H), 8.52 (m, 1H), 9.08 (t, J=5 Hz, 1H); MS (ESI/APCI−) m/e 360 (M−H)$^+$.

EXAMPLE 132

3-chloro-N-(3',6'-dihydro-2,4'-bipyridin-1'(2'H)-ylmethyl)benzamide

A mixture of 1',2',3',6'-tetrahydro-[2,4']bipyridinyl hydrochloride (20 mg, 0.10 mmol, Saari, W. S.; et al. J. Med. Chem. 1984, 27, 1182), paraformaldehyde (30 mg, 1 mmol), 3-chlorobenzamide (78 mg, 0.5 mmol, Lancaster), and 42 mg of potassium carbonate (0.3 mmol) in 2.5 mL absolute ethyl alcohol was heated to reflux under nitrogen overnight. The mixture was cooled to room temperature, filtered, and the solvent was removed. The residue was purified by flash column chromatography on silica gel (10% methanol:ethyl acetate) to give 20 mg (61%) pure compound. $^1$H NMR (500 MHz, DMSO-$d_6$) δ 2.58 (m, 2H), 2.79 (t, J=4 Hz, 2H), 3.30 (m, 2H), 4.30 (d, J=5 Hz, 2H), 6.71 (m, 1H), 7.22 (m, 1H), 7.52 (m, 2H), 7.62 (d, J=6 Hz, 1H), 7.73 (t, J=6 Hz, 1H), 7.85 (d, J=6 Hz, 1H), 7.92 (s, 1H), 8.52 (m, 1H), 9.08 (t, J=5 Hz, 1H); MS (ESI/APCI−) m/e 326 (M−H)$^+$.

EXAMPLE 133

N-(3',6'-dihydro-2,4'-bipyridin-1'(2'H)-ylmethyl)cyclohexanecarboxamide

A mixture of 1',2',3',6'-tetrahydro-[2,4']bipyridinyl hydrochloride (20 mg, 0.10 mmol, Saari, W. S.; et al. J. Med. Chem. 1984, 27, 1182), paraformaldehyde (30 mg, 1 mmol), cyclohexanecarboxylic acid amide (64 mg, 0.5 mmol, Aldrich), and 42 mg of potassium carbonate (0.3 mmol) in 2.5 mL absolute ethyl alcohol was heated to reflux under nitrogen overnight. The mixture was cooled to room temperature, filtered, and the solvent was removed. The residue was purified by flash column chromatography on silica gel (10% methanol:ethyl acetate) to give 19 mg (64%) pure compound. $^1$H NMR (500 MHz, DMSO-d$_6$) δ 1.19 (m, 4H), 1.26 (m, 2H), 1.61 (m, 1H), 1.68 (m, 3H), 2.18 (m, 1H), 2.55 (m, 2H), 2.68 (m, 2H), 3.18 (m, 2H), 4.02 (d, J=5 Hz, 2H), 6.68 (m, 1H), 7.22 (m, 1H), 7.52 (d, J=6 Hz, 1H), 7.73 (t, J=6 Hz, 1H), 8.02 (t, J=5 Hz, 1H), 8.52 (m, 1H); MS (ESI/APCI−) m/e 298 (M−H)$^+$.

EXAMPLE 134

N-(3',6'-dihydro-2,4'-bipyridin-1'(2'H)-ylmethyl)-3,4-difluorobenzamide

A mixture of 1',2',3',6'-tetrahydro-[2,4']bipyridinyl hydrochloride (20 mg, 0.10 mmol, Saari, W. S.; et al. J. Med. Chem. 1984, 27, 1182), paraformaldehyde (30 mg, 1 mmol), 3,4-difluorobenzamide (79 mg, 0.5 mmol, Lancaster), and 42 mg of potassium carbonate (0.3 mmol) in 2.5 mL absolute ethyl alcohol was heated to reflux under nitrogen overnight. The mixture was cooled to room temperature, filtered, and the solvent was removed. The residue was purified by flash column chromatography on silica gel (10% methanol:ethyl acetate) to give 18 mg (55%) pure compound. $^1$H NMR (500 MHz, DMSO-d$_6$) δ 2.58 (m, 2H), 2.79 (t, J=4 Hz, 2H), 3.32 (m, 2H), 4.28 (d, J=5 Hz, 2H), 6.71 (m, 1H), 7.22 (m, 1H), 7.55 (m, 2H), 7.83 (m, 2H), 7.95 (t, J=6 Hz, 1H), 8.52 (m, 1H) 8.95 (t, J=5 Hz, 1H); MS (ESI/APCI−) m/e 328 (M−H)$^+$.

EXAMPLE 135

N-(3',6'-dihydro-2,4'-bipyridin-1'(2'H)-ylmethyl)-3,5-dimethoxybenzamide

A mixture of 1',2',3',6'-tetrahydro-[2,4']bipyridinyl hydrochloride (20 mg, 0.10 mmol, Saari, W. S.; et al. J. Med. Chem. 1984, 27, 1182), paraformaldehyde (30 mg, 1 mmol), 3,5-dimethoxybenzamide (91 mg, 0.5 mmol, Aldrich), and 42 mg of potassium carbonate (0.3 mmol) in 2.5 mL absolute ethyl alcohol was heated to reflux under nitrogen overnight. The mixture was cooled to room temperature, filtered, and the solvent was removed. The residue was purified by flash column chromatography on silica gel (10% methanol:ethyl acetate) to give 19 mg (55%) pure compound. $^1$H NMR (500 MHz, DMSO-d$_6$) δ 2.59 (m, 2H), 2.79 (t, J=4 Hz, 2H), 3.30 (m, 2H), 3.79 (s, 3H), 3.80 (s, 3H), 4.25 (d, J=5 Hz, 2H), 6.65 (s, 1H), 6.71 (m, 1H), 7.02 (s, 2H), 7.22 (m, 1H), 7.52 (d, J=6 Hz, 1H), 7.75 (t, J=6 Hz), 8.52 (m, 1H), 8.88 (t, J=5 Hz, 1H); MS (ESI/APCI−) m/e 352 (M−H)$^+$.

EXAMPLE 136

N-(3-methylphenyl)-2-(4-phenyl-1-piperidinyl)acetamide

The procedure described in Example 35 was followed, substituting 4-phenylpiperidine for 4-(2-methoxyphenyl)piperidine to provide the title compound (99% yield). $^1$H NMR (300 MHz, DMSO-d$_6$) δ 1.76 (m, 4H), 2.28 (m, 5H), 2.51 (m, 1H), 2.98 (m, 2H), 3.12 (s, 2H), 6.88 (d, J=6 Hz, 1H), 7.19 (m, 2H), 7.29 (m, 4H), 7.46 (d, 2H), 9.61 (br s, 1H); MS (DCI/NH$_3$) m/e 310 (M+H)$^+$; Anal. calcd for C$_{20}$H$_{24}$N$_2$O.0.2 H$_2$O, C, 76.99; H, 7.88; N, 8.98. Found: C, 76.88, H, 7.85, N, 8.81

EXAMPLE 137

2-(3',6'-dihydro-2,4'-bipyridin-1'(2'H)-y)-N-(3-nitrophenyl)acetamide

The desired material was prepared according to the procedure of Example 124B by substituting the product from Example 124A with 2-chloro-N-(3-nitrophenyl)acetamide (Lancaster). Yield 48 mg (97%). $^1$H NMR (300 MHz, DMSO-d$_6$) δ 2.96 (br s, 2H), 3.45-3.75 (m, 2H), 4.05-4.20 (m, 2H), 4.38 (s, 2H), 6.75 (br s, 1H), 7.38 (m, 1H), 7.66 (m, 2H), 7.89 (m, 2H), 8.00 (d, J=6 Hz, 1H), 8.60 (m, 1H), 8.63 (br s, 1H), 10.45 (br s, 1H), 11.08 (br s, 1H); MS (ESI/APCI+) m/e 339 (M+H)$^+$.

EXAMPLE 138

N-1-adamantyl-2-[4-(3-cyano-2-pyridinyl)-1-piperazinyl]acetamide

EXAMPLE 138A

N-1-adamantyl-2-bromoacetamide

The procedure described in Example IA was followed, substituting 1-adamantane amine for 3-methylaniline to provide the title compound (77% yield) as a white solid. $^1$H NMR (300 MHz, DMSO-d$_6$) δ 1.61 (m, 6H), 1.91 (m, 6H), 2.01 (m, 3H), 3.76 (s, 2H), 7.74 (br s, 1H); MS (DCI/NH$_3$) m/e 272/274 (M+H)$^+$; 289/291 (M+NH$_4$)$^+$.

EXAMPLE 138B

N-1-adamantyl-2-[4-(3-cyano-2-pyridinyl)-1-piperazinyl]acetamide

The procedure described in Example 121B was followed, substituting the product from Example 138A for the product from Example 121A to provide the title compound (50% yield) as an colorless oil. $^1$H NMR (300 MHz, DMSO-d$_6$) δ 1.63 (m, 6H), 1.95 (m, 6H), 2.01 (m, 3H), 2.59 (m, 4H), 3.32 (s, 2H), 3.62 (m, 4H), 6.93 (dd, 1H, J=7.8, 5.1 Hz 1H), 8.06 (dd, 1H, J=7.5, 1.7 Hz), 8.41 (dd, 1H, J=4.8, 1.7 Hz); MS (DCI/NH$_3$) m/e (M+H)$^+$.

Maleate salt: white solid; Anal. calcd for C$_{22}$H$_{29}$N$_5$O.0.9 C$_4$H$_4$O$_4$.0.3 C$_4$H$_8$O$_2$: C, 63.07; H, 6.91; N, 13.72. Found: C, 63.41; H, 6.72; N, 13.45.

EXAMPLE 139

3-methyl-N-{[2-methyl-4-(2-pyridinyl)-1-piperazinyl]methyl}benzamide

EXAMPLE 139A 3-methyl-1-(2-pyridinyl)piperazine hydrobromide

A solution of 2-methylpiperazine (1.0 g, 0.01 mol, racemic mixture) and 2-bromopyridine (10 mL, 0.1 mol) was heated to 120° C. for 16 hours. The reaction mixture was cooled to room temperature and partitioned between ethyl acetate and water. The layers were separated, and the water layer was concentrated under reduced pressure. The residue was triturated with ethyl acetate, dichloromethane, and methanol to afford 460 mg (26% yield) of racemic 3-methyl-1-pyridin-2-yl-piperazine hydrobromide as an off-white solid. $^1$H NMR (300 MHz, DMSO-d$_6$) δ 1.27 (d, J=6.6 Hz, 3H), 2.90 (dd, J=10.5, 14.1 Hz, 1H), 3.10 (m, 2H), 3.40 (m, 2H), 4.32 (m, 2H), 6.77 (dd, J=4.8, 6.9 Hz, 1H), 6.98 (d, J=8.1 Hz, 1H), 7.64 (m, 1H), 8.15 (m, 1H), 8.63 (br s, 1H), 8.92 (br s, 1H); MS (APCI) m/e 178 (M+H)$_+$.

EXAMPLE 139B 3-methyl-N-{[2-methyl-4-(2-pyridinyl)-1-piperazinyl]methyl}benzamide A solution of the product from Example 139A (250 mg, 0.97 mmol), the product from Example 91A (201 mg, 0.97 mmol) and triethylamine (342 mg, 3.39 mmol) in acetonitrile (10 mL) was stirred at room temperature for 72 hours. The reaction mixture was poured into water and extracted with ethyl acetate. The ethyl acetate solution was then washed with additional water, a solution of saturated sodium bicarbonate, and brine before drying over sodium sulfate, filtering, and concentrating under reduced pressure. The residue was purified by flash column chromatography on silica gel (2-5% ethanol:ethyl acetate) to afford 216 mg (69% yield) of the title compound. $^1$H NMR (300 MHz, DMSO-d$_6$) δ 1.21 (d, J=5.4 Hz, 3H), 2.34 (s, 3H), 2.50 (m, 3H), 2.85 (m, 2H), 4.06 (br d, J=10.5 Hz, 2H), 4.29 (dd, J=13.5, 6.0 Hz, 1H), 4.43 (dd, J=13.5, 6.0 Hz, 1H), 6.58 (m, 1H), 6.82 (d, J=8.7 Hz, 1H), 7.34 (m, 2H), 7.48 (m, 1H), 7.63 (m, 2H), 8.07 (m, 1H), 8.54 (dd, J=6.0, 6.0 Hz, 1H); MS (ESI) m/e (M+H)$^+$.

EXAMPLE 140

N-(3-methylphenyl)-2-[2-methyl-4-(2-pyridinyl)-1-piperazinyl]acetamide

A solution of the product from Example 139A (250 mg, 0.97 mmol), the product from Example 1A (221 mg, 0.97 mmol), N,N-diisopropylethylamine (313 mg, 2.42 mmol), and toluene (8 mL) was heated at 60° C. for 16 hours and then cooled to room temperature. The reaction mixture was concentrated under reduced pressure, and the residue purified by flash column chromatography on silica gel (ethyl acetate) to afford 256 mg (81% yield) of the title compound. $^1$HNMR (300 MHz, DMSO-d$_6$) δ 1.06 (d, J=6.3 Hz, 3H), 2.27 (s, 3H), 2.58 (m, 2H), 2.80 (dd, J=12.3, 9.0 Hz, 1H), 2.84 (m, 1H), 3.10 (d, J=16.5 Hz, 1H), 3.11 (m, 1H), 3.38 (d, J=16.5 Hz, 1H), 4.00 (m, 2H), 6.63 (dd, J=8.1, 6.3 Hz, 1H), 6.84 (d, J=11.1 Hz, 1H), 6.89 (m, 1H), 7.18 (m, 1H), 7.44 (m, 2H), 7.52 (m, 1H), 8.10 (m, 1H), 9.63 (br s, 1H); MS (ESI) m/e 325 (M+H)$^+$.

EXAMPLE 141

3,5-dimethyl-N-{[4-(2-pyridinyl)-1-piperidinyl]methyl}benzamide

A mixture of the product from Example 36C (20 mg, 0.10 mmol), paraformaldehyde (30 mg, 1 mmol), 3,5-dimethylbenzamide (75 mg, 0.5 mmol), and 42 mg of potassium carbonate (0.3 mmol) in 2.5 mL absolute ethyl alcohol was heated to reflux under nitrogen overnight. The mixture was cooled to room temperature, filtered, and the solvent was removed. The residue was purified by flash column chromatography on silica gel (10% methanol:ethyl acetate) to give 23 mg (72%) pure compound. $^1$H NMR (500 MHz, DMSO-d$_6$) δ 1.73 (m, 2H), 1.82 (m, 2H), 2.29 (m, 2H), 2.32 (s, 6H), 2.60 (m, 1H), 2.95 (m, 2H), 4.18 (d, J=5 Hz, 2H), 7.18 (m, 2H), 7.25 (d, J=6 Hz, 1H), 7.50 (s, 2H), 7.68 (t, J=6 Hz, 1H), 8.48 (d, J=6 Hz, 1H), 8.62 (t, J=5 Hz, 1 H); MS (ESI/APCI−) m/e 322 (M−H)$^+$.

EXAMPLE 142

N-(3',6'-dihydro-2,4'-bipyridin-1'(2'H)-ylmethyl)-3,5-dimethylbenzamide

A mixture of 1',2',3',6'-tetrahydro-[2,4']bipyridinyl hydrochloride (20 mg, 0.10 mmol, Saari, W. S.; et al. J. Med. Chem. 1984, 27, 1182), paraformaldehyde (30 mg, 1 mmol), 3,5-dimethylbenzamide (75 mg, 0.5 mmol), and 42 mg of potassium carbonate (0.3 mmol) in 2.5 mL absolute ethyl alcohol was heated to reflux under nitrogen overnight. The mixture was cooled to room temperature, filtered, and the solvent was removed. The residue was purified by flash column chromatography on silica gel (10% methanol:ethyl acetate) to give 18 mg (56%) pure compound. $^1$H NMR (500 MHz, DMSO-d$_6$) δ2.33 (s, 6H), 2.56 (m, 2H), 2.78 (t, J=4 Hz, 2H), 3.28 (m, 2H), 4.18 (d, J=5 Hz, 2H), 6.71 (m, 1H), 7.18 (s, 1H), 7.22 (m, 1H), 7.50 (m, 3H), 7.75 (t, J=6 Hz, 1H), 8.52 (d, J=5 Hz, 1H), 8.62 (t, J=5 Hz, 1H), MS (ESI/APCI−) m/e 320 (M−H)$^+$.

EXAMPLE 143

3-methyl-N-[(3-methyl-3',6'-dihydro-2,4'-bipyridin-1'(2'H)-yl)methyl]benzamide

EXAMPLE 143A tert-butyl 3-methyl-3',6'-dihydro-2,4'-bipyridine-1'(2'H)-carboxylate A solution of 4-trifluoromethanesulfonyloxy-3,6-dihydro-2H-pyridine-1-carboxylic acid tert-butyl ester (8.10 g, 24.8 mmol; Bursavich, M. G.; et al. Org. Lett. 2001, 3, 2317) in tetrahydrofuran (50 mL) was treated with 3-methyl-2-pyridylzinc bromide (0.5 M in tetrahydrofuran, 65.0 mL, Aldrich), tetrakis(triphenylphosphine)-palladium(0) (280 mg, 0.24 mmol) and the mixture heated to 70° C. for 2 hours. The mixture was cooled to room temperature, concentrated under reduced pressure, the residue taken up in dichloromethane and washed with 1N sodium hydroxide. The organic phase was dried (magnesium sulfate), filtered and concentrated under reduced pressure. The residue was purified by flash column chromatography on silica gel (elution with 50% ethyl acetate: hexanes) to provide 5.50 g (82% yield) of the title compound as a light yellow oil. $^1$H NMR (300 MHz, DMSO-d$_6$) δ 1.44 (s, 9H), 2.32 (s, 3H), 2.44 (m, 2H), 3.54 (m, 2H), 3.99 (m, 2H), 5.88 (br s, 1H), 7.17 (dd, 1H, J=7.8, 4.8 Hz), 7.62 (br d, 1H, J=7.5 Hz), 8.36 (dd, 1H, J=4.8, 1.7 Hz); MS (DCI/NH$_3$) m/e 275 (M+H)$^+$; 292 (M+NH$_4$)$^+$.

EXAMPLE 143B 3-methyl-1',2',3',6'-tetrahydro-2,4'-bipyridine

The product from Example 143A (1.00 g, 3.64 mmol) in ethyl acetate (25 mL) was cooled to -78° C. and treated with a stream of hydrogen chloride gas for 10 minutes. The reaction mixture was allowed to warmed to room temperature with stirring. The solvent was removed under reduced pressure and the residue triturated with ethyl acetate, filtered and dried under vacuum overnight to provide the title compound as a white solid (HCl salt). $^1$H NMR (300 MHz, DMSO-d$_6$) δ 2.43 (s, 3H), 2.71 (m, 2H), 3.31 (m, 2H), 3.79 (m, 2H), 6.08

(br s, 1H), 7.66 (dd, 1H, J=6.8, 5.8 Hz), 8.18 (br d, 1H, J=6.6 Hz), 8.58 (d, 1H, J=5.1 Hz); MS (DCI/NH$_3$) m/e 175 (M+H)$^+$.

EXAMPLE 143C 3-methyl-N-[(3-methyl-3',6'-dihydro-2,4'-bipyridin-1'(2'H)-yl)methyl]benzamide A mixture of the product from Example 143B (trifluoroacetic acid salt; 29 mg, 0.1 mmol), paraformaldehyde (30 mg, 1 mmol), 3-methylbenzamide (68 mg, 0.5 mmol, Aldrich), and 42 mg of potassium carbonate (0.3 mmol) in 2.5 mL absolute ethyl alcohol was heated to reflux under nitrogen overnight. The mixture was cooled to room temperature, filtered, and the solvent was removed. The residue was purified by flash column chromatography on silica gel (10% methanol:ethyl acetate) to give 12.5 mg (39%) pure compound. $^1$H NMR (500 MHz, DMSO-d$_6$) δ 2.30 (s, 3H), 2.38 (s, 3H), 2.48 (m, 2H), 2.78 (m, 2H), 3.25 (m, 2H), 4.28 (d, J=6 Hz, 2H), 5.82 (m, 1H), 7.18 (t, J=6 Hz, 1H), 7.38 (m, 2H), 7.60 (t, J=6 Hz, 1H), 7.71 (m, 2H), 8.38 (d, J=6 Hz, 1H), 8.79 (t, J=6 Hz, 1H); MS (ESI/APCI–m/e 320) (M–H)$^+$.

EXAMPLE 144

N-[(3-cyano-3',6'-dihydro-2,4'-bipyridin-1'(2'H)-yl)methyl]-3-methylbenzamide

EXAMPLE 144A tert-butyl 3-cyano-3',6'-dihydro-2,4'-bipyridine-1'(2'H)-carboxylate A mixture of 4-trifluoromethanesulfonyloxy-3',6-dihydro-2H-pyridine-1-carboxylic acid tert-butyl ester (0.90 g, 2.7 mmol; Bursavich, M. G.; et al. Org. Lett. 2001, 3, 2317), lithium chloride (0.9 g, 20 mmol), hexamethylditin (1.0 mg, 3.05 mmol) and tetrakis(triphenylphosphine)palladium(0) (0.38 g, 0.32 mmol) in dioxane (40 mL) was heated was heated up under N$_2$ at 100° C. overnight. The mixture was cooled to room temperature, and concentrated. The residue was diluted with ethyl acetate (100 mL), filtered through Celite®, the filtrate washed with sodium bicarbonate solution (30 mL) and brine (30 mL). The organic phase was dried over magnesium sulfate, concentrated to give 1.3 g of crude product, which was used without purification. A mixture of the above crude solid, 2-chloro-3-cyanopyridine (1.1 equivalents), lithium chloride (0.9 g, 20 mmol), and tetrakis(triphenylphosphine)palladium(0) (0.34 g, 0.3 mmol) in N,N-dimethylformamide (35 mL) was heated up under N$_2$ at 120° C. overnight. The mixture was cooled to room temperature, and concentrated. The residue was diluted with ethyl acetate (100 mL), washed with water (2×30 mL), dried over magnesium sulfate, and concentrated. The residue was purified by flash column chromatography on silica gel to give 0.39 g of product. $^1$H NMR (300 MHz, DMSO-d$_6$) δ 1.40 (s, 9H), 2.60 (m, 2H), 3.55 (m, 2H), 4.05 (m, 2H), 6.50 (br s, 1H), 7.50 (m, 1H), 8.35 (m, 1H), 8.90 (m, 1H).

EXAMPLE 144B

1',2',3,6'-tetrahydro-2,4'-bipyridine-3-carbonitrile

To the product from Example 144A was added trifluoroacetic acid/dichloromethane (1:1, 10 mL) at room temperature. The mixture was stirred for 5 hours. The solvent was removed to give 0.55 g of product. $^1$H NMR (300 MHz, DMSO-d$_6$) δ 2.80 (m, 2H), 3.40 (m, 2H), 3.95 (m, 2H), 6.55 (br s, 1H), 7.60 (m, 1H), 8.40 (m, 1H), 8.90 (m, 1H), 9.00 (m, 2H); MS (ESI/APCI+) m/e 186 (M+H)$^+$.

EXAMPLE 144C

N-[(3-cyano-3',6'-dihydro-2,4'-bipyridin-1'(2'H)-yl)methyl]-3-methylbenzamide

A mixture of the product from Example 144B (30 mg, 0.1 mmol), paraformaldehyde (30 mg, 1 mmol), 3-methylbenzamide (70 mg, 0.5 mmol), and 42 mg of potassium carbonate (0.3 mmol) in 2.5 mL absolute ethyl alcohol was heated to reflux under nitrogen overnight. The mixture was cooled to room temperature, filtered, and the solvent was removed under reduced pressure. The residue was purified by flash column chromatography on silica gel (10% methanol:ethyl acetate) to give 10 mg (32%) pure compound. $^1$H NMR (500 MHz, DMSO-d$_6$) δ 2.36 (s, 3H), 2.62 (m, 2H), 2.79 (m, 2H), 3.32 (m, 2H), 4.24 (d, J=5 Hz, 2H), 4.66 (d, J=5 Hz, 1H), 6.50 (m, 1H), 7.35 (m, 2H), 7.49 (m, 1H), 7.72 (m, 2H), 8.29 (d, J=6 Hz, 1H), 8.78 (m, 1H); MS (ESI/APCI–) m/e 331 (M–H)$^+$.

EXAMPLE 145

N-(2,6-dimethylphenyl)-2-(3-methyl-3',6'-dihydro-2,4'-bipyridin-1'(2'H)-yl)acetamide A mixture of the product from Example 143B (trifluoroacetic acid salt; 23 mg, 0.08 mmol), 2-chloro-N-(2,6-dimethylphenyl)acetamide (20 mg, 0.1 mmol, Aldrich) and sodium carbonate (50 mg) in dimethylformamide/water (3:1, 1 mL) was shaken at room temperature for 18 hours. The resulting mixture was concentrated under reduced pressure. The residue was purified by preparative HPLC to provide 10 mg (28%) of the title compound as a trifluoroacetic acid salt. $^1$H NMR (300 MHz, DMSO-d$_6$) δ 2.20 (s, 6H), 2.40 (s, 3H), 2.80 (m, 2H), 3.50-3.70 (m, 2H), 4.00-4.15 (m, 2H), 4.39 (s, 2H), 5.92 (br s, 1H), 7.10 (m, 3H), 7.33 (m, 1H), 7.78 (m, 1H), 8.43 (m, 1H), 10.00 (br s, 1H), 10.42 (m, 1H); MS (ESI/APCI+) m/e 336 (M+H)$^+$.

EXAMPLE 146

N-(4-fluorophenyl)-2-(3-methyl-3',6'-dihydro-2,4'-bipyridin-1'(2'H)-yl)acetamide The desired material was prepared according to the procedure of Example 145 by substituting 2-chloro-N-(2,6-dimethylphenyl)acetamide with 2-chloro-N-(4-fluorophenyl)acetamide (Maybridge). Yield 9 mg (26%). 1H NMR (300 MHz, DMSO-d$_6$) δ 2.40 (s, 3H), 2.80 (m, 2H), 3.50-3.70 (m, 2H), 4.00-4.15 (m, 2H), 4.36 (s, 2H), 5.92 (br s, 1H), 7.20 (m, 2H), 7.35 (m, 1H), 7.63 (m, 2H), 7.80 (m, 1H), 8.43 (m, 1H), 10.45 (m, 1H), 10.62 (br s, 1H); MS (ESI/APCI+) m/e 326 (M+H)$^+$.

EXAMPLE 147

N-(2,4-difluorophenyl)-2-(3-methyl-3',6'-dihydro-2,4'-bipyridin-1'(2'H)-yl)acetamide The desired material was prepared according to the procedure of Example 145 by substituting 2-chloro-N-(2,6-dimethylphenyl)acetamide with 2-chloro-N-(2,4-difluorophenyl)acetamide (Maybridge). Yield 12 mg (33%). $^1$H NMR (300 MHz, DMSO-d$_6$) δ 2.40 (s, 3H), 2.80 (m, 2H), 3.50-3.70 (m, 2H), 4.00-4.15 (m, 2H), 4.38 (s, 2H), 5.90 (br s, 1H), 7.12 (m, 1H), 7.35 (m, 1H), 7.40 (m, 1H), 7.78 (m, 1H), 7.82 (m, 1H), 10.40 (m, 1H), 10.45 (br s, 1H); MS (ESI/APCI+) m/e 344 (M+H)$^+$.

EXAMPLE 148

2-(3-methyl-3',6'-dihydro-2,4'-bipyridin-1'(2'H)-yl)-N-(2-methylphenyl)acetamide The desired material was prepared according to the procedure of Example 145 by substituting 2-chloro-N-(2,6-dimethylphenyl)acetamide with 2-chloro-N-o-tolylacetamide (Maybridge). Yield 12 mg (34%). 1H NMR (300 MHz, DMSO-d$_6$) δ 2.22 (s, 3H), 2.40 (s, 3H), 2.80 (m, 2H), 3.50-3.70 (m, 2H), 4.00-4.15 (m, 2H), 4.38 (s, 2H), 5.92 (br s, 1H), 7.19 (m, 1H), 7.22 (m, 1H), 7.26 (m, 1H), 7.36 (m, 1H), 7.42 (m, 1H), 7.80 (m, 1H), 8.44 (m, 1H), 10.00 (br s, 1H), 10.42 (m, 1H); MS (ESI/APCI+) m/e 322 (M+H)$^+$.

EXAMPLE 149

2-(3-methyl-3',6'-dihydro-2,4'-bipyridin-1'(2'H)-yl)-N-[3-(trifluoromethyl)phenyl]acetamide The desired material was prepared according to the procedure of Example 145 by substituting 2-chloro-N-(2,6-dimethylphenyl)acetamide with 2-chloro-N-(3-trifluoromethylphenyl)acetamide (Maybridge). Yield 9 mg (23%). $^1$H NMR (300 MHz, DMSO-d$_6$) δ 2.40 (s, 3H), 2.80 (m, 2H), 3.50-3.70 (m, 2H), 4.00-4.15 (m, 2H), 4.37 (s, 2H), 5.92 (br s, 1H), 7.37 (m, 1H), 7.52 (m, 1H), 7.62 (m, 1H), 7.79 (m, 2H), 8.10 (m, 1H), 8.44 (m, 1H), 10.42 (m, 1H), 11.00 (br s, 1H); MS (ESI/APCI+) m/e 376 (M+H)$^+$.

EXAMPLE 150

N-(3-chloro-4-fluorophenyl)-2-(3-methyl-3',6'-dihydro-2,4'-bipyridin-1'(2'H)-yl)acetamide The desired material was prepared according to the procedure of Example 145 by substituting,2-chloro-N-(2,6-dimethylphenyl)acetamide with 2-chloro-N-(3-chloro-4-fluorophenyl)acetamide (Maybridge). Yield 9 mg (24%). $^1$H NMR (300 MHz, DMSO-d$_6$) δ 2.40 (s, 3H), 2.80 (m, 2H), 3.50-3.70 (m, 2H), 4.00-4.15 (m, 2H), 4.33 (s, 2H), 5.95 (br s, 1H), 7.36 (m, 1H), 7.44 (m, 2H), 7.78 (m, 1H), 7.92 (m, 1H), 8.44 (m, 1H), 10.42 (m, 1H), 10.82 (br s, 1H); MS (ESI/APCI+) m/e 360 (M+H)$^+$.

EXAMPLE 151

2-(3-methyl-3',6'-dihydro-2,4'-bipyridin-1'(2'H)-yl)-N-[4-(trifluoromethoxy)phenyl]acetamide The desired material was prepared according to the procedure of Example 145 by substituting 2-chloro-N-(2,6-dimethylphenyl)acetamide with 2-chloro-N-(4-trifluoromethoxyphenyl)acetamide (Maybridge). Yield 9 mg (22%). $^1$H NMR (300 MHz, DMSO-d$_6$) δ 2.40 (s, 3H), 2.80 (m, 2H), 3.50-3.70 (m, 2H), 4.00-4.15 (m, 2H), 4.30 (s, 2H), 5.92 (br s, 1H), 7.36 (m, 1H), 7.40 (m, 2H), 7.77 (m, 2H), 7.82 (m, 1H), 8.42 (m, 1H), 10.42 (m, 1H), 10.80 (br s, 1H); MS (ESI/APCI+) m/e 392 (M+H)$^+$.

EXAMPLE 152

2-(3-methyl-3',6'-dihydro-2,4'-bipyridin-1'(2'H)-yl)-N-[2-(trifluoromethyl)phenyl]acetamide The desired material was prepared according to the procedure of Example 145 by substituting 2-chloro-N-(2,6-dimethylphenyl)acetamide with 2-chloro-N-(2-trifluoromethylphenyl)acetamide (Maybridge). Yield 10 mg (26%). $^1$H NMR (300 MHz, DMSO-d$_6$) δ 2.40 (s, 3H), 2.80 (m, 2H), 3.50-3.70 (m, 2H), 4.00-4.15 (m, 2H), 5.92 (br s, 1H), 7.36 (m, 1H), 7.60 (m, 2H), 7.80 (m, 3H), 8.42 (m, 1H), 10.40 (br s, 1H), 10.42 (m, 1H); MS (ESI/APCI+) m/e 376 (M+H)$^+$.

EXAMPLE 153

N-(2,3-dichlorophenyl)-2-(3-methyl-3',6'-dihydro-2,4'-bipyridin-1'(2'H)-yl)acetamide The desired material was prepared according to the procedure of Example 145 by substituting 2-chloro-N-(2,6-dimethylphenyl)acetamide with 2-chloro-N-(3,4-dichlorophenyl)acetamide (Maybridge). Yield 10 mg (26%). 1H NMR (300 MHz, DMSO-d$_6$) δ 2.40 (s, 3H), 2.80 (m, 2H), 3.50-3.70 (m, 2H), 4.00-4.15 (m, 2H), 4.40 (s, 2H), 5.92 (br s, 1H), 7.37 (m, 1H), 7.42 (m, 1H), 7.58 (m, 1H), 7.77 (m, 1H), 7.81 (m, 1H), 8.42 (m, 1H), 10.42 (br s, 1H), 10.45 (m, 1H); MS (ESI/APCI+) m/e 377 (M+H)$^+$.

EXAMPLE 154

2-(3-methyl-3',6'-dihydro-2,4'-bipyridin-1'(2'H)-yl)-N-[4-(trifluoromethyl)phenyl]acetamide The desired material was prepared according to the procedure of Example 145 by substituting 2-chloro-N-(2,6-dimethylphenyl)acetamide with 2-chloro-N-(4-trifluoromethylphenyl)acetamide (Maybridge). Yield 11 mg (28%). $^1$H NMR (300 MHz, DMSO-d$_6$) δ 2.40 (s, 3H), 2.80 (m, 2H), 3.50-3.70 (m, 2H), 4.00-4.15 (m, 2H), 4.37 (s, 2H), 5.92 (br s, 1H), 7.36 (m, 1H), 7.78 (m, 3H), 7.82 (m, 2H), 8.42 (m, 1H), 10.42 (m, 1H), 10.98 (br s, 1H); MS (ESI/APCI+) m/e 376 (M+H)$^+$.

EXAMPLE 155

2-[4-(3-cyano-2-thienyl)-3,6-dihydro-1(2H)-pyridinyl]-N-(3-methylphenyl)acetamide

EXAMPLE 155A 2-(1,2,3,6-tetrahydro-4-pyridinyl)-3-thiophenecarbonitrile trifluoracetate The desired material was prepared according to the procedure of Examples 144A and 144B by substituting 2-bromo-3-methyl-pyridine with thiophene-3-carbonitrile. $^1$H NMR (300 MHz, DMSO-d$_6$) δ 2.80 (m, 2H), 3.40 (m, 2H), 3.90 (m, 2H), 6.45 (br s, 1H), 7.45 (m, 1H), 7.75 (m, 1H), 8.95 (m, 2H); MS (ESI/APCI+) m/e 191 (M+H)$^+$.

EXAMPLE 155B

2-[4-(3-cyano-2-thienyl)-3,6-dihydro-1(2H)-pyridinyl]-N-(3-methylphenyl)acetamide The desired material was prepared according to the procedure of Example 145 by substituting the product from Example 143B with the product from Example 155A, and 2-chloro-N-(2,6-dimethylphenyl)acetamide with the product from Example 33A. Yield 13 mg (36%). $^1$H NMR (300 MHz, DMSO-d$_6$) δ 2.30 (s, 3H), 2.90 (m, 2H), 3.50-4.20 (m, 4H), 4.30 (s, 2H), 6.43 (br s, 1H), 6.98 (m, 1H), 7.24 (m, 1H), 7.42 (m, 2H), 7.50 (m, 1H), 7.78 (m, 1H), 10.42 (m, 1H), 10.44 (br s, 1H); MS (ESI/APCI+) m/e 338 (M+H)$^+$.

EXAMPLE 156

2-(3-cyano-3',6'-dihydro-2,4'-bipyridin-1'(2'H)-yl)-N-(2,6-dimethylphenyl)acetamide The desired material was prepared according to the procedure of Example 145 by substituting the product of Example 143B with the product from Example 144B. Yield 10 mg (27%). $^1$H NMR (300 MHz, DMSO-d$_6$) δ 2.20 (s, 6H), 2.90 (m, 2H), 3.50-3.70 (m, 2H), 4.00-4.15 (m, 2H), 4.37 (s, 2H), 6.55 (br s, 1H), 7.20 (m, 3H), 7.55 (m, 1H), 8.40 (m, 1H), 8.80 (m, 1H), 10.00 (br s, 1H), 10.45 (m, 1H); MS (ESI/APCI+) m/e 347 (M+H)$^+$.

EXAMPLE 157

2-(3-cyano-3',6'-dihydro-2,4'-bipyridin-1'(2'H)-yl)-N-(4-fluorophenyl)acetamide

The desired material was prepared according to the procedure of Example 145 by substituting by substituting the product of Example 143B with the product from Example 144B, and 2-chloro-N-(2,6-dimethylphenyl)acetamide with 2-chloro-N-(4-fluorophenyl)acetamide (Maybridge). Yield 11 mg (31%). $^1$H NMR (300 MHz, DMSO-d$_6$) δ 2.95 (m, 2H), 3.50-3.70 (m, 2H), 4.00-4.15 (m, 2H), 4.37 (s, 2H), 6.55 (br s, 1H), 7.20 (m, 2H), 7.65 (m, 3H), 8.40 (m, 1H), 8.85 (m, 1H), 10.50 (m, 1H), 10.70 (br s, 1(ESI/APCI+) m/e 337 (M+H)$^+$.

EXAMPLE 158

2-(3-cyano-3',6'-dihydro-2,4'-bipyridin-1'(2'H)-yl)-N-(2,4-difluorophenyl)acetamide The desired material was prepared according to the procedure of Example 145 by substituting the product of Example 143B with the product from Example 144B, and 2-chloro-N-(2,6-dimethylphenyl)acetamide with 2-chloro-N-(2,4-difluorophenyl)acetamide (Maybridge). Yield 11 mg (29%). $^1$H NMR (300 MHz, DMSO-d$_6$) δ 2.95 (m, 2H), 3.50-3.70 (m, 2H), 4.00-4.15 (m, 2H), 4.35 (s, 2H), 6.55 (br s, 1H), 7.20 (m, 1H), 7.40 (m, 1H), 7.60 (m, 1H), 7.85 (m, 1H), 8.40 (m, 1H), 8.85 (m, 1H), 10.50 (m, 1H), 10.55 (br s, 1H), MS (ESI/APCI+) m/e 355 (M+H)$^+$.

EXAMPLE 159

2-(3-cyano-3',6'-dihydro-2,4'-bipyridin-1'(2'H)-yl)-N-(2-methylphenyl)acetamide

The desired material was prepared according to the procedure of Example 145 by substituting the product of Example 143B with the product from Example 144B, and 2-chloro-N-(2,6-dimethylphenyl)acetamide with 2-chloro-N-o-tolylacetamide (Maybridge). Yield 11 mg (31%). $^1$H NMR (300 MHz, DMSO-d$_6$) δ 2.20 (s, 3H), 2.95 (m, 2H), 3.50-3.70 (m, 2H), 4.00-4.15 (m, 2H), 4.35 (s, 2H), 6.60 (br s, 1H), 7.20 (m, 3H), 7.45 (m, 1H), 7.60 (m, 1H), 8.40 (m, 1H), 8.80 (m, 1H), 10.00 (br s, 1H), 10.55 (m, 1H); MS (ESI/APCI+) m/e 333 (M+H)$^+$.

EXAMPLE 160

2-(3-cyano-3',6'-dihydro-2,4'-bipyridin-1'(2'H)-yl)-N-[3-(trifluoromethyl)phenyl]acetamide The desired material was prepared according to the procedure of Example 145 by substituting the product of Example 143B with the product from Example 144B, and 2-chloro-N-(2,6-dimethylphenyl)acetamide with 2-chloro-N-(3-trifluoromethylphenyl)acetamide (Maybridge). Yield 11 mg (28%). $^1$H NMR (300 MHz, DMSO-d$_6$) δ 2.90 (m, 2H), 3.50-3.70 (m, 2H), 4.00-4.15 (m, 2H), 4.30 (s, 2H), 6.55 (br s, 1H), 7.60 (m, 3H), 7.75 (m, 1H), 8.10 (m, 1H), 8.40 (m, 1H), 8.80 (m, 1H), 10.50 (m, 1H), 10.95 (br s, 1H); MS (ESI/APCI+) m/e 387 (M+H)$^+$.

EXAMPLE 161

2-(3-cyano-3',6'-dihydro-2,4'-bipyridin-1'(2'H)-yl)-N-[4-(trifluoromethoxy)phenyl]acetamide The desired material was prepared according to the procedure of Example 145 by substituting the product of Example 143B with the product from Example 144B, and 2-chloro-N-(2,6-dimethylphenyl)acetamide with 2-chloro-N-(4-trifluoromethoxyphenyl)acetamide (Maybridge). Yield 11 mg (27%). $^1$H NMR (300 MHz, DMSO-d$_6$) δ 2.90 (m, 2H), 3.50-3.70 (m, 2H), 4.00-4.15 (m, 2H), 4.35 (s, 2H), 6.55 (br s, 1H), 7.40 (m, 2H), 7.60 (m, 1H), 7.75 (m, 2H), 8.40 (m, 1H), 8.80 (m, 1H), 10.50 (m, 1H), 10.80 (br s, 1H); MS (ESI/APCI+) m/e 403 (M+H)$^+$.

EXAMPLE 162

2-(3-cyano-3',6'-dihydro-2,4'-bipyridin-1'(2'H)-yl)-N-[2-(trifluoromethyl)phenyl]acetamide The desired material was prepared according to the procedure of Example 145 by substituting the product of Example 143B with the product from Example 144B, and 2-chloro-N-(2,6-dimethylphenyl)acetamide with 2-chloro-N-(2-trifluoromethylphenyl)acetamide (Maybridge). Yield 11 mg (28%). $^1$H NMR (300 MHz, DMSO-d$_6$) δ 2.90 (m, 2H), 3.50-3.70 (m, 2H), 4.00-4.15 (m, 2H), 4.35 (s, 2H), 6.55 (br s, 1H), 7.55 (m, 3H), 7.80 (m, 2H), 8.40 (m, 1H), 8.80 (m, 1H), 10.40 (br s, 1H), 10.50 (m, 1H); MS (ESI/APCI+) m/e 387 (M+H)$^+$.

EXAMPLE 163

2-(3-cyano-3',6'-dihydro-2,4'-bipyridin-1'(2'H)-yl)-N-(2,3-dichlorophenyl)acetamide The desired material was prepared according to the procedure of Example 145 by substituting the product of Example 143B with the product from Example 144B, and 2-chloro-N-(2,6-dimethylphenyl)acetamide with 2-chloro-N-(2,3-dichlorophenyl)acetamide (Maybridge). Yield 12 mg (30%). $^1$H NMR (300 MHz, DMSO-d$_6$) δ 2.90 (m, 2H), 3.50-3.70 (m, 2H), 4.00-4.15 (m, 2H), 4.35 (s, 2H), 6.55 (br s, 1H), 7.40

(m, 2H), 7.60 (m, 2H), 8.40 (m, 1H), 8.80 (m, 1H), 10.50 (m, 2H); MS (ESI/APCI+) m/e 388 (M+H)+.

EXAMPLE 164

3-methyl-N-{[4-(6-oxo-1(6H)-pyridazinyl)-1-piperidinyl]methyl}benzamide

The procedure described in Example 111 was followed, substituting the product from Example 40B for 4-(2-methoxyphenyl)piperidine to provide the title compound (99% yield). $^1$H NMR (300 MHz, DMSO-d$_6$) δ 1.74 (m, 2H), 1.88 (m, 2H), 2.37 (s, 3H), 2.39 (m, 2H), 2.99 (m, 2H), 4.19 (m, 2H), 4.71 (s, 1H), 6.91 (dd, J=9, 1.5 Hz, 1H), 7.38 (m, 3H), 7.69 (m, 2H), 7.96 (dd, J=9.0, 3.0 Hz, 1H), 8.75 (br s, 1H); MS (DCI/NH$_3$) m/e 327 (M+H)+.
Maleate salt: Anal. calcd for C$_{18}$H$_{22}$N$_4$O$_2$·1.25C$_4$H$_4$O$_4$·1.5 H$_2$O: C, 55.42; H, 6.07; N, 11.24. Found: C, 55.25; H, 5.88; N, 13.03.

EXAMPLE 165

N-(3',6'-dihydro-2,4'-bipyridin-1'(2'H)-ylmethyl)-1-adamantanecarboxamide

Prepared in the same manner as Example 115 substituting 1-adamantanecarboxamide (Aldrich) for 3-methoxybenzamide (43 mg, 6% yield). $^1$H NMR (300 MHz, DMSO-d$_6$) δ 1.66 (m, 6H), 1.80 (m, 6H), 1.95 (m, 3H), 2.30 (m, 2H), 2.66 (t, J=4.5 Hz, 2H), 3.15 (M, 2H), 4.06 (d, J=6 Hz, 2H), 6.68 (m, 1H), 7.21 (m, 1H), 7.51 (d, J=6 Hz, 1H), 7.72 (m, 2H), 8.51 (m, 1H); MS (DCI/NH$_3$) m/e 352 (M+H)+.

EXAMPLE 166

3-methyl-N-{[4-(1,3-thiazol-2-yl)-3,6-dihydro-1(2H)-pyridinyl]methyl}benzamide

EXAMPLE 166A tert-butyl 4-(1,3-thiazol-2-yl)-3,6-dihydro-1(2H)-pyridinecarboxylate The procedure described in Example 143A was followed, substituting 2-thiazolylzinc bromide for 3-methyl-2-pyridylzinc bromide to provide the title compound (56% yield). $^1$H NMR (300 MHz, CDCl$_3$) δ 1.5 (s, 9H), 2.7 (m, 2H), 3.33 (t, 2H, J=6 Hz), 4.10 (q, 2H, J=3 Hz), 6.60 (m, 1H), 7.21 (d, 1H, J=3 Hz), 7.78 (d, 1H, J=3 Hz); MS (DCI/NH$_3$) m/e 267 (M+H)+.

EXAMPLE 166B 4-(1,3-thiazol-2-yl)-1,2,3,6-tetrahydropyridine

A solution of the product from Example 1 66A (3.62 g, 13.6 mmol) in 25% trifluoroacetic acid/dichloromethane (30 mL) was stirred at room temperature for 2 hours. The reaction was concentrated under reduced pressure to afford brown oil (1.69 g, 74%). $^1$H NMR (300 MHz, CDCl$_3$) δ 2.55 (m, 2H), 3.12 (t, 2H, J=6 Hz), 3.59 (m, 2H), 6.63 (m, 1H), 7.20 (d, 1H, J=3 Hz), 7.75 (d, 1H, J=3 Hz); MS (DCI/NH$_3$) m/e 167 (M+H)+.

EXAMPLE 166C 3-methyl-N-{[4-(1,3-thiazol-2-yl)-3,6-dihydro-1(2H)-pyridinyl]methyl}benzamide The procedure described in Example 200 was followed, substituting the product from Example 166B for the product from Example 119A to provide the title compound as a yellow sticky residue 680 mg (36%). $^1$H NMR (300 MHz, CDCl$_3$) δ 2.4 (s, 3H), 2.8 (m, 2H), 2.95 (t, 2H, 4.5 Hz), 3.42 (m, 2H), 4.5 (d, 2H, J=6 Hz), 6.6 (m, 1H), 7.2 (d, 1H, J=3 Hz), 7.35 (dd, 2H, J=4.5 Hz, 1.5 Hz), 7.49 (m, 1H), 7.52 (s, 1H), 7.78 (d, 1H, J=3 Hz); MS (DCI/NH$_3$) m/e 314 (M+H)+.
Maleate salt: Anal. calcd for C$_{17}$H$_{19}$N$_3$OS·1.0 C$_4$H$_4$O$_4$·0.5 H$_2$O: C, 57.52; H, 5.52; N, 9.58. Found: C, 57.48; H, 5.33; N, 9.52.

EXAMPLE 167

2-[4-(3-cyano-2-pyridinyl)-1-piperazinyl]-N-1,2,3,4-tetrahydro-1-naphthalenylacetamide

EXAMPLE 167A 2-bromo-N-1,2,3,4-tetrahydro-1-naphthalenylacetamide

The procedure described in Example 1A was followed, substituting (±)-1,2,3,4-tetrahydro-1-naphthylamine hydrochloride for 3-methylaniline to provide the title compound (22% yield) as a white solid. $^1$H NMR (300 MHz, DMSO-d$_6$) δ 1.75 (m, 4H), 2.73 (m, 2H), 3.87 (ABq, 2H, J$_{AB}$=10.5 Hz, Δv$_{AB}$=8.5 Hz), 4.91 (m, 1H), 7.15 (m, 4H), 8.65 (br d, 1H, J=8.5 Hz); MS (DCI/NH$_3$) m/e 268/270 (M+H)+; 285/287 (M+NH$_4$)+.

EXAMPLE 167B

2-[4-(3-cyano-2-pyridinyl)-1-piperazinyl]-N-1,2,3,4-tetrahydro-1-naphthalenylacetamide The procedure described in Example 121B was followed, substituting the product from Example 167A for the product from Example 121A to provide the title compound (87% yield) as a white solid. $^1$H NMR (300 MHz, DMSO-d$_6$) δ 1.81 (m, 4H), 2.63 (m, 4H), 2.74 (m, 2H), 3.08 (ABq, 2H, J$_{AB}$=15.3 Hz, Δv$_{AB}$=8.8 Hz), 3.62 (m, 4H), 5.02 (m, 1H), 6.92 (dd, 1H, J=7.5, 4.8 Hz), 7.13 (m, 4H), 8.06 (dd, 1H, J=7.8, 2.0 Hz), 8.06 (m overlapped, 1H), 8.40 (dd, 1H, J=4.8, 2.0 Hz); MS (DCI/NH$_3$) m/e 376 (M+H)+; Anal. calcd for C$_{22}$H$_{25}$N$_5$O: C, 70.38; H, 6.71; N, 18.65. Found: C, 69.99; H, 6.85; N, 18.59.

EXAMPLE 168

2-[4-(3-cyano-2-pyridinyl)-1-piperazinyl]-N-[(1S)-1,2,3,4-tetrahydro-1-naphthalenyl]acetamide

EXAMPLE 168A 2-bromo-N-[(1S)-1,2,3,4-tetrahydro-1-naphthalenyl]acetamide

The procedure described in Example 1A was followed, substituting (S)-1,2,3,4-tetrahydro-1-naphthylamine (Lancaster) for 3-methylaniline to provide the title compound (87% yield) as a white solid. $^1$H NMR (300 MHz, DMSO-d$_6$) δ 1.79 (m, 4H), 2.73 (m, 2H), 3.87 (ABq, 2H, J$_{AB}$=10.9 Hz, Δv$_{AB}$=8.6 Hz), 4.93 (m, 1H), 7.15 (m, 4H), 8.65 (br d, 1H, J=8.5 Hz); MS (DCI/NH$_3$) m/e 268/270 (M+H)+; 285/287 (M+NH$_4$)+.

EXAMPLE 168B

2-[4-(3-cyano-2-pyridinyl)-1-piperazinyl]-N-[(1S)-1,2,3,4-tetrahydro-1-naphthalenyl]acetamide The procedure described in Example 121B was followed, substituting the product from Example 168A for the product from Example 121A to provide the title compound (67% yield) as a white solid. $[\alpha]^{23}_D$-39.37° (c 0.315, CHCl$_3$); $^1$H NMR (300 MHz, DMSO-d$_6$) δ 1.81 (m, 4H), 2.62 (m, 4H), 2.74 (m, 2H), 3.08 (ABq, 2H, J$_{AB}$=14.9 Hz, Δv$_{AB}$32 8.8 Hz), 3.61 (m, 4H), 5.00 (m, 1H), 6.92 (dd, 1H, J=7.8, 4.8 Hz), 7.12 (m, 4H), 8.06 (dd, 1H, J=7.8, 2.0 Hz), 8.06 (m, overlapped, 1H), 8.40 (dd, 1H, J=4.8, 2.0 Hz); MS (DCI/NH$_3$) m/e 376 (M+H)$^+$; Anal. calcd for C$_{22}$H$_{25}$N$_5$O: C, 70.38; H, 6.71; N, 18.65. Found: C, 70.00; H, 6.90; N, 18.26.

EXAMPLE 169

2-[4-(3-cyano-2-pyridinyl)-1-piperazinyl]-N-[(1R)-1,2,3,4-tetrahydro-1-naphthalenyl]acetamide

EXAMPLE 169A 2-bromo-N-[(1R)-1,2,3,4-tetrahydro-1-naphthalenyl]acetamide

The procedure described in Example 1A was followed, substituting (R)-1,2,3,4-tetrahydro-1-naphthylamine (Lancaster) for 3-methylaniline to provide the title compound (52% yield) as a white solid. $^1$H NMR (300 MHz, DMSO-d$_6$) δ 1.78 (m, 4H), 2.73 (m, 2H), 3.87 (ABq, 2H, J$_{AB}$=10.9 Hz, Δv$_{AB}$=8.6 Hz), 4.93 (m, 1H), 7.15 (m, 4H), 8.65 (br d, 1H, J=8.5 Hz); MS (DCI/NH$_3$) m/e 268/270 (M+H)$^+$; 285/287 (M+NH$_4$)$^+$.

EXAMPLE 169B

2-[4-(3-cyano-2-pyridinyl)-1-piperazinyl]-N-[(1R)-1,2,3,4-tetrahydro-1-naphthalenyl]acetamide The procedure described in Example 121B was followed, substituting the product from Example 169A for the product from Example 121A to provide the title compound (69% yield) as a white solid. $[\alpha]^{23}_D$+41.97° (c 0.305, CHCl$_3$); $^1$H NMR (300 MHz, DMSO-d$_6$) δ 1.79 (m, 4H), 2.63 (m, 4H), 2.74 (m, 2H), 3.08 (ABq, 2H, J$_{AB}$=15.3 Hz, Δv$_{AB}$=8.8 Hz), 3.61 (m, 4H), 5.01 (m, 1H), 6.92 (dd, 1H, J=7.8, 4.8 Hz), 7.12 (m, 4H), 8.06 (dd, 1H, J=7.8, 2.0 Hz), 8.06 (m, overlapped, 1H), 8.40 (dd, 1H, J=4.8, 2.0 Hz); MS (DCI/NH$_3$) m/e 376 (M+H)$^+$; Anal. calcd for C$_{22}$H$_{25}$N$_5$O.0.2 H$_2$O: C, 69.71; H, 6.75; N, 18.47. Found: C, 69.63; H, 6.75; N, 18.49.

EXAMPLE 170

N-(2,6-diethylphenyl)-2-[4-(2-pyridinyl)-1-piperidinyl]acetamide

To a 23° C. solution of 2,6-diethylaniline (59 mg, 0.394 mmol) and dichloromethane (1.5 mL) was added pyridine (52 mg, 0.656 mmol) and chloroacetyl chloride (37 mg, 0.328 mmol), and the reaction mixture vigorously shaken for 3 hours. To this reaction mixture was added a suspension of the product from Example 36C (hydrochloride salt, 50 mg, 0.253 mmol), sodium carbonate (115 mg, 1.08 mmol), N,N-dimethylformamide (2.2 mL) and water (1.1 mL), and the resultant mixture shaken overnight for 16 hours. The solvent was removed under reduced pressure, and the residue was suspended in a solution of dimethylsulfoxide (1.5 mL) and methanol (1.5 mL). This suspension was filtered through a pad of Celite®, and the filtrate was purified via preparative HPLC on a Waters Nova-Pak HR C18 column (40 mm×100 mm, 6 μm particle size) using a gradient of 10% to 100% acetonitrile:aqueous ammonium acetate (10 mM) over 12 minutes (15 minutes run time) at a flow rate of 70 mL/minute to provide the title compound (yield: 22.7 mg, 0.065 mmol, 26%). $^1$H NMR (300 MHz, DMSO-d$_6$) δ 1.12 (t, J=7.5 Hz, 6H), 1.90 (m, 4H), 2.32 (m, 2H), 2.50 (q, J=7.5 Hz, 4H), 2.70 (m, 1H), 3.05 (m, 2H), 3.14 (s, 2H), 7.09 (m, 2H), 7.19 (m, 2H), 7.32 (d, J=8.1 Hz, 1H), 7.72 (ddd, J=2.1, 7.5, 7.5 Hz, 1H), 8.49 (m, 1H), 9.23 (br s, 1H); MS (ESI) m/e 352 (M+H)$^+$; Anal. calcd for C$_{22}$H$_{29}$N$_3$O.0.25C$_2$H$_4$O$_2$.0.25H$_2$O: C, 72.84; H, 8.29; N, 11.33. Found: C, 72.71; H, 8.04; N, 11.59.

EXAMPLE 171

2-[4-(2-pyridinyl)-1-piperidinyl]-N-(2,4,6-trifluorophenyl)acetamide

The title compound was prepared according to the method of Example 170 substituting 2,4,6-trifluoroaniline in place of 2,6-diethylaniline (yield: 35.3 mg, 0.101 mmol, 40%). $^1$H NMR (300 MHz, DMSO-d$_6$) δ 1.86 (m, 4H), 2.27 (m, 2H), 2.67 (m, 1H), 3.01 (br d, J=10.5 Hz, 2H), 3.18 (s, 2H), 7.24 (m, 4H), 7.73 (ddd, J=2.1, 7.5, 7.5 Hz, 1H), 8.49 (m, 1H), 9.44 (br s, 1H); MS (ESI) m/e 350 (M+H)$^+$; Anal. calcd for C$_{18}$H$_{18}$F$_3$N$_3$O.0.1 C$_2$H$_4$O$_2$.0.1 H$_2$O: C, 61.20; H, 5.25; N, 11.77. Found: C, 61.22; H, 5.18; N, 11.78.

EXAMPLE 172

N-(4-chloro-2,6-dimethylphenyl)-2-[4-(2-pyridinyl)-1-piperidinyl]acetamide

The title compound was prepared according to the method of Example 170 substituting 4-chloro-2,6-dimethylaniline hydrochloride in place of 2,6-diethylaniline and adding one additional equivalent each of pyridine and sodium carbonate. (yield: 22.9 mg, 0.064 mmol, 25%). $^1$H NMR (300 MHz, DMSO-d$_6$) δ 1.90 (m, 4H), 2.05 (s, 3H), 2.14 (s, 6H), 2.30 (m, 2H), 2.67 (m, 1H), 3.04 (m, 2H), 3.16 (s, 2H), 4.67 (br s, 1H), 6.83 (s, 2H, min. rot.), 7.16 (s, 2H, maj. rot.), 7.20 (m, 1H), 7.29 (br d, J=7.5 Hz, 1H), 7.72 (ddd, J=2.1, 7.5, 7.5 Hz, 1H), 8.48 (m, 1H), 9.27 (br s, 1H), ; MS (ESI) m/e 358 (M+H)$^+$; Anal. calcd for C$_{20}$H$_{24}$ClN$_3$O.0.35C$_2$H$_4$O$_2$.0.15 H$_2$O: C, 65.15; H, 6.79; N, 11.01. Found: C, 65.19; H, 6.76; N, 11.02.

EXAMPLE 173

2-[4-(2-pyridinyl)-1-piperidinyl]-N-(2,4,6-trichlorophenyl)acetamide

The title compound was prepared according to the method of Example 170 substituting 2,4,6-trichloroaniline in place of 2,6-diethylaniline (yield: 21.2 mg, 0.053 mmol, 21%). $^1$H NMR (300 MHz, DMSO-d$_6$) δ 1.84 (m, 4H), 2.48 (m, 2H), 2.67 (m, 1H), 3.10 (br d, J=10.5 Hz, 2H), 3.17 (s, 2H), 7.21 (m, 1H), 7.30 (d, J=7.8 Hz, 1H), 7.72 (ddd, J=2.1, 7.5, 7.5 Hz, 1H), 7.77 (s, 2H), 8.48 (m, 1H); MS (ESI) m/e 400 (M+H)$^+$; Anal. calcd for C$_{18}$H$_{18}$Cl$_3$N$_3$O.0.1 C$_4$H$_4$O$_4$.0.55H$_2$O: C, 50.36; H, 4.44; N, 8.01. Found: C, 50.32; H, 4.17; N, 7.74.

EXAMPLE 174

N-(2,6-diethylphenyl)-2-(3',6'-dihydro-2,4'-bipyridin-1'(2'H)-yl)acetamide

The title compound was prepared according to the method of Example 170 substituting 1',2',3',6'-tetrahydro-[2,4']bipyridinyl hydrochloride (Saari, W. S.; et al. J. Med. Chem. 1984,

EXAMPLE 175

2-(3',6'-dihydro-2,4'-bipyridin-1'(2'H)-yl)-N-(2,4,6-trifluorophenyl)acetamide

The title compound was prepared according to the method of Example 170 substituting 2,4,6-trifluoroaniline in place of 2,6-diethylaniline and substituting 1',2',3',6'-tetrahydro-[2,4']bipyridinyl hydrochloride (Saari, W. S.; et al. J. Med. Chem. 1984, 27, 1182) in place of the product from Example 36C. The purification also employed 0.1% aqueous trifluoroacetic acid in place of aqueous ammonium acetate (10 mM). (yield: 59 mg, 0.084 mmol, 33%). $^1$H NMR (300 MHz, DMSO-$d_6$) δ 2.92 (m, 2H), 3.45 (m, 1H), 3.68 (m, 1H), 4.03 (m, 1H), 4.12 (m, 1H), 4.42 (s, 2H), 6.71 (br s, 1H), 7.37 (m, 3H), 7.66 (d, J=8.4 Hz, 1H), 7.85 (ddd, J=2.1, 7.5, 7.5 Hz, 1H), 8.58 (m, 1H), 10.44 (s, 1H); MS (ESI) m/e 348 (M+H)$^+$; Anal. calcd for $C_{18}H_{16}F_3N_3O.3.1\ C_2HF_3O_2$: C, 41.48; H, 2.75; N, 600. Found: C, 41.54; H, 2.57; N, 5.99.

EXAMPLE 176

N-(4-chloro-2,6-dimethylphenyl)-2-(3',6'-dihydro-2,4'-bipyridin-1'(2'H)-yl)acetamide The title compound was prepared according to the method of Example 170 substituting 4-chloro-2,6-dimethylaniline hydrochloride in place of 2,6-diethylaniline; substituting 1',2',3',6'-tetrahydro-[2,4']bipyridinyl hydrochloride (Saari, W. S.; et al. J. Med. Chem. 1984, 27, 1182) in place of the product from Example 36C; and, adding one additional equivalent each of pyridine and sodium carbonate. The purification also employed 0.1% aqueous trifluoroacetic acid in place of aqueous ammonium acetate (10 mM). (yield: 53 mg, 0.075 mmol, 29%). $^1$H NMR (300 MHz, DMSO-$d_6$) δ 2.18 (s, 6H), 2.92 (m, 2H), 3.46 (m, 1H), 3.68 (m, 1H), 4.03 (m, 1H), 4.14 (m, 1H), 4.38 (s, 2H), 6.73 (br s, 1H), 7.23 (s, 2H), 7.34 (m, 1H), 7.66 (br d, J=8.4 Hz, 1H), 7.85 (ddd, J=2.1, 7.5, 7.5 Hz, 1H), 8.59 (m, 1H), 10.0 (s, 1H); MS (ESI) m/e 356 (M+H)$^+$; Anal. calcd for $C_{20}H_{22}ClN_3O.3.1\ C_2HF_3O_2$: C, 44.36; H, 3.57; N, 5.92. Found: C, 44.31; H, 3.60; N, 5.91.

EXAMPLE 177

2-(3',6'-dihydro-2,4'-bipyridin-1'(2'H)-yl)-N-(2,4,6-trichlorophenyl)acetamide

The title compound was prepared according to the method of Example 170 substituting 2,4,6-trichloroaniline in place of 2,6-diethylaniline and substituting 1',2',3',6'-tetrahydro-[2,4']bipyridinyl hydrochloride (Saari, W. S.; et al. J. Med. Chem. 1984, 27, 1182) in place of the product from Example 36C. The purification also employed 0.1% aqueous trifluoroacetic acid in place of aqueous ammonium acetate (10 mM). (38 mg, 0.050 mmol, 20%). $^1$H NMR (300 MHz, DMSO-$d_6$) δ 2.92 (m, 2H), 3.46 (m, 1H), 3.68 (m, 1H), 4.02 (m, 1H), 4.14 (m, 1H), 4.42 (s, 2H), 6.72 (br s, 1H), 7.35 (m, 1H), 7.66 (br d, J=8.4 Hz, 1H), 7.84 (m, 3H), 8.58 (m, 1H), 10.73 (br s, 1H); MS (ESI) m/e 398 (M+H)$^+$; Anal. calcd for $C_{18}H_{16}Cl_3N_3O.3.15\ C_2HF_3O_2$: C, 38.61; H, 2.55; N, 5.56. Found: C, 38.65; H, 2.45; N, 5.61.

EXAMPLE 178

N-{[4-(2-pyridinyl)-1-piperazinyl]methyl}-3-(trifluoromethyl)benzamide

A mixture of 1-pyridin-2-ylpiperazine (16 mg, 0.1 mmol, Aldrich), paraformaldehyde (30 mg, 1 mmol), 3-trifluoromethylbenzamide (95 mg, 0.5 mmol), and 42 mg of potassium carbonate (0.3 mmol) in 2 mL absolute ethyl alcohol was heated to reflux under nitrogen overnight. The mixture was cooled to room temperature, filtered, and the solvent was removed under reduced pressure. The residue was purified by flash column chromatography on silica gel (10% methanol: ethyl acetate) to give 30 mg (55%) pure compound. $^1$H NMR (500 MHz, DMSO-$d_6$) δ 2.60 (t, J=4 Hz, 4H), 3.52 (t, J=4 Hz, 4H), 4.22 (d, J=5 hz, 1H), 6.62 (t, J=5 Hz, 1H), 6.81 (d, J=6 Hz, 1H), 7.51 (t, J=6 Hz, 1H), 7.75 (d, J=6 Hz, 1H), 7.92 (d, J=6 Hz, 1H), 8.12 (d, J=5 Hz, 1H), 8.10 (m, 2H), 9.05 (t, J=5 Hz, 1H); MS (ESI/APCI−) m/e 363 (M−H)$^+$.

EXAMPLE 179

3,5-dimethoxy-N-{[4-(2-pyridinyl)-1-piperazinyl]methyl}benzamide

A mixture of 1-pyridin-2-ylpiperazine (16 mg, 0.1 mmol, Aldrich), paraformaldehyde (30 mg, 1 mmol), 3,5-dimethoxybenzamide (91 mg, 0.5 mmol, Lancaster), and 42 mg of potassium carbonate (0.3 mmol) in 2 mL absolute ethyl alcohol was heated to reflux under nitrogen overnight. The mixture was cooled to room temperature, filtered, and the solvent was removed under reduced pressure. The residue was purified by flash column chromatography on silica gel (10% methanol:ethyl acetate) to give 38.5 mg (72%) pure compound. $^1$H NMR (500 MHz, DMSO-$d_6$) δ 2.59 (t, J=4 Hz, 4H), 3.48 (t, J=4 Hz, 4H), 3.78 (s, 6H), 4.20 (d, J=5 Hz, 1H), 6.62 (m, 2H), 6.81 (d, J=6 Hz, 1H), 7.03 (s, 2H), 7.50 (t, J=6 Hz, 1H), 8.10 (d, J=5 Hz, 1H), 8.78 (t, J=5 Hz, 1H); MS (ESI/APCI−) m/e 355 (M−H)$^+$.

EXAMPLE 180

N-{[4-(2-pyridinyl)-1-piperazinyl]methyl}cyclohexanecarboxamide

A mixture of 1-pyridin-2-ylpiperazine (16 mg, 0.1 mmol, Aldrich), paraformaldehyde (30 mg, 1 mmol), cyclohexanecarboxylic acid amide (64 mg, 0.5 mmol, Aldrich), and 42 mg of potassium carbonate (0.3 mmol) in 2 mL absolute ethyl alcohol was heated to reflux under nitrogen overnight. The mixture was cooled to room temperature, filtered, and the solvent was removed under reduced pressure. The residue was purified by flash column chromatography on silica gel (10% methanol:ethyl acetate) to give 30 mg (66%) pure compound. $^1$H NMR (500 MHz, DMSO-$d_6$) δ 1.05-1.40 (m, 5H), 1.59-1.68 (m, 5H), 2.15 (m, 1H), 2.48 (m, 4H), 3.45 (t, J=4 Hz, 4H), 3.95 (d, J=5 Hz, 1H), 6.62 (t, J=6 Hz, 1H), 6.81 (d, J=6 Hz, 1H), 7.53 (t, J=6 Hz, 1H), 8.01 (t, J=5 Hz, 1H), 8.10 (d, J=5 Hz, 1H); MS (ESI/APCI–) m/e 301 (M–H)+.

EXAMPLE 181

N-(2,6-dimethylphenyl)-2-[4-(2-pyridinyl)-1-piperazinyl]acetamide

A mixture of 1-pyridin-2-ylpiperazine (24 mg, 0.15 mmol, Aldrich), N-(2,6-dimethylphenyl)-2-chloroacetamide (39 mg, 0.20 mmol, Aldrich) and sodium carbonate (50 mg) in N,N-dimethylformamide/water (2:1, 2 mL) was shaken at room temperature for 18 hours. The resulting mixture was decanted, concentrated under reduced pressure and the residue purified by preparative HPLC to provide 43.7 mg (90.9%) of the desired product. $^1$H NMR (500 MHz, DMSO-$d_6$) δ 2.08 (s, 6H), 2.65 (t, J=4 Hz, 4H), 3.18 (s, 2H), 3.58 (t, J=4 Hz, 4H), 6.63 (t, J=5 Hz, 1H), 6.83 (d, J=5 Hz, 1H), 7.08 (s, 3H), 7.52 (t, J=5 Hz, 1H), 8.10 (d, J=5 Hz, 1H), 9.23 (s, 1H); MS (ESI/APCI+) m/e 325 (M+H)+.

EXAMPLE 182

N-(4-fluorophenyl)-2-[4-(2-pyridinyl)-1-piperazinyl]acetamide

A mixture of 1-pyridin-2-ylpiperazine (24 mg, 0.15 mmol, Aldrich), N-(4-fluorophenyl)-2-chloroacetamide (38 mg, 0.20 mmol, Maybridge) and sodium carbonate (50 mg) in N,N-dimethylformamide/water (2:1, 2 mL) was shaken at room temperature for 18 hours. The resulting mixture was decanted, concentrated under reduced pressure and the residue purified by preparative HPLC to provide 45 mg (95%) of the desired product. $^1$H NMR (500 MHz, DMSO-$d_6$) δ 2.60 (m, 4H), 3.18 (s, 2H), 3.58 (m, 4H), 6.63 (m, 1H), 6.83 (d, J=5 Hz, 1H), 7.14 (dd, J=8.7, 8.7 Hz, 2H), 7.55 (m, 1H), 7.66 (m, 2H), 8.18 (d, J=5 Hz, 1H), 9.80 (s, 1H); MS (ESI/APCI+) m/e 315 (M+H)+.

EXAMPLE 183

N-(2,4-difluorophenyl)-2-[4-(2-pyridinyl)-1-piperazinyl]acetamide

A mixture of 1-pyridin-2-ylpiperazine (24 mg, 0.15 mmol, Aldrich), N-(2,4-difluorophenyl)-2-chloroacetamide (41 mg, 0.20 mmol, Maybridge) and sodium carbonate (50 mg) in N,N-dimethylformamide/water (2:1, 2 mL) was shaken at room temperature for 18 hours. The resulting mixture was decanted, concentrated under reduced pressure and the residue purified by preparative HPLC to provide 37.3 mg (74.8%) of the desired product. $^1$H NMR (500 MHz, DMSO-$d_6$) δ 2.52 (t, J=4 Hz, 4H), 3.23 (s, 2H), 3.58 (t, J=4 Hz, 4H), 6.63 (t, J=5 Hz, 1H), 6.83 (d, J=6 Hz, 1H), 7.08 (t, J=6 Hz, 1H), 7.38 (t, J=6 Hz, 1H), 7.92 (m, 1H), 8.12 (d, J=5 Hz, 1H), 9.60 (s, 1H); MS (ESI/APCI+) m/e 333 (M+H)+.

EXAMPLE 184

N-(2-methylphenyl)-2-[4-(2-pyridinyl)-1-piperazinyl]acetamide

A mixture of 1-pyridin-2-ylpiperazine (24 mg, 0.15 mmol, Aldrich), N-(2-methyl-phenyl)-2-chloroacetamide (37 mg, 0.20 mmol, Maybridge) and sodium carbonate (50 mg) in N,N-dimethylformamide/water (2:1, 2 mL) was shaken at room temperature for 18 hours. The resulting mixture was decanted, concentrated under reduced pressure and the residue purified by preparative HPLC to provide 29.3 mg (63%) of the desired product. $^1$H NMR (500 MHz, DMSO-$d_6$) δ 2.23 (s, 3H), 2.62 (t, J=4 Hz, 4H), 3.20 (s, 2H), 3.58 (t, J=4 Hz, 4H), 6.63 (t, J=5 Hz, 1H), 6.83 (d, J=6 Hz, 1H), 7.05 (t, J=6 Hz, 1H), 7.10 (m, 2H), 7.58 (t, J=5 Hz, 1H), 7.78 (d, J=6 Hz, 1H), 8.12 (d, J=5 Hz, 1H), 9.40 (s, 1H); MS (ESI/APCI+) m/e 311 (M+H)+.

EXAMPLE 185

2-[4-(2-pyridinyl)-1-piperazinyl]-N-[3-(trifluoromethyl)phenyl]acetamide

A mixture of 1-pyridin-2-ylpiperazine (24 mg, 0.15 mmol, Aldrich), N-(3-trifluorophenyl)-2-chloroacetamide (48 mg, 020 mmol, Maybridge) and sodium carbonate (50 mg) in N,N-dimethylformamide/water (2:1, 2 mL) was shaken at room temperature for 18 hours. The resulting mixture was decanted, concentrated under reduced pressure and the residue purified by preparative HPLC to provide 27 mg (47%) of the desired product. $^1$H NMR (500 MHz, DMSO-$d_6$) δ 2.62 (t, J=4 Hz, 4H), 3.22 (s, 2H), 3.58 (t, J=4 Hz, 4H), 6.63 (t, J=5 Hz, 1H), 6.83 (d, J=6 Hz, 1H), 7.41 (d, J=6 Hz, 1H), 7.58 (m, 2H), 7.92 (d, J=6 Hz, 1H), 8.12 (d, J=5 Hz, 1H), 8.18 (s, 1H), 10.06 (s, 1H); MS (ESI/APCI+) m/e 365 (M+H)+.

EXAMPLE 186

N-(3-chlorophenyl)-2-[4-(2-pyridinyl)-1-piperazinyl]acetamide

A mixture of 1-pyridin-2-ylpiperazine (24 mg, 0.15 mmol, Aldrich), N-(3-chloro-phenyl)-2-chloroacetamide (41 mg, 0.20 mmol, Maybridge) and sodium carbonate (50 mg) in N,N-dimethylformamide/water (2:1, 2 mL) was shaken at room temperature for 18 hours. The resulting mixture was decanted, concentrated under reduced pressure and the residue purified by preparative HPLC to provide 16 mg (32%) of the desired product. $^1$H NMR (500 MHz, DMSO-$d_6$) δ 2.60 (t, J=4 Hz, 4H), 3.20 (s, 2H), 3.58 (t, J=4 Hz, 4H), 6.63 (t, J=5 Hz, 1H), 6.83 (d, J=6 Hz, 1H), 7.13 (d, J=6 Hz, 1H), 7.38 (t, J=6 Hz, 1H), 7.58 (m, 2H), 7.95 (s, 1H), 8.12 (d, J=5 Hz, 1H), 9.95 (s, 1H); MS (ESI/APCI+) m/e 331 (M+H)+.

EXAMPLE 187

N-benzyl-2-[4-(2-pyridinyl)-1-piperazinyl]acetamide

A mixture of 1-pyridin-2-ylpiperazine (24 mg, 0.15 mmol, Aldrich), N-benzyl-2-chloroacetamide (37 mg, 0.20 mmol, Maybridge) and sodium carbonate (50 mg) in N,N-dimethylformamide/water (2:1, 2 mL) was shaken at room temperature for 18 hours. The resulting mixture was decanted, concentrated under reduced pressure and the residue purified by preparative HPLC to provide 16 mg (32%) of the desired product. $^1$H NMR (500 MHz, DMSO-$d_6$) δ 2.58 (m, 4H), 3.05 (s, 2H), 3.52 (m, 4H), 4.35 (d, J=5 Hz, 2H), 6.63 (t, J=5 Hz, 1H), 6.82 (d, J=6 Hz, 1H), 7.28 (m, 5H), 7.55 (t, J=6 Hz, 1H), 8.12 (t, J=5 Hz, 1H), 8.35 (s, 1H); MS (ESI/APCI+) m/e 311 (M+H)+.

EXAMPLE 188

2-[4-(2-pyridinyl)-1-piperazinyl]-N-[4-(trifluoromethoxy)phenyl]acetamide

A mixture of 1-pyridin-2-ylpiperazine (24 mg, 0.15 mmol, Aldrich), N-(4-trifluoromethoxyphenyl)-2-chloroacetamide (51 mg, 0.20 mmol, Maybridge) and sodium carbonate (50 mg) in N,N-dimethylformamide/water (2:1, 2 mL) was shaken at room temperature for 18 hours. The resulting mixture was decanted, concentrated under reduced the residue was purified by preparative HPLC to provide 16 mg (32%) of the desired product. $^1$H NMR (500 MHz, DMSO-d$_6$) δ 2.60 (t, J=4 Hz, 4H), 3.21 (s, 2H), 3.58 (t, J=4 Hz, 4H), 6.63 (t, J=5 Hz, 1H), 6.83 (d, J=6 Hz, 1H), 7.35 (d, J=6 Hz, 2H), 7.55 (t, J=6 Hz, 1H), 7.76 (m, 2H), 8.12 (d, J=5 Hz, 1H), 9.98 (s, 1H); MS (ESI/APCI+) m/e 381 (M+H)$^+$.

EXAMPLE 189

2-[4-(2-pyridinyl)-1-piperazinyl]-N-[2-(trifluoromethyl)phenyl]acetamide

A mixture of 1-pyridin-2-ylpiperazine (24 mg, 0.15 mmol, Aldrich), N-(2-trifluoromethylphenyl)-2-chloroacetamide (48 mg, 0.20 mmol, Maybridge) and sodium carbonate (50 mg) in N,N-dimethylformamide/water (2:1, 2 mL) was shaken at room temperature for 18 hours. The resulting mixture was decanted, concentrated under reduced pressure and the residue purified by preparative HPLC to provide 41 mg (75%) of the desired product. $^1$H NMR (500 MHz, DMSO-d$_6$) δ 2.65 (t, J=4 Hz, 4H), 3.23 (s, 2H), 3.58 (t, J=4 Hz, 4H), 6.65 (t, J=5 Hz, 1H), 6.85 (d, J=6 Hz, 1H), 7.38 (t, J=6 Hz, 1H), 7.55 (t, J=6 Hz, 1H), 7.73 (m, 2H), 8.15 (d, J=5 Hz, 1H), 8.22 (d, J=6 Hz, 1H), 9.95 (s, 1H); MS (ESI/APCI+) m/e 365 (M+H)$^+$.

EXAMPLE 190

N-(4-chlorophenyl)-2-[4-(2-pyridinyl)-1-piperazinyl]acetamide

A mixture of 1-pyridin-2-ylpiperazine (24 mg, 0.15 mmol, Aldrich), N-(4-chlorophenyl)-2-chloroacetamide (41 mg, 0.20 mmol, Maybridge) and sodium carbonate (50 mg) in N,N-dimethylformamide/water (2:1, 2 mL) was shaken at room temperature for 18 hours. The resulting mixture was decanted, concentrated under reduced pressure and the residue purified by preparative HPLC to provide 42 mg (85%) of the desired product. $^1$H NMR (500 MHz, DMSO-d$_6$) δ b2.60 (t, J=4 Hz, 4H), 3.21 (s, 2H), 3.58 (t, J=4 Hz, 4H), 6.63 (t, J=5 Hz, 1H), 6.83 (d, J=6 Hz, 1H), 7.38 (d, J=6 Hz, 2H), 7.54 (t, J=6 Hz, 1H), 7.70 (d, J=6 Hz, 2H), 8.12 (d, J=5 Hz, 1H), 9.90 (s, 1H); MS (ESI/APCI+) m/e 331 (M+H)$^+$.

EXAMPLE 191

N-(2,3-dichlorophenyl)-2-[4-(2-pyridinyl)-1-piperazinyl]acetamide

A mixture of 1-pyridin-2-ylpiperazine (24 mg, 0.15 mmol, Aldrich), N-(2,3-dichlorophenyl)-2-chloroacetamide (48 mg, 0.20 mmol, Maybridge) and sodium carbonate (50 mg) in N,N-dimethylformamide/water (2:1, 2 mL) was shaken at room temperature for 18 hours. The resulting mixture was decanted, concentrated under reduced pressure the residue purified by preparative HPLC to provide 9 mg (16%) of the desired product as a trifluoroacetic acid salt. $^1$H NMR (500 MHz, DMSO-d$_6$) δ 2.62 (t, J=4 Hz, 4H), 3.23 (s, 2H), 3.58 (t, J=4 Hz, 4H), 6.63 (t, J=5 Hz, 1H), 6.83 (d, J=6 Hz, 1H), 7.55 (t, J=6 Hz, 1H), 7.68 (m, 2H), 7.88 (m, 2H), 8.12 (d, J=5 Hz, 1H), 10.12 (s, 1H); MS (ESI/APCI+) m/e 365 (M+H)$^+$.

EXAMPLE 192

N-(3,4-dichlorophenyl)-2-[4-(2-pyridinyl)-1-piperazinyl]acetamide

A mixture of 1-pyridin-2-ylpiperazine (24 mg, 0.15 mmol, Aldrich), N-(3,4-dichlorophenyl)-2-chloroacetamide (48 mg, 0.20 mmol, Maybridge) and sodium carbonate (50 mg) in N,N-dimethylformamide/water (2:1, 2 mL) was shaken at room temperature for 18 hours. The resulting mixture was decanted, concentrated under reduced pressure and the residue purified by preparative HPLC to provide 58 mg (41%) of the desired product. $^1$H NMR (500 MHz, DMSO-d$_6$) δ 2.65 (t, J=4 Hz, 4H), 3.23 (s, 2H), 3.58 (t, J=4 Hz, 4H), 6.65 (t, J=5 Hz, 1H), 6.85 (d, J=6 Hz, 1H), 7.41 (m, 2H), 7.55 (t, J=6 Hz, 1H), 8.12 (d, J=5 Hz, 1H), 8.25 (d, J=6 Hz, 1H), 10.08 (s, 1H); MS (ESI/APCI+) m/e 365 (M+H)$^+$.

EXAMPLE 193

2-[4-(2-pyridinyl)-1-piperazinyl]-N-[4-(trifluoromethyl)phenyl]acetamide

A mixture of 1-pyridin-2-ylpiperazine (24 mg, 0.15 mmol, Aldrich), N-(4-trifluoromethylphenyl)-2-chloroacetamide (48 mg, 0.20 mmol, Maybridge) and sodium carbonate (50 mg) in N,N-dimethylformamide/water (2:1, 2 mL) was shaken at room temperature for 18 hours. The resulting mixture was decanted, concentrated under reduced pressure and the residue purified by preparative HPLC to provide 20 mg (37%) of the desired product. $^1$H NMR (500 MHz, DMSO-d$_6$) δ 2.60 (t, J=4 Hz, 4H), 3.21 (s, 2H), 3.58 (t, J=4 Hz, 4H), 6.63 (t, J=5 Hz, 1H), 6.83 (d, J=6 Hz, 1H), 7.30 (m, 1H), 7.55 (m, 2H), 7.80 (m, 2H), 8.12 (d, J=5 Hz, 1H), 10.08 (s, 1H); MS (ESI/APCI+) m/e 365 (M+H)$^+$.

EXAMPLE 194

3-chloro-N-{[4-(2-pyridinyl)-1-piperazinyl]methyl}benzamide

A mixture of 1-pyridin-2-ylpiperazine (16 mg, 0.1 mmol, Aldrich), paraformaldehyde (30 mg, 1 mmol), 3-chlorobenzamide (78 mg, 0.5 mmol, Maybridge), and 42 mg of potassium carbonate (0.3 mmol) in 2 mL absolute ethyl alcohol was heated to reflux under nitrogen overnight. The mixture was cooled to room temperature, filtered, and the solvent was removed under reduced pressure. The residue was purified by flash column chromatography on silica gel (10% methanol: ethyl acetate) to give 26 mg (52%) pure compound; $^1$H NMR (500 MHz, DMSO-d$_6$) δ 2.58 (t, J=4 Hz, 4H), 3.50 (t, J=4 Hz, 4H), 4.19 (d, J=5 Hz, 1H), 6.62 (t, J=5 Hz, 1H), 6.81 (d, J=6 Hz, 1H), 7.51 (m, 2H), 7.61 (m, 1H), 7.82 (d, J=6 Hz, 1H), 7.92 (s, 1H), 8.12 (d, J=5 Hz, 1H), 8.93 (t, J=5 Hz, 1H); MS (ESI/APCI−) m/e 329 (M−H)$^+$.

EXAMPLE 195

4-fluoro-3-methyl-N-{[4-(2-pyridinyl)-1-piperazinyl]methyl}benzamide

A mixture of 1-pyridin-2-ylpiperazine (16 mg, 0.1 mmol, Aldrich), paraformaldehyde (30 mg, 1 mmol), 4-fluoro-3-methylbenzamide (77 mg, 0.5 mmol, Oakwood), and 42 mg of potassium carbonate (0.3 mmol) in 2 mL absolute ethyl alcohol was heated to reflux under nitrogen overnight. The mixture was cooled to room temperature, filtered, and the solvent was removed under reduced pressure. The residue was purified by flash column chromatography on silica gel (10% methanol:ethyl acetate) to give 25 mg (51%) pure compound. $^1$H NMR (500 MHz, DMSO-d$_6$) δ 2.25 (s, 3H), 2.58 (t, J=4 Hz, 4H), 3.52 (t, J=4 Hz, 4H), 4.18 (d, J=5 Hz, 1H), 6.61 (t, J=5 Hz, 1H), 6.81 (d, J=6 Hz, 1H), 7.21 (t, J=6 Hz, 1H), 7.51 (t, J=5 Hz, 1H), 7.75 (t, J=5 Hz, 1H), 7.82 (d, J=6 Hz, 1H), 8.12 (d, J=5 Hz, 1H), 8.76 (t, J=5 Hz, 1H); MS (ESI/APCI−) m/e 327 (M−H)$^+$.

EXAMPLE 196

N-(3',6'-dihydro-2,4'-bipyridin-1'(2'H)-ylmethyl)-4-fluoro-3-methylbenzamide

A mixture of 1',2',3',6'-tetrahydro-[2,4']bipyridinyl hydrochloride (20 mg, 0.10 mmol, Saari, W. S.; et al. J. Med. Chem. 1984, 27, 1182), paraformaldehyde (30 mg, 1 mmol), 4-fluoro-3-methylbenzamide (77 mg, 0.5 mmol, Oakwood), and 42 mg of potassium carbonate (0.3 mmol) in 2.5 mL absolute ethyl alcohol was heated to reflux under nitrogen overnight. The mixture was cooled to room temperature, filtered, and the solvent was removed under reduced pressure. The residue was purified by flash column chromatography on silica gel (10% methanol:ethyl acetate) to give 9 mg (28%) pure compound. $^1$H NMR (500 MHz, DMSO-$d_6$) δ 2.28 (s, 3H), 2.56 (m, 2H), 2.76 (m, 2H), 3.30 (m, 2H), 4.26 (d, J=5 Hz, 2H), 6.70 (m, 1H), 7.20 (m, 2H), 7.50 (d, J=6 Hz, 1H), 7.75 (m, 2H), 7.85 (d, J=6 Hz, 1H), 8.51 (m, 1H) 8.77 (t, J=5 Hz, 1 H); MS (ESI/APCI−) m/e 324 (M−H)$^+$.

EXAMPLE 197

3-methyl-N-{[4-(1,3-oxazol-2-yl)-3,6-dihydro-1(2H)-pyridinyl]methyl}benzamide

EXAMPLE 197A tert-butyl 4-(1,3-oxazol-2-yl)-3,6-dihydro-1(2H)-pyridinecarboxylate Oxazole (1.00 g, 14.5 mmol) in anhydrous tetrahydrofuran was treated with n-butyllithium (2.5 M, 6.4 mL, 15.9 mmol) at −78° C. Stirring continued and after 30 minutes, added zinc chloride (1M solution 43.0 mL, 43.4 mmol) and the reaction was allowed to warm to room temperature, and stirred for 1 hour. To this solution was added 4-trifluoromethanesulfonyloxy-3,6-dihydro-2H-pyridine-1-carboxylic acid tert-butylester (Bursavich, M. G.; et al. Org. Lett. 2001, 3, 2317, 4.8 g, 14.5 mmol) and stirred. A palladium catalyst solution was prepared separately by treating bis(triphenylphosphine)palladium(II)chloride (5% mole) (526.4 mg, 0.75 mmol) in tetrahydrofuran at room temperature with n-butyllithium (2.5M solution 1.6 mL, 1.5 mmol). The palladium catalyst was added to the reaction mixture containing the triflate and refluxed overnight. The reaction was cooled to room temperature, diluted with ethyl acetate, and partitioned with water. The organic phase was separated, washed with brine, dried over anhydrous magnesium sulfate and concentrated under reduced pressure to afford thick yellow oil (1.5 g, 41%) which solidified upon standing. $^1$H NMR (300 MHz, CDCl$_3$) δ 1.50 (s, 9H), 2.62 (m, 2H), 3.60 (t, 2H, J=6 Hz), 4.10 (m, 2H), 6.65 (m, 1H), 7.10 (d, 1H, J=0.25 Hz), 7.60 (d, 1H, J=0.25 Hz); MS (DCI/NH$_3$) m/e 251 (M+H)$^+$.

EXAMPLE 197B 4-(1,3-oxazol-2-yl)-1,2,3,6-tetrahydropyridine

The procedure described in Example 166B was followed, substituting the product from Example 197A for the product from Example 166A to provide the title compound as a brown oil (1.75 g, 92%). $^1$H NMR (300 MHz, CDCl$_3$) δ 2.90 (m, 2H), 3.45 (m, 2H), 3.95 (s, 2H), 6.70 (m, 1H), 7.28 (d, 1H, J=0.25 Hz), 7.68 (d, 1H, J=0.25 Hz); MS (DCI/NH$_3$) m/e 151 (M+H)$^+$.

EXAMPLE 197C 3-methyl-N-{[4-(1,3-oxazol-2-yl)-3,6-dihydro-1(2H)-pyridinyl]methyl}benzamide The procedure described in Example 200 was followed, substituting the product from Example 166B for the product from Example 119A to provide the title compound a as brown sticky residue (280 mg, 15%). $^1$H NMR (300 MHz, CDCl$_3$) δ 2.40 (s, 3H), 2.68 (m, 2H), 2.87 (t, 2H, J=6 Hz), 3.40 (q, 2H, J=4.5 Hz), 4.45 (d, 2H, J=6 Hz), 6.70 (m, 1H), 7.10 (d, 1H, J=0.25 Hz), 7.31 (d, 2H, J=6 Hz), 7.55 (m, 2H), 7.61 (s, 1H); MS (DCI/NH$_3$) m/e 298 (M+H)$^+$.

Maleate salt: Anal. calcd for C$_{17}$H$_{19}$N$_3$O$_2$.1.0 C$_4$H$_4$O$_4$: C, 61.01; H, 5.61; N, 10.16; Found: C, 60.65; H, 5.46; N, 9.91.

EXAMPLE 198

2-methyl-N-[(3-methyl-3',6'-dihydro-2,4'-bipyridin-1'(2'H)-yl)methyl]benzamide

A mixture of the product from Example 143B (trifluoroacetic acid salt, 29 mg, 0.1 mmol), paraformaldehyde (30 mg, 1 mmol), 2-methylbenzamide (68 mg, 0.5 mmol, Aldrich), and 42 mg of potassium carbonate (0.3 mmol) in 2.5 mL absolute ethyl alcohol was heated to reflux under nitrogen overnight. The mixture was cooled to room temperature, filtered, and the solvent was removed under reduced pressure. The residue was purified by flash column chromatography on silica gel (10% methanol:ethyl acetate) to give 12.5 mg (39%) pure compound. $^1$H NMR (500 MHz, DMSO-$d_6$) δ 2.32 (s, 3H), 2.37 (s, 3H), 2.48 (m, 2H), 2.80 (m, 2H), 3.27 (m, 2H), 4.26 (d, J=5 Hz, 2H), 5.82 (m, 1H), 7.15 (m, 1H), 7.24 (m, 2H), 7.35 (m, 2H), 7.60 (d, J=6 Hz, 1H), 8.15 (m, 1H), 8.35 (d, J=6 Hz, 1H), 8.61 (t, J=5 Hz, 1H); MS (ESI/APCI−) m/e 320 (M−H)$^+$.

EXAMPLE 199

2-[4-(3-cyano-2-pyridinyl)-1-piperidinyl]-N-(2,6-dimethylphenyl)acetamide

The product from Example 58D (trifluoroacetic acid salt, 30 mg, 0.1 mmol), N-(2,6-dimethylphenyl)-2-chloroacetamide (23 mg, 0.15 mmol, Aldrich) and sodium carbonate (50 mg) in N,N-dimethylformamide/water (2:1, 2 mL) was shaken at room temperature for 18 hours. The resulting mixture was decanted, concentrated under reduced pressure. The residue was purified by preparative HPLC to provide 7 mg (28%) of the desired product. $^1$H NMR (500 MHz, DMSO-$d_6$) δ 1.82 (m, 2H), 2.05 (m, 2H), 2.12 (s, 6H), 2.35 (m, 2H), 3.05 (m, 3H), 3.15 (s, 2H), 7.05 (m, 3H), 7.45 (dd, J=6 Hz, 1H), 8.25 (d, J=6 Hz, 1H), 8.79 (dd, J=6 Hz, 1H), 9.21 (s, 1H); MS (ESI/APCI+) m/e 349 (M+H)$^+$.

EXAMPLE 200

2-(1-{[(3-methylbenzoyl)amino]methyl}-4-piperidinyl)pyridinium N-oxide

2-Piperidin-4-ylpyridinium N-oxide hydrochloride (from Example 119A) (4.16 g, 16.4 mmol) in toluene/dioxane (60 mL/6 mL) was treated with powdered potassium carbonate (2.69 g, 19.37 mmol) at room temperature and stirred for 30 minutes. To this mixture was added 3-methylbenzamide (7.89 g, 58.4 mmol) and 37% aqueous formaldehyde (4.7 mL, 58 mmol). The reaction mixture was heated at 80° C. for 3 hours, cooled to room temperature, treated with additional portions of 3-methylbenzamide (2.63 g, 19.5 mmol) and 37% formaldehyde (1.57 mL, 19.5 mmol). The reaction mixture was stirred at 80° C. for 1 hour, cooled, and concentrated under reduced pressure. Toluene was used to remove the water (2×75 mL). To the residue was added 3% methanol:dichloromethane and inorganic salts were filtered off. The filtrate was concentrated under reduced pressure. The residue was purified by flash column chromatography using 10% methanol:dichloromethane followed by 15% methanol:dichloromethane to provide the title compound as a solid. mp 177-180° C.; $^1$H NMR (300 MHz, DMSO-d$_6$) δ 1.52 (m, 2H), 1.89 (m, 2H), 2.33 (m, 2H), 2.38 (s, 3H), 2.96 (m, 2H), 3.19 (m, 1H), 4.17 (d, J=6 Hz, 2H), 7.31 (m, 5H), 7.69 (m, 2H), 8.23 (m, 1H), 8.71 (m, 1H); MS (DCI/NH$_3$) m/e 310 (M+H−16)$^+$; Anal. calcd for C$_{19}$H$_{23}$N$_3$O$_2$: C, 70.13; H, 7.12; N, 12.91. Found C, 69.94; H, 7.19; N, 12.96.

EXAMPLE 201

N-(3-methylphenyl)-2-[4-(3-methyl-2-pyridinyl)-1-piperazinyl]acetamide

EXAMPLE 201A 1-(3-methyl-2-pyridinyl)piperazine

To a slurry of 2-bromo-3-methylpyridine (3.30 mL, 29.6 mmol) in n-butanol was added piperazine (25.0 g, 290 mmol) and the reaction heated to reflux for 3 days. The mixture was cooled and the solvent removed under reduced pressure. The residue was partitioned between water and ethyl acetate. The organic phase was dried (sodium sulfate) and concentrated. The residue was purified by flash column chromatography on silica gel (elution with 15% methanol:dichloromethane) to provide the title compound as a yellow oil.

$^1$H NMR (300 MHz, CDCl$_3$) δ 2.28 (s, 3H), 3.01 (m, 4H), 3.11 (m, 4H), 6.84 (dd, 1H, J=7.1, 4.8 Hz), 7.39 (m, 1H), 8.16 (m, 1H); MS (DCI/NH$_3$) m/e 178 (M+H)$^+$.

EXAMPLE 201B

N-(3-methylphenyl)-2-[4-(3-methyl-2-pyridinyl)-1-piperazinyl]acetamide

The procedure described in Example 33C was followed, substituting the product from Example 201A for the product from Example 33B to provide the title compound. $^1$H NMR (300 MHz, DMSO-d$_6$) δ 2.23 (s, 3H), 2.28 (s, 3H), 2.68 (m, 4H), 3.13 (m, 4H), 3.18 (s, 2H), 6.90 (m, 2H), 7.18 (dd, 1H, J=7.8, 7.8 Hz), 7.47 (m, 3H), 8.10 (dd, 1H, J=4.7, 1.7 Hz), 9.65 (br s, 1H); MS (DCI/NH$_3$) m/e 325 (M+H)$^+$; Anal. calcd for C$_{19}$H$_{24}$N$_4$O: C, 70.34; H, 7.46; N, 17.27. Found: C, 70.13; H, 7.36; N, 17.20.

EXAMPLE 202

2-[4-(3-cyano-2-pyridinyl)-1-piperazinyl]-N-[4-(trifluoromethyl)phenyl]acetamide 2-Chloro-N-(4-trifluoromethylphenyl)acetamide (820 mg, 3.45 mmol, Maybridge) and N,N-diisopropylamine (2.5 mL) in toluene (50 mL) were treated with 2-piperazin-1-ylnicotinonitrile (800 mg, 4.25 mmol, Chess) and heated to 60° C. for 18 hours. The mixture was allowed to cool to room temperature, transferred to a separatory funnel and washed with saturated aqueous sodium bicarbonate. The organic phase was dried (sodium sulfate), filtered, and the filtrate concentrated under reduced pressure. The residue was purified by flash column chromatography on silica gel (gradient elution with 20% to 40% ethyl acetate:hexanes) to provide 1.05 g (78% yield) of the title compound as a white solid. $^1$H NMR (300 MHz, DMSO-d$_6$) δ 2.69 (m, 4H), 3.26 (s, 2H), 3.68 (m, 4H), 6.93 (dd, 1H, J=7.5, 4.7 Hz), 7.68 (AA'BB', 2H, J=8.8 Hz), 7.88 (AA'BB', 2H, J=8.5 Hz), 8.07 (dd, 1H, J=7.8, 2.0 Hz), 8.42 (dd, 1H, J=4.7, 2.0 Hz), 10.14 (br s, 1H); MS (DCI/NH$_3$) m/e 390 (M+H)$^+$;

Anal. calcd for C$_{19}$H$_{18}$F$_3$N$_5$O: C, 58.61; H, 4.66; N, 17.99. Found: C, 58.35; H, 4.45; N, 18.02.

EXAMPLE 203

N-(2-ethyl-6-methylphenyl)-2-[4-(2-pyridinyl)-1-piperidinyl]acetamide

The title compound was prepared according to the method of Example 170 substituting 2-ethyl-6-methylaniline in place of 2,6-diethylaniline (yield: 48.5 mg, 0.144 mmol, 28%). $^1$H NMR (300 MHz, DMSO-d$_6$) δ 1.08 (t, J=7.5 Hz, 3H), 1.90 (m, 4H), 2.14 (s, 3H), 2.32 (m, 2H), 2.50 (q, J=7.5 Hz, 2H), 2.68 (m, 1H), 3.04 (br d, J=11.4 Hz, 2H), 3.15 (s, 2H), 7.10 (m, 3H), 7.21 (ddd, J=1.5, 4.5, 7.5 Hz, 1H), 7.30 (d, J=8.4 Hz, 1H), 7.72 (ddd, J=2.1, 7.5, 7.5 Hz, 1H), 8.28 (m, 1H), 9.22 (br s, 1H); MS (ESI) m/e 338 (M+H)$^+$; Anal. calcd for C$_{21}$H$_{27}$N$_3$O.0.3 H$_2$O: C, 73.56; H, 8.11; N, 12.26. Found: C, 73.46; H, 7.93; N, 12.07.

EXAMPLE 204

N-(2-isopropyl-6-methylphenyl)-2-[4-(2-pyridinyl)-1-piperidinyl]acetamide

The title compound was prepared according to the method of Example 170 substituting 2-isopropyl-6-methylaniline in place of 2,6-diethylaniline (yield: 45.3 mg, 0.129 mmol, 25%). $^1$H NMR (300 MHz, DMSO-d$_6$) δ 1.13 (d, J=7.2 Hz, 6H), 1.90 (m, 4H), 2.14 (s, 3H), 2.32 (m, 2H), 2.70 (m, 1H), 3.05 (m, 3H), 3.16 (s, 2H), 7.06 (m, 1H), 7.18 (m, 3H), 7.29 (d, J=8.4 Hz, 1H), 7.72 (ddd, J=2.1, 7.5, 7.5 Hz, 1H), 8.48 (m, 1H), 9.22 (br s, 1H); MS (ESI) m/e 352 (M+H)$^+$; Anal. calcd for C$_{22}$H$_{29}$N$_3$O.0.35 H$_2$O: C, 73.85; H, 8.37; N, 11.74. Found: C, 74.04; H, 8.41; N, 11.58.

EXAMPLE 205

N-(2-chloro-6-methylphenyl)-2-[4-(2-pyridinyl)-1-piperidinyl]acetamide

The title compound was prepared according to the method of Example 170 substituting 2-chloro-6-methylaniline in place of 2,6-diethylaniline (yield: 62.8 mg, 0.183 mmol, 36%). $^1$H NMR (300 MHz, DMSO-d$_6$) δ 1.88 (m, 4H), 2.20 (s, 3H), 2.30 (m, 2H), 2.68 (m, 1H), 3.12 (m, 2H), 3.17 (s, 2H), 7.21 (m, 2H), 7.29 (d, J=8.4 Hz, 1H), 7.36 (m, 1H), 7.73 (ddd, J=2.1, 7.5, 7.5 Hz, 1H), 8.48 (m, 1H), 9.43 (br s, 1H); MS (ESI) m/e 344 (M+H)$^+$; Anal. calcd for $C_{19}H_{22}ClN_3O\cdot0.1$ $CH_2Cl_2$: C, 65.11; H, 6.35; N, 11.93. Found: C, 64.83; H, 6.04; N, 11.88.

EXAMPLE 206

N-(2-methoxy-6-methylphenyl)-2-[4-(2-pyridinyl)-1-piperidinyl]acetamide

The title compound was prepared according to the method of Example 170 substituting 2-methoxy-6-methylaniline in place of 2,6-diethylaniline (yield: 38.1 mg, 0.112 mmol, 22%). 1H NMR (300 MHz, DMSO-d$_6$) δ 1.87 (m, 4H), 2.14 (s, 3H), 2.29 (m, 2H), 2.69 (m, 1H), 3.08 (m, 4H), 3.72 (s, 31H), 6.84 (m, 2H), 7.13 (dd, J=8.4, 8.4 Hz, 1H), 7.20 (ddd, J=1.5, 4.5, 7.5 Hz, 1H), 7.31 (d, J=8.4 Hz, 1H), 7.72 (ddd, J=2.1, 7.5, 7.5 Hz, 1H), 8.48 (m, 1H), 8.94 (br s, 1H); MS (ESI) m/e 340 (M+H)$^+$; Anal. calcd for $C_{20}H_{25}N_3O\cdot0.4\ H_2O$: C, 69.30; H, 7.50; N, 12.12. Found: C, 69.45; H, 7.48; N, 11.82.

EXAMPLE 207

2-(3',6'-dihydro-2,4'-bipyridin-1'(2'H)-yl)-N-(2-ethyl-6-methylphenyl)acetamide

The title compound was prepared according to the method of Example 170 substituting 2-ethyl-6-methylaniline in place of 2,6-diethylaniline and substituting 1',2',3',6'-tetrahydro-[2,4']bipyridinyl hydrochloride in place of the product from example 36C. (yield: 50.2 mg, 0.150 mmol, 29%). 1H NMR (300 MHz, DMSO-d$_6$) δ 1.09 (t, J=7.5 Hz, 3H), 216 (s, 3H), 2.52 (m, 2H), 2.68 (m, 2H), 2.82 (t, J=5.7 Hz, 2H), 3.28 (s, 2H), 3.36 (m, 2H), 6.73 (m, 1H), 7.08 (m, 3H), 7.23 (ddd, J=1.0, 5.1, 7.5 Hz, 1H), 7.57 (d, J=7.5 Hz, 1H), 7.75 (ddd, J=2.1, 7.5, 7.5 Hz, 1H), 8.54 (m, 1H), 9.23 (br s, 1H); MS (ESI) m/e 336 (M+H)$^+$; Anal. calcd for $C_{21}H_{25}N_3O\cdot0.3$ $CH_2Cl_2$: C, 70.88; H, 7.15; N, 11.64. Found: C, 70.92; H, 7.06; N, 11.78.

EXAMPLE 208

2-(3',6'-dihydro-2,4'-bipyridin-1'(2'H)-yl)-N-(2-isopropyl-6-methylphenyl)acetamide The title compound was prepared according to the method of Example 170 substituting 2-isopropyl-6-methylaniline in place of 2,6-diethylaniline and substituting 1',2',3',6'-tetrahydro-[2,4']bipyridinyl hydrochloride (Saari, W. S.; et al. J. Med. Chem. 1984, 27, 1182) in place of the product from Example 36C. (yield: 37.4 mg, 0.110 mmol, 21%). $^1$H NMR (300 MHz, DMSO-d$_6$) δ 1.12 (d, J=6.9 Hz, 6H), 2.15 (s, 3H), 2.67 (m, 2H), 2.82 (t, J=5.7 Hz, 2H), 3.07 (m, 1H), 3.27 (s, 2H), 3.37 (m, 2H), 6.73 (m, 1H), 7.06 (dd, J=3.0, 9.0 Hz, 1H), 7.15 (m, 2H), 7.23 (ddd, J=1.0, 5.1, 7.5 Hz, 1H), 7.56 (d, J=8.4 Hz, 1H), 7.76 (ddd, J=2.1, 7.5, 7.5 Hz, 1H), 8.53 (m, 1H), 9.21 (br s, 1H); MS (ESI) m/e 350 (M+H)$^+$. Anal. calcd for $C_{22}H_{27}N_3O\cdot0.3\ C_2H_4O_2\cdot0.1H_2O$: C, 73.51; H, 7.75; N, 11.38. Found: C, 73.42; H, 7.67; N, 11.40.

EXAMPLE 209

N-(2-chloro-6-methylphenyl)-2-(3',6'-dihydro-2,4'-bipyridin-1'(2'H)-yl)acetamide The title compound was prepared according to the method of Example 170 substituting 2-chloro-6-methylaniline in place of 2,6-diethylaniline and substituting 1',2',3',6'-tetrahydro-[2,4']bipyridinyl hydrochloride (Saari, W. S.; et al. J. Med. Chem. 1984, 27, 1182) in place of the product from Example 36C. (yield: 49.5 mg, 0.145 mmol, 28%). $^1$H NMR (300 MHz, DMSO-d$_6$) δ 2.20 (s, 3H), 2.68 (m, 2H), 2.83 (t, J=5.7 Hz, 2H), 3.29 (s, 2H), 3.38 (m, 2H), 6.72 (m, 1H), 7.22 (m, 3H), 7.35 (dd, J=2.1, 7.5 Hz, 1H), 7.57 (d, J=8.4 Hz, 1H), 7.76 (ddd, J=2.1, 7.5, 7.5 Hz, 1H), 8.53 (m, 1H), 9.43 (br s, 1H); MS (ESI) m/e 342 (M+H)$^+$. Anal. calcd for $C_{19}H_{20}ClN_3O\cdot0.25\ C_2H_4O_2$: C, 65.63; H, 5.93; N, 11.98. Found: C, 65.44; H, 5.72; N, 11.88.

EXAMPLE 210

2-(3',6'-dihydro-2,4'-bipyridin-1'(2'H)-yl)-N-(2-methoxy-6-methylphenyl)acetamide The title compound was prepared according to the method of Example 170 substituting 2-methoxy-6-methylaniline in place of 2,6-diethylaniline and substituting 1',2',3',6'-tetrahydro-[2,4']bipyridinyl hydrochloride (Saari, W. S.; et al. J. Med. Chem. 1984, 27, 1182) in place of the product from Example 36C. (yield: 50.3 mg, 0.149 mmol, 29%). $^1$H NMR (300 MHz, DMSO-d$_6$) δ 2.13 (s, 3H), 2.70 (m, 2H), 2.82 (t, J=5.7 Hz, 2H), 3.24 (s, 2H), 3.35 (m, 2H), 3.74 (s, 3H), 6.74 (m, 1H), 6.86 (dd, J=8.4, 13.8, 1H), 7.14 (dd, J=7.5, 7.5 Hz, 1H), 7.24 (ddd, J=1.0, 5.1, 7.5 Hz, 1H), 7.58 (d, J=8.4 Hz, 1H), 7.78 (ddd, J=2.1, 7.5, 7.5 Hz, 1H), 8.54 (m, 1H), 8.94 (br s, 1H); MS (ESI) m/e 338 (M+H)$^+$. Anal. calcd for $C_{20}H_{23}N_3O\cdot0.05\ CH_2Cl_2$: C, 70.48; H, 6.81; N, 12.30. Found: C, 70.40; H, 6.67; N, 12.38.

EXAMPLE 211

3-chloro-N-[(3-methyl-3',6'-dihydro-2,4'-bipyridin-1'(2'H)-yl)methyl]benzamide

A mixture of the product from Example 143B (trifluoroacetic acid salt, 29 mg, 0.1 mmol), paraformaldehyde (30 mg, 1 mmol), 3-chlorobenzamide (78 mg, 0.5 mmol, Maybridge), and 42 mg of potassium carbonate (0.3 mmol) in 2.5 mL absolute ethyl alcohol was heated to reflux under nitrogen overnight. The mixture was cooled to room temperature, filtered, and the solvent was removed under reduced pressure. The residue was purified by flash column chromatography on silica gel (10% methanol:ethyl acetate) to give 8.6 mg (25%) pure compound. $^1$H NMR (500 MHz, DMSO-d$_6$) δ 2.28 (s, 3H), 2.45 (m, 2H), 2.73 (m, 2H), 3.23 (m, 2H), 4.28 (d, J=6 Hz, 2H), 5.80 (m, 1H), 7.15 (m, 1H), 7.52 (t, J=6 Hz, 1H), 7.61 (m, 2H), 7.86 (d, J=6 Hz, 1H), 7.94 (m, 1H), 8.34 (d, J=6 Hz, 1H), 8.95 (t, J=6 Hz, 1H); MS (ESI/APCI−) m/e 340 (M−H)$^+$.

EXAMPLE 212

3-fluoro-N-[(3-methyl-3',6'-dihydro-2,4'-bipyridin-1'(2'H)-yl)methyl]benzamide

A mixture of the product from Example 143B (trifluoroacetic acid salt, 29 mg, 0.1 mmol), paraformaldehyde (30 mg, 1 mmol), 3-fluorobenzamide (70 mg, 0.5 mmol, Aldrich), and 42 mg of potassium carbonate (0.3 mmol) in 2.5 mL absolute ethyl alcohol was heated to reflux under nitrogen overnight. The mixture was cooled to room temperature, filtered, and the solvent was removed under reduced pressure under reduced pressure. The residue was purified by flash column chromatography on silica gel (10% methanol:ethyl acetate) to give 24 mg (74%) pure compound. $^1$H NMR (500 MHz, DMSO-d$_6$) δ 2.30 (s, 3H), 2.47 (m, 2H), 2.76 (m, 2H), 3.25 (m, 2H), 4.28 (d, J=6 Hz, 2H), 5.80 (m, 1H), 7.14 (m, 1H), 7.39 (t, J=6 Hz, 1H), 7.55 (m, 2H), 7.69 (d, J=6 Hz, 1H), 7.76 (d, J=6 Hz, 1H), 8.34 (d, J=6 Hz, 1H), 8.91 (t, J=6 Hz, 1H); MS (ESI APCI–) m/e 324 (M–H)$^+$.

EXAMPLE 213

3-methyl-N-{[(2S)-2-methyl-4-(2-pyridinyl)-1-piperazinyl]methyl}benzamide

EXAMPLE 213A

(3S)-3-methyl-1-(2-pyridinyl)piperazine

A solution of (S)-(+)-2-methylpiperazine (0.50 g, 0.005 mol, CAS 74879-18-8, Aldrich 39,717-2, 99%) and 2-bromopyridine (5 mL, 0.05 mol) was heated to 120° C. for 14 hours. The reaction mixture was cooled to 23° C. and partitioned between ethyl acetate and water. The layers were separated, and the water layer extracted twice more with ethyl acetate. The aqueous phase was adjusted to pH ~11 with a solution of saturated sodium bicarbonate and solid sodium carbonate. Sodium chloride was added, and the saturated aqueous solution was extracted with ethyl acetate (2×) and dichloromethane (2×). The combined organic extracts were dried over sodium sulfate, filtered, and concentrated under reduced pressure to afford 0.6 g (67% yield) of the title compound. $^1$H NMR (400 MHz, DMSO-d$_6$) δ 1.02 (d, J=6.0 Hz, 3H), 2.27 (dd, J=12, 10 Hz, 1H), 2.67 (m, 3H), 2.92 (m, 1H), 4.07 (m, 2H), 6.58 (dd, J=8, 6 Hz, 1H), 6.77 (d, J=8 Hz, 1H), 7.49 (m, 1H), 8.08 (m, 1H); MS (ESI) m/e 178 (M+H)$^+$.

EXAMPLE 213B

3-methyl-N-{[(2S)-2-methyl-4-(2-pyridinyl)-1-piperazinyl]methyl}benzamide

A solution of the product from Example 213A (250 mg, 1.40 mmol), the product from Example 91A (291 mg, 1.40 mmol) and triethylamine (354 mg, 3.50 mmol) in acetonitrile (10 mL) was stirred at 23° C. for 72 hours. The reaction mixture was poured into water and extracted with ethyl acetate. The ethyl acetate solution was then washed with additional water, a solution of saturated sodium bicarbonate, and brine. The organic phase was dried over sodium sulfate, filtered, and concentrated under reduced pressure. The residue was purified by flash column chromatography on silica gel (2-5% ethanol:ethyl acetate) to afford 396 mg (87% yield) of the title compound. $^1$H NMR (300 MHz, DMSO-d$_6$) δ 1.21 (d, J=5.4 Hz, 3H), 2.34 (s, 3H), 2.50 (m, 3H), 2.85 (m, 2H), 4.06 (br d, J=10.5 Hz, 2H), 4.29 (dd, J=13.5, 6.0 Hz, 1H), 4.43 (dd, J=13.5, 6.0 Hz, 1H), 6.58 (m, 1H), 6.82 (d, J8.7 Hz, 1H), 7.34 (m, 2H), 7.48 (m, 1H), 7.63 (m, 2H), 8.07 (m, 1H), 8.54 (dd, J=6.0, 6.0 Hz, 1H); MS (ESI) m/e 325 (M+H)$^+$; Anal. calcd for C$_{19}$H$_{24}$N$_4$O: C, 70.34; H, 7.46; N, 17.27. Found: C, 70.07; H, 7.55; N, 17.03.

EXAMPLE 214

N-(3-methylphenyl)-2-[(2S)-2-methyl-4-(2-pyridinyl)-1-piperazinyl]acetamide

A solution of the product from Example 213A (100 mg, 0.562 mmol), the product from Example 1A (128 mg, 0.562 mmol) and N,N-diisopropylethylamine (109 mg, 0.843 mmol) in toluene (5 mL) was heated at 60° C. for 16 hours and then cooled to 23° C. The reaction mixture was concentrated under reduced pressure, and the residue purified by flash column chromatography on silica gel (elution with ethyl acetate) to afford 125 mg (68% yield) of the title compound. $^1$H NMR (300 MHz, DMSO-d$_6$) δ 1.06 (d, J=6.3 Hz, 3H), 2.27 (s, 3H), 2.58 (m, 2H), 2.80 (dd, J=12.3, 9.0 Hz, 1H), 2.84 (m, 1H), 3.10 (d, J=16.5 Hz, 1H), 3.11 (m, 1H), 3.38 (d, J=16.5 Hz, 1H), 4.00 (m, 2H), 6.63 (dd, J=8.1, 6.3 Hz, 1H), 6.84 (d, J=11.1 Hz, 1H), 6.89 (m, 1H), 7.18 (m, 1H), 7.44 (m, 2H), 7.52 (m, 1H), 8.10 (m, 1H), 9.63 (br s, 1H); MS (ESI) m/e 325 (M+H)$^+$; Anal. calcd for C$_{19}$H$_{24}$N$_4$O: C, 70.34; H, 7.46; N, 17.27. Found: C, 70.25; H, 7.62; N, 17.29.

EXAMPLE 215

3-methyl-N-{[(2R)-2-methyl-4-(2-pyridinyl)-1-piperazinyl]methyl}benzamide

EXAMPLE 215A

(3R)-3-methyl-1-(2-pyridinyl)piperazine

A solution of (R)-(–)-2-methylpiperazine (0.50 g, 0.005 mol, CAS 75336-86-6, Aldrich 39,716-4, 99%) and 2-bromopyridine (5 mL, 0.05 mol) was heated to 120° C. for 14 hours. The reaction mixture was cooled to 23° C. and partitioned between a large volume of ethyl acetate and water. The layers were separated, and then additional water was added to the ethyl acetate solution. Drops of 1N Hydrochloric acid solution were added to the water/ethyl acetate mixture with vigorous mixing until all of the product was transferred to the aqueous phase. The layers were separated, and the combined aqueous phases concentrated under reduced pressure, and azeotroped with toluene/methanol (5×) to afford 1.29 g (>99% yield) of 3-(R)-methyl-1-pyridin-2-yl-piperazine hydrobromide. $^1$H NMR (300 MHz, DMSO-d$_6$) δ 1.27 (d, J=6.6 Hz, 3H), 2.90 (dd, J=10.5, 14.1 Hz, 1H), 3.10 (m, 2H), 3.40 (m, 2H), 4.32 (m, 2H), 6.77 (dd, J=4.8, 6.9 Hz, 1H), 6.98 (d, J=8.1 Hz, 1H), 7.64 (m, 1H), 8.15 (m, 1H), 8.63 (br s, 1H), 8.92 (br s, 1H); MS (ESI) m/e 178 (M+H)$^+$.

EXAMPLE 215B

3-methyl-N-{[(2R)-2-methyl-4-(2-pyridinyl)-1-piperazinyl]methyl}benzamide

A solution of the product from Example 215A (250 mg, 0.97 mmol), the product from Example 91A (201 mg, 0.97 mmol) and triethylamine (342 mg, 3.39 mmol) in acetonitrile (10 mL) was stirred at 23° C. for 72 hours. The reaction mixture was poured into water and extracted with ethyl acetate. The ethyl acetate solution was then washed with additional water, a solution of saturated sodium bicarbonate and brine. The organic phase was dried over sodium sulfate, filtered and concentrated under reduced pressure. The residue was purified by flash column chromatography on silica gel (2-5% ethanol:ethyl acetate) to afford 245 mg (78% yield) of the title compound. $^1$H NMR (300 MHz, DMSO-d$_6$) δ 1.21 (d, J=5.4 Hz, 3H), 2.34 (s, 3H), 2.50 (m, 3H), 2.85 (m, 2H), 4.06 (br d, J=10.5 Hz, 2H), 4.29 (dd, J=13.5, 6.0 Hz, 1H), 4.43 (dd, J=13.5, 6.0 Hz, 1H), 6.58 (m, 1H), 6.82 (d, J=8.7 Hz, 1H), 7.34 (m, 2H), 7.48 (m, 1H), 7.63 (m, 2H), 8.07 (m, 1H), 8.54

185

(dd, J=6.0, 6.0 Hz, 1H); MS (ESI) m/e 325 (M+H)⁺; Anal. calcd for $C_{19}H_{24}N_4O$: C, 70.34; H, 7.46; N, 17.27. Found: C, 70.61; H, 7.41; N, 16.95.

EXAMPLE 216

N-(3-methylphenyl)-2-[(2R)-2-methyl-4-(2-pyridinyl)-1-piperazinyl]acetamide

A solution of the product from 215A (250 mg, 0.97 mmol), the product from Example 1A (221 mg, 0.97 mmol) and N,N-diisopropylethylamine (313 mg, 2.42 mmol) in toluene (8 mL) was heated at 60° C. for 16 hours and then cooled to 23° C. The reaction mixture was concentrated under reduced pressure, and the residue purified by flash column chromatography on silica gel (elution with ethyl acetate) to afford 261 mg (83% yield) of the title compound. ¹H NMR (300 MHz, DMSO-d₆) δ 1.06 (d, J=6.3 Hz, 3H), 2.27 (s, 3H), 2.58 (m, 2H), 2.80 (m, 1H), 2.84 (m, 1H), 3.10 (d, J=16.5 Hz, 1H), 3.11 (m, 1H), 3.38 (d, J=16.5 Hz, 1H), 4.00 (m, 2H), 6.63 (dd, J=8.1, 6.3 Hz, 1H), 6.84 (d, J=11.1 Hz, 1H), 6.89 (m, 1H), 7.18 (m, 1H), 7.44 (m, 2H), 7.52 (m, 1H), 8.10 (m, 1H), 9.63 (br s, 1H); MS (ESI) m/e 325 (M+H)⁺; Anal. calcd for $C_{19}H_{24}N_4O \cdot 0.3\ H_2O$: C, 69.19; H, 7.52; N, 16.99. Found: C, 69.09; H, 7.42; N, 16.92.

EXAMPLE 217

3-methoxy-N-[(3-methyl-3',6'-dihydro-2,4'-bipyridin-1'(2'H)-yl)methyl]benzamide A mixture of the product from Example 143B (trifluoroacetic acid salt, 29 mg, 0.1 mmol), paraformaldehyde (30 mg, 1 mmol), 3-methoxybenzamide (76 mg, 0.5 mmol, Lancaster), and 42 mg of potassium carbonate (0.3 mmol) in 2.5 mL absolute ethyl alcohol was heated to reflux under nitrogen overnight. The mixture was cooled to room temperature, filtered, and the solvent was removed under reduced pressure under reduced pressure. The residue was purified by flash column chromatography on silica gel (10% methanol:ethyl acetate) to give 25 mg (75%) pure compound. ¹H NMR (500 MHz, DMSO-d₆) δ 2.30 (s, 3H), 2.47 (m, 2H), 2.76 (m, 2H), 3.25 (m, 2H), 3.79 (s, 3H), 4.27 (d, J=6 Hz, 2H), 5.80 (m, 1H), 7.11 (d, J=6 Hz, 1H), 7.14 (t, J=6 Hz, 1H), 7.38 (t, J=6 Hz, 1H), 7.45 (s, 1H), 7.49 (d, J=6 Hz, 1H), 7.59 (d, J=6 Hz, 1H), 8.34 (d, J=6 Hz, 1H), 8.81 (t, J=6 Hz, 1H); MS (ESI APCI−) m/e 336 (M−H)⁺.

EXAMPLE 218

4-fluoro-N-[(3-methyl-3',6'-dihydro-2,4'-bipyridin-1'(2'H)-yl)methyl]benzamide A mixture of the product from Example 143B (trifluoroacetic acid salt, 29 mg, 0.1 mmol), paraformaldehyde (30 mg, 1 mmol), 4-fluorobenzamide (70 mg, 0.5 mmol, Aldrich), and 42 mg of potassium carbonate (0.3 mmol) in 2.5 mL absolute ethyl alcohol was heated to reflux under nitrogen overnight. The mixture was cooled to room temperature, filtered, and the solvent was removed under reduced pressure under reduced pressure. The residue was purified by flash column chromatography on silica gel (10% methanol:ethyl acetate) to give 30 mg (94%) pure compound. ¹H NMR (500 MHz, DMSO-d₆) δ 2.30 (s, 3H), 2.46 (m, 2H), 2.77 (m, 2H), 3.24 (m, 2H), 4.28 (d, J=5 Hz, 2H), 5.80 (m, 1H), 7.14 (t, J=5 Hz, 1H), 7.30 (t, J=6 Hz, 2H), 7.58 (d, J=5 Hz, 1H), 7.98 (t, J=6 Hz, 2H), 8.34 (d, J=5 Hz, 1H), 8.85 (t, J=5 Hz, 1H); MS (ESI APCI−) m/e 324 (M−H)⁺.

EXAMPLE 219

2-(3-chloro-3',6'-dihydro-2,4'-bipyridin-1'(2'H)-yl)-N-(2,6-dimethylphenyl)acetamide

EXAMPLE 219A tert-butyl 4-(3-chloro-2-pyridinyl)-4-hydroxy-1-piperidinecarboxylate

To a solution of 1,4-diazabicyclo[2.2.2]octane (DABCO, 680 mg, 6.06 mmol) in diethyl ether (20 mL) at −78° C. was added n-butyllithium (2.5M in hexanes, 3.0 mL) and stirring continued for 20 minutes. To this mixture was added 3-chloropyridine (700 mg, 6.16 mmol) as a solution in diethyl ether (5 mL). After 30 minutes, tert-butyl 4-oxo-1-piperidinecarboxylate (1.3o g, 6.52 mmol) was added as a solution in diethyl ether (1 mL). The reaction mixture was stirred at −78° C. for 2.5 hours then warmed to −50° C. and quenched with water. The mixture was allowed to warm to room temperature overnight. The layers were separated and the organic phase dried, filtered and concentrated under reduced pressure. The residue was purified by flash column chromatography on silica gel (gradient elution with 20% to 99% ethyl acetate: hexanes) to provide the title compound (110 mg, 9% yield). ¹H NMR (500 MHz, CDCl₃) δ 1.38 (br d, 2H, J=13.7 Hz), 1.50 (s, 9H), 2.73 (ddd, 2H, J=13.1, 13.1, 5.3 Hz), 3.31 (br m, 2H), 4.09 (br m, 2H), 7.25 (m, 1H), 7.74 (dd, 1H, J=7.8, 1.3 Hz), 8.46 (dd, 1H, J=4.7, 1.6 Hz).

EXAMPLE 219B tert-butyl 3-chloro-3',6'-dihydro-2,4'-bipyridine-1'(2'H)-carboxylate

The procedure described in Example 237B was followed, substituting the product from Example 219A for the product from Example 237A to provide the title compound (42 mg, 50%). ¹H NMR (500 MHz, DMSO-d₆) δ 1.44 (s, 9H), 2.47 (m, 2H), 3.54 (m, 2H), 4.02 (m, 2H), 6.14 (br s, 1H), 7.33 (dd, 1H, J=8.1, 4.7 Hz), 7.93 (ddd, 1H, J=8.1, 1.6 Hz), 8.51 (dd, 1H, J=4.5, 1.4 Hz); MS (DCI/NH₃) m/e 295 (M+H)⁺.

EXAMPLE 219C

3-chloro-1',2',3',6'-tetrahydro-2,4'-bipyridine

The procedure described in Example 166B was followed, substituting the product from Example 219B for the product from Example 166A to provide the title compound. MS (DCI/NH₃) m/e 195 (M+H)⁺.

EXAMPLE 219D

2-(3-chloro-3',6'-dihydro-2,4'-bipyridin-1'(2'H)-yl)-N-(2,6-dimethylphenyl)acetamide A mixture of the product from Example 219C (30 mg, 0.1 mmol), N-(2,6-dimethylphenyl)-2-chloroacetamide (23 mg, 0.15 mmol, Aldrich) and sodium carbonate (50 mg) in N,N-dimethylformamide/water (2:1, 2 mL) was shaken at room temperature for 18 hours. The resulting mixture was decanted, concentrated under reduced pressure. The residue was purified by preparative HPLC to provide 20 mg (59%) of the desired product. ¹H NMR (500 MHz, DMSO-d₆) δ 2.18 (s, 6H), 2.49 (m, 2H), 2.85 (m, 2H), 4.38 (m, 2H), 6.25 (s, 1H), 7.09 (m, 3H), 7.40 (dd, J=6 Hz, 1H), 8.00 (d, J=6 Hz, 1H), 8.56 (dd, J=6 Hz, 1H), 10.00 (s, 1H); MS (ESI APCI+) m/e 356 (M+H)+.

EXAMPLE 220

2-(3-chloro-3',6'-dihydro-2,4'-bipyridin-1'(2'H)-yl)-N-(2-methylphenyl)acetamide A mixture of the product from Example 219C (30 mg, 0.1 mmol), N-(2-methyl-phenyl)-2-chloroacetamide (21 mg, 0.15 mmol, Maybridge) and sodium carbonate (50 mg) in N,N-dimethylformamide/water (2:1, 2 mL) was shaken at room temperature for 18 hours. The resulting mixture was decanted, concentrated under reduced pressure. The residue was purified by preparative HPLC to provide 21 mg (64%) of the desired product. $^1$H NMR (500 MHz, DMSO-$d_6$) δ 2.24 (s, 3H), 2.75-2.85 (m, 2H), 2.86 (m, 2H), 3.05 (m, 2H), 4.32 (m, 2H), 6.25 (s, 1H), 7.00-7.25 (m, 3H), 7.45 (m, 2H), 8.00 (d, J=6 Hz, 1H), 8.55 (dd, J=6 Hz, 1H), 10.00 (s, 1H); MS (ESI APCI+) m/e 342 (M+H)+.

EXAMPLE 221

N-(3',6'-dihydro-2,4'-bipyridin-1'(2'H)-ylmethyl)-1-naphthamide

The procedure described in Example 115 was followed, substituting napthalene-1-carboxamide for 3-methoxybenzamide to provide the title compound (28% yield). This compound (164 mg) in ethanol was treated with maleic acid (55.5 mg), stirred for 10 minutes then concentrated under reduced pressure to give yellowish sticky solid which was dissolved in dichloromethane, and the compound was precipitated using diethyl ether, filtered and then washed with diethyl ether, dried to give the maleate salt (144 mg). $^1$H NMR (300 MHz, DMSO-$d_6$) δ 2.86 (m, 2H), 3.4 (m, 2H), 3.91 (m, 2H), 4.57 (m, 2H), 6.12 (s, 2H), 6.76 (m, 1H), 7.32 (m, 1H), 7.61 (m, 4H), 7.80 (m, 2H), 8.02 (m, 1H), 8.10 (d, J=9 Hz, 1H), 8.28 (m, 1H), 8.58 (m, 1H), 9.55 (m, 1H); MS (DCI/NH$_3$) m/e 324 (M+H)+; Anal. calcd for $C_{22}H_{21}N_3O·_{1.2}C_4H_4O_4$: C, 66.68; H, 5.39; N, 8.70. Found; C, 66.38; H, 5.43; N, 8.75.

EXAMPLE 222

N-{[4-(3-cyano-2-pyridinyl)-1-piperazinyl]methyl}-3-fluorobenzamide

The procedure described in Example 200 was followed, substituting 2-piperazin-1-ylnicotinonitrile for the product in Example 119A and 3-fluorobenzamide for 3-methylbenzamide to provide the title compound (80% yield). $^1$H NMR (300 MHz, DMSO-$d_6$) δ 2.66 (m, 4H), 3.59 (m, 4H), 4.22 (d, J=6.1 Hz, 2H), 6.91 (dd, J=7.6, 4.9 Hz, 1H), 7.39 (tdd, J=8.5, 8.5, 2.6, 1.0 Hz, 1H), 7.53 (td, J=8.0, 5.8 Hz, 1H), 7.68 (ddd, J=10.0, 2.5, 1.4 Hz, 2H), 7.74 (dt, J=7.7, 1.2 Hz, 1H), 8.39 (dd, J=4.9, 1.9 Hz, 1H), 8.91 (t, J=6.1 Hz, 1H); MS (DCI/NH$_3$) m/e 340 (M+H)+; Anal. calcd for $C_{18}H_{18}N_5OF$: C, 63.70; H, 5.35; N, 20.60. Found: C, 63.54; H, 5.22; N, 20.47.

EXAMPLE 224

3-methyl-N-{[4-(1,3-thiazol-2-yl)-1-piperidinyl]methyl}benzamide

The product from Example 166C (490 mg) was hydrogenated with 10% Pd/C catalyst under hydrogen gas pressure (60 psi) for 42 hours in methanol. The mixture was filtered and concentrated under reduced pressure. The residue was purified by flash column chromatography on silica gel (5% ethanol:ethyl acetate) to provide the title compound (100 mg, 22%). $^1$H NMR (300 MHz, CDCl$_3$) δ 1.85 (dq, 2H, J=12, 6 Hz), 2.20 (m, 2H), 2.40 (s, 3H), 2.48 (m, 2H), 3.10 (m, 3H), 4.35 (d, 2H, J=6 Hz), 6.50 (m, 1H), 7.20 (d, 1H, J=3.3 Hz), 7.35 (m, 2H), 7.60 (m, 2H), 7.70 (d, 1H, J=3.3 Hz); MS (DCI/NH$_3$) m/e 316 (M+H)+.

Maleate salt: Anal. calcd for $C_{17}H_{21}N_3OS·1.2 C_4H_4O_4$: C, 57.11; H, 5.85; N, 9.48. Found: C, 57.48; H, 5.33; N, 9.52.

EXAMPLE 225

2-(1-{2-[(4-fluoro-2-methylphenyl)amino]-2-oxoethyl}-4-piperidinyl)pyridinium N-oxide

EXAMPLE 225A 2-bromo-N-(4-fluoro-2-methylphenyl)acetamide

The procedure described in Example 1A was followed, substituting 4-fluoro-2-methylphenylamine for 3-methylaniline to provide the title compound as a pink solid. $^1$H NMR (300 MHz, DMSO-$d_6$) δ 2.20 (s, 3H), 4.06 (s, 2H), 7.01 (ddd, 1H, J=8.8, 8.8, 3.0 Hz), 7.10 (dd, 1H, J=9.5, 3.0 Hz), 7.34 (dd, 1H, J=8.8, 5.4 Hz), 9.74 (br s, 1H); MS (DCI/NH$_3$) m/e 246/248 (M+H)+; 263/265 (M+NH$_4$)+.

EXAMPLE 225B 2-(1-{2-[(4-fluoro-2-methylphenyl)amino]-2-oxoethyl}-4-piperidinyl)pyridinium N-oxide A mixture of the product from Example 225A (0.64 g, 2.6 mmol), the product from Example 119A (0.63 g, 2.5 mmol) and K$_2$CO$_3$ (720 mg, 5.2 mmol) in N,N-dimethylformamide (12 mL) was heated at 40° C. for overnight. The reaction mixture was cooled and the solvent removed under reduced pressure. The residue was partitioned between brine and ethyl acetate. The aqueous layer was extracted with ethyl acetate (3×200 mL). The combined organics were dried over magnesium sulfate and concentrated. The residue was purified by flash column chromatography on silica gel using 4% methanol:dichloromethane to give the desired product as a off-white solid. (649 mg, 76%). $^1$H NMR (300 MHz, DMSO-$d_6$) δ 1.68 (m, 2H), 1.92 (d, J=5.8 Hz, 2H), 2.24 (s, 3H), 2.36 (m, 2H), 3.04 (d, J=11.5 Hz, 2H), 3.17 (s, 2H), 3.29 (m, 2H), 7.03 (m, 1H), 7.11 (dd, J=9.7, 2.9 Hz, 1H), 7.35 (m, 2H), 7.67 (dd, J=8.8, 5.8 Hz, 11H), 8.26 (m, 1H), 9.40 (s, 1H); MS (DCI/NH$_3$) m/e 328 (M+H−16)+; 344 (M+H)+.

Maleate salt (856 mg): Anal. calcd for $C_{19}H_{22}N_3O_2F·1.0 C_4H_4O_4·0.75 H_2O$: C, 58.41; H, 5.86; N, 8.88. Found: C, 58.02; H, 5.83; N, 8.67.

EXAMPLE 226

2-(1-{2-[(4-fluoro-3-methylphenyl)amino]-2-oxoethyl}-4-piperidinyl)pyridinium N-oxide The procedure described in Example 225B was followed, substituting the product from Example 27A for the product from Example 225A to provide the title compound. (139 mg, 57%). $^1$H NMR (300 MHz, DMSO-$d_6$) δ 1.68 (m, 2H), 1.92 (d, J=5.8 Hz, 2H), 2.22 (s, 3H), 2.46 (m, 2H), 3.04 (m, 2H), 3.25 (s, 3H), 7.03 (t, J=6, 1H), 7.35 (m, 2H), 7.44 (dd, J=4.5, 1.5 Hz, 1H), 7.48 (m, 1H), 7.54 (dd, J=4.5, 1.5 Hz, 1H), 8.26 (d, J=4.5, 1H), 9.79 (s, 1H); MS (DCI/NH$_3$) m/e 328 (M+H−16)$^+$; 344 (M+H)$^+$.

Maleate salt (171 mg): Anal. calcd for C$_{19}$H$_{22}$N$_3$O$_2$F.1.0 C$_4$H$_4$O$_4$: C, 60.12; H, 5.12; N, 9.15. Found: C, 59.91; H, 5.79; N, 9.05.

EXAMPLE 227

2-(1-{2-[(3-fluorophenyl)amino]-2-oxoethyl}-4-piperidinyl)pyridinium N-oxide

The procedure described in Example 225B was followed, substituting the product from Example 254A for the product from Example 225A to provide the title compound. (157 mg, 68%). $^1$H NMR (300 MHz, DMSO-d$_6$) δ 1.68 (m, 2H), 1.92 (d, J=5.8 Hz, 2H), 2.30 (m, 2H), 3.01 (m, 2H), 3.19 (s, 2H), 3.25 (m, 1H), 6.89 (m, 1H), 7.35 (m, 3H), 7.42 (m, 2H), 7.68 (m, 1H), 8.26 (d, J=4.5, 1H), 9.91 (s, 1H); MS (DCI/NH$_3$) m/e 330 (M+H)$^+$.

Maleate salt (190 mg): Anal. calcd for C$_{18}$H$_{20}$N$_3$O$_2$F.1.0 C$_4$H$_4$O$_4$.0.2 H$_2$O: C, 58.84; H, 5.48; N, 9.36. Found: C, 58.52; H, 5.45; N, 9.04.

674532 EXAMPLE 228

2-(1-{2-[(2-fluoro-5-methylphenyl)amino]-2-oxoethyl}-4-piperidinyl)pyridinium N-oxide

EXAMPLE 228A 2-chloro-N-(2-fluoro-5-methylphenyl)acetamide

The procedure described in Example 22A was followed, substituting 2-fluoro-5-methylphenylamine for 3,4,5-trimethoxyaniline to provide the title compound (83% yield) as a white solid. $^1$H NMR (400 MHz, DMSO-d$_6$) δ 2.28 (s, 3H), 4.34 (s, 2H), 6.98 (m, 1H), 7.14 (dd, 1H, J=11.1, 8.6 Hz), 7.69 (d, 1H, J=7.4 Hz), 9.99 (br s, 1H); MS (DCI/NH$_3$) m/e 202 (M+H)$^+$; 219 (M+NH$_4$)$^+$.

EXAMPLE 228B 2-(1-{2-[(2-fluoro-5-methylphenyl)amino]-2-oxoethyl}-4-piperidinyl)pyridinium N-oxide The procedure described in Example 225B was followed, substituting the product from Example 228A for the product from Example 225A to provide the title compound. (88 mg, 36.6%). $^1$H NMR (300 MHz, DMSO-d$_6$) δ 1.63 (m, 2H), 1.95 (d, J=12 Hz, 2H), 2.27 (s, 3H), 3.50 (m, 2H), 3.01 (d, J=12 Hz, 2H), 3.20 (s, 2H), 3.30 (m, 1H), 6.93 (m, 1H), 7.15 (dd, J=9, 3 Hz, 1H), 7.31 (m, 2H), 7.42 (m, 1H), 7.84 (m, 1H), 8.26 (m, 1H), 9.59 (s, 1H); MS (DCI/NH$_3$) m/e 328 (M+H−16)$^+$; 344 (M+H)$^+$.

Maleate salt (190 mg): Anal. calcd for C$_{19}$H$_{22}$N$_3$O$_2$F.1.0 C$_4$H$_4$O$_4$.0.2 H$_2$O: C, 58.84; H, 5.48; N, 9.36. Found: C, 58.52; H, 5.45; N, 9.04.

EXAMPLE 229

2-(1-{1-methyl-2-[(3-methylphenyl)amino]-2-oxoethyl}-4-piperidinyl)pyridinium N-oxide

EXAMPLE 229A 2-bromo-N-(3-methylphenyl)propanamide

The procedure described in Example 1A was followed, substituting 2-bromopropionyl chloride for bromoacetyl chloride to provide the title compound (92% yield) as a white solid.

$^1$H NMR (300 MHz, DMSO-d$_6$) δ 1.74 (d, 3H, J=6.8 Hz), 2.28 (s, 3H), 4.69 (q, 1H, J=6.8 Hz), 6.90 (d, 1H, J=7.5 Hz), 7.20 (dd, 1H, J=7.8, 7.8 Hz), 7.37 (br d, 1H, J=8.5 Hz), 7.44 (br s, 1H), 10.22 (br s, 1H); MS (DCI/NH$_3$) m/e 242/244 (M+H)$^+$; 259/261 (M+NH$_4$)$^+$.

EXAMPLE 229B 2-(1-{1-methyl-2-[(3-methylphenyl)amino]-2-oxoethyl}-4-piperidinyl)pyridinium N-oxide The procedure described in Example 225B was followed, substituting the product from Example 229A for the product from Example 225A to provide the title compound. (153 mg, 64.6%). $^1$H NMR (300 MHz, DMSO-d$_6$) δ 1.20 (d, J=6 Hz, 2H), 1.41 (d, J=6 Hz, 1H), 1.65 (m, 2H), 1.91 (m, 2H), 2.28 (s, 3H), 2.29 (m, 1H), 2.45 (m, 1H), 3.30 (m, 3H), 6.88 (d, J=7.5 Hz, 1H), 7.19 (t, J=7.5 Hz, 1H), 7.31 (m, 2H), 7.45 (m, 3H), 8.24 (m, 1H), 9.68 (s, 1H), 9.94 (s, 1H); MS (DCI/NH$_3$) m/e 324 (M+H−16)$^+$; 340 (M+H)$^+$.

Maleate salt (187 mg): Anal. calcd for C$_{20}$H$_{25}$N$_3$O$_2$.1.0 C$_4$H$_4$O$_4$.1.2 H$_2$O: C, 60.42; H, 6.63; N, 8.81. Found: C, 60.41; H, 6.38; N, 8.01.

EXAMPLE 230

2-(1-{2-[(4-fluorophenyl)amino]-2-oxoethyl}-4-piperidinyl)pyridinium N-oxide

The procedure described in Example 225B was followed, substituting N-chloroacetyl-4-fluoroaniline (Avacado) for the product from Example 225A to provide the title compound (45% yield). $^1$H NMR (300 MHz, DMSO-d$_6$) δ 1.68 (m, 2H), 1.92 (d, J=5.8 Hz, 2H), 2.30 (m, 2H), 3.01 (m, 2H), 3.19 (s, 2H), 3.25 (m, 1H), 6.89 (m, 1H), 7.35 (m, 3H), 7.42 (m, 2H), 7.68 (m, 1H), 8.26 (d, J=4.5, 1H), 9.91 (s, 1H); MS (DCI/NH$_3$) m/e 314 (M+H−16)$^+$; 330 (M+H)$^+$. Maleate salt (190 mg): Anal. calcd for C$_{18}$H$_{20}$N$_3$O$_2$F.1.0 C$_4$H$_4$O$_4$.1.1 H$_2$O: C, 57.88; H, 5.53; N, 8.80. Found: C, 57.49; H, 5.56; N, 8.72.

EXAMPLE 231

2-(1-{2-[(2-fluorophenyl)amino]-2-oxoethyl}-4-piperidinyl)pyridinium N-oxide

The procedure described in Example 225B was followed, substituting the product from Example 28A for the product from Example 225A to provide the title compound. (126 mg, 54%). $^1$H NMR (300 MHz, DMSO-d$_6$) δ 1.68 (m, 2H), 1.92 (d, J=6 Hz, 2H), 2.30 (m, 2H), 3.01 (m, 2H), 3.19 (s, 2H), 3.25 (m, 1H), 7.15 (m, 1H), 7.30 (m, 3H), 7.42 (m, 2H), 7.68 (m, 1H), 8.26 (d, J=4.5, 1H), 9.81 (s, 1H); MS (DCI/NH$_3$) m/e 314 (M+H−16)$^+$; 330 (M+H)$^+$.

Maleate salt (190 mg): Anal. calcd for C$_{18}$H$_{20}$N$_3$O$_2$F.1.0 C$_4$H$_4$O$_4$.0.2 H$_2$O: C, 58.84; H, 5.48; N, 9.36. Found: C, 59.04; H, 5.60; N, 9.20.

EXAMPLE 232

N-(3-methylphenyl)-2-{4-[3-(trifluoromethyl)-2-pyridinyl]-1-piperazinyl}acetamide

EXAMPLE 232A

1-[3-(trifluoromethyl)-2-pyridinyl]piperazine

A solution of 2-chloro-3-trifluoromethylpyridine (6.57 g, 36.2 mmol) and piperazine (31.48 g, 365.5 mmol) in n-butanol was heated to 115° C. After 48 hours, the mixture was cooled to room temperature, the solvent removed under reduced pressure and the residue partitioned between water and ethyl acetate. The organic phase was dried (sodium sulfate), filtered and concentrated under reduced pressure. The residue was purified by flash column chromatography on silica gel (elution with 15% methanol:dichloromethane) to provide 3.35 g (40% yield) of the title compound as a tan solid. $^1$H NMR (300 MHz, DMSO-d$_6$) δ 2.80 (m, 4H), 3.10 (m, 4H), 7.15 (ddd, 1H, J=7.8, 4.7, 1.0 Hz), 8.03 (dd, 1H, J=7.8, 1.7 Hz), 8.50 (ddd, 1H, J=4.8, 2.0, 0.7 Hz); MS (DCI/NH$_3$) m/e 232 (M+H)$^+$.

EXAMPLE 232B

N-(3-methylphenyl)-2-{4-[3-(trifluoromethyl)-2-pyridinyl]-1-piperazinyl}acetamide The product from Example 33A (1.30 mg, 7.08 mmol) and N,N-diisopropylamine (5.0 mL) in toluene (50 mL) were treated with the product from Example 232A (2.00 mg, 8.65 mmol) and heated to 60° C. for 18 hours. The mixture was allowed to cool to room temperature, transferred to a separatory funnel and washed with saturated aqueous sodium bicarbonate. The organic phase was dried (sodium sulfate), filtered, and the filtrate concentrated under reduced pressure. The residue was purified by flash column chromatography on silica gel (gradient elution with 25% to 50% ethyl acetate:hexanes) to provide of the title compound as a white solid. $^1$H NMR (300 MHz, DMSO-d$_6$) δ 2.28 (s, 3H), 2.67 (m, 4H), 3.18 (s, 2H), 3.27 (m, 4H), 6.88 (br d, 1H, J=8.1 Hz), 7.18 (m, 2H), 7.45 (m, 2H), 8.06 (dd, 1H, J=7.8, 2.0 Hz), 8.53 (m, 1H), 9.65 (br s, 1H); MS (DCI/NH$_3$) m/e 379 (M+H)$^+$.

Maleate salt 2.45 g, 70% yield): white solid; IH NMR (300 MHz, CD$_3$OD) δ 2.33 (s, 3H), 3.50 (m, 8H), 4.06 (s, 2H), 6.26 (s, 2H), 6.97 (br d, 1H, J=8.1 Hz), 7.21 (dd, 1H, J=7.8, 7.8 Hz), 7.29 (ddd, 1H, J=7.8, 5.1, 1.0 Hz), 7.40 (m, 2H), 8.09 (dd, 1H, J=7.8, 1.4 Hz), 8.57 (ddd, 1H, J=4.8, 2.0, 0.7 Hz); Anal. calcd for C$_{19}$H$_{21}$F$_3$N$_4$O.1.0 C$_4$H$_4$O$_4$: C, 55.87; H, 5.10; N, 11.33. Found: C, 55.55; H, 5.00; N, 10.99.

EXAMPLE 233

N-(3-methylphenyl)-2-[4-(1,3-thiazol-2-yl)-3,6-dihydropyridin-1 (2H)-yl]acetamide The procedure described in Example 33C was followed, substituting the product from Example 166B for the product from Example 33B to provide the title compound as a yellow sticky residue (450 mg, 62%). $^1$H NMR (300 MHz, CDCl$_3$) δ 2.3 (s, 3H), 3.8 (m, 2H), 2.9 (m, 2H), 3.31 (s, 2H), 3.4 (m, 2H), 6.6 (m, 1H), 6.9 (m, 1H), 7.2 (m, 1H), 7.25 (d, 1H, J=3 Hz), 7.4 (m, 2H), 7.8 (d, 1H, J=3 Hz), 9.15 (br s, 1H); MS (DCI/NH$_3$) m/e 314 (M+H)$^+$.

Maleate salt: Anal. calcd for C$_{17}$H$_{19}$N$_3$OS.1.0 C$_4$H$_4$O$_4$: C, 58.73; H, 5.40; N, 9.78. Found: C, 58.69; H, 5.49; N, 9.44.

EXAMPLE 234

N-(3-methylphenyl)-2-(4-thien-2-yl-3,6-dihydropyridin-1 (2H)-yl)acetamide

EXAMPLE 234A tert-butyl 4-hydroxy-4-thien-2-ylpiperidine-1-carboxylate

2-Thienyllithium (27.6 mL, 27.6 mmol) in tetrahydrofuran (30 mL) was treated slowly with 4-oxo-piperidinel-carboxylic acid tert-butylester (5.0 g, 25 mmol) in 15 mL tetrahydrofuran) at −78° C. The mixture was warmed to room temperature and stirred for 3.5 hours. The reaction was quenched by pouring over ice, extracted with ethyl acetate, dried over magnesium sulfate, filtered and concentrated under reduced pressure to afford greenish oil (5.68 g, 81%) which solidified upon standing. $^1$H NMR (300 MHz, DMSO-d$_6$) δ 1.4 (s, 9H), 1.8 (m, 4H), 3.10 (br s, 2H), 3.8 (m, 2H), 5.5 (s, 1H), 6.9 (m, 2H), 7.38 (dd, 1H, J=6, 3 Hz); MS (DCI/NH$_3$) m/e 284 (M+H)$^+$.

EXAMPLE 234B 4-thien-2-yl-1,2,3,6-tetrahydropyridine

The product from Example 234A (3 g, 10.59 mmol) was treated with 99% formic acid (7 mL) and stirred at room temperature overnight. The mixture was quenched saturated sodium bicarbonate (pH 8.5-9), extracted with ethyl acetate, dried over magnesium sulfate, filtered and concentrated under reduced pressure to afford reddish oil (700 mg, 40%). $^1$H NMR (300 MHz, CDCl$_3$) δ 2.45 (m, 2H), 3.10 (t, 2H, J=6 Hz), 2.45 (m, 2H), 6.18 (m, 1H), 6.95 (d, 2H, J=3 Hz), 7.18 (t, 1H, J=3 Hz); MS (DCI/NH$_3$) m/e 166 (M+H)$^+$.

EXAMPLE 234C

N-(3-methylphenyl)-2-(4-thien-2-yl-3,6-dihydropyridin-1 (2H)-yl)acetamide

The procedure described in Example 33C was followed, substituting the product from Example 234B for the product from Example 33B to provide the title compound as a yellow solid (220 mg, 50%). $^1$H NMR (300 MHz, DMSO-d$_6$) δ 2.10 (s, 3H), 2.45 (m, 2H), 2.75 (t, 2H, J=6 Hz), 3.2 (m, 4H), 6.1 (m, 1H), 6.9 (d, 1H, J=9 Hz), 7.0 (dd, 1H, J=6, 4.5 Hz), 7.05 (dd, 1H, J=3, 0.75 Hz), 7.18 (t, 1H, J=7.5 Hz), 7.40 (dd, 1H, J=3, 0.75 Hz), 7.5 (m, 2H), 9.4 (s, 1H); MS (DCI/NH$_3$) m/e 313 (M+H)$^+$.

Maleate salt: Anal. calcd for C$_{18}$H$_{20}$N$_2$OS.1.0 C$_4$H$_4$O$_4$.0.4 H$_2$O: C,60.65; H,5.74; N,6.43. Found: C,60.44; H,5.44; N,6.18.

EXAMPLE 235

3-methyl-N-[(4-thien-2-yl-3,6-dihydropyridin-1 (2H)-yl)methyl]benzamide

The procedure described in Example 200 was followed, substituting the product from Example 234B for the product from Example 119A to provide the title compound as a yellow sticky residue (84 mg). $^1$H NMR (300 MHz, CDCl$_3$) δ 2.35 (s, 3H), 2.78 (t, 2H, J=6 Hz), 3.2 (m, 2H), 4.12 (d, 1H, J=6 Hz), 4.7 (t, 2H, J=6 Hz), 5.62 (t, 1H, J=6 Hz), 6.1 (m, 1H), 7.0 (m, 2H), 7.38 (d, 3H, J=6 Hz), 7.7 (m, 2H), 9.0 (t, 1H, J=6 Hz); MS (DCI/NH$_3$) m/e 313 (M+H)$^+$.

Maleate salt: Anal. calcd for C$_{18}$H$_{20}$N$_2$OS.1.0 C$_4$H$_4$O$_4$: C, 61.67; H, 5.65; N, 6.54; Found: C, 62.03, H, 5.05, N, 6.24.

EXAMPLE 236

2-(1-{2-[(3-chlorophenyl)amino]-2-oxoethyl}piperidin-4-yl)pyridinium N-oxide

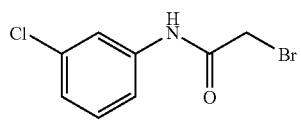

EXAMPLE 236A 2-bromo-N-(3-chlorophenyl)acetamide

The procedure described in Example 1A was followed, substituting 3-chloroaniline for 3-methylaniline to provide the title compound as a white solid. $^1$H NMR (300 MHz, DMSO-d$_6$) δ 4.05 (s, 2H), 7.15 (ddd, 1H, J=7.8, 2.0, 1.4 Hz), 7.36 (dd, 1H, J=7.8, 7.8 Hz), 7.44 (ddd, 1H, J=8.1, 2.0, 1.4 Hz), 7.79 (dd, 1H, J=2.0, 2.0 Hz), 10.57 (br s, 1H).

EXAMPLE 236B 2-(1-{2-[(3-chlorophenyl)amino]-2-oxoethyl}piperidin-4-yl)pyridinium N-oxide The procedure described in Example 225B was followed, substituting the product from Example 236A for the product from Example 225A to provide the title compound. (226 mg, 66%). $^1$H NMR (300 MHz, DMSO-d$_6$) δ 1.68 (m, 2H), 1.92 (d, J=5.7 Hz, 2H), 2.30 (m, 2H), 3.01 (m, 2H), 3.19 (s, 2H), 3.25 (m, 1H), 6.89 (m, 1H), 7.35 (m, 3H), 7.42 (m, 2H), 7.68 (m, 1H), 8.26 (d, J=4.5, 1H), 9.91 (s, 1H); MS (DCI/NH$_3$), m/e 330 (M+H−16)$^+$, 346 (M+H)$^+$.

Maleate salt (294 mg): Anal. calcd for C$_{18}$H$_{20}$N$_3$O$_2$Cl.1.0 C$_4$H$_4$O$_4$.0.2 H$_2$O: C, 57.21; H, 5.24; N, 9.01. Found: C, 57.28; H, 5.16; N, 8.70.

EXAMPLE 237

2-[4-(1-methyl-1H-imidazol-2-yl)-3,6-dihydropyridin-1(2H)-yl]-N-(3-methylphenyl)acetamide

EXAMPLE 237A tert-butyl 4-hydroxy-4-(1-methyl-1H-imidazol-2-yl)piperidine-1-carboxylate 1-Methylimidazole (4.1 mL, 50 mmol) in dry tetrahydrofuran was treated with n-butyllithium (25 mL, 50 mmol) at room temperature and heated at 40° C. for 3 hours. The reaction was cooled to −78° C. and 4-oxo-piperidine-1-carboxylic acid tert-butylester (9.96 g, 50 mmol) added. The mixture was allowed to warm to room temperature, stirred for 6 hours the heated to 40° C. for an additional 3 hours. The reaction was cooled to room temperature, quenched with water and extracted with ethyl acetate. The organic phases were dried over magnesium sulfate, filtered and concentrated under reduced pressure. The crude material was recrystallized from methanol to provide the title compound (8.2 g, 84%) as white solid. $^1$H NMR (300 MHz, CDCl$_3$) δ 1.45 (s, 9H), 1.8 (d, 2H, J=15 Hz), 2.1 (m, 2H), 3.3 (t, 3H, J=15 Hz), 3.8 (s, 4H), 6.8 (dd, 2H, J=9, 3 Hz); MS (DCI/NH$_3$) m/e 282 (M+H)$^+$.

EXAMPLE 237B tert-butyl 4-(1-methyl-1H-imidazol-2-yl)-3,6-dihydropyridine-1(2H)-carboxylate The product from Example 237A (5 g, 17.8 mmol) was taken in toluene and treated with (methoxycarbonylsulfamoyl)triethylammonium hydroxide, inner salt (Burgess Reagent, 6.35 g, 26.7 mmol) and heated to 90° C. for 6 hours. The reaction was cooled to room temperature and partitioned between ethyl acetate/water. The organic phase was dried over magnesium sulfate, filtered and concentrated under reduced pressure to afford 4.1 g (87%) of the title compound as a brown oily residue. $^1$H NMR (300 MHz, CDCl$_3$) δ 1.42 (s, 9H), 2.63 (m, 2H), 3.61 (t, 2H, J=6 Hz), 3.7 (s, 3H), 4.1 (d, 2H, J=3 Hz), 6.02 (br s, 1H), 6.9 (d, 1H, J=1.5 Hz), 7.1 (d, 1H, J=1.5 Hz); MS (DCI/NH$_3$) m/e 264 (M+H)$^+$.

EXAMPLE 237C 4-(1-methyl-1H-imidazol-2-yl)-1,2,3,6-tetrahydropyridine

The procedure described in Example 166B was followed, substituting the product from Example 237B for the product from Example 166A to provide the title compound as a yellow sticky residue (1.28 g, 41%). $^1$H NMR (300 MHz, CDCl$_3$) δ 2.6 (m, 2H), 3.1 (t, 2H, J=6 Hz), 3.6 (m, 2H), 3.7 (s, 3H), 6.0 (m, 1H), 6.82 (d, 1H, J=1.5 Hz), 7.0 (d, 1H, J=1.5 Hz); MS (DCI/NH$_3$) m/e 164 (M+H)$^+$.

EXAMPLE 237D

2-[4-(1-methyl-1H-imidazol-2-yl)-3,6-dihydropyridin-1(2H)-yl]-N-(3-methylphenyl)acetamide The procedure described in Example 33C was followed, substituting the product from Example 237C for the product from Example 33B to provide the title compound 300 mg (51%) as a yellow oil; $^1$H NMR (300 MHz, DMSO-d$_6$) δ 2.30 (s, 3H), 2.5 (s, 2H), 2.6 (br s, 2H), 2.75 (m, 2H), 3.20 (s, 3H), 3.75 (s, 2H), 6.3 (br s, 1H), 6.9 (m, 2H), 7.2 (m, 2H), 7.42 (m, 2H), 9.65 (s, 1H); MS (DCI/NH$_3$) m/e 311 (M+H)$^+$.

Maleate salt: Anal. calcd for C$_{18}$H$_{22}$N$_4$O.1.3 C$_4$H$_4$O$_4$.1.7 H$_2$O: C, 56.65; H, 6.27; N, 11.39. Found: C, 56.57; H, 6.53; N, 11.23.

EXAMPLE 238

N-(3-methylphenyl)-2-[4-(3-nitropyridin-2-yl)piperazin-1-yl]acetamide

EXAMPLE 238A 1-(3-nitropyridin-2-yl)piperazine

To a solution of 2-chloro-3-nitropyridine (10.05 g, 63.39 mmol) in isopropyl alcohol (350 mL) at room temperature was added piperazine (27.48 g, 319.0 mmol) in one portion. After 2 hours, the solvent was removed under reduced pressure and the residue partitioned between water and dichloromethane. The organic phase was dried (sodium sulfate), filtered and concentrated to a bright yellow solid. This material was used without further purification. $^1$H NMR (300 MHz, CDCl$_3$) δ 1.74 (s, 1H), 2.98 (m, 4H), 3.43 (m, 4H), 6.73 (dd, 1H, J=8.1, 4.8 Hz), 8.11 (dd, 1H, J=8.1, 1.7 Hz), 8.32 (dd, 1H, J=4.4, 1.7 Hz); MS (DCI/NH$_3$) m/e 209 (M+H)$^+$.

EXAMPLE 238B

N-(3-methylphenyl)-2-[4-(3-nitropyridin-2-yl)piperazin-1-yl]acetamide

The procedure described in Example 232B was followed, substituting the product from Example 238A for the product from Example 232A to provide the title compound (84% yield) as a yellow solid. $^1$H NMR (300 MHz, CDCl$_3$) δ 2.36 (s, 3H), 2.74 (m, 4H), 3.20 (s, 2H), 3.56 (m, 4H), 6.80 (dd, 1H, J=8.1, 4.4 Hz), 6.94 (br d, 1H, J=7.8 Hz), 7.23 (dd, 1H, J=7.5, 7.5 Hz), 7.39 (m, 2H), 8.15 (dd, 1H, J=8.1, 1.7 Hz), 8.35 (dd, 1H, J=4.8, 2.0 Hz), 9.01 (br s, 1H); MS (DCI/NH$_3$) m/e 356 (M+H)$^+$; Anal. calcd for C$_{18}$H$_{21}$N$_5$O$_3$: C, 60.83; H, 5.96; N, 19.71. Found: C, 60.66; H, 5.97; N, 19.70.

EXAMPLE 239

2-[4-(3-chloropyridin-2-yl)piperazin-1-yl]-N-(3-methylphenyl)acetamide

EXAMPLE 239A 1-(3-chloropyridin-2-yl)piperazine

A solution of piperazine (29.1 g, 338 mmol), 2,3-dichloropyridine (5.00 g, 33.8 mmol), and n-butanol (220 mL) was refluxed for 3 days. The reaction mixture was cooled to 23° C. and concentrated under reduced pressure. The residue was slurried with ethyl acetate and water. The ethyl acetate layer was poured off and dried over sodium sulfate, filtered, and concentrated to afford 4.8 g (72% yield) of the title compound. $^1$H NMR (300 MHz, DMSO-d$_6$) δ 2.83 (m, 4H), 3.15 (m, 4H), 6.97 (dd, 1H, J=4.5, 7.5 Hz), 7.77 (dd, 1H, J=1.5, 7.5 Hz), 8.21 (dd, 1H, J=1.5, 4.5 Hz)); MS (ESI) m/e 198 (M+H)$^+$.

EXAMPLE 239B

2-[4-(3-chloropyridin-2-yl)piperazin-1-yl]-N-(3-methylphenyl)acetamide

The procedure described in Example 232B was followed, substituting the product from Example 239A for the product from Example 232A. The reaction mixture was concentrated under reduced pressure, and the residue was purified by chromatography (Prep Nova-Pak HR C18 column, 6 m 60 A, 25×100 mm, eluent gradient from 25% to 95% acetonitrile: water with a constant 0.1% trifluoroacetic acid) to afford 109 mg (23% yield) of the trifluoroacetic acid salt: an amorphous solid mp 45-55° C. $^1$H NMR (300 MHz, DMSO-d$_6$) δ 2.29 (s, 3H), 3.40 (br m, 8H), 3.80 (br m, 1H), 4.19 (br m, 1H), 6.96 (br d, 1H, J=7.5 Hz), 7.09 (dd, 1H, J=4.5, 7.5 Hz), 7.24 (dd, 1H, J=7.8, 7.8 Hz), 7.40 (m, 2H), 7.88 (dd, 1H, J=2.1, 8.1 Hz), 8.28 (dd, 1H, J=2.1, 4.8 Hz); MS (ESI) m/e 345 (M+H)$^+$. Anal. calcd for C$_{18}$H$_{21}$ClN$_4$O.1.1 C$_2$HF$_3$O$_2$: C, 51.59; H, 4.74; N, 11.91. Found: C, 51.58; H, 4.81; N, 11.99.

EXAMPLE 240

2-(1-{2-oxo-2-[(2,4,6-tribromo-3-methylphenyl)amino]ethyl}piperidin-4-yl)pyridinium N-oxide

EXAMPLE 240A 2-bromo-N-(2,4,6-tribromo-3-methylphenyl)acetamide

To a solution of 3-methyl-2,4,6-tribromoaniline (4.36 g, 12.7 mmol) in toluene (40 mL) at room temperature was added bromoacetyl chloride (1.20 mL, 14.6 mmol) and the slurry heated to 100° C. for 24 h. The reaction was cooled, filtered, washed with and placed on a high vacuum pump to provide 2.88 g (49%) of the title compound as a white solid. mp 207-209° C.; $^1$H NMR (300 MHz, DMSO-d$_6$) δ 2.52 (s, 3H) 4.07 (s, 2H) 8.05 (s, 1H) 10.38 (s, 1H); $^{13}$C NMR (100 MHz, DMSO-d$_6$) δ 24.2, 28.6, 121.3, 123.4, 127.2, 134.3, 134.9, 137.6, 164.4; MS (DCI/NH$_3$) m/e 482 (M+NH$_4$)$^+$; Anal. calcd for C$_9$H$_7$Br$_4$NO: C, 23.26; H, 1.52; N, 3.01. Found: C, 23.30; H, 1.45; N, 2.94.

EXAMPLE 240B 2-(1-{2-oxo-2-[(2,4,6-tribromo-3-methylphenyl)amino]ethyl}piperidin-4-yl)pyridinium N-oxide The procedure described in Example 225B was followed, substituting the product from Example 240A for the product from Example 225A to provide the title compound. (290 mg, 51%). $^1$H NMR (300 MHz, DMSO-d$_6$) δ 1.75 (m, 2H), 1.92 (m, 2H), 2.30 (m, 2H), 2.54 (s, 3H), 3.12 (m, 1H), 3.15 (s, 2H), 3.31 (m, 1H), 7.30 (m, 3H), 7.40 (m, 2H), 8.26 (dd, J=4.5, 1.5 Hz, 1H), 9.78 (s, 1H); MS (DCI/NH$_3$) m/e 545 (M+H−16)$^+$; m/e 563 (M+H)$^+$.

Maleate salt (294 mg): Anal. calcd for C$_{25}$H$_{16}$N$_3$O$_2$Br$_3$.1.0 C$_4$H$_4$O$_4$: C, 40.60; H, 3.59; N, 7.48. Found: C, 40.85; H, 3.54; N, 7.27.

EXAMPLE 241

2-{4-[3-(aminomethyl)pyridin-2-yl]piperazin-1-yl}-N-(3-methylphenyl)acetamide

A solution of Example 5 (349 mg, 1.04 mmol) in 20 mL of 20% anhydrous ammonia in methanol was added Raney nickel (1.51 g) and the reaction stirred at room temperature under 60 psi of hydrogen pressure for 16 hours. The mixture was then filtered and concentrated under reduced pressure. The residue was purified by flash column chromatography on silica gel (elution with 10% methanol:dichloromethane) to provide the title compound (340 mg, 96% yield) as a light yellow semi-solid. $^1$H NMR (300 MHz, DMSO-d$_6$) δ 2.33 (s, 3H), 2.79 (m, 4H), 3.20 (m, 4H), 3.25 (s, 2H), 3.87 (s, 2H), 6.94 (br d, 1H, J=7.5 Hz), 7.09 (dd, 1H, J=7.5, 4.8 Hz), 7.20 (dd, 1H, J=7.5, 7.5 Hz), 7.40 (m, 2H), 7.79 (d, 1H, J=7.5 Hz), 8.17 (dd, 1H, 4.8, 1.7 Hz); MS (DCI/NH$_3$) m/e 340.

Maleate salt: white solid; $^1$H NMR (300 MHz, CD$_3$OD) δ 2.33 (s, 3H), 2.96 (m, 4H), 3.27 (m, 4H), 3.43 (s, 2H), 4.25 (s, 2H), 6.25 (s, 2H), 6.95 (br d, 1H, J=7.5 Hz), 7.21 (m, 2H), 7.40 (m, 2H), 7.81 (dd, 1H, J=7.5, 1.7 Hz), 8.38 (dd, 1H, J=4.8, 1.7 Hz); $^{13}$C NMR (100 MHz, DMSO-d$_6$) δ 21.1, 37.8, 49.7, 52.5, 116.5, 118.8, 119.9, 121.8, 124.2, 128.2, 128.5, 135.8, 137.4, 137.9, 138.3, 147.5, 160.5, 167.1; Anal. calcd for C$_{19}$H$_{25}$N$_5$O.1.2 C$_4$H$_4$O$_4$.0.2 H$_2$O C$_4$H$_4$O$_4$: C, 59.27; H; 6.31; N, 14.52. Found: C, 59.61; H, 6.48; N, 14.42.

EXAMPLE 242

2-[4-(2-isopropoxyphenyl)piperazin-1-yl]-N-(3-methylphenyl)acetamide

EXAMPLE 242A 1-isopropoxy-2-nitrobenzene

A solution of 2-nitrophenol (10 g, 71.9 mmol) and potassium carbonate (21.85 g, 158.1 mmol) in N,N-dimethylformamide:acetone (1:2, 150 mL) was heated under reflux and isopropyl bromide (14.8 mL, 158 mmol) was added dropwise (in 30 minutes) during reflux and stirred overnight. The reaction was cooled to room temperature and partitioned between water and ethyl acetate. The organic phase was dried over magnesium sulfate, filtered and concentrated under reduced pressure. The residue was purified by flash column chromatography on silica gel (10% ethyl acetate:hexanes) to provide the title compound as a golden yellow oil (11.5 g, 88%). $^1$H NMR (300 MHz, CDCl$_3$) δ 1.4 (d, 6H, J=6 Hz), 4.7 (septet, 1H, J=6 Hz), 6.98 (m, 1H), 7.09 (d, 1H, J=9 Hz), 7.45 (m, 1H), 7.78 (dd, 1H, 3 Hz); MS (DCI/NH$_3$) m/e 182 (M+H)$^+$.

EXAMPLE 242B 2-isopropoxyaniline

The product from Example 242A (5.00 g, 27.5) was reduced under hydrogen pressure (60 psi) using 10% Pd/C catalyst in methanol. The catalyst was filtered and solution was concentrated under reduced pressure to afford 3.75 g (90%) of the desired product as brown oil. $^1$H NMR (400 MHz, CDCl$_3$) δ 1.35 (d, 6H, J=6.1 Hz), 3.77 (br s, 2H), 4.52 (m, 1H), 6.75 (m, 4H), ; MS (DCI/NH$_3$) m/e 152 (M+H)$^+$.

EXAMPLE 242C 1-(2-isopropoxyphenyl)piperazine

The product from Example 242B (3.5 g, 23.2 mmol) was added slowly to bis-2-chloroethylaime hydrochloride (4.96 g, 27.78 mmol) at room temperature and refluxed for 48 hours. The reaction was cooled to room temperature and sodium carbonate added (9 g) and refluxed for another 48 hours. The mixture was cooled to room temperature, filtered and the white solid partitioned between dichloromethane and 3N sodium hydroxide. The organic phase was dried over magnesium sulfate, filtered and concentrated under reduced pressure to afford 3.2 g (63%) pink oil. $^1$H NMR (300 MHz, CDCl$_3$) δ 1.4 (d, 6H, J=6 Hz), 1.5-1.6 (m, 4H), 2.45-2.65 (m, 4H), 3.43 (m, 1H), 6.6-6.8 (m, 2H), 6.81-6.91 (m, 2H); MS (DCI/NH$_3$) m/e 221 (M+H)$^+$.

EXAMPLE 242D

2-[4-(2-isopropoxyphenyl)piperazin-1-yl]-N-(3-methylphenyl)acetamide

The procedure described in Example 33C was followed, substituting the product from Example 242C for the product from Example 33B to provide the title compound as a yellow oil (223 mg, 28%). $^1$H NMR (300 MHz, CDCl$_3$) δ 1.22 (d, 6H, J=6 Hz), 2.25 (s, 3H), 2.65-2.70 (m, 4H), 3.2-3.35 (m, 4H), 3.38 (s, 2H), 4.6 (m, 1H), 6.85-6.91 (m, 5H), 7.2 (t, 1H, J=9 Hz), 7.4-7.48 (m, 2H), 9.62 (s, 1H); MS (DCI/NH$_3$) m/e 368 (M+H)$^+$.

Maleate salt: Anal. calcd for C$_{22}$H$_{29}$N$_3$O$_2$.0.7C$_4$H$_4$O$_4$: C, 66.38; H, 7.14; N, 9.36. Found: C, 66.50; H, 6.95; N, 9.16.

EXAMPLE 243

2-(4-{2-[(3-methylphenyl)amino]-2-oxoethyl}piperazin-1-yl)nicotinamide

A solution of the product from Example 5 (500 mg, 1.49 mmol) in 2N sodium hydroxide (15 mL) and ethanol (15 mL) was heated to 100° C. for 16 hours. The reaction was cooled, concentrated and the residue partitioned between ethyl acetate and water. The organic phase was dried (sodium sulfate), filtered and concentrated under reduced pressure to provide 18 mg (3% yield) of the title compound as a yellow semi-solid. $^1$H NMR (300 MHz, CD$_3$OD) δ2.32 (s, 3H), 2.77 (m, 4H), 3.23 (s, 2H), 3.42 (m, 4H), 6.94 (br d, 1H, J=7.8 Hz), 7.00 (dd, 1H, J=7.5, 4.8 Hz), 7.19 (dd, 1H, J=7.8, 7.8 Hz), 7.39 (m, 2H), 7.95 (dd, 1H, J=7.5, 2.0 Hz), 8.29 (dd, 1H, J=4.7, 2.0 Hz); MS (DCI/NH$_3$) m/e 354 (M+H)$^+$.

Maleate salt: yellow solid; $^1$H NMR (300 MHz, CD$_3$OD) δ 2.33 (s, 3H), 3.44 (m, 4H), 3.65 (m, 4H), 4.03 (s, 2H), 6.28 (s, 2H), 6.98 (br d, 1H, J=7.5 Hz), 7.06 (dd, 1H, J=7.8, 5.1 Hz), 7.21 (dd, 1H, J=7.8, 7.8 Hz), 7.40 (m, 2H), 7.94 (dd, 1H, J=7.5, 1.7 Hz), 8.33 (dd, 1H, J=4.8, 1.7 Hz); Anal. calcd for C$_{19}$H$_{23}$N$_5$O$_2$.1.3 C$_4$H$_4$O$_4$: C, 57.64; H, 5.64; N, 13.89. Found: C, 57.60; H, 5.61; N, 13.61.

EXAMPLE 244

N-(3-methylphenyl)-2-[(2S)-2-methyl-4-pyridin-2-ylpiperazin-1-yl]ethanethioamide A solution of the product from Example 214 (200 mg, 0.62 mmol) in dry toluene (6 mL) was treated with 2,4-bis(4-methoxyphenyl)-1,3-dithia-2,4-diphosphetane-2,4-disulphide (Lawesson's reagent, 125 mg, 0.31 mmol) and heated at 65° C. for 1 hour. The mixture was allowed to cool to room temperature and concentrated under reduced pressure. The residue was purified by flash column chromatography on silica gel (elution with 75% hexanes:ethyl acetate) to provide 173 mg (82% yield) of the title compound as a yellow oil. $^1$H NMR (300 MHz, CDCl$_3$) δ 1.17 (d, J=6.1 Hz, 3H) 2.39 (s, 3H) 2.75 (dd, J=12.4, 9.8 Hz, 1H) 2.81 (m, 1H) 2.96 (m, 2H) 3.26 (t, J=5.5 Hz, 1H) 3.56 (d, J=17.6 Hz, 1H) 3.88 (d, J=17.6 Hz, 1H) 4.04 (m, 2H) 6.67 (t, J=6.1 Hz, 1H) 6.69 (d, J=8.5 Hz, 1H) 7.08 (d, J=7.5 Hz, 1H) 7.30 (t, J=7.8 Hz, 1H) 7.52 (ddd, J=8.7, 7.0, 2.0 Hz, 1H) 7.67 (s, 1H) 7.74 (d, J=8.1 Hz, 1H) 8.22 (dd, J=4.9, 1.9 Hz, 1H) 11.25 (s, 1H); MS (DCI/NH$_3$) m/e 341.2 (M+H)$^+$.

Maleate salt: yellow solid; $^1$H NMR (300 MHz, DMSO-d$_6$) δ 1.13 (m, 3H) 2.34 (s, 3H) 3.06 (m, 2H) 3.31 (m, 3H) 3.79 (m, 2H) 4.05 (m, 2H) 6.22 (s, 2H) 6.69 (m, 1H) 6.94 (d, J=7.8 Hz, 1H) 7.11 (d, J=7.5 Hz, 1H) 7.32 (t, J=7.1 Hz, 1H) 7.58 (d, J=6.8 Hz, 1H) 7.63 (s, 1H) 7.71 (d, J=7.5 Hz, 1H) 8.11 (d, J=4.1 Hz, 1H) 11.54 (s, 1H); Anal. calcd for C$_{20}$H$_{25}$N$_3$O$_2$.1.5 C$_4$H$_4$O$_4$: C, 58.35; H, 5.88; N, 10.89. Found: C, 58.35; H, 5.99; N, 10.41.

EXAMPLE 245

2-(1-{[(4-bromo-3-methylbenzoyl)amino]methyl}piperidin-4-yl)pyridinium N-oxide

The procedure described in Example 200 was followed, substituting 4-bromo-3-methylbenzamide (Lancaster) for 3-methylbenzamide to provide the title compound (10% yield) as a white solid. $^1$H NMR (300 MHz, DMSO-d$_6$) δ 1.54 (m, 2H) 1.89 (m, 2H) 2.34 (m, 2H) 2.41 (s, 3H) 2.95 (m, 2H) 3.21 (m, 1H) 4.16 (d, J=5.8 Hz, 2H) 7.29 (m, 2H) 7.39 (m, 1H) 7.63 (dd, J=8.1, 2.0 Hz, 1H) 7.69 (d, J=8.1 Hz, 1H) 7.87 (d, J=2.0 Hz, 1H) 8.23 (m, 1H) 8.80 (t, J=5.9 Hz, 1H); MS (DCI/NH$_3$) m/e 404/406 (M+H)$^+$; 388/390 (M−16)$^+$; Anal. calcd for C$_{19}$H$_{22}$BrN$_3$O$_2$.0.8 H$_2$O: C, 54.50; H, 5.68; N, 10.04. Found: C, 54.38; H, 5.15; N, 9.75.

EXAMPLE 246

2-[4-(3-cyanopyridin-2-yl)piperazin-1-yl]-N-[3-(methylthio)phenyl]acetamide

The procedure described in Example 145 was followed, substituting 2-chloro-N-(3-methylsulfanylphenyl)acetamide for the product from Example 143B to provide the title compound as a yellow sticky residue (420 mg, 82%). $^1$H NMR (300 MHz, CDCl$_3$) δ 2.5 (s, 3H), 2.7 (t, 4H, J=6 Hz), 3.22 (s, 2H), 3.8 (t, 4H, J=6 Hz), 6.82 (dd, 1H, J=9, 6 Hz), 7.0-7.7 (m, 3H), 7.55 (m, 1H), 7.80 (dd, 1H, J=9, 3 Hz), 8.38 (dd, 1H, J=6, 3 Hz), 9.07 (br s, 1H); MS (DCI/NH$_3$) m/e 368 (M+H)$^+$.

Maleate salt: Anal. calcd for C$_{19}$H$_{21}$N$_5$OS.1.0 C$_4$H$_4$O$_4$: C, 57.13; H, 5.21; N, 14.48. Found: C, 57.02; H, 5.20; N, 14.45.

EXAMPLE 247

N-(3-tert-butylphenyl)-2-[4-(3-cyanopyridin-2-yl) piperazin-1-yl]acetamide

EXAMPLE 247A

N-(3-tert-butylphenyl)-2-chloroacetamide

The procedure described in Example 33A was followed, substituting 3-t-butylaniline for 3-methylaniline to provide the title compound (86% yield) as a white solid. $^1$H NMR (300 MHz, DMSO-d$_6$) δ 1.27 (s, 9H), 4.23 (s, 2H), 7.12 (ddd, 1H, J=8.1, 2.0, 1.4 Hz), 7.25 (dd, 1H, J=7.8, 7.8 Hz), 7.47 (ddd, 11H, J=8.1, 2.0, 1.0 Hz), 7.56 (dd, 1H, J=2.0, 2.0 Hz), 10.22 (br s, 1H); MS (DCI/NH$_3$) m/e 225 (M+H)$^+$; 243 (M+NH$_4$)$^+$.

EXAMPLE 247B

N-(3-tert-butylphenyl)-2-[4-(3-cyanopyridin-2-yl) piperazin-1-yl]acetamide 1-(2-cyanopyridyl)piperazine (850 mg, 4.52 mmol, Chess) and N,N-diisopropylamine (5.0 mL) in toluene (20 mL) were treated with the product from Example 247A (810 mg, 3.59 mmol) and heated to 60° C. for 18 hours. The mixture was allowed to cool to room temperature, transferred to a separatory funnel and washed with saturated aqueous sodium bicarbonate. The organic phase was dried (sodium sulfate), filtered, and the filtrate concentrated under reduced pressure. The residue was purified by flash column chromatography on silica gel (elution with 25% ethyl acetate:hexanes) to provide 984 mg (73% yield) of the title compound as a light yellow solid. $^1$H NMR (300 MHz, DMSO-d$_6$) δ 1.27 (s, 9H), 2.68 (m, 4H), 3.20 (s, 2H), 3.68 (m, 4H), 6.93 (dd, 1H, J=7.5, 4.8 Hz), 7.09 (m, 1H), 7.22 (dd, 1H, J=7.8, 7.8 Hz), 7.52 (m, 1H), 7.63 (dd, 1H, J=2.0, 2.0 Hz), 8.07 (dd, 1H, J=7.8, 2.0 Hz), 8.42 (dd, 1H, J=4.7,2.0 Hz), 9.71 (br s, 1H); MS (DCI/NH$_3$) m/e 378 (M+H)$^+$; Anal. calcd for C$_{22}$H$_{27}$N$_5$O: C, 70.00; H, 7.21; N, 18.55. Found: C, 69.76; H, 7.16; N, 18.29.

EXAMPLE 248

2-[4-(2-hydroxyphenyl)piperazin-1-yl]-N-(3-methylphenyl)acetamide

The procedure described in Example 232B was followed, substituting 2-(1-piperazino)phenol for the product from Example 232A to provide the title compound (80% yield) as a light tan solid. $^1$H NMR (300 MHz, DMSO-d$_6$) δ 2.28 (s, 3H), 2.68 (m, 4H), 3.01 (m, 4H), 3.16 (s, 2H), 6.78 (m, 5H), 7.18 (dd, 1H, J=7.8, 7.8 Hz), 7.45 (m, 2H), 8.90 (s, 1H), 9.63 (s, 1H); MS (DCI/NH$_3$) m/e 326 (M+H)$^+$; Anal. calcd for C$_{19}$H$_{23}$N$_3$O$_2$: C, 70.13; H, 7.12; N, 12.91. Found: C, 69.95; H, 7.09; N, 12.85.

EXAMPLE 249

2-[14-(3-hydroxyphenyl)piperazin-1-yl]-N-(3-methylphenyl)acetamide

The procedure described in Example 232B was followed, substituting 3-(1-piperazino)phenol for the product from Example 232A to provide the title compound (77% yield) as a white solid. $^1$H NMR (300 MHz, DMSO-d$_6$) δ 2.27 (s, 3H), 2.64 (m, 4H), 3.14 (m, 4H), 3.16 (s, 2H), 6.20 (dd, 1H, J=8.5, 2.7 Hz), 6.31 (dd, 1H, J=2.0, 2.0 Hz), 6.38 (dd, 1H, J=8.1, 2.0 Hz), 6.87 (d, 1H, J=7.5 Hz), 6.98 (dd, 1H, J=8.1, 8.1 Hz), 7.18 (dd, 1H, J=7.8, 7.8 Hz), 7.44 (m, 2H), 9.09 (s, 1H), 9.64 (s, 1H); MS (DCI/NH$_3$) m/e 326 (M+H)$^+$; Anal. calcd for C$_{19}$H$_{23}$N$_3$O$_2$: C, 70.13; H, 7.12; N, 12.91. Found: C, 69.91; H, 7.19; N, 12.69.

EXAMPLE 250

2-[4-(4-hydroxyphenyl)piperazin-1-yl]-N-(3-methylphenyl)acetamide

The procedure described in Example 232B was followed, substituting 4-(1-piperazino)phenol for the product from Example 232A to provide the title compound (39% yield) as a light yellow solid. $^1$H NMR (300 MHz, DMSO-d$_6$) δ 2.27 (s, 3H), 2.64 (m, 4H), 3.03 (m, 4H), 3.15 (s, 2H), 6.64 (AA'BB', 2H, J=8.8 Hz), 6.79 (AA'BB', 2H, J=8.8 Hz), 6.87 (d, 1H, J=7.5 Hz), 7.18 (dd, 1H, J=7.8, 7.8 Hz), 7.44 (m, 2H), 8.79 (s, 1H), 9.63 (s, 1H); MS (DCI/NH$_3$) m/e 326 (M+H)$^+$; Anal. calcd for C$_{19}$H$_{23}$N$_3$O$_2$: C, 70.13; H, 7.12; N, 12.91. Found: C, 69.82; H, 7.21; N, 12.81S.

EXAMPLE 251

2-[4-(2-ethoxyphenyl)piperazin-1-yl]-N-(3-methylphenyl)acetamide

The procedure described in Example 232B was followed, substituting 1-(2-ethoxyphenyl)piperazine for the product from Example 232A to provide the title compound (84% yield) as a white solid. $^1$H NMR (300 MHz, DMSO-d$_6$) δ 1.34 (t, 3H, J=6.8 Hz), 2.28 (s, 3H), 2.67 (m, 4H), 3.06 (m, 4H), 3.17 (s, 2H), 4.01 (q, 2H, J=7.1 Hz), 6.90 (m, 5H), 7.18 (dd, 1H, J=7.5, 7.5 Hz), 7.45 (m, 2H), 9.64 (s, 1H); MS (DCI/NH$_3$) m/e 354 (M+H)$^+$. Anal. calcd for C$_{20}$H$_{25}$N$_3$O.0.20 H$_2$O: C, 70.64; H, 7.73; N, 11.77. Found: C, 70.74; H, 7.56; N, 11.78.

EXAMPLE 252

N-(3-methylphenyl)-2-{4-[2-(methylthio)phenyl] piperazin-1-yl}acetamide

The procedure described in Example 232B was followed, substituting 1-(2-methylsulfanylphenyl)piperazine for the product from Example 232A to provide the title compound (84% yield) as a yellow oil. $^1$H NMR (300 MHz, DMSO-d$_6$) δ 2.28 (s, 3H), 2.36 (s, 3H), 2.68 (m, 4H), 2.97 (m, 4H), 3.18 (s, 2H), 6.88 (d, 1H, J=7.8 Hz), 7.12 (m, 5H)7.45 (m, 2H), 9.64 (s, 1H); MS (DCI/NH$_3$) m/e 356 (M+H)$^+$.

Maleate salt: white solid; Anal. calcd for C$_{20}$H$_{25}$N$_3$OS.1.0 C$_4$H$_4$O$_4$: C, 61.13; H, 6.20; N, 8.91. Found: C, 60.78; H, 6.11; N, 8.81.

EXAMPLE 253

2-[4-(2-fluorophenyl)piperazin-1-yl]-N-(3-methylphenyl)acetamide

The procedure described in Example 232B was followed, substituting 1-(2-fluorophenyl)piperazine for the product from Example 232A to provide the title compound (84% yield) as a tan solid. $^1$H NMR (300 MHz, DMSO-d$_6$) δ 2.28 (s, 3H), 2.69 (m, 4H), 3.09 (m, 4H), 3.18 (s, 2H), 6.88 (d, 1H, J=7.8 Hz), 7.06 (m, 4H), 7.18 (dd, 1H, J=7.8, 7.8 Hz), 7.45 (m, 2H), 9.65 (s, 1H); MS (DCI/NH$_3$) m/e 328 (M+H)$^+$; Anal. calcd for C$_{19}$H$_{22}$FN$_3$O: C, 69.70; H, 6.77; N, 12.83. Found: C, 69.52; H, 6.73; N, 12.80.

EXAMPLE 254

2-[4-(3-cyanopyridin-2-yl)piperazin-1-yl]-N-(3-fluorophenyl)acetamide

EXAMPLE 254A 2-chloro-N-(3-fluorophenyl)acetamide

The procedure described in Example 33A was followed, substituting 3-fluorophenylamine for 3-methylaniline to provide the title compound as a white solid. $^1$H NMR (300 MHz, CDCl$_3$) δ 4.19 (s, 2H), 6.88 (dddd, 1H, J=8.1, 8.1, 2.7, 1.0 Hz), 7.19 (ddd, 1H, J=8.1, 2.0, 1.0 Hz), 7.31 (ddd, 1H, J=8.1, 8.1, 6.4 Hz), 7.52 (ddd, 1H, J=10.6, 2.3, 2.3 Hz), 8.26 (br s, 1H); MS (DCI/NH$_3$) m/e 187 (M+H)$^+$; 205 (M+NH$_4$)$^+$.

EXAMPLE 254B

2-[4-(3-cyanopyridin-2-yl)piperazin-1-yl]-N-(3-fluorophenyl)acetamide

The procedure described in Example 247B was followed, substituting the product from Example 254A for the product from Example 247A to provide the title compound (81% yield) as a tan solid. $^1$H NMR (300 MHz, DMSO-d$_6$) δ 2.68 (m, 4H), 3.23 (s, 2H), 3.68 (m, 4H), 6.89 (m, 1H), 6.93 (dd, 1H, J=7.8, 4.8 Hz), 7.34 (ddd, 1H, J=8.0, 8.0, 6.6 Hz), 7.42 (ddd, 1H, J=8.1, 1.5, 1.5 Hz), 7.65 (ddd, 1H, J=11.7, 2.4, 2.4 Hz), 8.07 (dd, 1H, J=7.5, 2.0 Hz), 8.42 (dd, 1H, J=4.8, 2.0 Hz), 9.98 (br s, 1H); MS (DCI/NH$_3$) m/e 340 (M+H)$^+$; Anal. calcd for C$_{18}$H$_{18}$FN$_5$O: C, 63.71; H, 5.35; N, 20.64. Found: C, 63.59; H, 5.11; N, 20.56.

EXAMPLE 255

N-(3-bromophenyl)-2-[4-(3-cyanopyridin-2-yl)piperazin-1-yl]acetamide

EXAMPLE 255A

N-(3-bromophenyl)-2-chloroacetamide

The procedure described in Example 33A was followed, substituting 3-bromophenylamine for 3-methylaniline to provide the title compound (100% yield) as a white solid. $^1$H NMR (300 MHz, CDCl$_3$) δ 4.19 (s, 2H), 7.24 (m, 1H), 7.31 (m, 1H), 7.47 (m, 1H), 7.81 (dd, 1H, J=1.9, 1.9 Hz), 8.20 (br s, 1H); MS (DCI/NH$_3$) m/e 248/250 (M+H)$^+$; 263/265 (M+NH$_4$)$^+$.

EXAMPLE 255B

N-(3-bromophenyl)-2-[4-(3-cyanopyridin-2-yl)piperazin-1-yl]acetamide

The procedure described in Example 247B was followed, substituting the product from Example 255A for the product from Example 247A to provide the title compound (84% yield) as a tan solid. $^1$H NMR (300 MHz, DMSO-d$_6$) δ 2.68 (m, 4H), 3.22 (s, 2H), 3.69 (m, 4H), 6.93 (dd, J=7.5, 4.8 Hz, 1H), 7.26 (m, 2H), 7.62 (ddd, J=7.1, 2.0, 2.0 Hz, 1H), 8.00 (m, 1H), 8.07 (dd, 1H, J=7.5, 1.7 Hz), 8.42 (dd, 1H, J=4.7, 1.7 Hz), 9.94 (br s, 1H); MS (DCI/NH$_3$) m/e 400/402 (M+H)$^+$; Anal. calcd for C$_{18}$H$_{18}$BrN$_5$O: C, 54.01; H, 4.53; N, 17.50. Found: C, 54.02; H, 4.37; N, 17.63.

EXAMPLE 256

N-(3-methylphenyl)-2-(4-pyridin-2-ylpiperazin-1-yl)ethanethioamide

A solution of the product from Example 4 (250 mg, 0.81 mmol) in dry toluene (6 mL) was treated with 2,4-bis(4-methoxyphenyl)-1,3-dithia-2,4-diphosphetane-2,4-disulphide (Lawesson's reagent, 163 mg, 0.4 mmol) and heated at 65° C. for 1 hour. The mixture was allowed to cool to room temperature and concentrated under reduced pressure. The residue was purified by flash column chromatography on silica gel (elution with 75% hexanes:ethyl acetate) to provide 185 mg (70% yield) of the title compound as an off-white solid. $^1$H NMR (300 MHz, CDCl$_3$) δ 2.39 (s, 3H) 2.77 (m, 4H) 3.65 (m, 6H) 6.68 (m, 2H) 7.08 (d, J=7.5 Hz, 1H) 7.30 (t, J=7.8 Hz, 1H) 7.51 (ddd, J=8.7, 7.0, 2.0 Hz, 1H) 7.67 (s, 1H) 7.75 (d, J=8.1 Hz, 1H) 8.21 (ddd, J=4.9, 1.9, 0.7 Hz, 1H) 11.04 (br s, 1H); MS (DCI/NH$_3$) m/e 327 (M+H)$^+$; Anal. calcd for C$_{18}$H$_{22}$N$_4$S: C, 66.22; H, 6.79; N, 17.16. Found: C, 66.15; H, 6.79; N, 17.00.

EXAMPLE 257

2-[4-(2-aminophenyl)piperazin-1-yl]-N-(3-methylphenyl)acetamide

A solution of the product from Example 7 (299 mg, 0.636 mmol) in methanol (20 mL) was treated with 10% palladium on carbon and placed under 60 psi of hydrogen at room temperature for 80 minutes. The heterogeneous mixture was filtered, concentrated under reduced pressure and the residue portioned between 2N sodium hydroxide and dichloromethane. The organic phase was dried (sodium sulfate), filtered and concentrated under reduced pressure to provide the title compound (160 mg, 78% yield) as a light tan solid, which darkens upon standing. $^1$H NMR (300 MHz, DMSO-d$_6$) δ 2.28 (s, 3H), 2.69 (m, 4H), 2.87 (m, 4H), 3.17 (s, 2H), 4.69 (s, 2H), 6.55 (ddd, 1H, J=7.5, 7.5 1.7 Hz), 6.66 (dd, 1H, J=7.8, 1.4 Hz), 6.80 (ddd, 1H, J=7.5, 7.5, 1.4 Hz), 6.88 (m, 1H), 6.92 (dd, 1H, J=7.8, 1.4 Hz), 7.19 (dd, 1H, J=7.8, 7.8 Hz), 7.46 (m, 2H), 9.63 (s, 1H); MS (DCI/NH$_3$) m/e 325 (M+H)$^+$, Anal. calcd for C$_{19}$H$_{24}$N$_4$O.0.05 CH$_2$Cl$_2$: C, 69.62; H, 7.39; N, 17.05. Found: C, 69.52; H, 7.32; N, 17.13.

EXAMPLE 258

N-(3-nitrophenyl)-2-(4-pyridin-2-ylpiperazin-1-yl)acetamide 1-(2-pyridinyl)piperazine (0.65 mL, 4.3 mmol, Aldrich) and N,N-diisopropylamine (5.0 mL) in toluene (20 mL) were treated with 2-chloro-N-(3-nitrophenyl)acetamide (750 mg, 3.49 mmol, Lancaster) and heated to 60° C. for 18 hours. The mixture was allowed to cool to room temperature, transferred to a separatory funnel and washed with saturated aqueous sodium bicarbonate. The organic phase was dried (sodium sulfate), filtered, and the filtrate concentrated under reduced pressure. The residue was purified by flash column chromatography on silica gel (elution with 25% ethyl acetate:hexanes) to provide 900 mg (76% yield) of the title compound as a tan solid. $^1$H NMR (300 MHz, DMSO-d$_6$) δ 2.62 (m, 4H), 3.24 (s, 2H), 3.56 (m, 4H), 6.63 (ddd, 1H, J=7.1, 4.7, 0.7 Hz), 6.83 (dd, 1H, J=8.8 Hz), 7.52 (ddd, 1H, J=8.5, 7.1, 2.0), 7.61 (dd, 1H, J=8.5, 8.5 Hz), 7.92 (ddd, 1H, J=8.1, 2.4, 1.0 Hz), 8.04 (ddd, 1H, J=8.5, 2.4, 1.0 Hz), 8.11 (ddd, 1H, J=4.8, 1.7, 0.7 Hz), 8.70 (dd, 1H, J=2.0, 2.0 Hz), 10.27 (br s, 1H); MS

EXAMPLE 259

2-[4-(2-cyanophenyl)piperazin-1-yl]-N-(3-nitrophenyl)acetamide

The procedure described in Example 258 was followed, substituting 2-piperazin-1-ylbenzonitrile (Chess) for 1-(2-pyridinyl)piperazine to provide the title compound (58% yield) as a white solid. $^1$H NMR (300 MHz, DMSO-$d_6$) δ 2.74 (m, 4H), 3.24 (m, 4H), 3.29 (s, 2H), 7.10 (ddd, 1H, J=7.5, 7.5, 0.7 Hz), 7.19 (d, 1H, J=8.5 Hz), 7.61 (m, 2H), 7.70 (dd, 1H, J=7.8, 1.7 Hz), 7.93 (ddd, 1H, J=8.5, 2.4, 1.0 Hz), 8.04 (ddd, 1H, J=8.5, 2.4, 1.0 Hz), 8.70 (dd, 1H, J=2.0, 2.0 Hz), 10.28 (br s, 1H); MS (DCI/NH$_3$) m/e 366 (M+H)$^+$; Anal. calcd for $C_{19}H_{19}N_5O_3$: C, 62.46; H, 5.24; N, 19.17. Found: C, 62.41; H, 5.02; N, 19.08.

EXAMPLE 260

N-(3-cyanophenyl)-2-(4-pyridin-2-ylpiperazin-1-yl)acetamide

The procedure described in Example 258 was followed, substituting 2-chloro-N-(3-cyanophenyl)acetamide (Maybridge) for 2-chloro-N-(3-nitrophenyl)acetamide to provide the title compound (79% yield) as a white solid. $^1$H NMR (300 MHz, DMSO-$d_6$) δ 2.61 (m, 4H), 3.22 (s, 2H), 3.56 (m, 4H), 6.63 (ddd, 1H, J=7.1, 5.1, 0.7 Hz), 6.83 (d, 1H, J=8.5 Hz), 7.52 (m, 3H), 7.95 (m, 1H), 8.11 (ddd, 1H, J=4.7, 2.0, 0.7 Hz), 8.15 (m, 1H), 10.10 (br s, 1H); MS (DCI/NH$_3$) m/e 322 (M+H)$^+$; Anal. calcd for $C_{18}H_{19}N_5O$: C, 67.27; H, 5.96; N, 21.79. Found: C, 67.27; H, 5.97; N, 21.73.

EXAMPLE 261

N-(3-cyanophenyl)-2-[4-(2-cyanophenyl)piperazin-1-yl]acetamide

The procedure described in Example 258 was followed, substituting 2-chloro-N-(3-cyanophenyl)acetamide (Maybridge) for 2-chloro-N-(3-nitrophenyl)acetamide and substituting 2-piperazin-1-ylbenzonitrile (Chess) for 1-(2-pyridinyl)piperazine to provide the title compound (74% yield) as a white solid. $^1$H NMR (300 MHz, DMSO-$d_6$) δ 2.73 (m, 4H), 3.23 (m, 4H), 3.27 (s, 2H), 7.10 (ddd, 1H, J=7.8, 7.8, 1.0 Hz), 7.19 (d, 1H, J=8.5 Hz), 7.53 (m, 2H), 7.61 (ddd, 1H, J=8.5, 7.5, 1.7 Hz), 7.70 (dd, 1H, J=7.8, 1.7 Hz), 7.94 (m, 1H), 8.14 (m, 1H), 10.11 (br s, 1H); MS (DCI/NH$_3$) m/e 346 (M+H)$^+$; Anal. calcd for $C_{20}H_{19}N_5O \cdot 0.1\ H_2O \cdot 0.05\ CH_2Cl_2$: C, 68.52; H, 5.54; N, 19.93. Found: C, 68.52; H, 5.52; N, 19.81.

EXAMPLE 262

2-[4-(3-cyanopyridin-2-yl)piperazin-1-yl]-N-(pentafluorophenyl)acetamide

EXAMPLE 262A 2-chloro-N-(pentafluorophenyl)acetamide

The procedure described in Example 22A was followed, substituting pentafluorophenylamine for 3,4,5-trimethoxyaniline to provide the title compound (94% yield) as a tan solid. $^1$H NMR (300 MHz, DMSO-$d_6$) δ 3.31 (s, 2H), 10.48 (br s, 1H); MS (DCI/NH$_3$) m/e 259 (M+H)$^+$; 277 (M+NH$_4$)$^+$.

EXAMPLE 262B

2-[4-(3-cyanopyridin-2-yl)piperazin-1-yl]-N-(pentafluorophenyl)acetamide

The procedure described in Example 247B was followed, substituting the product from Example 262A for the product from Example 247A to provide the title compound (71% yield) as an oil. $^1$H NMR (300 MHz, DMSO-$d_6$) δ 2.69 (m, 4H), 3.32 (s, 2H), 3.69 (m, 4H), 6.93 (dd, 1H, J=7.8, 4.8 Hz), 8.07 (dd, 1H, J=7.8, 2.0 Hz), 8.42 (dd, 1H, J=4.8, 1.7 Hz), 9.93 (br s, 1H); MS (DCI/NH$_3$) m/e 412.

Maleate salt: white solid; $^1$H NMR (300 MHz, CD$_3$OD) δ 3.18 (m, 4H), 3.84 (s, 2H), 3.87 (m, 4H), 6.28 (s, 2H), 6.98 (dd, 1H, J=7.8, 5.1 Hz), 7.99 (dd, 1H, J=7.8, 2.0 Hz), 8.42 (dd, 1H, J=4.7, 1.7 Hz); Anal. calcd for $C_{18}H_{14}F_5N_5O \cdot 1.0\ C_4H_4O_4$: C, 50.10; H, 3.44; N, 13.28. Found: C, 49.81; H, 3.41; N, 12.90.

EXAMPLE 263

2-[4-(3-cyanopyridin-2-yl)piperazin-1-yl]-N-(1,3-dimethyl-1H-pyrazol-5-yl)acetamide The procedure described in Example 247B was followed, substituting 2-chloro-N-(2,5-dimethyl-2H-pyrazol-3-yl)acetamide (Maybridge) for the product from Example 247A to provide the title compound (84% yield) as an oil. MS (DCI/NH$_3$) m/e 340 (M+H)$^+$.

Maleate salt: white solid; $^1$H NMR (300 MHz, CD$_3$OD) δ 2.19 (s, 3H), 3.26 (m, 4H), 3.67 (s, 3H), 3.88 (m, 6H), 6.12 (s, 1H), 6.27 (s, 2H), 7.00 (dd, 1H, J=7.5, 4.7 Hz), 8.00 (dd, 1H, J=7.8, 2.0 Hz), 8.43 (dd, 1H, J=5.1, 2.0 Hz); Anal. calcd for $C_{17}H_{21}N_7O \cdot 1.0\ C_4H_4O_4$: C, 55.38; H, 5.53; N, 21.53. Found: C, 55.07; H, 5.65; N, 21.30.

EXAMPLE 264

N-(3-benzylphenyl)-2-[4-(3-cyanopyridin-2-yl)piperazin-1-yl]acetamide

EXAMPLE 264A

N-(3-benzylphenyl)-2-chloroacetamide

The procedure described in Example 33A was followed, substituting 3-benzylphenylamine for 3-methylaniline to provide the title compound (84% yield) as a white solid. $^1$H NMR (300 MHz, DMSO-$d_6$) δ 3.92 (s, 2H), 4.21 (s, 2H), 6.98 (d, 1H, J=7.5 Hz), 7.24 (m, 6H), 7.39 (m, 1H), 7.44 (d, 1H, J=8.1 Hz), 10.22 (br s, 1H); MS (DCI/NH$_3$) m/e 260 (M+H)$^+$; 277 (M+NH$_4$)$^+$.

EXAMPLE 264B

N-(3-benzylphenyl)-2-[4-(3-cyanopyridin-2-yl)piperazin-1-yl]acetamide

The procedure described in Example 247B was followed, substituting the product from Example 264A for the product from Example 247A to provide the title compound (86% yield) as an oil. $^1$H NMR (300 MHz, DMSO-$d_6$) δ 2.67 (m, 4H), 3.18 (s, 2H), 3.67 (m, 4H), 3.90 (s, 2H), 6.92 (m, 2H), 7.22 (m, 6H), 7.50 (m, 2H), 8.07 (dd,1H, J=7.8, 2.0 Hz), 8.41 (dd, 1H, J=4.7, 2.0 Hz), 9.72 (br s, 1H); MS (DCI/NH$_3$) m/e 412 (M+H)$^+$.

Maleate salt: white solid; $^1$H NMR (300 MHz, DMSO-d$_6$) δ 3.35 (m, 4H), 3.90 (m, 6H), 3.95 (s, 2H), 6.26 (s, 2H), 7.01 (m, 2H), 7.21 (m, 6H), 7.44 (m, 2H), 8.01 (dd, 1H, J=7.5, 1.7 Hz), 8.43 (dd, 1H, J=5.1, 2.0 Hz); Anal. calcd for C$_{25}$H$_{25}$N$_5$O.1.0 C$_4$H$_4$O$_4$: C, 66.02; H, 5.54; N, 13.27. Found: C, 65.68; H, 5.49; N, 13.08.

EXAMPLE 265

2-[4-(2-chlorophenyl)piperazin-1-yl]-N-(3-methylphenyl)acetamide

The procedure described in Example 232B was followed, substituting 1-(2-chlorophenyl)piperazine for the product from Example 232A to provide the title compound (92% yield) as a light yellow solid. $^1$H NMR (300 MHz, DMSO-d$_6$) δ 2.28 (s, 3H), 2.71 (m, 4H), 3.05 (m, 4H), 3.20 (s, 2H), 6.87 (br d, 1H, J=7.7 Hz), 7.04 (ddd, 1H, J=8.0, 7.4, 1.5 Hz), 7.19 (m, 2H), 7.30 (ddd, 1H, J=8.0, 7.4, 1.5 Hz), 7.40 (dd, 1H, J=8.0, 1.5 Hz)7.46 (m, 2H), 9.64 (br s, 1H); MS (DCI/NH$_3$) m/e 344 (M+H)$^+$; Anal. calcd for C$_{19}$H$_{22}$ClN$_3$O: C, 66.37; H, 6.45; N, 12.22. Found: C, 66.40; H, 6.50; N, 12.22.

EXAMPLE 266

2-[4-(3-cyanopyrazin-2-yl)piperazin-1-yl]-N-(3-methylphenyl)acetamide

The procedure described in Example 232B was followed, substituting 3,4,5,6-tetrahydro-2H-[1,2']bipyrazinyl-3'-carbonitrile for the product from Example 232A to provide the title compound (82% yield) as a light yellow solid. $^1$H NMR (300 MHz, DMSO-d$_6$) δ 2.28 (s, 3H), 2.69 (m, 4H), 3.20 (s, 2H), 3.80 (m, 4H), 6.88 (br d, 1H, J=7.5 Hz), 7.18 (dd, 1H, J=7.8, 7.8 Hz), 7.44 (br d, 1H, J=7.8 Hz), 7.47 (br s, 1H), 8.11 (d, 1H, J=2.4 Hz), 8.45 (d, 1H, J=2.0 Hz), 9.69 (br s, 1H); MS (DCI/NH$_3$) m/e 337 (M+H)$^+$; Anal. calcd for C$_{18}$H$_{20}$N$_6$O: C, 64.27; H, 5.99; N, 24.98. Found: C, 64.04; H, 6.10; N, 24.60.

EXAMPLE 267

2-(4-pyridin-2-ylpiperazin-1-yl)-N-(2-{[(4-pyridin-2-ylpiperazin-1-yl)acety]amino}phenyl)acetamide The procedure described in Example 181 was followed, substituting 2-chloro-N-[2-(2-chloroacetylamino)phenyl]acetamide (Aldrich) for N-(2,5-dimethylphenyl)-2-chloroacetamide and using 2.4 equivalents of 1-pyridin-2-yl-piperazine to provide the title compound (74% yield) as a light tan solid. $^1$H NMR (300 MHz, DMSO-d$_6$) δ 2.59 (m, 8H), 3.18 (s, 4H), 3.52 (m, 8H), 6.63 (dd, 2H, J=5.1, 5.1 Hz), 6.78 (d, 2H, J=8.5 Hz), 7.20 (dd, 2H, J=5.8, 3.4 Hz), 7.51 (dd, 2H, J=8.5, 8.5 Hz), 7.60 (dd, 2H, J=5.8, 3.7 Hz), 8.10 (d, 2H, J=3.7 Hz), 9.64 (br s, 2H); MS (DCI/NH$_3$) m/e 515 (M+H)$^+$; Anal. calcd for C$_{28}$H$_{34}$N$_8$O$_2$.0.4 C$_4$H$_8$O$_2$.0.1 H$_2$O: C, 64.44; H, 6.83; N, 20.31. Found: C, 64.42; H, 6.67; N, 20.12.

EXAMPLE 268

N-(3-methylphenyl)-2-(4-pyridin-2-ylpiperidin-1-yl)ethanethioamide

A solution of the product from Example 36D (77 mg, 0.25 mmol) in dry toluene (3 mL) was treated with 2,4-bis(4-methoxyphenyl)-1,3-dithia-2,4-diphosphetane-2,4-disulphide (Lawesson's reagent, 51 mg, 0.13 mmol) and heated at 65° C. for 1 hour. The mixture was allowed to cool to room temperature and concentrated under reduced pressure. The residue was purified by flash column chromatography on silica gel (elution with 5% methanol:dichloromethane) to provide 40 mg (0.12 mmol, 49% yield) of the title compound as a yellow oil. $^1$H NMR (300 MHz, DMSO-d$_6$) δ 1.85 (m, 2H) 1.96 (dq, J=12.4, 12.4, 12.4, 3.6 Hz, 2H) 2.34 (s, 3H) 2.39 (m, 2H) 2.70 (tt, J=11.8, 11.8, 3.7, 3.9 Hz, 1H) 2.96 (m, 2H) 3.55 (s, 2H) 7.09 (d, J=7.80 Hz, 1H) 7.22 (ddd, J=7.5, 4.7, 1.0 Hz, 1H) 7.31 (t, J=7.7 Hz, 1H) 7.32 (d, J=7.8 Hz, 1H) 7.65 (s, 1H) 7.71 (dd, J=7.8, 1.7 Hz, 1H) 7.73 (dt, J=7.8, 7.8, 1.7 Hz, 1H) 8.50 (dd, J=5.0, 1.2 Hz, 1H) 11.34 (s, 1H); MS (DCI/NH$_3$) m/e 326.1 (M+H)$^+$. Anal. calcd for C$_{19}$H$_{23}$N$_3$S: C, 70.12; H, 7.12; N, 12.91. Found: C, 69.87; H, 7.11; N, 12.78.

EXAMPLE 269

2-[4-(1-methyl-1H-imidazol-2-yl)piperidin-1-yl]-N-(3-methylphenyl)acetamide

The procedure described in Example 224 was followed, substituting the product from Example 237D for the product from Example 166C to provide the title compound as a pale yellow oil (13 mg). $^1$H NMR (300 MHz, DMSO-d$_6$) δ 1.7-1.85 (m, 4H), 2.5-2.35 (m, 4H), 2.75 (m, 1H), 2.85-2.95 (m, 2H), 3.1 (s, 3H), 3.6 (s, 3H), 6.65 (d, 1H, J=3 Hz), 6.85-6.95 (m, 1H), 6.95 (d, 1H, J=3 Hz), 7.2 (m, 1H), 7.5 (m, 2H), 9.6 (s, 1H); MS (DCI/NH$_3$) m/e 313 (M+H)$^+$.

EXAMPLE 270

N-(3-methylphenyl)-2-[4-(1,3-thiazol-2-yl)piperidin-1-yl]acetamide

The procedure described in Example 224 was followed, substituting the product from Example 233 for the product from Example 166C to provide the title compound (35 mg) as pale yellow oil. $^1$H NMR (300 MHz, DMSO-d$_6$) δ 1.8-1.95 (m, 2H), 2.0-2.15 (m, 2H), 2.22 (s, 3H), 2.25-2.35 (m, 2H), 2.85-2.98 (m, 2H), 3.0 (m, 1H), 3.15 (s, 2H), 6.82 (d, 1H, J=9 Hz), 7.18 (t, 1H, J=7.5 Hz), 7.45 (m, 2H), 7.6 (d, 1H, J=3 Hz,), 7.7 (d, 1H, J=3 Hz), 9.6 (br s, 1H); MS (DCI/NH$_3$) m/e 316 (M+H)$^+$.

EXAMPLE 271

N-(4-iodo-3-methylphenyl)-2-(4-pyridin-2-ylpiperidin-1-yl)acetamide

EXAMPLE 271 A 2-bromo-N-(4-iodo-3-methylphenyl)acetamide

The procedure described in Example 1A was followed, substituting 4-iodo-3-methylaniline for 3-methylaniline to provide the title compound as a white solid. $^1$H NMR (300 MHz, DMSO-d$_6$) δ 2.33 (s, 3H), 4.02 (s, 2H), 7.20 (dd, 1H, J=8.5, 2.4 Hz), 7.56 (d, 1H, J=2.4 Hz), 7.74 (d, 1H, J=8.5 Hz), 10.40 (br s, 1H); MS (DCI/NH$_3$) m/e 353/355 (M+H)$^+$; 371.373 (M+NH$_4$)$^+$.

EXAMPLE 271 B

N-(4-iodo-3-methylphenyl)-2-(4-pyridin-2-ylpiperidin-1-yl)acetamide

The procedure described in Example 225B was followed, substituting the product from Example 271A for the product from Example 225A to provide the title compound. (290 mg, 51%). $^1$H NMR (300 MHz, DMSO-d$_6$) δ 1.83 (m, 4H), 2.28 (m, 2H), 2.33 (s, 3H), 2.64 (m, 1H), 2.98 (m, 2H), 3.12 (s, 2H), 7.20 (m, 2H), 7.30 (m, 2H), 7.65 (d, J=3 Hz, 1H), 7.73 (m, 2H), 9.76 (br s, 1H); MS (DCI/NH$_3$) m/e 436 (M+H)$^+$; Anal. calcd for C$_{19}$H$_{22}$N$_3$OI: C, 52.42; H, 5.09; N, 9.65. Found: C, 52.30; H, 5.14; N, 9.29.

EXAMPLE 272

2-(4-fluoro-4-phenylpiperidin-1-yl)-N-(3-methylphenyl)acetamide

EXAMPLE 272A tert-butyl 4-hydroxy-4-phenylpiperidine-1-carboxylate

The procedure described in Example 234A was followed, substituting phenyllithium for 2-thienyllithium to provide the title compound as a pale yellow oil (6 g, 87%). $^1$H NMR (300 MHz, CDCl$_3$) δ 1.5 (s, 9H), 1.65-1.71 (m, 2H), 1.9-1.98 (M, 1H), 2.42 (t, 1H, J=6 Hz), 3.22-3.25 (m, 1H), 3.43 (d, 2H, J=3 Hz), 3.7 (t, 1H, J=6 Hz), 7.30-7.39 (m, 2H), 7.43-7.48 (m, 2H), 7.58-7.60 (m 1H); MS (DCI/NH$_3$) m/e 278 (M+H)$^+$.

EXAMPLE 272B tert-butyl 4-fluoro-4-phenylpiperidine-1-carboxylate

To a solution of (diethylamino)sulfur trifluoride (0.9 mL, 7.2 mmol) in dichloromethane at −70° C. was added the product from Example 272A (1 g, 3.6 mmol) as a solution in dichloromethane (10 mL). After 1 hour, the mixture was slowly warmed to −10° C. and stirred for 2 hours. The reaction was quenched with water (20 mL) and saturated potassium carbonate (7 mL) followed by extraction with diethyl ether. The organic phases were combined, washed with brine, dried over magnesium sulfate, filtered and concentrated under reduced pressure. The residue was purified by flash column chromatography on silica gel (30% ethyl acetate:hexanes) to afford the title compound as a yellow oil (200 mg, 25%). $^1$H NMR (300 MHz, CDCl$_3$) δ 1.5 (s, 9H), 1.9-1.96 (m, 2H), 2.0-2.10 (m, 2H), 3.18-3.26 (m, 2H), 3.5-3.62 (m, 2H), 7.3 (m, 1H), 7.35-7.4 (m, 4H); MS (DCI/NH$_3$) m/e 280 (M+H)$^+$.

EXAMPLE 272C 4-fluoro-4-phenylpiperidine

The procedure described in Example 166B was followed, substituting the product from Example 272B for the product from Example 166A to provide the title compound as a yellow oily residue (200 mg). $^1$H NMR (300 MHz, CDCl$_3$) δ 2.20-2.30 (m, 2H), 2.45-2.55 (m, 2H), 3.10 (t, 2H, J=6 Hz), 3.50-3.55 (m, 1H), 7.30-7.40 (m, 4H); MS (DCI/NH$_3$) m/e 180 (M+H)$^+$.

EXAMPLE 272D 2-(4-fluoro-4-phenylpiperidin-1-yl)-N-(3-methylphenyl)acetamide The procedure described in Example 33C was followed, substituting the product from Example 272C for the product from Example 33B to provide the title compound as a yellow oil(155 mg, 42%). $^1$H NMR (300 MHz, CDCl$_3$) δ 1.48 (br s, 1H), 2.35 (m, 4H), 2.65 (m, 2H), 2.85 (t, 2H, J=6 Hz), 3.22 (s, 2H), 3.38 (m, 2H), 6.85 (m, 1H), 7.2 (m, 1H), 7.35-7.45 (m, 7H), 9.2 (br s, 1H); MS (DCI/NH$_3$) m/e 327 (M+H)$^+$; Anal. calcd for C$_{20}$H$_{23}$FN$_2$O: C, 73.59; H, 7.10; N, 8.58. Found: C, 73.70; H, 7.19; N, 8.80.

EXAMPLE 273

2-[4-(5-hydroxypyridin-2-yl)piperidin-1-yl]-N-(3-methylphenyl)acetamide

EXAMPLE 273A 5-(benzyloxy)-2-bromopyridine

6-Chloropyridin-3-ol (6 g, 46 mmol) in N,N-dimethylformamide (50 mL) was treated with benzylbromide (5.5 mL, 46 mmol) and potassium carbonate (12.8 mmol) and the reaction mixture heated to 40° C. for 18 hours. The reaction was cooled to room temperature, poured into brine (200 mL) and extracted with ethyl acetate (200 mL). The organic layer was washed with brine (3×100 mL), dried over magnesium sulfate, filtered, and concentrated under reduced pressure to give 5-benzyloxy-2-chloropyridine. This crude product was dissolved in propionitrile (50 mL) and treated with trimethylsilylbromide (12.36 mL, 92 mmol) and the reaction mixture was heated at 100° C. for 113 hours. The reaction mixture was cooled to room temperature and poured into 2.0 M sodium hydroxide solution to which 50 g of ice had been added. The aqueous phase was extracted with diethyl ether, (3×75 mL). The organic layers were combined and washed with water (2×100 mL) and brine (75 mL), dried over magnesium sulfate, filtered, and concentrated under reduced pressure. The crude residue (light brown oil) was purified by flash column chromatography on silica gel using 8% ethyl acetate:hexanes as eluent to give 4.72 g of the title compound as a light yellow solid. $^1$H NMR (300 MHz, DMSO-d$_6$) δ 5.19 (s, 2H), 7.42 (m, 6H), 7.57 (d, J=6 Hz, 1H), 8.19 (d, J=3 Hz, 1H), MS (DCI/NH$_3$) m/e 365 (M+H)$^+$.

EXAMPLE 273B tert-butyl 5-(benzyloxy)-3',6'-dihydro-2,4'-bipyridine-1'(2'H)-carboxylate The product from Example 273A (0.33 g, 17.7 mmol) in diethyl ether (10 mL) was added rapidly to a solution of 2.5M n-butyllithium (0.98 mL, 1.56 mmol) in diethyl ether (8 mL) at −78° C. The resulting brown solution was stirred at −78° C. for 10 minutes. To this was added 0.5M zinc chloride solution (2.75 mL, 1.37 mmol) and the reaction mixture was warmed to 0° C. and stirred at 0° C. for 15 minutes. To this reaction mixture was added 4-trifluoromethanesulfonyloxy-3,6-dihydro-2H-pyridine-1-carboxylic acid tert-butyl ester (Bursavich, M. G.; et al. Org. Lett. 2001, 3, 2317, 0.5 g, 1.5 mmol) and tetrakis(triphenylphosphine)palladium(0) (175 mg, 0.15 mmol). The reaction was heated to 60° C. for 4 hours. The mixture was cooled to room temperature and the solvent removed under reduced pressure. The residue was partitioned between ethyl acetate (50 mL) and 1N sodium hydroxide (50 mL). The inorganic salts were filtered, and the filtrate washed with brine (50 mL), dried (magnesium sulfate) and concentrated on the rotary evaporator to give brown oil. The crude compound was purified by flash column chromatography on silica gel using 80% hexanes: ethyl acetate as eluent to give 0.209 g (47% yield) of desired product as white solid. $^1$H NMR (300 MHz, DMSO-d$_6$) δ 1.42 (s, 9H), 2.52 (m, 2H), 3.51 (t, J=6 Hz, 2H), 4.01 (m, 2H), 5.19 (s, 2H), 6.52 (m, 1H), 7.41 (m, 7H), 8.31 (d, J=1.5 Hz, 1H), MS (DCI/NH$_3$) m/e 367 (M+H)$^+$.

EXAMPLE 273C 5-(benzyloxy)-1',2',3',6'-tetrahydro-2,4'-bipyridine

The product from Example 273B (200 mg, 0.54 mmol) in dichloromethane (8 mL) was cooled to 0° C. and treated with trifluoroacetic acid (0.35 mL, 4.3 mmol) for 2 hours; warmed to room temperature for 2 hours and the solvent removed by rotary evaporator. Toluene was added to the residue and then removed under reduced pressure (2×50 mL) to give desired product as colorless oil. $^1$H NMR (300 MHz, DMSO-$d_6$) δ 2.72 (m, 2H), 3.32 (m, 2H), 3.79 (m, 2H), 5.20 (s, 2H), 6.55 (m, 1H), 7.41 (m, 6H), 7.59 (d, J=9 Hz, 1H), 8.34 (d, J=1.5 Hz, 1H), 8.82 (s, 1H); MS (DCI/NH$_3$) m/e 267 (M+H)$^+$.

EXAMPLE 273D

2-[5-(benzyloxy)-3',6'-dihydro-2,4'-bipyridin-1'(2'H)-yl]-N-(3-methylphenyl)acetamide A mixture of the product from Example 273C (175 mg, 0.46 mmol), the product from Example 1A (125 mg, 0.54 mmol) and potassium carbonate (164 mg, 1.1 mmol) in N,N-dimethylformamide (8 mL) was stirred at room temperature for 18 hours. The reaction mixture was poured into water (30 mL) and extracted with ethyl acetate (30 mL). The organic layer was washed with brine (2×30 mL) and dried over magnesium sulfate, filtered and concentrated under reduced pressure and purified by flash column chromatography using 70% hexanes:ethyl acetate to give the desired product 105 mg (55% yield). $^1$H NMR (300 MHz, DMSO-$d_6$) δ 2.27 (s, 3H), 2.60 (m, 2H), 2.76 (t, J=4.5 Hz, 2H), 3.27 (m, 2H), 3.97 (d, J=6 Hz, 2H), 5.19 (s, 2H), 6.54 (m, 1H), 6.87 (m, 2H), 7.18 (t, J=6 Hz, 2H), 7.42 (m, 7H), 8.31 (d, J=3 Hz, 1H), 9.52 (s, 0.5H), 9.64 (s, 0.5H); MS (DCI/NH$_3$) m/e 414 (M+H)$^+$.

EXAMPLE 273E

2-[4-(5-hydroxypyridin-2-yl)piperidin-1-yl]-N-(3-methylphenyl)acetamide

The product from Example 273D (105 mg, 0.2 mmol) in methanol (50 mL) was treated with 10% Pd/C (58 mg) at 60 psi for 16 hours. The catalyst was filtered and the filtrate was concentrated under reduced pressure to give pale yellow foamy solid. This crude product was purified by flash column chromatography on silica gel using 4% ethanol:ethyl acetate to give the title compound 50 mg (64% yield). $^1$H NMR (300 MHz, CDCl$_3$) δ 1.93 (m, 4H), 2.31 (s, 3H), 2.41 (m, 2H), 2.71 (m, 1H), 3.04 (m, 2H), 3.16 (s, 2H), 6.92 (d, J=7.5 Hz, 1H), ), 7.20 (m, 4H), 7.40 (d, J=9 Hz, 2H), 8.26 (m, 1H), 9.24 (br s, 1H); MS (DCI/NH$_3$) m/e 326 (M+H)$^+$; Anal. calcd for C$_{19}$H$_{23}$N$_3$O$_2$: C, 70.13; H, 7.12; N, 12.91. Found: C, 69.97; H, 7.17; N, 12.68.

EXAMPLE 274

N-(5-fluoro-1,3-benzothiazol-2-yl)-2-[4-(3-methoxyphenyl)piperazin-1-yl]acetamide The procedure described in Example 247B was followed, substituting 2-bromo-N-(5-fluorobenzothiazol-2-yl)acetamide (Maybridge) for the product from Example 247A and substituting 1-(2-methoxyphenyl)piperazine for 1-(2-cyanopyridyl)piperazine to provide the title compound (62% yield) as an oil. $^1$H NMR (300 MHz, CD$_3$OD); δ 2.77-2.86 (m, 4H), 3.10-3.19 (m, 4H), 3.32 (s, 2H), 3.86 (s, 3H), 6.86- 7.06 (m, 3H), 7.08-7.25 (m, 2H), 7.65 (dd, J=3.0, 6.0 Hz, 1.0H), 7.70-7.76 (m, 1H); MS (DCI/NH$_3$) m/e 401; Anal. calcd for C$_{20}$H$_{21}$N$_4$O$_2$SF: C, 59.98; H, 5.29; N, 14.12. Found: C, 60.12; H, 5.58; N, 14.12.

EXAMPLE 275

2-[4-(2-methoxyphenyl)piperazin-1-yl]-N-(1-methyl-1H-benzimidazol-2-yl)acetamide The procedure described in Example 247B was followed, substituting 2-chloro-N-(1-methyl-1H-benzoimidazol-2-yl) acetamide (Caroti, P.; et al. Farmaco 1989, 44, 227) for the product from Example 247A and substituting 1-(2-methoxyphenyl)piperazine for 1-(2-cyanopyridyl)piperazine to provide the title compound (44% yield) as a yellow oil. $^1$H NMR (300 MHz, CD$_3$OD); δ 2.81-2.84 (m, 4H), 3.05-3.10 (m, 4H), 3.38 (s, 2H), 3.75 (s, 3H), 3.85 (s, 3H), 6.85-7.05 (m, 4H), 7.22-7.37 (m, 2H), 7.42-7.58 (m, 2H); MS (DCI/NH$_3$) m/e 380; Anal. calcd for C$_{21}$H$_{25}$N$_5$O$_2$: C, 65.82; H, 6.61; N, 17.87. Found: C, 65.69; H, 6.69; N, 18.24.

EXAMPLE 276

N-(3-methylphenyl)-2-[4-(3-methylthien-2-yl)-3,6-dihydropyridin-1(2H)-yl]acetamide

EXAMPLE 276A tert-butyl 4-(3-methylthien-2-yl)-3,6-dihydropyridine-1(2H)-carboxylate The procedure described in Example 143A was followed, substituting 3-methyl-2-thienylzinc bromide for 3-methyl-2-pyridylzinc bromide to provide the title compound as a yellow oil (2.67 g, 54%). $^1$H NMR (300 MHz, CDCl$_3$) δ 1.5 (s, 9H), 1.6 (s, 3H), 2.5 (m, 2H), 3.6 (t, 2H, J=6 Hz), 4.03 (m, 2H), 5.8 (m, 1H), 6.8 (d, 1H, J=6 Hz), 7.15 (d, 1H, J=6 Hz); MS (DCI/NH$_3$) m/e 280 (M+H)$^+$.

EXAMPLE 276B 4-(3-methylthien-2-yl)-1,2,3,6-tetrahydropyridine

The procedure described in Example 166B was followed, substituting the product from Example 276A for the product from Example 166A to provide the title compound as a yellow oil (450 mg, 46%). $^1$H NMR (300 MHz, CDCl$_3$) δ 2.22 (s, 3H), 2.78-2.80 (m, 2H), 3.44-3.47 (m, 2H), 3.85-3.90 (m, 2H), 5.79-5.81 (m, 1H), 6.83 (d, 1H, J=6 Hz), 7.18 (d, 1H, J=6 Hz), 9.6 (br s, 1H); MS (DCI/NH$_3$) m/e 180 (M+H)$^+$.

EXAMPLE 276C

N-(3-methylphenyl)-2-[4-(3-methylthien-2-yl)-3,6-dihydropyridin-1(2H)-yl]acetamide The procedure described in Example 33C was followed, substituting the product from Example 272C for the product from Example 33B to provide the title compound as a colorless oil (370 mg, 49%). $^1$H NMR (300 MHz, CDCl$_3$) δ 2.30 (s, 3H), 2.35 (s, 3H), 2.61 (m, 2H), 2.83 (t, 2H, J=6 Hz), 3.25 (s, 2H), 3.38 (m, 2H), 5.82 (m, 1H), 6.82 (d, 1H, J=6 Hz), 6.95 (d, 1H, J=9 Hz), 7.10 (d, 1H, J=6 Hz), 7.20 (d, 1H, J=9 Hz), 7.40 (m, 2H), 9.15 (br s, 1H); MS (DCI/NH$_3$) m/e 327 (M+H)$^+$.

Maleate salt: Anal. calcd for C$_{19}$H$_{22}$N$_2$OS.1.0 C$_4$H$_4$O$_4$: C, 62.42; H, 5.92; N, 6.33; Found: C, 62.23, H, 5.96, N, 6.18.

EXAMPLE 277

2-(1-{2-[(3,5-dichlorophenyl)amino]-2-oxoethyl}piperidin-4-yl)pyridinium N-oxide The procedure described in Example 225B was followed, substituting 2-bromo-N-(3,5-dichlorophenyl)acetamide (Maybridge) for the product from Example 225A to provide the title compound. Isolated as an acetate salt (36 mg, 34%). $^1$H NMR (300 MHz, DMSO-$d_6$) δ 1.71 (m, 2H), 1.92 (m, 2H), 2.30 (m, 2H), 2.98 (m, 2H), 3.19 (s, 2H), 3.25 (m, 1H), 7.30 (m, 2H), 7.42 (m, 1H), 7.80 (d, J=3 Hz, 2H), 8.26 (d, J=4.5, 1H), 10.05 (s, 1H); MS (DCI/NH$_3$) m/e 365 (M+H−16)$^+$; 381 (M+H)$^+$; Anal. calcd for $C_{18}H_{19}Cl_2N_3O_2 \cdot 1.0\ C_2H_4O_2$: C, 54.55; H, 5.26; N, 9.54. Found: C, 54.85; H, 5.02; N, 10.23.

EXAMPLE 278

2-(1-{2-[(2,3-dichlorophenyl)amino]-2-oxoethyl}piperidin-4-yl)pyridinium N-oxide The procedure described in Example 225B was followed, substituting 2-bromo-N-(2,3-dichlorophenyl)acetamide for the product from Example 225A to provide the title compound. Isolated as an acetate salt (25 mg, 22%). $^1$H NMR (300 MHz, DMSO-$d_6$) δ 1.71 (m, 2H), 1.99 (m, 2H), 2.43 (m, 2H), 3.03 (m, 2H), 3.25 (s, 2H), 3.35 (m, 1H), 7.38 (m, 5H), 8.26 (dd, J=4.5, 1.5, 2H), 10.15 (s, 1H); MS (DCI/NH$_3$) m/e 365 (M+H−16)+; 381 (M+H)$^+$;

Anal. calcd for $C_{18}H_{19}C_{12}N_3O_2 \cdot 1.0\ C_2H_4O_2$: C, 54.55; H, 5.26; N, 9.54. Found: C, 55.62; H, 4.92; N, 10.50.

EXAMPLE 279

2-(1-{2-[(2-methoxy-6-methylphenyl)amino]-2-oxoethyl}piperidin-4-yl)pyridinium N-oxide A solution of 2-methoxy-6-methylaniline (4 equivalents) in dichloromethane (0.2 M) was treated with pyridine (8 equivalents) followed by bromoacetyl chloride (1 equivalent). After 3 hours at room temperature, the mixture was treated with sodium carbonate (12 equivalents) and the product from Example 119A (3 equivalents) in dioxane:water (2:1). The heterogeneous mixture was heated to 40° C. overnight. The reaction mixture was cooled to room temperature, concentrated under reduced pressure and the residue triturated with 5% methanol:dichloromethane. The solid inorganic material was filtered and the filtrated concentrated and purified by HPLC. Isolated as an acetate salt. (45 mg, 44%). $^1$H NMR (300 MHz, DMSO-$d_6$) δ 1.71 (m, 2H), 1.99 (m, 4H), 2.15 (m, 3H), 2.30 (m, 2H), 3.10 (m, 1H), 3.15 (s, 2H), 3.75 (s, 3H), 6.86 (dd, J=9, 1.5 Hz, 2H), 7.16 (t, J=9 Hz, 1H), 7.30 (m, 2H), 7.45 (m, 1H), 8.26 (dd, J=4.5, 1.5 Hz, 1H), 8.95 (s, 1H); MS (DCI/NH$_3$) m/e 340 (M+H−16)$^+$; 356 (M+H)$^+$.

EXAMPLE 280

2-{1-[2-(1,1'-biphenyl-3-ylamino)-2-oxoethyl]piperidin-4-yl}pyridinium N-oxide

EXAMPLE 280A

N-1,1'-biphenyl-3-yl-2-chloroacetamide

The procedure described in Example 22A was followed, substituting biphenyl-3-ylamine for 3,4,5-trimethoxyaniline to provide the title compound.

MS (DCI) m/e 346 (M+H)$^+$.

EXAMPLE 280B

2-{1-[2-(1,1'-biphenyl-3-ylamino)-2-oxoethyl]piperidin-4-yl}pyridinium N-oxide

The procedure described in Example 225B was followed, substituting the product from Example 280A for the product from Example 225A to provide the title compound as an amorphous solid. (38.5 mg, 26%). $^1$H NMR (300 MHz, CDCl$_3$) δ 1.73 (m, 2H) 2.09 (m, 2H) 2.55 (m, 2H) 3.08 (m, 2H) 3.22 (s, 2H) 3.48 (m, 1H) 7.19 (m, 4H) 7.39 (m, 3H) 7.61 (m, 5H) 8.28 (d, J=6.10 Hz, 114) 9.21 (s, 1H); MS (ESI) m/e 390 (M+H)$^+$; Anal. calcd for $C_{24}H_{25}N_3O_2$: C, 74.39; H, 6.50; N, 10.80. Found: C, 73.87; H, 7.13; N, 10.58.

EXAMPLE 281

2-(1-{2-[(3-ethylphenyl)amino]-2-oxoethyl}piperidin-4-yl)pyridinium N-oxide

EXAMPLE 281A 2-chloro-N-(3-ethylphenyl)acetamide

The procedure described in Example 22A was followed, substituting 3-ethylphenylamine for 3,4,5-trimethoxyaniline to provide the title compound (8.0 g, 100%). $^1$H NMR (300 MHz, CDCl$_3$) δ 1.25 (m, 3H), 2.68 (m, 2H), 4.35 (m, 2H), 7.02 (d, J=5.4 Hz, 1H), 7.40 (m, 3H), 8.18 (br s, 1H); MS (DCI/NH$_3$) m/e 198 (M+H)$^+$.

EXAMPLE 281 B 2-(1-{2-[(3-ethylphenyl)amino]-2-oxoethyl}piperidin-4-yl)pyridinium N-oxide The procedure described in Example 225B was followed, substituting the product from Example 281 A for the product from Example 225A to provide the title compound as an amorphous solid. (38 mg, 26%). $^1$H NMR (300 MHz, CDCl$_3$) δ 1.24 (t, J=7.6 Hz, 3H), 1.70 (m, 8H), 2.64 (m, 3H), 4.26 (s, 2H), 6.91 (s, 1H), 7.25 (m, 3H), 7.42 (m, 2H), 7.60 (m, 1H), 8.28 (d, J=6.1 Hz, 1H); MS (ESI) m/e 340 (M+H)$^+$.

EXAMPLE 282

2-{1-[2-(2,3-dihydro-1H-inden-5-ylamino)-2-oxoethyl]piperidin-4-yl}pyridinium N-oxide A solution of 5-aminoindan (190 mg, 1.43 mmol) in dichloromethane (7 mL) was treated with pyridine (300 μL, 3.71 mmol) followed by bromoacetyl chloride (30 μL, 0.36 mmol). After 3 hours at room temperature, the mixture was treated with sodium carbonate (450 mg, 4.25 mmol) and the product from Example 119A (225 mg, 1.05 mmol) in dioxane:water (2:1, 7 mL). The heterogeneous mixture was heated to 40° C. overnight. The mixture was cooled and diluted with dichloromethane. The potassium carbonate was removed by filtration and the filtrate was concentrated under reduced pressure. The residue was diluted 1:10 with 20% aqueous ethanol and loaded on a strongly acidic ion exchange resin (Biorad AG 50W-X2). The resin was washed to neutral with water, and the product was eluted with 10 mL of 5% ammonium hydroxide in 20% aqueous ethanol. The solution was lyophilized to provide (50% yield) of the title compound as a white solid. $^1$H NMR (300 MHz, DMSO-$d_6$) δ 1.69 (ddd, J=12.3, 12.3, 12.1, 3.7 Hz, 2H), 1.91 (d, J=11.5 Hz, 2H), 2.00

(dq, J=7.6, 7.4 Hz, 2H), 2.30 (t, J=11.5 Hz, 2H), 2.81 (q, J=7.8 Hz, 4H), 2.99 (d, J=11.2 Hz, 2H), 3.13 (s, 2H), 3.28 (m, 1H), 7.14 (d, J=8.1 Hz, 1H), 7.33 (m, 3H), 7.45 (dd, J=7.5, 2.4 Hz, 1H), 7.55 (s, 1H), 8.25 (dd, J=6.3, 1.5 Hz, 1H), 9.57 (s, 1H); MS (DCI/NH$_3$) m/e 352 (M+H)$^+$; Anal. calcd for C$_{21}$H$_{25}$N$_3$O.0.2 K$_2$CO$_3$.0.4 H$_2$O: C, 65.92; H, 6.73; N, 10.88. Found: C, 66.07; H, 6.65; N, 10.75.

EXAMPLE 283

2-{1-[2-oxo-2-(5,6,7,8-tetrahydronaphthalen-1-ylamino)ethyl]piperidin-4-yl}pyridinium N-oxide The procedure described in Example 282 was followed, substituting 5,6,7,8-tetrahydronaphthalen-1-ylamine for 5-aminoindan to provide the title compound (70% yield) as a white solid. $^1$H NMR (300 MHz, DMSO-d$_6$) δ 1.71 (m, 6H), 1.96 (d, J=11.5 Hz, 2H), 2.37 (t, J=10.7 Hz, 2H), 2.61 (t, J=6.1 Hz, 2H), 2.72 (t, J=5.9 Hz, 2H), 3.04 (d, J=11.2 Hz, 2H), 3.16 (s, 2H), 3.29 (m, 1H), 6.87 (d, J=7.8 Hz, 1H), 7.07 (t, J=7.8 Hz, 1H), 7.33 (m, 2H), 7.42 (dd, J=8.8, 2.4 Hz, 1H), 7.61 (d, J=7.8 Hz, 1H), 8.27 (d, J=6.1 Hz, 1H), 9.34 (s, 1H); MS (DCI/NH$_3$) m/e 366 (M+H)$^+$; Anal. calcd for C$_{22}$H$_{27}$N$_3$O$_2$.0.3 K$_2$CO$_3$.1.0 H$_2$O: C, 63.03; H, 6.88; N, 9.89. Found: C, 62.82; H, 6.79; N, 9.71.

EXAMPLE 284

2-(1-{2-[(3-isopropoxyphenyl)amino]-2-oxoethyl}piperidin-4-yl)pyridinium N-oxide The procedure described in Example 279 was followed, substituting 3-isopropoxyaniline for 2-methoxy-6-methylaniline to provide the title compound. (74 mg, 52.8%). $^1$H NMR (300 MHz, DMSO-d$_6$) δ 1.26 (d, J=6 Hz, 6H), 1.70 (m, 2H), 1.91 (m, 2H), 2.30 (m, 2H), 3.01 (m, 2H), 3.15 (m, 1H), 3.31 (m, 1H), 4.55 (m, 1H), 6.62 (m, 1H), 7.16 (m, 2H), 7.30 (m, 3H), 7.45 (m, 1H), 8.15 (dd, J=6, 1.5 Hz, 1H), 9.65 (s, 1H); MS (DCI/NH$_3$) m/e 354 (M+H−16)$^+$; 370 (M+H)$^+$; Anal. calcd for C$_{21}$H$_{27}$N$_3$O$_3$.0.4 H$_2$O: C, 66.96; H, 7.44; N, 11.16. Found: C, 66.69; H, 7.56; N, 10.80.

EXAMPLE 285

2-(1-{2-[(3,5-dimethylphenyl)amino]-2-oxoethyl}piperidin-4-yl)pyridinium N-oxide

EXAMPLE 285A 2-chloro-N-(3,5-dimethylphenyl)acetamide

The procedure described in Example 22A was followed, substituting 3,5-dimethylphenylamine for 3,4,5-trimethoxyaniline to provide the title compound (6.38 g, 79%). $^1$H NMR (300 MHz, CDCl$_3$) δ 2.34 (s, 6H), 4.17 (s, 2H), 6.82 (s, 1H), 7.17 (s, 1H), 7.26 (s, 1H), 8.11 (s, 1H); MS (ESI) m/e 198 (M+H)$^+$.

EXAMPLE 285B 2-(1-{2-[(3,5-dimethylphenyl)amino]-2-oxoethyl}piperidin-4-yl)pyridinium N-oxide The procedure described in Example 225B was followed, substituting the product from Example 285A for the product from Example 225A to provide the title compound as an amorphous solid. (38 mg, 26%). $^1$H NMR (300 MHz, CDCl$_3$) δ 1.88 (d, J=3.39 Hz, 2H), 2.05 (d, J=12.55 Hz, 2H), 2.28 (s, 6H), 2.43 (m, 2H), 3.11 (m, 3H), 3.21 (s, 2H), 6.78 (s, 1H), 7.21 (s, 2H), 7.41 (m, 2H), 7.60 (d, J=4.07 Hz, 1H), 8.34 (d, J=6.44 Hz, 1H); MS (ESI) m/e 340 (M+H)$^+$.

EXAMPLE 286

2-(1-{2-[(4-bromo-2-methylphenyl)amino]-2-oxoethyl}piperidin-4-yl)pyridinium N-oxide The procedure described in Example 282 was followed, substituting 4-bromo-2-methylphenylamine for 5-aminoindan to provide the title compound (60% yield) as a white solid. $^1$H NMR (300 MHz, DMSO-d$_6$) δ 1.67 (ddd, J=24.6, 12.2, 3.6 Hz, 2H), 1.96 (d, J=12.5 Hz, 2H), 2.25 (s, 3H), 2.37 (t, J=11.7 Hz, 2H), 3.04 (d, J=11.5 Hz, 2H), 3.18 (s, 2H), 3.26 (m, 1H), 7.37 (m, 5H), 7.76 (d, J=8.8 Hz, 1H), 8.26 (m, 1H), 9.46 (s, 1H); MS (DCI/NH$_3$) m/e 404/406 (M+H)$^+$; Anal. calcd for C$_{19}$H$_{22}$BrN$_3$O$_2$.0.1 K$_2$CO$_3$: C, 54.87; H, 5.30; Found: C, 54.72; H, 5.38; N, 9.73.

EXAMPLE 287

2-[1-(2-oxo-2-{[3-(trifluoromethoxy)phenyl]amino}ethyl)piperidin-4-yl]pyridinium N-oxide The procedure described in Example 282 was followed, substituting 3-trifluoromethoxyphenylamine for 5-aminoindan to provide the title compound (77% yield) as a white solid. $^1$H NMR (300 MHz, DMSO-d$_6$) δ 1.68 (q, J=11.9 Hz, 1H), 1.69 (q, J=12.4 Hz, 1H), 1.91 (d, J=11.9 Hz, 2H), 2.31 (t, J=11.5 Hz, 2H), 3.00 (d, J=11.5 Hz, 2H), 3.19 (s, 2H), 3.28 (m, 1H), 7.05 (m, J=8.3, 2.4, 1.0, 0.9 Hz, 1H), 7.31 (m, 2H), 7.44 (m, 2H), 7.62 (ddd, J=8.2, 2.0, 1.0 Hz, 1H), 7.85 (s, 1H), 8.26 (d, J=5.8 Hz, 1H), 10.01 (s, 1H); MS (DCI/NH$_3$) m/e 396 (M+H)$^+$; Anal. calcd for C$_{19}$H$_{20}$F$_3$N$_3$O$_3$.0.4 H$_2$O: C, 56.69; H, 5.21; N, 10.44. Found: C, 56.71; H, 5.04; N, 10.19.

EXAMPLE 288

2-(1-{2-[(5-methyl-2-nitrophenyl)amino]-2-oxoethyl}piperidin-4-yl)pyridinium N-oxide The procedure described in Example 282 was followed, substituting 2-methyl-5-nitrophenylamine for 5-aminoindan to provide the title compound (75% yield) as a yellow solid. $^1$H NMR (300 MHz, CDCl$_3$) δ 1.70 (q, J=11.9 Hz, 1H), 1.71 (q, J=12.4 Hz, 1H), 2.21 (d, J=13.2 Hz, 2H), 2.40 (s, 3H), 2.62 (t, J=11.9 Hz, 2H), 3.11 (d, J=11.9 Hz, 2H), 3.28 (s, 2H), 3.55 (tt, J=12.0, 3.4 Hz, 1H), 7.19 (ddd, J=12.9, 6.4, 2.7 Hz, 1H), 7.31 (m, 2H), 7.91 (dd, J=8.1, 2.4 Hz, 1H), 8.28 (d, J=6.4 Hz, 1H), 9.08 (d, J=2.4 Hz, 1H), 9.55 (s, 1H); MS (DCI/NH$_3$) m/e 371 (M+H)$^+$; Anal. calcd for C$_{19}$H$_{22}$N$_4$O$_4$.1.1 H$_2$O: C, 58.48; H, 6.25; N, 14.36. Found: C, 58.44; H, 6.20; N, 14.30.

EXAMPLE 289

2-(1-{2-[(2,6-dimethylphenyl)amino]-2-oxoethyl}piperidin-4-yl)pyridinium N-oxide

EXAMPLE 289A 2-chloro-N-(2,6-dimethylphenyl)acetamide

The procedure described in Example 22A was followed, substituting 2,6-dimethylphenylamine for 3,4,5-trimethoxyaniline to provide the title compound (7.21 g, 89%)

¹H NMR (300 MHz, CDCl₃) δ 2.25 (s, 6H), 4.26 (s, 2H), 6.65 (t, J=7.46 Hz, 1H), 6.95 (d, J=7.46 Hz, 2H), 7.84 (s, 3H); MS (ESI) m/e 198 (M+H)⁺.

EXAMPLE 289B 2-(1-{2-[(2,6-dimethylphenyl)amnino]-2-oxoethyl}piperidin-4-yl)pyridinium N-oxide The procedure described in Example 225B was followed, substituting the product from Example 289A for the product from Example 225A to provide the title compound as an amorphous solid. (27 mg, 8%). ¹H NMR (300 MHz, CD₃OD) δ 1.88 (dd, J=12.4, 3.6 Hz, 2H), 2.07 (m, 2H), 2.22 (s, 6H), 2.50 (m, 2H), 3.11 (m, 3H) 3.21 (s, 2H), 7.10 (m, 1H), 7.42 (m, 2H), 7.58 (m, 1H), 7.86 (m, 1H), 7.93 (d, J=2.0 Hz, 1H), 8.34 (d, J=6.4 Hz, 1H); MS (ESI) m/e 354 (M+H)⁺.

EXAMPLE 290

2-(1-{2-[(2,6-dichloro-3-methylphenyl)amino]-2-oxoethyl}piperidin-4-yl)pyridinium N-oxide The procedure described in Example 282 was followed, substituting 2,6-dichloro-3-methylphenylamine for 5-aminoindan to provide the title compound (64% yield) as an off-white solid. ¹H NMR (300 MHz, CDCl₃) δ 1.72 (q, J=12.4 Hz, 1H), 1.73 (q, J=12.3 Hz, 1H), 2.17 (d, J=12.9 Hz, 2H), 2.39 (s, 3H), 2.56 (t, J=11.9 Hz, 2H), 3.25 (d, J=12.2 Hz, 2H), 3.27 (s, 2H), 3.58 (t, J=12.2, 3.3 Hz, 1H), 6.57 (d, J=8.1 Hz, 1H), 7.17 (m, 4H), 8.27 (d, J=6.4 Hz, 1H), 9.03 (s, 1H); MS (DCI/NH₃) m/e 394 (M+H)⁺; Anal. calcd for C₁₉H₂₁Cl₂N₃O₂.1.3 H₂O: C, 54.63; H. 5.69; N. 10.06. Found: C, 54.51; H. 5.13; N. 9.70.

EXAMPLE 291

2-{1-[2-(1,3-benzodioxol-5-ylamino)-2-oxoethyl]piperidin-4-yl}pyridinium N-oxide

EXAMPLE 291 A

N-1,3-benzodioxol-5-yl-2-chloroacetamide

The procedure described in Example 33A was followed, substituting benzo[1,3]dioxol-5-ylamine for 3-methylaniline to provide the title compound (92% yield) as a brown solid. ¹H NMR (300 MHz, CDCl₃) δ 4.2 (s, 2H), 5.98 (s, 2H), 6.78 (d, 1H, J=9 Hz,), 6.83 (dd 1H, J=9 Hz, 3 Hz), 7.22 (d, 1H, J=3 Hz,), 8.10 (br s, 1H); MS (DCI/NH₃) m/e 213 (M+H)⁺.

EXAMPLE 291B

2-{1-[2-(1,3-benzodioxol-5-ylamino)-2-oxoethyl]piperidin-4-yl}pyridinium N-oxide The procedure described in Example 225B was followed, substituting the product in Example 291A for the product from Example 225A to provide the title compound as a white solid (25 mg, 21%). ¹H NMR (300 MHz, CDCl₃) δ 1.65-1.7 (m, 2H), 2.15-2.19 (m, 2H), 2.45 (t, 2H, J=12 Hz), 3.05 (m, 2H), 3.10-3.15 (m, 2H), 3.45 (m, 1H), 5.9 (s, 2H), 6.76 (d, 1H, J=9 Hz), 6.75-6.85 (m, 1H), 7.12-7.18 (m, 1H), 7.32-7.38 (m, 3H), 8.25 (d, 1H, J=6 Hz,), 9.08 (br s, 1H); MS (DCI/NH₃) m/e 356 (M+H)⁺; Anal. calcd for C₁₉H₂₁N₃O₄.0.5 H₂O: C, 62.63; H, 6.09; N, 11.53. Found: C, 63.01; H, 5.96; N, 11.12.

EXAMPLE 292

2-[1-(2-{[3-(methylthio)phenyl]amino}-2-oxoethyl)piperidin-4-yl]pyridinium N-oxide The procedure described in Example 225B was followed, substituting 2-chloro-N-(3-methylsulfanylphenyl)acetamide for the product from Example 225A to provide the title compound as a pale yellow oil (17 mg, 21%). ¹H NMR (300 MHz, DMSO-d₆) δ 1.60-1.78 (m, 2H), 1.63-1.95 (m, 2H), 2.12-2.18 (m, 2H), 2.70 (s, 3H), 2.9-3.12 (m, 2H), 3.22-3.30 (m, 3H), 6.9-7.0 (m, 1H), 7.2-7.3 (m, 2H), 7.3-7.35 (m, 2H), 7.62 (t, 1H, J=3 Hz), 7.8 (s, 1H), 8.23-8.27 (m, 1H), 9.75 (s, 1H); MS (DCI/NH₃) m/e 358 (M+H)⁺.

EXAMPLE 293

2-(1-{2-[(5-chloro-2-methylphenyl)amino]-2-oxoethyl}piperidin-4-yl)pyridinium N-oxide

EXAMPLE 293A 2-chloro-N-(5-chloro-2-methylphenyl)acetamide

The procedure described in Example 33A was followed, substituting 5-chloro-2-methylphenylamine for 3-methylaniline to provide the title compound (1.7 g, 55%) as a white solid. ¹H NMR (300 MHz, DMSO-d₆) δ 2.0 (s, 3H), 5.10 (s, 2H), 6.42 (dd, 1H, J=9, 3 Hz), 6.60 (d, 1H, J=3 Hz), 6.90 (d, 1H, J=9 Hz); MS (DCI/NH₃) m/e 219 (M+H)⁺.

EXAMPLE 293B 2-(1-{2-[(5-chloro-2-methylphenyl)amino]-2-oxoethyl}piperidin-4-yl)pyridinium N-oxide The procedure described in Example 225B was followed, substituting the product from Example 293A for the product from Example 225A to provide the title compound as a brown powder (15 mg, 13%). ¹H NMR (300 MHz, CDCl₃) δ 1.68-1.73 (m, 2H), 2.15-2.22 (m, 2H), 2.25 (s, 3H), 2.6 (t, 2H, J=12 Hz), 3.05-3.18 (m, 2H), 3.22 (s, 2H), 3.50-3.60 (m, 1H), 7.05 (dd, 1H, J=6 Hz, 3 Hz), 7.10 (d, 1H, 9 Hz,), 7.18-7.2 (m, 1H), 7.22-7.28 (m, 2H), 8.22 (d, 2H, J=6 Hz), 9.38 (br s, 1H); MS (DCI/NH₃) m/e 360 (M+H)⁺; Anal. calcd for C₁₉H₂₂ClN₃O₂.0.5 H₂O: C, 61.87; H, 6.28; N, 11.39. Found: C, 61.76; H, 6.22; N, 11.10.

EXAMPLE 294

2-(1-{2-[(2,5-dimethoxyphenyl)amino]-2-oxoethyl}piperidin-4-yl)pyridinium N-oxide

EXAMPLE 294A 2-chloro-N-(2,5-dimethoxyphenyl)acetamide

The procedure described in Example 33A was followed, substituting 2-chloro-N-(2,5-dimethoxyphenyl)aniline for 3-methylaniline to provide the title compound (1.6 g, 55% yield) as a brown solid. ¹H NMR (300 MHz, CDCl₃) δ 3.73 (s, 3H), 3.8 (s, 3H), 4.4 (s, 2H), 6.33 (dd, 1H, J=9, 3 Hz), 6.45 (d, 1H, J=3 Hz), 6.65 (dd, 1H, J=9, 3 Hz); MS (DCI/NH$_3$) m/e 230 (M+H)$^+$.

EXAMPLE 294B 2-(1-{2-[(2,5-dimethoxyphenyl)amino]-2-oxoethyl}piperidin-4-yl)pyridinium N-oxide The procedure described in Example 225B was followed, substituting the product from Example 294A for the product from Example 225A to provide the title compound as a pale yellow oil (27 mg, 77%). $^1$H NMR (300 MHz, CDCl$_3$) δ 1.40-1.51 (m, 2H), 1.65-1.80 (m, 2H), 2.15-2.20 (m, 2H), 2.50-2.60 (m, 2H), 3.10-3.18 (m, 2H), 3.50-3.60 (m, 1H), 3.80 (s, 3H), 3.85 (s, 3H), 6.60 (dd, 1H, J=6 Hz, 3 Hz), 6.80 (d, 1H, J=9 Hz), 7.20-7.25 (m, 1H), 7.30-7.39 (m, 2H), 8.15 (d, 1H, J=3 Hz,), 8.38 (d, 1H, J=6 Hz), 9.8 (br s, 1H); MS (DCI/NH$_3$) m/e 372 (M+H)$^+$.

Maleate salt: Anal. calcd for C$_{20}$H$_{25}$N$_3$O$_4$.2.0 C$_4$H$_4$O$_4$.1.3 H$_2$O: C, 53.64; H, 5.72; N, 6.70. Found: C, 53.26; H, 5.95; N, 6.45.

EXAMPLE 295

2-(1-{2-[(3,5-dimethoxyphenyl)amino]-2-oxoethyl}piperidin-4-yl)pyridinium N-oxide

EXAMPLE 295A 2-chloro-N-(3,5-dimethoxyphenyl)acetamide

The procedure described in Example 33A was followed, substituting 2-chloro-N-(3,5-dimethoxyphenyl)aniline for 3-methylaniline to provide the title compound (1.8 g, 60% yield) as a white solid. $^1$H NMR (300 MHz, CDCl$_3$) δ 3.80 (s, 6H), 4.20 (s, 2H), 6.15 (t, 1H, J=3 Hz), 6.78 (d, 2H, J=3 Hz), 8.15 (br s, 1H); MS (DCI/NH$_3$) m/e 230 (M+H)$^+$.

EXAMPLE 295B 2-(1-{2-[(3,5-dimethoxyphenyl)amino]-2-oxoethyl}piperidin-4-yl)pyridinium N-oxide The procedure described in Example 225B was followed, substituting the product from Example 295A for the product from Example 225A to provide the title compound as a yellow solid (50 mg). $^1$H NMR (300 MHz, CDCl$_3$) δ 1.42 (d, 2H, J=6 Hz), 1.50-1.60 (m, 2H), 2.20-2.50 (m, 2H), 3.10-3.18 (m, 1H), 3.22-3.41 (m, 2H), 3.62-3.70 (m, 2H), 3.80 (s, 6H), 6.15 (m, 1H), 6.82 (s, 1H), 7.20-7.35 (m, 4H), 8.02 (s, 1H), 8.25 (d, 1H, J=6 Hz,); MS (DCI/NH$_3$) m/e 372 (M+H)$^+$; Anal. calcd for C$_{20}$H$_{25}$N$_3$O$_4$.2.24 H$_2$O: C, 58.34; H, 7.22; N, 10.20. Found: C, 58.73; H, 7.50; N, 9.79.

EXAMPLE 296

2-[1-(2-{[3-(dimethylamino)phenyl]amino}-2-oxoethyl)piperidin-4-yl]pyridinium N-oxide The procedure described in Example 282 was followed, substituting N,N-dimethylbenzene-1,3-diamine for 5-aminoindan. The residue was purified by flash column chromatography on silica gel (elution with 5% methanol:dichloromethane) to provide 60 mg (48% yield) of the title compound as a clear oil. $^1$H NMR (300 MHz, CDCl$_3$) δ 1.70 (q, J=12.4 Hz, 1H), 1.71 (q, J=12.2 Hz, 1H), 2.15 (d, J=12.9 Hz, 2H), 2.53 (t, J=11.9 Hz, 2H), 2.96 (s, 6H), 3.08 (d, J=13.6 Hz, 2H), 3.18 (s, 2H), 3.55 (tt, J=12.0, 3.4 Hz, 1H), 6.49 (dd, J=8.0, 2.2 Hz, 1H), 6.72 (d, J=8.1 Hz, 1H), 7.17 (m, 2H), 7.24 (t, J=2.4 Hz, 1H), 7.28 (d, J=4.4 Hz, 2H), 9.05 (s, 1H); MS (DCI/NH$_3$) m/e 355 (M+H)$^+$; Anal. calcd for C$_{20}$H$_{26}$N$_4$O$_2$.0.3 CH$_2$Cl$_2$: C, 64.18; H, 7.06; N, 14.75. Found: C, 64.32; H, 7.04; N, 14.79.

EXAMPLE 297

2-(1-{2-[(3-isopropylphenyl)amino]-2-oxoethyl}piperidin-4-yl)pyridinium N-oxide

EXAMPLE 297A 2-chloro-N-(3-isopropylphenyl)acetamide

The procedure described in Example 22A was followed, substituting 3-iso-propylphenylamine for 3,4,5-trimethoxyaniline to provide the title compound (7.12 g, 92%). $^1$H NMR (300 MHz, CDCl$_3$) δ 1.24 (dd, J=10.3, 7.0 Hz, 6H), 2.91 (m, 1H), 4.19 (s, 2H), 7.05 (d, J=7.8 Hz, 1H), 7.39 (m, 3H), 8.18 (s, 1H); MS (ESI) m/e 212 (M+H)$^+$.

EXAMPLE 297B 2-(1-{2-[(3-isopropylphenyl)amino]-2-oxoethyl}piperidin-4-yl)pyridinium N-oxide The procedure described in Example 225B was followed, substituting the product from Example 297A for the product from Example 225A to provide the title compound as an amorphous solid. (160 mg, 30%). $^1$H NMR (300 MHz, CD$_3$OD) δ 1.25 (d, J=6.8 Hz, 6H), 1.86 (dd, J=12.7, 3.6 Hz, 2H), 2.05 (m, 2H), 2.44 (m, 2H), 2.89 (m, 1H), 3.13 (m, 3H), 3.23 (s, 2H), 7.00 (d, J=7.8 Hz, 1H), 7.24 (t, J=7.8 Hz, 1H), 7.40 (m, 3H), 7.48 (s, 1H), 7.60 (d, J=4.4 Hz, 1H), 8.34 (d, J=6.4 Hz, 1H); MS (ESI) m/e 354 (M+H)$^+$; Anal. calcd for C$_{21}$H$_{27}$N$_3$O$_2$.0.4 CH$_2$Cl$_2$.2.0 H$_2$O: C, 52.29; H, 6.15; N, 7.82. Found: C, 52.21; H, 6.14; N, 8.15.

EXAMPLE 298

2-(1-{2-[(3-chloro-2-methylphenyl)amino]-2-oxoethyl}piperidin-4-yl)pyridinium N-oxide

EXAMPLE 298A 2-chloro-N-(3-chloro-2-methylphenyl)acetamide

The procedure described in Example 22A was followed, substituting 3-chloro-2-methylphenylamine for 3,4,5-trimethoxyaniline to provide the title compound (7.3 g, 95%). $^1$H NMR (300 MHz, CDCl$_3$) δ 2.35 (s, 3H), 4.26 (s, 2H), 7.19 (m, 1H), 7.26 (m, 1H), 7.73 (d, J=8.1 Hz, 1H), 8.26 (s, 1H); MS (ESI) m/e 219 (M+H)$^+$.

EXAMPLE 298

2-(1-{2-[(3-chloro-2-methylphenyl)amino]-2-oxoethyl}piperidin-4-yl)pyridinium N-oxide The procedure described in Example 225B was followed, substituting the product from Example 298A for the product from Example 225A to provide the title compound as an amorphous solid. (25 mg, 18%). $^1$H NMR (300 MHz, CD$_3$OD) δ 1.64 (dd, J=12.2, 3.7 Hz, 2H), 1.87 (m, 2H), 2.05 (d, J=12.9 Hz, 2H), 2.33 (s, 3H), 2.89 (m, 2H), 3.21 (m, 3H), 7.23 (m, 2H), 7.39 (m, 2H), 7.58 (m, 2H), 8.34 (d, J=6.4 Hz, 1H); MS (ESI) m/e 360 (M+H)$^+$.

EXAMPLE 299

3-methyl-N-[2-(4-pyridin-2-ylpiperazin-1-yl)ethyl]benzamide

To a solution of 3-methylbenzamide (360 mg, 5.0 mmol) in dichloromethane (5 mL) at 0° C. was added 1-(3-dimethylaminopropyl)-3-ethylcarbodiimide hydrochloride (1.06 g, 5.5 mmol). After 15 minutes, ethanolamine (333 μL, 5.5 mmol) was added and the mixture was stirred at room temperature for 6 hours. The mixture was diluted with 50 mL ethyl acetate. The organic layer was washed with 2× saturated aqueous ammonium chloride (25 mL), 2× saturated aqueous sodium bicarbonate (25 mL), 2× brine (25 mL), dried over magnesium sulfate, filtered and evaporated. The product was a white solid (476 mg, 53%).

To a solution of the resulting alcohol (55 mg, 0.31 mmol) and pyridine (33 μL, 0.37 mmol) in dichloromethane (0.5 mL) at 0° C. was added methanesulfonyl chloride (43 mg, 0.37 mmol). After 1 hour at room temperature, the mixture was diluted with 10 mL ethyl acetate. The organic layer was washed with 2× dilute aqueous ammonium chloride (5 mL), 2× brine (5 mL), dried over magnesium sulfate, filtered and evaporated. The residue was dissolved in N,N-dimethylformamide (1 mL) and treated with 1-pyridin-2-ylpiperazine (48 μL, 0.31 mmol) and N,N-diisopropylethylamine (155 μL, 0.78 mmol). After 24 hours at 100° C., the mixture was cooled and concentrated. The residue was purified by flash column chromatography on silica gel (elution with 1-2.5% methanol:dichloromethane) to provide 45 mg (45% yield) of the title compound as a white solid. $^1$H NMR (300 MHz, CDCl$_3$) δ 2.40 (s, 3H), 2.66 (m, 6H), 3.60 (m, 6H), 6.65 (m, 2H), 6.84 (s, 1H), 7.31 (m, 2H), 7.49 (ddd, J=8.7, 7.0, 2.0 Hz, 1H), 7.55 (m, 1H), 7.63 (s, 1H), 8.20 (ddd, J=5.0, 2.0, 0.9 Hz, 1H); MS (DCI/NH$_3$) m/e 325 (M+H)$^+$; Anal. calcd for C$_{19}$H$_{24}$N$_4$O.0.2 H$_2$O: C, 69.57; H, 7.50; N, 17.08. Found: C, 69.41; H, 7.21; N, 17.10.

EXAMPLE 300

2-(1-{[(2,3-dibromo-5-methylbenzoyl)amino]methyl}piperidin-4-yl)pyridinium N-oxide

EXAMPLE 300A 2,3-dibromo-5-methylbenzoic acid

To a solution of 3-bromo-5-methylanthranilic acid (2.3 g, 10 mmol) in acetic acid (12 mL) at 0° C. was added 18% hydrobromic acid (30 mL, 30 mmol) followed by drop wise addition of a solution of sodium nitrite (690 mg, 10 mmol) in water (5 mL). After 10 min, this solution was added to a mixture of copper (I) bromide (2.15 g, 15 mmol) in 48% hydrobromic acid (7 mL) at 0° C. The mixture was allowed to warm to ambient temperature (15 minutes) and then refluxed at 50° C. until evolution of N$_2$ was completed. The mixture was then extracted with ethyl acetate, washed with water, brine, dried with anhydrous magnesium sulfate and concentrated under reduced pressure to provide 2.8 g of crude of the title compound. $^1$H NMR (300 MHz, DMSO-d$_6$) δ 2.27 (s, 3H), 7.43 (s, 1H), 7.72 (s, 1H), 13.60 (br s, 1H); MS (DCI/NH$_3$) m/e 310 (M+NH$_4$)$^+$.

EXAMPLE 300B 2,3-dibromo-5-methylbenzamide

A mixture of the product from Example 300A (1.5 g, 5 mmol), 1-(3-dimethylaminopropyl)-3-ethylcarbodiimide hydrochloride (EDCI, 1.43 g, 7.5 mmol) and 1-hydroxybenzotriazole (675 mg, 5 mmol) in chloroform (30 mL) was stirred for 90 minutes and then added to 10% ammonium hydroxide (10 mL) and the stirring was continued for additional 6 hours. Chloroform was then removed under reduced pressure and the precipitated solid was filtered, washed with water and dried under reduced pressure to provide 1.45 g of the title compound. $^1$H NMR (300 MHz, DMSO-d$_6$) δ 2.27 (s, 3H), 7.20 (m, 1H), 7.60 (br s, 1H), 7.64 (m, 1H), 7.89 (br s, 1H); MS (DCI/NH$_3$) m/e 309 (M+NH$_4$)$^+$.

EXAMPLE 300C 2-(1-{[(2,3-dibromo-5-methylbenzoyl)amino]methyl}piperidin-4-yl)pyridinium N-oxide The procedure described in Example 200 was followed, substituting the product from Example 300B for 3-methylbenzamide to give the title compound (30% yield) as a white solid. $^1$H NMR (300 MHz, DMSO-d$_6$) δ 1.53 (m, 2H), 1.90 (m, 2H), 2.30 (s, 3H), 2.47 (m, 2H), 2.93 (m, 2H), 3.22 (m, 1H), 4.15 (d, 2H, J=6.1 Hz), 7.29 (m, 4H), 7.66 (dd, 1H, J=2.0, 1.0 Hz), 8.24 (m, 1H), 8.77 (t, 1H, J=6.1 Hz); MS (DCI/NH$_3$) m/e 484 (M+H)$^+$.

EXAMPLE 301

2-{1-[(benzoylamino)methyl]piperidin-4-yl}pyridinium N-oxide

The procedure described in Example 200 was followed, substituting benzamide for 3-methylbenzamide to provide the title compound (27 mg, 30% yield). $^1$H NMR (300 MHz, CD$_3$OD) δ 1.71 (dd, J=12.4, 3.6 Hz, 2H), 2.04 (m, 2H), 2.54 (m, 2H), 3.12 (m, 3H), 3.37 (s, 2H), 7.46 (m, 5H), 7.87 (m, 3H), 8.33 (d, J=6.4 Hz, 1H); MS (ESI) m/e 312 (M+H)$^+$; Anal. calcd for C$_{18}$H$_{21}$N$_3$O$_2$.2.0 H$_2$O: C, 62.23; H, 7.25; N, 12.10. Found: C, 61.91; H, 7.27; N, 12.03.

EXAMPLE 302

2-(1-{[(4-chloro-3-methylbenzoyl)amino]methyl}piperidin-4-yl)pyridinium N-oxide

The procedure described in Example 200 was followed, substituting 4-chloro-3-methylbenzamide for 3-methylbenzamide to provide the title compound (60 mg, 56% yield). $^1$H NMR (300 MHz, DMSO-d$_6$) δ 2.38 (m, 6H), 2.51 (m, 2H), 2.73 (m, 1H), 2.88 (s, 3H), 4.80 (s, 2H), 7.34 (m, 1H), 7.52 (m, 2H), 7.71 (m, 2H), 7.90 (m, 2H), 9.21 (br s, 1H); MS (ESI) m/e 360 (M+H)$^+$; Anal. calcd for C$_{19}$H$_{22}$ClN$_3$O$_2$.1.0 C$_2$HF$_3$O$_2$: C, 53.23; H, 4.89; N, 8.87. Found: C, 52.84; H, 4.57; N, 8.62.

764284 EXAMPLE 303

2-(1-{[(4-fluoro-3-methylbenzoyl)amino]methyl}piperidin-4-yl)pyridinium N-oxide

The procedure described in Example 200 was followed, substituting 4-fluoro-3-methylbenzamide (Oakwood) for 3-methylbenzamide to provide the title compound. (82 mg, 82.8%). $^1$H NMR (300 MHz, DMSO-$d_6$) δ 1.52 (m, 2H), 1.89 (d, J=12 Hz, 2H), 2.29 (s, 3H), 2.36 (t, J=12 Hz, 2H), 2.95 (d, J=12 Hz, 2H), 3.19 (m, 1H), 4.17 (d, J=6 Hz, 2H), 7.27 (m, 3H), 7.39 (dd, J=7.5, 1.5 Hz, 1H), 7.75 (m, 1H), 7.85 (dd, 7.5, 1.5 Hz, 1H), 8.23 (dd, J=6, 1.5 Hz, 1H), 8.72 (t, J=6 Hz, 1H); MS (DCI/NH$_3$) m/e 328 (M+H−16)$^+$; 344 (M+H)$^+$; Anal. calcd for $C_{19}H_{22}N_3FO_2$: C, 66.54; H, 6.46; N, 12.24. Found: C, 66.20; H, 6.31; N, 12.18.

EXAMPLE 304

2-[1-({[3-chloro-4-(trifluoromethoxy)benzoyl] amino}methyl)piperidin-4-yl]pyridinium N-oxide The procedure described in Example 200 was followed, substituting 3-chloro-4-methoxybenzamide (Oakwood) for 3-methylbenzamide. (98 mg, 62%). $^1$H NMR (300 MHz, DMSO-$d_6$) δ 1.52 (m, 2H), 1.89 (d, J=12 Hz, 2H), 2.36 (t, J=12 Hz, 2H), 2.95 (d, J=12 Hz, 2H), 3.20 (m, 1H), 4.18 (d, J=6 Hz, 2H), 7.27 (m, 3H), 7.39 (dd, J=7.5, 1.5 Hz, 1H), 7.75 (m, 1H), 7.85 (dd, 7.5, 1.5 Hz, 1H), 8.23 (dd, J=6, 1.5 Hz, 1H), 8.72 (t, J=6 Hz, 1H); MS (DCI/NH$_3$) m/e 414 (M+H−16)$^+$; 430 (M+H)$^+$; Anal. calcd for $C_{19}H_{19}ClF_3O_3$: C, 53.09; H, 4.46; N, 9.78. Found C, 52.73; H, 4.34; N, 9.51.

EXAMPLE 305

2-(1-{[(3-ethoxybenzoyl)amino]methyl}piperidin-4-yl)pyridinium N-oxide

The procedure described in Example 200 was followed, substituting 3-ethoxybenzamide for 3-methylbenzamide. (65 mg, 47%). $^1$H NMR (300 MHz, DMSO-$d_6$) δ 1.34 (t, J=7.5 Hz, 3H), 1.52 (m, 2H), 1.89 (d, J=12 Hz, 2H), 2.36 (t, J=12 Hz, 2H), 2.95 (d, J=12 Hz, 2H), 3.20 (m, 1H), 4.08 (q, J=6 Hz, 2H), 4.18 (d, J=6 Hz, 2H), 7.08 (m, 1H), 7.27 (m, 2H), 7.39 (m, 4H), 8.23 (dd, J=6 Hz, 1.5 Hz, 1H), 8.72 (t, J=6 Hz, 1H); MS (DCI/NH$_3$) m/e 340 (M+H−16)$^+$; 356 (M+H)$^+$; Anal. calcd for $C_{20}H_{25}N_3O_3$.0.75 $H_2O$: C, 65.11; H, 7.24; N, 11.39. Found: C, 65.00; H, 7.08; N, 11.01.

EXAMPLE 306

2-(1-{[(3,5-dichlorobenzoyl)amino]methyl}piperidin-4-yl)pyridinium N-oxide

The procedure described in Example 200 was followed, substituting 3,5-dichlorobenzamide (Lancaster) for 3-methylbenzamide. (46 mg, 33.3%). $^1$H NMR (300 MHz, DMSO-$d_6$) δ 1.52 (m, 2H), 1.89 (d, J=12 Hz, 2H), 2.36 (t, J=12 Hz, 2H), 2.95 (d, J=12 Hz, 2H), 3.20 (m, 1H), 4.18 (d, J=6 Hz, 2H), 7.29 (m, 2H), 7.39 (m, 1H), 7.83 (t, J=1.5 Hz, 1H), 7.92 (d, J=1.5 Hz, 2H), 8.23 (dd, J=6 Hz, 1.5 Hz, 1H), 8.98 (t, J=6 Hz, 1H); MS (DCI/NH$_3$) m/e 365 (M+H−16)$^+$; 381 (M+H)$^+$; Anal. calcd for $C_{18}H_{19}Cl_2N_3O_2$: C, 56.85; H, 5.04; N, 11.05. Found: C, 56.56; H, 5.20; N, 10.79.

EXAMPLE 307

2-[1-({[4-methyl-3-(trifluoromethyl)benzoyl] amino}methyl)piperidin-4-yl]pyridinium N-oxide The procedure described in Example 200 was followed, substituting 4-Methyl-3-trifluoromethylbenzamide (Apollo) for 3-methylbenzamide. (75 mg, 66.3%). $^1$H NMR (300 MHz, DMSO-$d_6$) δ 1.52 (m, 2H), 1.89 (d, J=12 Hz, 2H), 2.36 (t, J=12 Hz, 2H), 2.95 (d, J=12 Hz, 2H), 3.20 (m, 1H), 3.25 (s, 3H), 4.18 (d, J=6 Hz, 2H), 7.29 (m, 2H), 7.39 (m, 1H), 7.58 (d, J=9 Hz, 1H), 8.08 (d, J=9 Hz, 1H), 8.19 (s, 1H), 8.23 (dd, J=6, 1.5 Hz, 1H), 8.98 (t, J=6 Hz, 1H); MS (DCI/NH$_3$) m/e 378 (M+H−16)$^+$; 394 (M+H)$^+$; Anal. calcd for $C_{20}H_{22}F_3N_3O_2$.0.3 $H_2O$: C, 60.23; H, 5.71; N, 10.53. Found: C, 60.03; H, 5.62; N, 10.18.

EXAMPLE 308

2-(1-{[(3,4-dimethylbenzoyl)amino] methyl}piperidin-4-yl)pyridinium N-oxide

The procedure described in Example 200 was followed, substituting 3,4-dimethylbenzamide (Lancaster) for 3-methylbenzamide. (85 mg, 89%). $^1$H NMR (300 MHz, DMSO-$d_6$) δ 1.52 (m, 2H), 1.89 (d, J=12 Hz, 2H), 2.28 (s, 6H), 2.36 (m, 2H), 2.95 (d, J=12 Hz, 2H), 3.20 (m, 1H), 4.18 (d, J=6 Hz, 2H), 7.21 (d, J=9 Hz, 1H), 7.29 (m, 2H), 7.39 (m, 1H), 7.62 (d, J=9 Hz, 1H), 7.68 (s, 1H), 8.23 (dd, J=6, 1.5 Hz, 1H), 8.64 (t, J=6 hz, 1H); MS (DCI/NH$_3$) m/e 324 (M+H−16)$^+$; 340 (M+H)$^+$; Anal. calcd for $C_{20}H_{25}N_3O_2$.0.3 $H_2O$: C, 69.66; H, 7.48; N, 12.19. Found: C, 69.39; H, 7.41; N, 11.94.

EXAMPLE 309

2-(1-{[(3-chloro-4-fluorobenzoyl)amino] methyl}piperidin-4-yl)pyridinium N-oxide The procedure described in Example 200 was followed, substituting 3-chloro-4-fluorobenzamide (Maybridge) for 3-methylbenzamide. (85 mg, 89%). $^1$H NMR (300 MHz, DMSO-$d_6$) δ 1.52 (m, 2H), 1.89 (d, J=12 Hz, 2H), 2.36 (m, 2H), 2.95 (d, J=12 Hz, 2H), 3.20 (m, 1H), 4.18 (d, J=6 Hz, 2H), 7.24 (m, 2H), 7.39 (dd, J=6, 1.5 Hz, 1H), 7.53 (t, J=9 Hz, 1H), 7.93 (m, 1H), 8.13 (dd, J=6, 1.5 Hz, 1H), 8.23 (dd, J=6, 1.5 Hz, 1H), 8.90 (t, J=6 hz, 1H); MS (DCI/NH$_3$) m/e 348 (M+H−16)$^+$; 364 (M+H)$^+$; Anal. calcd for $C_{18}H_{19}N_3O_2ClF$.0.8 $H_2O$: C, 57.16; H, 5.49; N, 11.11. Found: C, 57.26; H, 5.40; N, 10.53.

EXAMPLE 310

2-(1-{[(pyridin-2-ylcarbonyl)amino] methyl}piperidin-4-yl)pyridinium N-oxide

The procedure described in Example 200 was followed, substituting picolinamide for 3-methylbenzamide. (51 mg, 57%). $^1$H NMR (300 MHz, DMSO-$d_6$) δ 1.52 (m, 2H), 1.89 (d, J=12 Hz, 2H), 2.36 (m, 2H), 2.98 (d, J=12 Hz, 2H), 3.18 (m, 1H), 4.22 (d, J=6 Hz, 2H), 7.27 (m, 2H), 7.28 (dd, J=6, 1.5 Hz, 1H), 7.63 (m, 1H), 8.03 (m, 1H), 8.22 (dd, J=6, 1.5 Hz, 1H), 8.23 (dd, J=6, 1.5 Hz, 1H), 8.68 (dd, J=6, 1.5 Hz, 1H), 9.02 (t, J=6 Hz, 1H); MS (DCI/NH$_3$) m/e 297 (M+H−16)$^+$; 313 (M+H)$^+$; Anal. calcd for $C_{17}H_{20}N_4O_2$.0.3 $H_2O$: C, 64.25; H, 6.53; N, 17.63. Found: C, 64.10; H, 6.51; N, 17.35.

EXAMPLE 311

2-(1-{[(3,5-dimethylbenzoyl)amino] methyl}piperidin-4-yl)pyridinium N-oxide

The procedure described in Example 200 was followed, substituting 3,5-dimethylbenzamide for 3-methylbenzamide. (140 mg, 60%). $^1$H NMR (300 MHz, CD$_3$OD) δ 1.76 (dd, J=12.4, 3.6 Hz, 2H), 2.11 (d, J=12.6 Hz, 2H), 2.36 (s, 6H), 2.66 (m, 2H), 3.23 (d, J=12.2 Hz, 2H), 3.47 (m, 1H), 4.38 (s, 2H), 7.22 (s, 1H), 7.41 (m, 1H), 7.52 (m, 2H), 7.56 (m, 2H), 8.34 (d, J=6.4 Hz, 1H); MS (ESI) m/e 340 (M+H)+.

EXAMPLE 312

2-(1-{[(3-vinylbenzoyl)amino]methyl}piperidin-4-yl)pyridinium N-oxide

The procedure described in Example 200 was followed, substituting 3-vinylbenzamide for 3-methylbenzamide. (84 mg, 67%). $^1$H NMR (300 MHz, CD$_3$OD) δ 1.75 (dd, J=12.6, 3.7 Hz, 2H), 2.10 (d, J=12.6 Hz, 2H), 2.63 (m, 2H), 3.21 (m, 2H), 3.46 (m, 1H), 4.38 (s, 2H), 5.34 (d, J=11.2 Hz, 1H), 5.90 (d, J=17.3 Hz, 1H), 6.81 (dd, J=17.6, 10.9 Hz, 1H), 7.50 (m, 5H), 7.76 (d, J=7.5 Hz, 1H), 7.95 (s, 1H), 8.33 (d, J=6.4 Hz, 1H), MS (ESI) m/e 338 (M+H)+.

EXAMPLE 313

2-(1-{[(4-bromo-3-methylbenzoyl)amino]methyl}-1,2,3,6-tetrahydropyridin-4-yl)pyridinium N-oxide

EXAMPLE 313A

2-[1-(tert-butoxycarbonyl)-4-hydroxypiperidin-4-yl]pyridinium N-oxide

To a solution of 4'-hydroxy-3',4',5',6'-tetrahydro-2'H-[2,4']bipyridinyl-1'-carboxylic acid tert-butyl ester (Saari, W. S.; et al. J. Med. Chem. 1984, 27, 1182, 4.00 g, 14.4 mmol) in dichloromethane (100 mL) at room temperature was added m-chloroperbenzoic acid (4.70 g, 27.3 mmol) and the reaction stirred for 16 hours. The reaction was quenched with a sodium metabisulfite solution and washed with saturated sodium carbonate. The organic phase was dried (sodium sulfate), filtered and concentrated under reduced pressure. The residue was purified by flash column chromatography on silica gel (gradient elution with dichloromethane to 10% methanol:dichloromethane) to provide the title compound (94% yield) as a white solid. $^1$H NMR (300 MHz, DMSO-d$_6$) δ 1.41 (s, 9H), 1.84 (br d, 2H, J=11.5 Hz), 2.13 (ddd, 2H, J=12.9, 12.9, 4.7 Hz), 3.17 (br s, 2H), 3.87 (br s, 2H), 7.30 (br s, 1H), 7.43 (m, 1H), 7.51 (ddd, 1H, J=7.5, 7.5, 1.4 Hz), 7.64 (dd, 1H, J=7.8, 1.7 Hz), 8.32 (dd, 1H, J=6.5, 1.4 Hz); MS (DCI/NH$_3$) m/e 295 (M+H)+.

EXAMPLE 313B

2-[1-(tert-butoxycarbonyl)-1,2,3,6-tetrahydropyridin-4-yl]pyridinium N-oxide

The procedure described in Example 237B was followed, substituting the product from Example 313A for the product from Example 237A to provide the title compound (40% yield) as a yellow oil. $^1$H NMR (300 MHz, DMSO-d$_6$) δ 1.43 (s, 9H), 3.32 (m, 2H), 3.49 (m, 2H), 4.01 (br s, 2H), 6.27 (br s, 1H), 7.36 (m, 3H), 8.20 (m, 1H); MS (DCI/NH$_3$) m/e 261 (M+H−16)+; 277 (M+H)+.

EXAMPLE 313C 2-(1,2,3,6-tetrahydropyridin-4-yl)pyridinium N-oxide

The procedure described in Example 166B was followed, substituting the product from Example 313B for the product from Example 166A to provide the title compound as a yellow oil. $^1$H NMR (300 MHz, DMSO-d$_6$) δ 2.78 (m, 2H), 3.28 (m, 2H), 3.79 (m, 2H), 6.36 (s, 1H), 7.38 (m, 3H), 8.26 (m, 1H); MS (DCI/NH$_3$) m/e 161 (M+H−16)+; 177 (M+H)+.

EXAMPLE 313D 2-(1-{[(4-bromo-3-methylbenzoyl)amino]methyl}-1,2,3,6-tetrahydropyridin-4-yl)pyridinium The procedure described in Example 200 was followed, substituting the product from Example 313C amide for the product from Example 119A and 4-bromo-3-methylbenzamide (Lancaster) for 3-methylbenzamide to provide the title compound (6% yield) as a yellow solid. $^1$H NMR (300 MHz, CD$_3$OD); δ 2.63-2.75 (m, 2H), 2.86-2.99 (m, 2H), 3.30 (s, 3H), 3.36-3.44 (m, 2H), 4.39 (s, 2H), 6.23 (m, 1H), 7.37-7.51 (m, 2H), 7.52-7.61 (m, 2H), 7.66 (d, J=9.0 Hz, 1H), 7.68 (d, J=3.6 Hz, 1H), 8.27 (d, J=8.0 Hz, 1H); MS (DCI/NH$_3$) m/e 386/388 (M+H−16)+; 402/404 (M+H)+.

EXAMPLE 314

2-{1-[(2-naphthoylamino)methyl]piperidin-4-yl}pyridinium N-oxide

The procedure described in Example 200 was followed, substituting naphthalene-2-carboxylic acid amide for 3-methylbenzamide to provide the title compound (75 mg, 56% yield) as a white solid. $^1$H NMR (300 MHz, DMSO-d$_6$) δ 1.56 (q, J=12.2 Hz, 1H), 1.57 (q, J=11.9 Hz, 1H), 1.92 (d, J=11.2 Hz, 2H), 2.41 (t, J=11.2 Hz, 2H), 3.02 (d, J=11.5 Hz, 2H), 3.25 (m, J=12.9 Hz, 1H), 4.24 (d, J=5.8 Hz, 2H), 7.30 (m, 2H), 7.40 (dd, J=7.5, 2.4 hz, 1H), 7.62 (m, 2H), 8.01 (m, 4H), 8.24 (d, J=5.8 Hz, 1H), 8.51 (s, 1H), 8.97 (s, 1H); MS (DCI/NH$_3$) m/e 362 (M+H)+; Anal. calcd for C$_{22}$H$_{23}$N$_3$O$_2$.0.2 CH$_2$Cl$_2$.1.2 H$_2$O: C, 66.65; H, 6.50; N, 10.50. Found: C, 66.62; H, 6.20; N, 10.19.

EXAMPLE 315

2-(1-{[(thien-2-ylcarbonyl)amino]methyl}piperidin-4-yl)pyridinium N-oxide

The procedure described in Example 200 was followed, substituting thiophene-2-carboxylic acid amide for 3-methylbenzamide. (100 mg, 56.6%). $^1$H NMR (300 MHz, DMSO-d$_6$) δ 1.52 (m, 2H), 1.89 (d, J=12 Hz, 2H), 2.36 (m, 2H), 2.98 (d, J=12 Hz, 2H), 3.18 (m, 1H), 4.12 (d, J=6 Hz, 2H), 7.18 (dd, J=4.5, 3.0, 1H), 7.28 (m, 2H), 7.39 (dd, J=9.0, 3 Hz, 1H), 7.78 (dd, J=4.5, 1.5 Hz, 1H), 7.85 (dd, J=4.5, 1.5 Hz, 1H), 8.22 (dd, J=6, 1.5 Hz, 1H), 8.79 (t, J=6 Hz, 1H); MS (DCI/NH$_3$) m/e 297 (M+H−16)+; 313 (M+H)+.

EXAMPLE 316

2-[1-({[(6-chloropyridin-3-yl)carbonyl]amino}methyl)piperidin-4-yl]pyridinium N-oxide The procedure described in Example 200 was followed, substituting 6-chloronicotinamide for 3-methylbenzamide. $^1$H NMR (300 MHz, DMSO-d$_6$) δ 1.52 (m, 2H), 1.89 (d, J=12 Hz, 2H), 2.36 (m, 2H), 2.98 (d, J=12 Hz, 2H), 3.22 (m, 1H), 4.19 (d, J=6 Hz, 2H), 7.29 (m, 2H), 7.30 (dd, J=6, 1.5 Hz, 1H), 7.65 (d, J=9 Hz, 1H), 8.26 (m, 2H), 8.88 (d, J=3 Hz, 1H), 9.02 (t, J=6 Hz, 1H); MS (DCI/NH$_3$) m/e 331 (M+H−16)+; Anal. calcd for C$_{17}$H$_{19}$N$_4$O$_2$Cl.0.4 H$_2$O: C, 57.68; H, 5.64; N, 15.83. Found: C, 57.63; H, 65.45; N, 15.60.

EXAMPLE 317

2-(1-{[(3-cyanobenzoyl)amino]methyl}piperidin-4-yl)pyridinium N-oxide

The procedure described in Example 200 was followed, substituting 3-cyanobenzamide for 3-methylbenzamide. (55 mg, 55%). $^1$H NMR (300 MHz, CD$_3$OD) δ 1.73 (dd, J=12.5, 3.6 Hz, 2H), 2.11 (m, 2H), 2.69 (d, J=2.0 Hz, 2H), 3.27 (m, 2H), 3.46 (m, 1H), 4.43 (s, 2H), 7.41 (d, J=2.4 Hz, 1H), 7.56 (m, 2H), 7.70 (t, J=7.8 Hz, 1H), 7.96 (d, J=8.8 Hz, 1H), 8.18 (d, J=8.1 Hz, 1H), 8.24 (s, 1H), 8.34 (d, J=6.4 Hz, 1H), MS (ESI) m/e 337 (M+H)$^+$.

EXAMPLE 318

2-(1-{[(2,3-dibromo-5-methylbenzoyl)amino]methyl}-1,2,3,6-tetrahydropyridin-4-yl)pyridinium N-oxide The procedure described in Example 200 was followed, substituting the product from Example 300B for 3-methylbenzamide and the product from Example 313C for the product from Example 119A to give the title compound (4% yield) as a yellow solid. $^1$H NMR (300 MHz, CD$_3$OD); δ 2.35 (s, 3H), 2.65-2.73 (m, 2H), 2.80-2.85 (s, 2H), 3.10 (t, J=9 hz, 2H), 3.45-3.58 (m, 2H), 6.21 (m, 1H), 7.21 (d, J=3.1 Hz, 1H), 7.40-7.65 (m, 4H), 8.25 (d, J=9.0 Hz, 1H); MS (ESI–) m/e 479 (M–H)$^+$.

EXAMPLE 319

2-(1-{[(4-bromobenzoyl)amino]methyl}piperidin-4-yl)pyridinium N-oxide

The procedure described in Example 200 was followed, substituting 4-bromobenzamide for 3-methylbenzamide to provide the title compound (87 mg, 60% yield) as a white solid. $^1$H NMR (300 MHz, DMSO-d$_6$) δ 1.55 (q, J=1 1.9 Hz, 2H), 1.90 (d, J=11.9 Hz, 2H), 2.36 (t, J=11.9 Hz, 2H), 2.98 (d, J=11.5 Hz, 2H), 3.24 (m,1H), 4.18 (d, J=4.8 Hz, 2H), 7.29 (m, 2H), 7.39 (dd, J=7.8, 2.7 Hz, 1H), 7.69 (m, 2H), 7.84 (m, 2H), 8.24 (d, J=5.8 Hz, 1H), 8.89 (br s, 1H); MS (DCI/NH$_3$) m/e 390/392 (M+H)$^+$.

EXAMPLE 320

2-(1-{[(3-chloro-4-methylbenzoyl)amino]methyl}piperidin-4-yl)pyridinium N-oxide

The procedure described in Example 200 was followed, substituting 3-chloro-4-methylbenzamide for 3-methylbenzamide to provide the title compound (66 mg, 50% yield) as a white solid. $^1$H NMR (300 MHz, DMSO-d$_6$) δ 1.55 (q, J=11.9 Hz, 2H), 1.90 (d, J=11.9 Hz, 2H), 2.36 (t, J=11.9 Hz, 2H), 2.39 (s, 3H), 2.98 (d, J=11.5 Hz, 2H), 3.24 (m, 1H), 4.18 (d, J=4.8 Hz, 2H), 7.29 (m, 2H), 7.39 (dd, J=7.8,2.7 Hz, 1H), 7.48 (d, J=6.7 Hz, 1H), 7.80 (d, J=6.8 Hz, 1H), 7.94 (s, 1H), 8.24 (d, J=5.8 Hz, 1H), 8.89 (br s, 1H); MS (DCI/NH$_3$) m/e 360 (M+H)$^+$.

EXAMPLE 321

2-(1-{[methyl(3-methylbenzoyl)amino]methyl}piperidin-4-yl)pyridinium N-oxide

To a solution of the product from Example 200 (90 mg, 0.28 mmol) in N,N-dimethylformamide (4 mL) at cooled to 0° C. was added sodium hydride (121 mg, 0.88 mmol). To this mixture methyl iodide (106 mg, 0.35 mmol) was added. After 40 minutes at room temperature, the mixture was neutralized with acetic acid and concentrated. The residue was purified by flash column chromatography on silica gel (elution with 5-10% methanol:dichloromethane) to provide 85 mg (60% yield) of the title compound as a white solid. $^1$H NMR (300 MHz, DMSO-d$_6$) δ 1.52 (q, J=11.8, Hz, 2H), 1.89 (d, J=9.2 Hz, 2H), 2.04 (t, J=11.5 Hz, 2H), 2.35 (s, 3H), 2.77 (d, J=4.4 Hz, 3H), 2.92 (m, 2H), 3.16 (m, 1H), 3.32 (s, 2H), 7.24 (m, 1H), 7.30 (m, 4H), 7.40 (m, 1H), 7.62 (m, 1H), 8.24 (d, J=6.1 Hz, 1H); MS (DCI/NH$_3$) m/c 340 (M+H)$^+$.

EXAMPLE 322

2-(1-{[(3-nitrobenzoyl)amino]methyl}piperidin-4-yl) pyridinium N-oxide

The procedure described in Example 200 was followed, substituting 3-nitrobenzamide for 3-methylbenzamide to provide the title compound (28 mg, 26% yield) as an oil. $^1$H NMR (300 MHz, CD$_3$OD) δ 1.74 (m, 2H), 2.11 (m, 2H), 2.69 (m, 2H), 3.26 (m, 2H), 3.45 (m, 1H), 4.35 (s, 2H), 7.50 (m, 4H), 7.73 (m, 3H), 7.87 (d, J=8.1 Hz, 1H), 8.34 (d, J=6.4 Hz, 1H); MS (ESI) m/e 357 (M+H)$^+$; Anal. calcd for C$_{18}$H$_{20}$N$_4$O$_4$.2.0 C$_2$HF$_3$O$_2$: C, 45.21; H, 3.79; N, 9.59. Found: C, 45.58; H, 4.00; N, 9.72.

EXAMPLE 323

2-(1-{[(2-chloro-5-methylbenzoyl)amino]methyl}piperidin-4-yl)pyridinium N-oxide

The procedure described in Example 200 was followed, substituting 2-chloro-5-methylbenzamide for 3-methylbenzamide to provide the title compound (31 mg, 29% yield) as an oil. $^1$H NMR (300 MHz, CD$_3$OD) δ 1.74 (m, 2H), 2.08 (d, J=11.9 Hz, 1H), 2.35 (m, 2H), 2.67 (m, 2H), 2.84 (m, 1H), 3.15 (m, 2H), 3.42 (m, 2H), 4.34 (m, 2H), 7.34 (m, 4H), 7.55 (m, 2H), 7.71 (s, 1H), 8.34 (d, J=6.4 Hz, 1H); MS (ESI) m/e 360 (M+H)$^+$; Anal. calcd for C$_{19}$H$_{22}$ClN$_3$O$_2$.2.0 C$_2$HF$_3$O$_2$: C, 46.99; H, 4.11; N, 7.15. Found: C, 47.23; H, 3.96; N, 7.02.

EXAMPLE 324

2-(1-{[(3-methoxy-2-methylbenzoyl)amino]methyl}piperidin-4-yl)pyridinium N-oxide

EXAMPLE 324A 3-methoxy-2-methylbenzamide

A reaction mixture containing 3-methoxy-2-methylbenzoic acid (2 g, 12.04 mmol), 1-(3-dimethylaminopropyl)-3-ethylcarbodiimide hydrochloride (2.76 g, 14.4 mmol), 1-hydroxybenzotriazole hydrate (1.95 g, 14.4 mmol) in chloroform was stirred at room temperature for 1 hour. The reaction was quenched with 30% ammonium hydroxide solution (35 mL) and stirring continued for another 1.5 hours. The layers were separated, the organic phase dried over magnesium sulfate, filtered and concentrated under reduced pressure. The residue was purified by flash column chromatography on silica gel (50% ethyl acetate/hexanes) to afford a white powder (1.2 g, 60%). $^1$H NMR (300 MHz, CDCl$_3$) δ 2.3 (s, 3H), 3.82 (s, 3H), 6.9 (d, 1H, J=9 Hz), 7.02 (d, 1H, J=9 Hz), 7.18 (t, 1H, J=9 Hz); MS (DCI/NH$_3$) m/e 166 (M+H)$^+$.

EXAMPLE 324B 2-(1-{[(3-methoxy-2-methylbenzoyl)amino]methyl}piperidin-4-yl)pyridinium N-oxide The procedure described in Example 200 was followed, substituting the product in Example 325A for 3-methylbenzamide to provide the title compound (45 mg, 16%) as a white solid. $^1$H NMR (300 MHz, CDCl$_3$) δ 1.45-1.55 (m, 2H), 2.05-2.15 (m, 2H), 2.25 (s, 3H), 2.55-2.65 (m, 2H), 3.05-3.10 (m, 2H), 3.40-3.50 (m, 1H), 3.81 (s, 3H), 4.40 (d, 2H, J=6 Hz), 6.4 (br s, 1H), 6.85 (d, 1H, J=9 Hz,), 7.0 (d, 1H, J=9 Hz), 7.10-7.20 (m, 2H), 7.25-7.32 (m, 2H), 8.20 (d, 1H, J=6 Hz); MS (DCI/NH$_3$) m/e 356 (M+H)$^+$; Anal. calcd for C$_{20}$H$_{25}$N$_3$O$_3$: C, 67.58; H, 7.09; N, 11.82. Found: C, 67.29; H, 7.20; N, 11.87.

EXAMPLE 325

2-(1-{[(4-chloro-3-methoxybenzoyl)amino]methyl}piperidin-4-yl)pyridinium N-oxide

EXAMPLE 325A 4-chloro-3-methoxybenzamide

The procedure described in Example 325A was followed, substituting 3-methoxy-4-chlorobenzoic acid for 3-methoxy-2-methylbenzoic acid to provide the title compound (1.5 g, 75% yield) as a white solid. $^1$H NMR (300 MHz, DMSO-d$_6$) δ 3.9 (s, 3H), 7.42-7.52 (m, 2H), 7.6 (d, 1H, J=3 Hz), 8.08 (s, 2H); MS (DCI/NH$_3$) m/e 203 (M+NH$_4$)$^+$.

EXAMPLE 325B 2-(1-{[(4-chloro-3-methoxybenzoyl)amino]methyl}piperidin-4-yl)pyridinium N-oxide The procedure described in Example 200 was followed, substituting the product in Example 326A for 3-methylbenzamide to provide the title compound (75 mg, 17%) as a yellow solid. $^1$H NMR (300 MHz, CDCl$_3$) δ 1.6-1.68 (m, 2H), 2.05-2.20 (m, 2H), 2.50-2.65 (m, 2H), 3.05-3.20 (m, 2H), 3.42-3.55 (m, 1H), 3.98 (s, 3H), 4.40 (d, 2H, J=6 Hz), 6.65 (br s, 1H), 7.15 (m, 1H), 7.2-7.35 (m, 3H), 7.40 (d, 1H, J=9 Hz), 7.45 (d, 1H, J=3 Hz), 8.22 (d, 1H, J=6 Hz); MS (DCI/NH$_3$) m/e 376 (M+H)$^+$; Anal. calcd for C$_{19}$H$_{22}$ClN$_3$O$_3$: C, 60.72; H, 5.90; N, 11.18. Found: C, 60.44; H, 5.84; N, 10.97.

EXAMPLE 326

N-(3-methylphenyl)-2-(3-pyridin-2-ylpiperidin-1-yl)acetamide

EXAMPLE 326A tert-butyl 5',6'-dihydro-2,3'-bipyridine-1'(2'H)-carboxylate

The procedure described in Example 328C was followed, substituting 2-pyridylzinc bromide for 2-thiazolylzinc bromide to provide the title compound (92%). MS (DCI/NH$_3$) m/e 261 (M+H)$^+$.

EXAMPLE 326B tert-butyl 3-pyridin-2-ylpiperidine-1-carboxylate

The procedure described in Example 328D was followed, substituting the product from Example 326A for the product from Example 328C to provide the title compound (93%). MS (DCI/NH$_3$) m/e 263 (M+H)$^+$.

EXAMPLE 326C 2-piperidin-3-ylpyridine

The procedure described in Example 328E was followed, substituting the product from Example 326B for the product from Example 328D to provide the title compound.

EXAMPLE 326D

N-(3-methylphenyl)-2-(3-pyridin-2-ylpiperidin-1-yl)acetamide

The procedure described in Example 33C was followed, substituting the product from Example 326C for the product from Example 33B to provide the title compound (xx %). $^1$H NMR (300 MHz, CDCl$_3$) δ 1.71 (m, 4H), 2.04 (m, 1H), 2.36 (s, 3H), 2.43 (m, 1H), 2.65 (m, 1H), 2.92 (m, 1H), 3.15 (m, 3H), 6.91 (d, J=7.5 Hz, 1H), 7.19 (m, 3H), 7.39 (m, 2H), 7.638 (t, J=7.5 Hz, 1H), 8.53 (m, 1H), 9.25 (bs, 1H); MS (DCI/NH$_3$) m/e 310 (M+H)$^+$; Anal. calcd for C$_{19}$H$_{23}$N$_3$O: C, 73.76; H, 7.49; N, 13.58. Found: C, 73.93; H, 7.42; N, 13.53.

EXAMPLE 327

N-(3-methylphenyl)-2-(3-pyridin-2-ylpyrrolidin-1-yl)acetamide

The procedure described in Example 232B was followed, substituting 2-pyrrolidin-3-ylpyridine for the product from Example 232A to provide the title compound (21% yield) as a yellow oil. $^1$H NMR (300 MHz, CD$_3$OD); δ 2.06-2.12 (m, 1H), 2.15-2.23 (m, 4H), 2.84-2.98 (m, 1H), 3.0-3.10 (m, 2H), 3.12-3.20 (m, 1H), 3.25 (d, J=12.0 Hz, 1H), 3.45 (d, J=12.0 Hz, 1H), 3.50-3.65 (m, 1H), 6.93 (d, J=9.0 Hz, 1H), 7.06-7.13 (m, 2H), 7.18-7.23 (m, 2H), 7.62 (ddd, J=6.5, 6.1, 3.3 Hz, 1H). 8.59 (d, 6.0 Hz, 1H), 7.38 (s, 1H); MS (DCI/NH$_3$) m/e 296; Anal. calcd for C$_{18}$H$_{21}$N$_3$O: C, 73.19; H, 7.17; N, 14.23. Found: C, 72.88; H, 7.01; N, 13.91.

EXAMPLE 328

N-(1-methyl-1H-benzimidazol-2-yl)-2-[3-(1,3-thiazol-2-yl)piperidin-1-yl]acetamide

EXAMPLE 328A tert-butyl 3-oxopiperidine-1-carboxylate

A solution of 1-benzylpiperidin-3-one (22.06 g, 116.6 mmol, Acros), 20% palladium hroxide on carbon (2.50 g), di-tert-butyl dicarbonate (22.37 g, 102.5 mmol) and triethylamine (13.9 mL) in methanol (200 mL) was placed under 60 psi of hydrogen at 50° C. for 40 minutes. The solution was cooled to room temperature, filtered and concentrated to provide the title compound. $^1$H NMR (300 MHz, DMSO-d$_6$) δ 1.48 (s, 9H), 1.99 (m, 2H), 2.47 (m, 2H), 3.59 (m, 2H), 4.00 (s, 2H); MS (DCI/NH$_3$) m/e 200 (M+H)$^+$; 217 (M+NH$_4$)$^+$.

EXAMPLE 328B tert-butyl 5-{[(trifluoromethyl)sulfonyl]oxy}-3,6-dihydropyridine-1(2H)-carboxylate A mixture of diisopropylamine (13.1 mL, 110 mmol) and tetrahydrofuran (150 mL) was cooled to −10° C. To the mixture was added n-butyllithium (2.5M in hexane, 44 mL, 110 mmol) via syringe. The mixture was stirred for 30 minutes, cooled to −78° C. and a solution of the product from Example 328A (16 g, 80 mmol) was added as a solution in tetrahydrofuran (50 mL). The mixture was stirred for 15 minutes and then added solution of N-phenyl-bis-trifluoromethnaesulfonamide (35.0 g, 110 mmol) dissolved in tetrahydrofuran (60 mL). The reaction was allowed to warm to room temperature, quenched with saturated sodium bicarbonate solution (75 mL) and diluted with diethyl ether. The layers were separated and the organic phase washed with brine, dried with magnesium sulfate and concentrated under reduced pressure. The residue was purified by flash column chromatography (silica gel, 5% ethyl acetate:hexanes) to obtain desired triflate as an oil (7.8 g, 24%). MS (DCI/NH$_3$) m/e 333 (M+H)$^+$.

EXAMPLE 328C tert-butyl 5-(1,3-thiazol-2-yl)-3,6-dihydropyridine-1 (2H)-carboxylate To the mixture of 2-thiazolylzinc bromide (20 mL, 10 mmol) in dry tetrahydrofuran (30 mL) at 0° C. was added the product from Example 328B (3.3 gm, 10 mmol) and tetrakis (tripehynlphosphine) palladium (0) (10% mole 1.1 g). The mixture was heated at 50° C. for 1 hour, cooled to room temperature, quenched with brine and extracted with ethyl acetate. The organic layer was dried with magnesium sulfate, filtered and concentrated under reduced pressure. The residue was purified by flash column chromatography (silica gel, 25% ethyl acetate:hexanes) to obtain desired product 1.4 g (60%) as colorless oil. MS (DCI/NH$_3$) m/e 265 (M+H)$^+$.

EXAMPLE 328D tert-butyl 3-(1,3-thiazol-2-yl)piperidine-1-carboxylate

A solution of the product from Example 328C in methanol (50 mL) and 20% palladium over carbon (0.7 g) was placed under 1 atmosphere of hydrogen pressure for 4 days at room temperature. The reaction was filtered and concentrated under reduced pressure to provide the title compound (1.42 g, 100%). MS (DCI/NH$_3$) m/e 267 (M+H)$^+$.

EXAMPLE 328E 3-(1,3-thiazol-2-yl)piperidine

A solution of the product from Example 328D (1.2 g, 4.5 mmol) in 25% trifluoroacetic acid/dichloromethane (10 mL) was stirred at room temperature for 2 hours. The reaction was concentrated under reduced pressure to provide the title compound 0.70 g (76%) as yellow color oil. This compound was used directly in the next reaction.

EXAMPLE 328F

N-(1-methyl-1H-benzimidazol-2-yl)-2-[3-(1,3-thiazol-2-yl)piperidin-1-yl]acetamide The procedure described in Example 247B was followed, substituting 2-chloro-N-(1-methyl-1H-benzoimidazol-2-yl) acetamide (Caroti, P.; et al. Farmaco 1989, 44, 227) for the product from Example 247A and substituting the product from Example 328E for 1-(2-cyanopyridyl)piperazine to provide the title compound (23%) as a yellow oil. $^1$H NMR (300 MHz, CD$_3$OD); δ 1.80-1.88 (m, 1H), 1.90-1.95 (m, 2H), 2.05-2.10 (m, 1H), 2.45-2.68 (m, 4H), 2.98-3.05 (m, 2H), 3.21-3.26 (m, 1H), 3.65 (s, 3H), 7.20-7.38 (m, 2H), 7.42-7.58 (m, 3H), 7.65 (d, J=3.1 Hz, 1H); Anal. calcd for C$_{18}$H$_{21}$N$_5$OS: C, 60.21; H, 6.01; N, 19.50. Found: C, 60.20; H, 5.84; N, 19.16.

EXAMPLE 329

N-(1-methyl-1H-benzimidazol-2-yl)-2-[3-(1,3-thiazol-2-yl)pyrrolidin-1-yl]acetamide

EXAMPLE 329A tert-butyl 3-oxopyrrolidine-1-carboxylate

The procedure described in Example 328A was followed, substituting 1-benzylpyrrolidin-3-one (Acros) for 1-benzylpiperidin-3-one to provide the title compound. MS (DCI/NH$_3$) m/e 186 (M+H)$^+$; 203 (M+NH$_4$)$^+$.

EXAMPLE 329B tert-butyl 3-{[(trifluoromethyl)sulfonyl]oxy}-2,5-dihydro-1H-pyrrole-1-carboxylate The procedure described in Example 328B was followed, substituting the product from Example 329A for the product from Example 328A to provide the title compound. $^1$H NMR (300 MHz, CDCl$_3$) δ 5.71-5.76 (m, 1H), 4.22 (m, 4H), 1.48 (s, 9H); MS (DCI/NH$_3$) m/e 318 (M+H)$^+$.

EXAMPLE 329C tert-butyl 3-(1,3-thiazol-2-yl)-2,5-dihydro-1H-pyrrole-1-carboxylate The procedure described in Example 143A was followed, substituting 2-thiazolylzinc bromide for 3-methyl-2-pyridylzinc bromide and the product from Example 329B for 4-trifluoromethanesulfonyloxy-3,6-dihydro-2H-pyridine-1-carboxylic acid tert-butyl ester to provide the title compound. MS (DCI/NH$_3$) m/e 253 (M+H)$^+$; 270 (M+NH$_4$)$^+$.

EXAMPLE 329D tert-butyl 3-(1,3-thiazol-2-yl)pyrrolidine-1-carboxylate

The procedure described in Example 224 was followed, substituting the product from Example 329B for the product from Example 166C to provide the title compound (45% yield) as a yellow oil. $^1$H NMR (300 MHz, DMSO-d$_6$) δ 1.47 (s, 9H), 2.36 (m, 2H), 3.73 (m, 5H), 7.25 (d, 1H, J=3.4 Hz), 7.71 (d, 1H, J=3.1 Hz); MS (DCI/NH$_3$) m/e 255 (M+H)$^+$.

EXAMPLE 329E 2-pyrrolidin-3-yl-1,3-thiazole

The procedure described in Example 166B was followed, substituting the product from Example 329C for the product from Example 166A to provide the title compound (81% yield) as a yellow solid. $^1$H NMR (300,MHz, DMSO-d$_6$) δ 2.12 (m, 1H), 2.43 (m, 1H), 3.35 (m, 3H), 3.64 (m, 1H), 3.98 (m, 1H), 7.71 (d, 1H, J=3.4 Hz), 7.78 (d, 1H, J=3.1 Hz), 8.99 (br s, 1H); MS (DCI/NH$_3$) m/e 155 (M+H)$^+$.

EXAMPLE 329F

N-(1-methyl-1H-benzimidazol-2-yl)-2-[3-(1,3-thiazol-2-yl)pyrrolidin-1-yl]acetamide The procedure described in Example 247B was followed, substituting 2-chloro-N-(1-methyl-1H-benzoimidazol-2-yl) acetamide (Caroti, P.; et al. Farmaco 1989, 44, 227) for the product from Example 247A and substituting the product from Example 329D for 1-(2-cyanopyridyl)piperazine to provide the title compound (23% yield) as a yellow oil. $^1$H NMR (300 MHz, CD$_3$OD); δ 2.51-2.65 (m, 1H), 2.68-3.25 (m, 1H), 3.62 (s, 2H), 3.85 (t, J=3.0 Hz, 1H), 4.15-4.24 (m, 4H), 4.92 (s, 3H), 7.13-7.25 (m, 4H), 7.58 (d, J=3.0 Hz, 1H), 7.80 (d, J=3.0 Hz, 1H); MS (DCI/NH$_3$) m/e 242; Anal. calcd for C$_{17}$H$_{19}$N$_5$OS: C, 59.80; H, 5.61; N, 20.51. Found: C, 59.61; H, 5.42; N, 20.86.

EXAMPLE 330

2-(2-benzylpyrrolidin-1-yl)-N-(3-fluorophenyl)acetamide

The procedure described in Example 247B was followed, substituting the product from Example 254A for the product from Example 247A and substituting 3-benzylpyrrolidine (Array) for 1-(2-cyanopyridyl)piperazine to provide the title compound (21% yield) as a yellow oil. $^1$H NMR (300 MHz, CD$_3$OD); δ 1.58-1.92 (m, 4H), 2.38-2.42 (m, 1H), 2.58-2.70 (m, 1H), 2.83-3.02 (m, 2H), 3.10 (d, J=12.0 Hz, 1H), 3.09-3.23 (m, 1H), 3.25-3.31 (m, 1H), 3.58 (d, J=12.0 Hz, 1H), 6.80-6.85 (m, 1H), 7.12-7.37 (m, 6H), 7.55 (dt, J=9.0, 3.0 Hz, 1H); MS (DCI/NH$_3$) m/e 313; Anal. calcd for C$_{19}$H$_{21}$N$_2$OF.0.10 H$_2$O: C, 72.63; H, 6.80; N, 8.92. Found: C, 72.51; H, 6.88; N, 8.82.

Example 331

N-(4-fluorophenyl)-2-(3-thien-2-ylpyrrolidin-1-yl) acetamide

Example 331A tert-butyl 3-thien-2-yl-2,5-dihydro-1H-pyrrole-1-carboxylate

To a solution of the product from Example 329B (3.65 gm, 11.5 mmol) in tetrahydrofuran (20 mL) added a solution of 2-thienylzinc bromide (40 mL, 20 mmol, 0.5 M soln.) in dry tetrahydrofuran followed by addition of tetrakis(triphenylphosphine) palladium (0) (9% mole, 1.20 g) under inert atmosphere at room temperature. The mixture was heated at 50° C. for 2 hours. The reaction was cooled to room temperature, quenched with aqueous sodium bicarbonate and extracted with ethyl acetate (3×30 ml). The organic layers were combined, washed with brine, dried with sodium sulfate concentrated under reduced pressure and purified by flash column chromatography (silica gel, 10:1 hexanes:ethyl acetate) to provide the desired compound as an oil (1.50 g, 54%). $^1$H NMR (300 MHz, CDCl$_3$) δ 7.23 (d, J=5 Hz, 1H), 7.00 (dd, J=5 Hz, 3 Hz, 1H), 6.94 (m, 1H), 5.93-5.99 (m, 1H), 4.25-4.49 (m, 4H), 1.50 (m, 9H); MS (DCI/NH$_3$) m/e 252 (M+H)$^+$.

Example 331B tert-butyl 3-thien-2-ylpyrrolidine-1-carboxylate

A solution of the product from Example 331A (1.25 g, 5 mmol) in methanol (100 mL) was treated with 20% palladium on carbon (0.7 g) and placed under 60 psi of hydrogen pressure at room temperature overnight. The solution was filtered and concentrated to give the desired compound (1.10 g, 92%). $^1$H NMR (300 MHz, CDCl$_3$) δ 7.17 (d, J=5, 1 Hz, 1H), 6.95 (dd, J=5, 4 Hz, 1H), 6.87 (m, 1H), 3.39-3.82 (m, 5H), 2.32 (m, 1H), 2.02 (m, 1H), 1.47 (m, 9H); MS (DCI/NH$_3$) m/e 254 (M+H)$^+$.

Example 331C 3-thien-2-ylpyrrolidine

The product from Example 331B (1.3 g, 5.13 mmol) was treated with 50% trifluoroacetic acid/dichloromethane (20 mL) for 2 hours at room temperature. The reaction was concentrated under reduced pressure, basified with 2N sodium hydroxide and extracted with dichloromethane (3×20 mL). The organic layer was combined, washed with brine and dried to give the desired product (0.62 g, 79%) as a yellow oil. $^1$H NMR (300 MHz, CDCl$_3$) δ 7.14 (d, J=5, 1 Hz, 1H), 6.93 (dd, J=5, 4 Hz, 1H), 6.83 (m, 1H), 3.51 (m, 1H), 3.33 (m, 1H), 3.14 (m, 1H), 3.05 (m, 1H), 2.91 (m, 1H), 2.28 (m, 1H), 1.91 (m, 1H); MS (DCI/NH$_3$) m/e 154 (M+H)$^+$.

Example 331D

N-(4-fluorophenyl)-2-(3-thien-2-ylpyrrolidin-1-yl) acetamide

The procedure described in Example 247B was followed, substituting the product from Example 331C for 1-(2-cyanopyridyl)piperazine and substituting 2-chloro-N-(4-fluorophenyl)acetamide (Maybridge) for 247A to provide the title compound (23% yield). $^1$H NMR (300 MHz, DMSO-d$_6$) δ 2.14 (m, 1H), 3.20-4.00 (m, 6H), 4.33 (s, 2H), 7.03 (m, 2H), 7.21 (dd, 2H, J=8.8, 8.8 Hz), 7.46 (dd, 1H, J=5.1, 1.0 Hz), 7.61 (m, 2H), 10.50 (br s, 1H), 10.66 (s, 1H); MS (DCI/NH$_3$) m/e 305 (M+H)$^+$.

In Vitro

Data

Functional Activity of D$_4$

Efficacies and potencies of compounds of the present invention at the human D$_4$ receptor were determined using a stable cell line containing the human D$_{4.4}$ receptor and a chimeric G protein in HEK-293 cells. This cell line allows a robust calcium signal detectable using a calcium fluorescent dye and a fluorescent imaging plate reader (FLIPR) (Coward et al., Anal. Biochem. 270: 242-248, 1999). Cells were plated (20000/well) into 96 well dishes and cultured for 48 hours. Media is removed, Fluo-4 dye added and cells incubated 1 hour at room temperature. Cells are washed with phosphate buffered saline to remove excess dye and the compounds to be tested are added to the wells and signal measured in FLIPR. Percent efficacy is the maximum response produced by the compound in relation to the maximum effect of 10 μM dopamine. The EC$_{50}$ is the effective concentration of the compound that causes 50% of the compound's maximum response.

Chimeric G-proteins allow a high-throughput signaling assay of Gi-coupled receptors, P. Coward, S. Chan, H. Wada, G. Humpries and B. Conklin, Analytical Biochemistry 270, 242-248 (1999).

Representative compounds of the present invention exhibited $EC_{50s}$ in the range of about 0.8 nM to about 5200 nM.

In Vivo Data

Rat Penile Erection Model

Wistar rats were used as a primary animal model to study penile erection in vivo. All experiments were carried out between 9:00 AM and 3:00 PM in a diffusely illuminated testing room with a red light. Animals were weighed and allowed to adapt to the testing room for 60 minutes before the beginning of experiments. Rats were placed individually in a transparent cage (20×30×30 cm) after drug injection. The number of penile erections were recorded by direct observation for a period of 60 minutes after drug dosing, and the number of animals exhibiting 1 or more erections was expressed as incidence (%). (L)-Ascorbic acid in saline (1 mg/mL) was used as vehicle and apomorphine was used as a positive control at a dose of 0.1 μmol/kg.

Representative compounds of the present invention induced a minimum of 30% incidence of penile erections in rats after subcutaneous administration at doses of 0.003 μmol/kg to 3 μmol/kg.

The in vitro and in vivo data demonstrates that compounds of the present invention are dopamine $D_4$ receptor agonists that induce penile erections in mammals.

Compounds of the present invention are dopamine $D_4$ receptor agonists and are useful for the treatment of male sexual dysfunction, female sexual dysfunction, attention deficit hyperactivity disorder, Alzheimer's disease, drug abuse, Parkinson's disease, anxiety, schizophrenia, mood disorders and depression, as described in: The dopamine $D_4$ receptor: a controversial therapeutic target, N.J. Hrib, Drugs of the future 25:587-611 (2000); Dopamine and sexual behavior, M. Melis and A. Argiolas, Neuroscience and Biobehavioral Reviews 19:19-38 (1995); and Dopamine receptors: from structure to function, C. Missale, S. R. Nash, S. Robinson, M. Jabber and M. Caron, Physiological Reviews 78: 189-225 (1998).

Compounds of the present invention are dopamine $D_4$ receptor agonists and are useful for the treatment of cardiovascular disorders. Dopamine and dopaminergic agents have been reported to exert pharmacologically significant cardiovascular effects on blood pressure and heart rate and are useful in the treatment of cardiovascular disorders, as described in: Chen F F, and Lin M T, Effects of dopamine, apomorphine gamma-hydroxybutyric acid, haloperidol, and pimozide on reflex bradycardia in rats, Journal of Pharmacology and Experimental Therapeutics (1980) 214: 427-432; and it has been reported that primate data support the potential clinical utility of dopamine receptor agonists in treating cardiovascular disease, as described in: Hahn, R A and Mac-Donald B R, Primate cardiovascular responses meditated by dopaminine receptors: effects of N,N-dipropyldopamine and LY171555, Journal of Phamacology and Experimental Therapeutics (1984) 229: 132-138.

Compounds of the present invention are dopamine $D_4$ receptor agonists and are useful for the treatment of inflammation. Dopaminergic agents can exert anti-inflammatory effects and are useful for the treatment of diseases where inflammation plays a deleterious role, as described in: Bendele A M, Spaethe S M, Benslay D N, and Bryant H U, Anti-inflammatory activity of pergolide, a dopamine receptor agonist, in Journal of Pharmacology of Pharmacology and Experimental Therapeutics (1991) 259 169-175. Dopaminergic agents can also be of utility in the treatment of cancers, as described in: Lissoni P, Mandala M, Giani L, Malugani F, Secondino S, Zonato S, Rocco F, Gardani G, Efficacy of Bromocriptine in the Treatment of Metastatic Breast Cancer and Prostate Cancer-related Hyperprolactinemia, Neuroendocrinology Letters (2000) 21 405-408.

The term agonist, as used herein, means a compound of the present invention that exhibits 30% or greater efficacy in the in vitro assay described herein.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The present invention provides pharmaceutical compositions which comprise compounds of the present invention formulated together with one or more non-toxic pharmaceutically acceptable carriers.

Dosage forms for topical administration of a compound of the present invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

When used in the above or other treatments, a therapeutically effective amount of one of the compounds of the present invention can be employed in pure form or, where such forms exist, in pharmaceutically acceptable salt, ester, amide, or prodrug form. Alternatively, the compound can be administered as a pharmaceutical composition containing the compound of interest in combination with one or more pharmaceutically acceptable carriers. The phrase "therapeutically effective amount" of the compound of the present invention means a sufficient amount of the compound to treat disorders, at a reasonable benefit/risk ratio applicable to any medical treatment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of the present invention administered to a mammal, and particularly a human, may range from about 0.001 to about 30 mg/kg/day. For purposes of oral administration, more preferable doses can be in the range of from 0.01 to about 10 mg/kg/day. If desired, the effective daily dose can be divided into multiple doses for purposes of administration; consequently, single dose compositions may contain such amounts or submultiples thereof to make up the daily dose.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Suspensions, in addition to the active compounds, may contain agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of the present invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

The present invention contemplates pharmaceutically active compounds either chemically synthesized or formed by in vivo biotransformation to compounds of formula (I).

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The term "pharmaceutically acceptable salt, ester, amide, and prodrug" as used herein, refers to carboxylate salts, amino acid addition salts, zwitterions, esters, amides, and prodrugs of compounds of formula (I) which are within the scope of sound medical judgement, suitable for use in contact with the tissues of humans and lower animals without undue toxicity, irritation, allergic response, and the like, are commensurate with a reasonable benefit/risk ratio, and are effective for their intended use.

The compounds of the present invention can be used in the form of pharmaceutically acceptable salts derived from inorganic or organic acids. The term "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. The salts can be prepared in situ during the final isolation and purification of the compounds of the present invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, sulfate, bis(tartrate), tartrate, (L) tartrate, bis((L) tartrate), (D) tartrate, bis((L) tartrate), (DL) tartrate, bis((DL) tartrate), mesotartrate, bis(meso tartrate), thiocyanate, phosphate, glutamate, bicarbonate, p-toluenesulfonate and undecanoate. Examples of acids which can be employed to form pharmaceutically acceptable acid addition salts include such inorganic acids as hydrochloric acid, hydrobromic acid, sulphuric acid and phosphoric acid and such organic acids as maleic acid, fumaric acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Preferred salts of the compounds of the present invention include phosphate, tris and acetate.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to compounds of formula (I), for example, by hydrolysis in blood.

The term "pharmaceutically acceptable ester" or "ester" as used herein, refers to esters of compounds of the present invention which hydrolyze in vivo and include those that break down readily in the human body to leave the parent compound or a salt thereof. Examples of pharmaceutically acceptable, non-toxic esters of the present invention include $C_1$-to-$C_6$ alkyl esters and $C_5$-to-$C_7$ cycloalkyl esters, although $C_1$-to-$C_4$ alkyl esters are preferred. Esters of the compounds of formula (I) may be prepared according to conventional methods.

The term "pharmaceutically acceptable amide" or "amide" as used herein, refers to non-toxic amides of the present invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) may be prepared according to conventional methods.

What is claimed is:

1. A method of treating sexual dysfunction in a mammal comprising administering to said mammal in need of such treatment a therapeutically effective amount of a compound of formula (I)

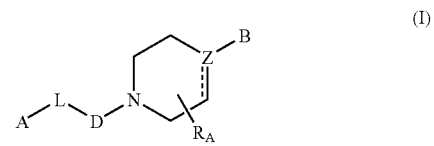

or a pharmaceutically acceptable salt thereof, wherein
  A is selected from the group consisting of aryl, arylalkyl, cycloalkyl, cycloalkylalkyl, heterocycle, and heterocyclealkyl;
  L is selected from the group consisting of —N($R_7$)C(O)—, and —C(O)N($R_7$)—, wherein the left end of said —N($R_7$)C(O)—, or —C(O)N($R_7$)—, is attached to A and the right end is attached to D;
  D is selected from the group consisting of alkylene, fluoroalkylene, and hydroxyalkylene;
  Z is selected from the group consisting of C and $CR_B$, wherein $R_B$ is hydrogen;
  $R_A$ is selected from the group consisting of hydrogen and alkyl;
  ⸺ is a bond when Z is C and ⸺ is absent when Z is $CR_B$;
  B is selected from the group consisting of:

R₁, R₂, R₃, R₄ and R₅ are each independently selected from the group consisting of hydrogen, alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, —NZ₁Z₂, (NZ₃Z₄)carbonyl, and (NZ₃Z₄)sulfonyl;

Z₁ and Z₂ are each independently selected from the group consisting of hydrogen, alkyl, alkylcarbonyl, alkylsulfonyl, aryl, arylalkyl, arylalkylsulfonyl, arylsulfonyl, and formyl;

Z₃ and Z₄ are each independently selected from the group consisting of hydrogen, alkyl, aryl, and arylalkyl;

X is selected from the group consisting of N(R₆), O and S;

Y is selected from the group consisting of C(R₄) and N;

R₆ is selected from the group consisting of hydrogen and alkyl; and

R₇ is selected from the group consisting of hydrogen and alkyl.

2. The method according to claim 1 wherein

A is aryl;

B is

Z is N;

— is absent; and

L is —N(R₇)C(O)—.

3. The method according to claim 1 wherein

A is aryl wherein the aryl is phenyl substituted with 0, 1, 2, 3, 4, or 5 substituents selected from the group consisting of alkenyl, alkoxy, alkoxycarbonyl, alkyl, alkythio, benzyl, cyano, halogen, haloalkoxy, haloalkyl, methylenedioxy, nitro, phenyl, and —NZ₁Z₂;

B is

R₁, R₂, R₃, and R₄ are hydrogen;

Z is CR$_B$;

— is absent;

D is —CH₂—; and

L is —N(R₇)C(O)—.

4. The method according to claim 1 wherein

A is aryl;

B is

Z is CR$_B$;

— is absent; and

L is —C(O)N(R₇)—.

5. The method according to claim 1 wherein

A is aryl wherein the aryl is phenyl substituted with 0, 1, 2, 3, 4, or 5 substituents selected from the group consisting of alkenyl, alkoxy, alkoxycarbonyl, alkyl, alkythio, benzyl, cyano, halogen, haloalkoxy, haloalkyl, methylenedioxy, nitro, phenyl, and —NZ₁Z₂;

B is

R₁ is selected from the group consisting of hydrogen, alkyl, cyano, haloalkyl, halogen, nitro, (NZ₃Z₄)alkyl, and (NZ₃Z₄)carbonyl;

R₂ and R₄ are hydrogen;

R₃ is selected from the group consisting of hydrogen and hydroxy;

Z is CR$_B$;

R$_B$ id hydrogen;

— is absent;

D is —CH₂—; and

L is —C(O)N(R₇)—.

6. The method according to claim 1 wherein
A is aryl;
B is

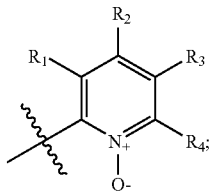

Z is CR$_B$;
— is absent; and
L is —C(O)N(R$_7$)—.

7. The method according to claim 1 wherein
A is aryl wherein the aryl is phenyl substituted with 0, 1, 2, 3, 4, or 5 substituents selected from the group consisting of alkenyl, alkoxy, alkoxycarbonyl, alkyl, alkylthio, benzyl, cyano, halogen, haloalkoxy, haloalkyl, methylenedioxy, nitro, phenyl, and —NZ$_1$Z$_2$;
B is

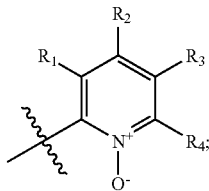

R$_1$, R$_2$, R$_3$, and R$_4$ are hydrogen;
Z is CR$_B$;
R$_B$ is hydrogen;
— is absent;
D is —CH$_2$—; and
L is —C(O)N(R$_7$)—.

8. The method according to claim 1 wherein the compound of formula (I) is selected from the group consisting of
N-(3-methylphenyl)-2-[4-(2-pyridinyl)-1-piperidinyl]acetamide;
N-(4-bromophenyl)-2-[4-(2-pyridinyl)-1-piperidinyl]acetamide;
N-(2,6-dimethylphenyl)-2-[4-(2-pyridinyl)-1-piperidinyl]acetamide;
N-(2-nitrophenyl)-2-[4-(2-pyridinyl)-1-piperidinyl]acetamide;
N-(3-nitrophenyl)-2-[4-(2-pyridinyl)-1-piperidinyl]acetamide;
N-(2,4-difluorophenyl)-2-[4-(2-pyridinyl)-1-piperidinyl]acetamide;
N-(2,5-dimethylphenyl)-2-[4-(2-pyridinyl)-1-piperidinyl]acetamide;
N-(2-methylphenyl)-2-[4-(2-pyridinyl)-1-piperidinyl]acetamide;
N-(4-methylphenyl)-2-[4-(2-pyridinyl)-1-piperidinyl]acetamide;
2-[4-(2-pyridinyl)-1-piperidinyl]-N-[3-(trifluoromethyl)phenyl]acetamide;
ethyl 4-({[4-(2-pyridinyl)-1-piperidinyl]acetyl}amino)benzoate;
N-(3-chloro-4-methylphenyl)-2-[4-(2-pyridinyl)-1-piperidinyl]acetamide;
N-(2-cyanophenyl)-2-[4-(2-pyridinyl)-1-piperidinyl]acetamide;
N-(3-chlorophenyl)-2-[4-(2-pyridinyl)-1-piperidinyl]acetamide;
2-[4-(3-cyano-2-pyridinyl)-1-piperidinyl]-N-(3-methylphenyl)acetamide;
N-(4-fluorophenyl)-2-[4-(2-pyridinyl)-1-piperidinyl]acetamide;
N-(3,5-dichlorophenyl)-2-[4-(2-pyridinyl)-1-piperidinyl]acetamide;
N-(2,3-dichlorophenyl)-2-[4-(2-pyridinyl)-1-piperidinyl]acetamide;
2-[4-(2-pyridinyl)-1-piperidinyl]-N-[2-(trifluoromethyl)phenyl]acetamide;
N-(3-chloro-4-fluorophenyl)-2-[4-(2-pyridinyl)-1-piperidinyl]acetamide;
2-[4-(2-pyridinyl)-1-piperidinyl]-N-[4-(trifluoromethoxy)phenyl]acetamide;
N-Cyclohexyl-2-(3',4',5',6'-tetrahydro-2'H-[2,4']bipyridinyl-1'-yl)acetamide;
N-{[4-(2-methoxyphenyl)-1-piperidinyl]methyl}-3-methylbenzamide;
3-methyl-N-{[4-(2-pyridinyl)-1-piperidinyl]methyl}benzamide;
2-(1-{2-[(3-methylphenyl)amino]-2-oxoethyl}piperidin-4-yl)pyridiniumn N-oxide;
N-{[4-(2-pyridinyl)-1-piperidinyl]methyl}-3-(trifluoromethyl)benzamide;
3,5-dimethoxy-N-{[4-(2-pyridinyl)-1-piperidinyl]methyl}benzamide;
N-{[4-(2-pyridinyl)-1-piperidinyl]methyl }cyclohexanecarboxamide;
3,4-difluoro-N-{[4-(2-pyridinyl)-1-piperidinyl]methyl}benzamide;
3-chloro-N-{[4-(2-pyridinyl)-1-piperidinyl]methyl}benzamide;
N-(3-methylphenyl)-2-(4-phenyl-1-piperidinyl)acetamide;
3,5-dimethyl-N-{[4-(2-pyridinyl)-1-piperidinyl]methyl}benzamide;
N-(2,6-diethylphenyl)-2-[4-(2-pyridinyl)-1-piperidinyl]acetamide;
2-[4-(2-pyridinyl)-1-piperidinyl]-N-(2,4,6-trifluorophenyl)acetamide;
N-(4-chloro-2,6-dimethylphenyl)-2-[4-(2-pyridinyl)-1-piperidinyl]acetamide;
2-[4-(2-pyridinyl)-1-piperidinyl]-N-(2,4,6-trichlorophenyl)acetamide;
2-[4-(3-cyano-2-pyridinyl)-1-piperidinyl]-N-(2,6-dimethylphenyl)acetamide;
N-(2-ethyl-6-methylphenyl)-2-[4-(2-pyridinyl)-1-piperidinyl]acetamide;
N-(2-isopropyl-6-methylphenyl)-2-[4-(2-pyridinyl)-1-piperidinyl]acetamide;
N-(2-chloro-6-methylphenyl)-2-[4-(2-pyridinyl)-1-piperidinyl]acetamide;
N-(2-methoxy-6-methylphenyl)-2-[4-(2-pyridinyl)-1-1piperidinyl]acetamide;
2-(1-{2-[(4-fluoro-2-methylphenyl)amino]-2-oxoethyl}-4-piperidinyl)pyridinium N-oxide;
2-(1-{2-[(4-fluoro-3-methylphenyl)amino]-2-oxoethyl}-4-piperidinyl)pyridinium N-oxide;
2-(1-{2-[(3-fluorophenyl)amino]-2-oxoethyl}-4-piperidinyl)pyridinium N-oxide;
2-(1-{2-[(2-fluoro-5-methylphenyl)amino]-2-oxoethyl}-4-piperidinyl)pyridinium N-oxide;

2-(1-{1-methyl-2-[(3-methylphenyl)amino]-2-oxoethyl}-4-piperidinyl)pyridinium N-oxide;
2-(1-{2-[(4-fluorophenyl)amino]-2-oxoethyl}-4-piperidinyl)pyridinium N-oxide;
2-(1-{2-[(2-fluorophenyl)amino]-2-oxoethyl}-4-piperidinyl)pyridinium N-oxide;
2-(1-{2-[(3-chlorophenyl)amino]-2-oxoethyl}piperidin-4-yl)pyridinium N-oxide;
2-(1-{2-oxo-2-[(2,4,6-tribromo-3-methylphenyl)amino]ethyl}piperidin-4-yl)pyridinium N-oxide;
2-(1-{[(4-bromo-3-methylbenzoyl)amino]methyl}piperidin-4-yl)pyridinium N-oxide;
N-(3-methylphenyl)-2-(4-pyridin-2-ylpiperidin-1-yl)ethanethioamide;
2-(1-{2-[(3,5-dichlorophenyl)amino]-2-oxoethyl}piperidin-4-yl)pyridinium N-oxide;
2-(1-{2-[(2,3-dichlorophenyl)amino]-2-oxoethyl}piperidin-4-yl)pyridinium N-oxide;
2-(1-{2-[(2-methoxy-6-methylphenyl)amino]-2-oxoethyl}piperidin-4-yl)pyridinium N-oxide;
2-{1-[2-(1,1'-biphenyl-3-ylamino)-2-oxoethyl]piperidin-4-yl}pyridinium N-oxide;
2-(1-{2-[(3-ethylphenyl)amino]-2-oxoethyl}piperidin-4-yl)pyridinium N-oxide;
2-{1-[2-(2,3-dihydro-1H-inden-5-ylamino)-2-oxoethyl]piperidin-4-yl}pyridinium N-oxide;
2-{1-[2-oxo-2-(5,6,7,8-tetrahydronaphthalen-1-ylamino)ethyl]piperidin-4-yl}pyridinium N-oxide;
2-(1-{2-[(3-isopropoxyphenyl)amino]-2-oxoethyl}piperidin-4-yl)pyridinium N-oxide;
2-(1-{2-[(3,5-dimethylphenyl)amino]l-2-oxoethyl}piperidin-4-yl)pyridinium N-oxide;
2-(1-{2-[(4-bromo-2-methylphenyl)amino]-2-oxoethyl}piperidin-4-yl)pyridinium N-oxide;
2-[1-(2-oxo-2-{[3-(trifluoromethoxy)phenyl]amino}ethyl)piperidin-4-yl]pyridinium N-oxide;
2-(1-{2-[(5-methyl-2-nitrophenyl)amino]-2-oxoethyl}piperidin-4-yl)pyridinium N-oxide;
2-(1-{2-[(2,6-dimethylphenyl)amino]-2-oxoethyl}piperidin-4-yl)pyridinium N-oxide;
2-(1-{2-[(2,6-dichloro-3-methylphenyl)amino]-2-oxoethyl}piperidin-4-yl)pyridinium N-oxide;
2-[1-(2-{[3-(methylthio)phenyl]amino}-2-oxoethyl)piperidin-4-yl]pyridinium N-oxide;
2-(1-{2-[(5-chloro-2-methylphenyl)amino]-2-oxoethyl}piperidin-4-yl)pyridinium N-oxide;
2-(1-{2-[(2,5-dimethoxyphenyl)amino]-2-oxoethyl}piperidin-4-yl)pyridinium N-oxide;
2-(1-{2-[(3,5-dimethoxyphenyl)amino]-2-oxoethyl}piperidin-4-yl)pyridinium N-oxide;
2-[1-(2-{[3-(dimethylamino)phenyl]amino}-2-oxoethyl)piperidin-4-yl]pyridinium N-oxide;
2-(1-{2-[(3-isopropylphenyl)amino]-2-oxoethyl}piperidin-4-yl)pyridinium N-oxide;
2-(1-{2-[(3-chloro-2-methylphenyl)amino]-2-oxoethyl}piperidin-4-yl)pyridinium N-oxide;
2-(1-{[(2,3-dibromo-5-methylbenzoyl)amino]methyl}piperidin-4-yl)pyridinium N-oxide;
2-{1-[(benzoylamino)methyl]piperidin-4-yl}pyridinium N-oxide;
2-(1-{[(4-chloro-3-methylbenzoyl)amino]methyl}piperidin-4-yl)pyridinium N-oxide;
2-(1-{[(4-fluoro-3-methylbenzoyl)amino]methyl}piperidin-4-yl)pyridinium N-oxide;
2-[1-({[3-chloro-4-(trifluoromethoxy)benzoyl]amino}methyl)piperidin-4-yl]pyridinium N-oxide;
2-(1-{[(3-ethoxybenzoyl)amino]methyl}piperidin-4-yl)pyridinium N-oxide;
2-(1-{[(3,5-dichlorobenzoyl)amino]methyl}piperidin-4-yl)pyridinium N-oxide;
2-[1-({[4-methyl-3-(trifluoromethyl)benzoyl]amino}methyl)piperidin-4-yl]pyridinium N-oxide;
2-(1-{[(3,4-dimethylbenzoyl)amino]methyl}piperidin-4-yl)pyridinium N-oxide;
2-(1-{[(3-chloro-4-fluorobenzoyl)amino]methyl}piperidin-4-yl)pyridinium N-oxide;
2-(1-{[(pyridin-2-ylcarbonyl)amino]methyl}piperidin-4-yl)pyridinium N-oxide;
2-(1-{[(3,5-dimethylbenzoyl)amino]methyl}piperidin-4-yl)pyridinium N-oxide;
2-(1-{[(3-vinylbenzoyl)amino]methyl}piperidin-4-yl)pyridinium N-oxide;
2-(1-{[(4-bromo-3-methylbenzoyl)amino]methyl}-1,2,3,6-tetrahydropyridin-4-yl)pyridinium N-oxide;
2-(1-{[(3-cyanobenzoyl)amino]methyl}piperidin-4-yl)pyridinium N-oxide;
2-(1-{[(4-bromobenzoyl)amino]methyl}piperidin-4-yl)pyridinium N-oxide;
2-(1-{[(3-chloro-4-methylbenzoyl)amino]methyl}piperidin-4-yl)pyridinium N-oxide;
2-(1-{[methyl(3-methylbenzoyl)amino]methyl}piperidin-4-yl)pyridinium N-oxide;
2-(1-{[(3-nitrobenzoyl)amino]methyl}piperidin-4-yl)pyridinium N-oxide;
2-(1-{[(2-chloro-5-methylbenzoyl)amino]methyl}piperidin-4-yl)pyridinium N-oxide;
2-(1-{[(3-methoxy-2-methylbenzoyl)amino]methyl}piperidin-4-yl)pyridinium N-oxide;
2-(1-{[(4-chloro-3-methoxybenzoyl)amino]methyl}piperidin-4-yl)pyridinium N-oxide; and
N-(3-methylphenyl)-2-(3-pyridin-2-ylpiperidin-1-yl)acetamide.

9. The method according to claim 1 wherein the compound of formula (I) is 2-(1-{[(3-methylbenzoyl)amino]methyl}-4-piperidinyl)pyridinium N-oxide.

* * * * *